US007122557B2

(12) United States Patent
Pinto et al.

(10) Patent No.: US 7,122,557 B2
(45) Date of Patent: Oct. 17, 2006

(54) SULFONYL-AMIDINO-CONTAINING AND TETRAHYDROPYRIMIDINO-CONTAINING COMPOUNDS AS FACTOR XA INHIBITORS

(75) Inventors: Donald J. Pinto, Kennett Square, PA (US); Jennifer X. Qiao, Princeton, NJ (US); Timur Gungor, Pennington, NJ (US); Patrick Y. S. Lam, Chadds Ford, PA (US); Yun-Long Li, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 170 days.

(21) Appl. No.: 10/801,518

(22) Filed: Mar. 16, 2004

(65) Prior Publication Data
US 2004/0209863 A1    Oct. 21, 2004

Related U.S. Application Data

(60) Provisional application No. 60/455,709, filed on Mar. 18, 2003.

(51) Int. Cl.
*A61K 31/437* (2006.01)
*C07D 471/04* (2006.01)
(52) U.S. Cl. ..................... 514/303; 546/120
(58) Field of Classification Search ............... None
See application file for complete search history.

(56) References Cited

U.S. PATENT DOCUMENTS

| | | | |
|---|---|---|---|
| 3,340,269 A | 9/1967 | Blatter | |
| 3,365,459 A | 1/1968 | Blatter | |
| 3,423,414 A | 1/1969 | Blatter | |
| 5,342,851 A | 8/1994 | Sanfilippo et al. | |
| 5,976,532 A * | 11/1999 | Coller et al. | 424/133.1 |
| 5,998,424 A | 12/1999 | Galemmo, Jr. et al. | |
| 6,020,357 A | 2/2000 | Pinto et al. | |
| 6,060,491 A | 5/2000 | Pruitt et al. | |
| 6,191,159 B1 | 2/2001 | Pinto | |
| 6,413,980 B1 * | 7/2002 | Fevig et al. | 514/300 |
| 6,750,225 B1 * | 6/2004 | Pinto et al. | 514/303 |

FOREIGN PATENT DOCUMENTS

| | | |
|---|---|---|
| WO | WO 98/28269 | 7/1998 |
| WO | WO 98/28282 | 7/1998 |
| WO | WO 98/57934 | 12/1998 |
| WO | WO 98/57937 | 12/1998 |
| WO | WO 98/57951 | 12/1998 |
| WO | WO 99/32454 | 7/1999 |
| WO | WO 99/32477 | 7/1999 |
| WO | WO 99/50255 | 10/1999 |
| WO | WO 00/39108 | 7/2000 |
| WO | WO 00/39131 | * 7/2000 |
| WO | WO 00/59902 | 10/2000 |
| WO | WO 01/05784 | 1/2001 |
| WO | WO 01/19798 | 3/2001 |
| WO | WO 01/32628 | 5/2001 |

OTHER PUBLICATIONS

Fevig, et al, STN International (2006) HCAPLUS Database, Columbus, OH, Accession No. 2000:457072.*
Freistein, STN International Search Report, Jan. 9, 2006.*
Bauer, K.A., "Fondaparinux: a new synthetic and selective inhibitor of Factor Xa", Best Practice & Research Clinical Haematology, vol. 17, No. 1, pp. 89-104, 2004.
Elodi et al., "Optimization of Conditions for the Catalytic Effect of The Factor IXa—Factor VIII Complex: Probable role of the complex in the amplification of blood coagulation", Thrombosis Research, vol. 15, pp. 617-623, 1979.
Gresele et al., "Novel approaches to the treatment of thrombosis", TRENDS in Pharmacological Sciences, vol. 23, No. 1, pp. 25-32, Jan. 2002.
Kaiser, B., "Visions & Reflections—Factor Xa—a promising target for drug development", Cell. Mol. Life Sci., vol. 59, pp. 189-192, 2002.
Linkins et al., "New Anticoagulants", Seminars in Thrombosis and Hemostasis, vol. 29, No. 6, pp. 619-631, 2003.
Rauch et al., "Thrombus Formation on Atherosclerotic Plaques: Pathogenesis and Clinical Consequences", Annals of Internal Medicine, vol. 134, No. 3., pp. 224-238, Feb. 6, 2001.
Ruef et al., "New antithrombotic drugs on the horizon", Expert Opin. Investig. Drugs, vol. 12, No. 5, pp. 781-797, 2003.
Wang et al., "Inhibition of Factor Xa Reduces Ischemic Brain Damage After Thromboembolic Stroke in Rats", Stroke, pp. 468-474, Feb. 2003.
Weitz et al., "Thrombophilia and New Anticoagulant Drugs", Hematology, pp. 424-438, 2004.
Wong et al., "Nonpeptide Factor Xa Inhibitors III: Effects of DPC423, an Orally-Active Pyrazole Antithrombotic Agent, on Arterial Thrombosis in Rabbits", vol. 303, No. 3, pp. 993-1000, 2002.

* cited by examiner

*Primary Examiner*—Kamal A. Saeed
*Assistant Examiner*—Andrew B. Freistein
(74) *Attorney, Agent, or Firm*—Jing G. Sun; David H. Vance

(57) ABSTRACT

The present application describes sulfonyl-amidino-containing and tetrahydropyrimidino-containing compounds and derivatives thereof of Formula I:

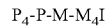

$P_4$-P-M-$M_4$I or pharmaceutically acceptable salt forms thereof, wherein M is a ring, P is an optional ring, and $P_4$ and $M_4$ are as defined below. Compounds of the present invention are useful as inhibitors of trypsin-like serine proteases, specifically factor Xa.

19 Claims, No Drawings

SULFONYL-AMIDINO-CONTAINING AND TETRAHYDROPYRIMIDINO-CONTAINING COMPOUNDS AS FACTOR Xa INHIBITORS

CROSS-REFERENCE TO RELATED APPLICATIONS

The present application claims the priority benefit of U.S. Provisional Application No. 60/455,709, filed Mar. 18, 2003, which is expressly incorporated fully herein by reference.

FIELD OF THE INVENTION

This invention relates generally to sulfonyl-amidino-containing and tetrahydropyrimidino-containing compounds and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

U.S. Pat. Nos. 3,365,459, 3,340,269, and 3,423,414 illustrate anti-inflammatory inhibitors of the following formula:

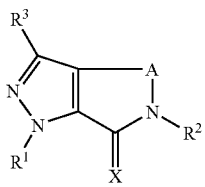

wherein A is 2–3 carbon atoms, X can be O, and $R^1$ and $R^3$ can be substituted or unsubstituted aromatic groups. None of these patents, however, exemplify or suggest compounds of the present invention.

U.S. Pat. No. 5,342,851 depicts thiazole platelet aggregation inhibitors including those of the following formula:

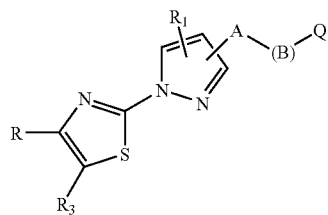

wherein A is a linker, B can be a linker or a ring, Q is a ring or an amino group, R, $R_1$, and $R_3$ are a variety of groups. This patent, however, does not exemplify or suggest compounds of the present invention.

WO00/39131 describes heterobicyclic Factor Xa inhibitors of which the following is an example formula:

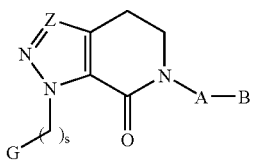

wherein Z is C or N, G is a mono- or bicyclic group, A is a cyclic moiety and B is a basic group or a cyclic moiety. Compounds specifically described in WO00/39131 are not considered to be part of the present invention.

WO98/28269, WO98/28282, WO99/32454, U.S. Pat. Nos. 6,020,357, and 6,271,237 describe Factor Xa inhibitors of the following formula:

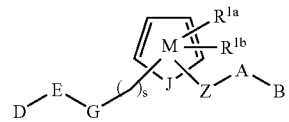

wherein ring M is a heterocycle, Z is a linker, A is a ring, B is a basic or cyclic group, D is a basic moiety, and E is a ring. Compounds specifically described in WO98/28269, WO98/28282, WO99/32454, U.S. Pat. Nos. 6,020,357, and 6,271,237 are not considered to be part of the present invention.

WO98/57951 describes Factor Xa inhibitors of the following formula:

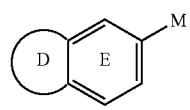

wherein ring M can be a variety of heterocycles and rings D-E represent a heterobicyclic group. Compounds specifically described in WO98/57951 are not considered to be part of the present invention.

WO98/57934 and U.S. Pat. No. 6,060,491 describe Factor Xa inhibitors of the following formula:

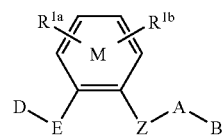

wherein ring M is a 6-membered heteroaryl, Z is a linker, A is a ring, B is a basic or cyclic group, D is a basic moiety, and E is a ring. Compounds specifically described in WO98/57934 and U.S. Pat. No. 6,060,491 are not considered to be part of the present invention.

WO98/57937 and U.S. Pat. No. 5,998,424 describe Factor Xa inhibitors of the following formula:

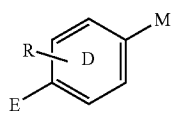

wherein ring M is a variety of rings, ring D is an aromatic ring, and R and E are non-basic groups. Compounds specifically described in WO98/57937 and U.S. Pat. No. 5,998,424 are not considered to be part of the present invention.

WO99/50255 and U.S. Pat. No. 6,191,159 describe pyrazoline and triazoline Factor Xa inhibitors of the following formulas:

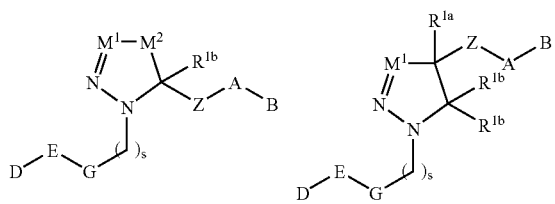

Compounds specifically described in WO99/50255 and U.S. Pat. No. 6,191,159 are not considered to be part of the present invention.

WO00/59902 describes Factor Xa inhibitors of the following formula:

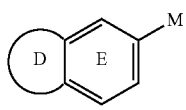

wherein ring M can be a variety of rings all of which are substituted with Z-A-B, Z is a linker, A is a ring, B is a sulfonyl-containing heterobicycle, and rings D-E represent a heterobicyclic group or a 6-membered ring. Compounds specifically described in WO00/59902 are not considered to be part of the present invention.

WO01/32628 describes cyano-pyrroles, cyano-imidazoles, cyano-pyrazoles, and cyano-triazoles that are Factor Xa inhibitors. Compounds specifically described in WO01/32628 are not considered to be part of the present invention.

WO01/05784 describes Factor Xa inhibitors of the following formulas:

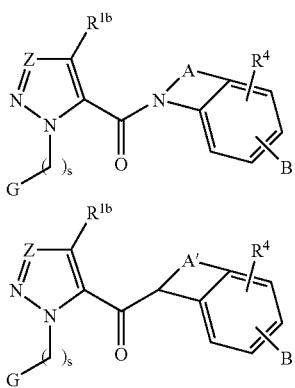

wherein Z is C or N, G is a mono- or bicyclic ring M, A is a linker, B is a basic or cyclic group. Compounds specifically described in WO01/05784 are not considered to be part of the present invention.

WO00/39108 describes Factor Xa inhibitors of the following formula:

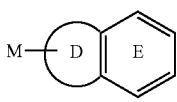

wherein ring M can be a variety of heterocycles and rings D-E represent a heterobicyclic group. Compounds specifically described in WO00/39108 are not considered to be part of the present invention.

WO01/19798 describes factor Xa inhibitors of the following formula:

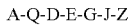

A-Q-D-E-G-J-Z wherein A, D, G, and X can be phenyl or heterocycle. However, none of the presently claimed compounds are exemplified or suggested in WO01/19798.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

Accordingly, the present invention provides novel sulfonyl-amidino-containing and tetrahydropyrimidino-containing compounds and derivatives thereof that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a mammal in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder.

The present invention provides a novel method, comprising: administering a compound of the present invention or a pharmaceutically acceptable salt form thereof in an amount effective to treat a thromboembolic disorder.

The present invention provides novel lactam-containing compounds and derivatives thereof for use in therapy.

The present invention provides the use of novel lactam-containing compounds for the manufacture of a medicament for the treatment of a thromboembolic disorder.

These and other objects, which will become apparent during the following detailed description, have been achieved by the inventors' discovery that sulfonyl-amidino-containing and tetrahydropyrimidino-containing compounds of Formula I:

$$P_4\text{-}P\text{-}M\text{-}M_4 \qquad\qquad I$$

wherein $P_4$, $P$, $M$, and $M_4$ are defined below, or pharmaceutically acceptable salt or prodrug forms thereof, are effective factor Xa inhibitors.

DETAILED DESCRIPTION

In a first aspect, the present invention provides a novel compound of formula I:

$$P_4\text{-}P\text{-}M\text{-}M_4 \qquad\qquad I$$

or a stereoisomer or pharmaceutically acceptable salt thereof, wherein;

M is a 3–10 membered carbocycle or a 4–10 membered heterocycle, consisting of: carbon atoms and 1–3 heteroatoms selected from O, $S(O)_p$, N, and $NZ^2$;

ring M is substituted with 0–3 $R^{1a}$ and 0–2 carbonyl groups, and there are 0–3 ring double bonds;

P is fused onto ring M and is a 5, 6, or 7 membered carbocycle or a 5, 6, or 7 membered heterocycle, consisting of: carbon atoms and 1–3 heteroatoms selected from O, $S(O)_p$, and N;

ring P is substituted with 0–3 $R^{1a}$ and 0–2 carbonyl groups, and there are 0–3 ring double bonds;

alternatively, ring P is absent and $P_4$ is directly attached to ring M, provided that when ring P is absent, $P_4$ and $M_4$ are attached to the 1,2, 1,3, or 1,4 positions of ring M;

one of $P_4$ and $M_4$ is -Z-A-B and the other -$G_1$-G;

G is a group of formula IIa or IIb:

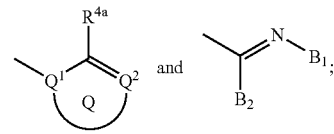

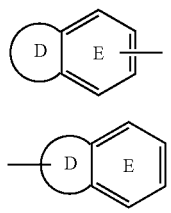

ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1–3 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyls and 1–2 R and there are 0–3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, —CN, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, $C(=NR^8)NR^7R^9$, $NHC(=NR^8)NR^7R^9$, $ONHC(=NR^8)NR^7R^9$, $NR^8CH(=NR^7)$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rNR^7C(O)R^7$, $(CR^8R^9)_rOR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$;

alternatively, when 2 R groups are attached to adjacent atoms, they combine to form methylenedioxy or ethylenedioxy;

A is selected from: $C_{3-10}$ carbocycle substituted with 0–2 $R^4$, and 5–12 membered heterocycle consisting of: carbon atoms and 1–4 heteroatoms selected from the group consisting of N, O, and $S(O)_p$ and substituted with 0–2 $R^4$;

B is selected from provided that Z and B are attached to different atoms on A and that the $R^{4a}$ shown is other than OH;

$Q^1$ and $Q^2$ are each N;

alternatively, one of $Q^1$ and $Q^2$ is $CR^3$ and $R^{4a}$ is $NR^2R^{2a}$ or $NR^{3a}B_1$, provided that when one of $Q^1$ and $Q^2$ is $CR^3$, then this $R^3$ group optionally forms a ring with the $R^2$ group of $R^{4a}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

ring Q is a 5–8 membered ring consisting of, in addition to the $Q^1$—$CR^{4a}=Q^2$ group shown, carbon atoms and 0–2 heteroatoms selected from N, O, and $S(O)_p$, and the ring is substituted with an additional 0–2 $R^{4a}$;

$B_1$ is selected from $SO_2R^{3b}$, $C(O)R^{3b}$, $SO_2NR^3R^{3b}$, $C(O)NR^3R^{3b}$, $OR^2$, $SR^2$, —CN, and $NO_2$;

$B_2$ is $NR^2R^{2d}$ or $CR^3R^2R^{2d}$;

alternatively, $CR^3R^2R^{2d}$ forms a 5–8 membered ring consisting of: carbon atoms and 0–2 heteroatoms selected from N, O, and $S(O)_p$, and this ring is substituted with 0–2 $R^{4b}$;

alternatively, $NR^2R^{2d}$ forms a 5–8 membered ring consisting of: carbon atoms and 0–2 additional heteroatoms selected from N, O, and $S(O)_p$, and this ring is substituted with 0–2 $R^{4b}$;

alternatively, when $B_1$ is $SO_2R^{3b}$ and $B_2$ is $NR^2R^{2d}$, $R^{3b}$ and $R^{2d}$ combine to form a 5–8 membered ring consisting of: carbon atoms and 0–2 additional heteroatoms selected from N, O, and $S(O)_p$, and this ring is substituted with 0–2 $R^{4b}$;

alternatively, when $B_1$ is $C(O)R^{3b}$ and $B_2$ is $NR^2R^{2d}$, $R^{3b}$ and $R^{2d}$ combine to form a 5–8 membered ring consisting of: carbon atoms and 0–2 additional heteroatoms selected from N, O, and $S(O)_p$, and this ring is substituted with 0–2 $R^{4b}$;

alternatively, when $B_2$ is $NR^2R^{2d}$, $B_1$ and $R^{2d}$ combine to form a 5–8 membered ring consisting of: carbon atoms and 0–2 additional heteroatoms selected from N, O, and $S(O)_p$, and this ring is substituted with 0–2 $R^{4b}$ and the $R^2$ group of $NR^2R^{2d}$, in addition to the groups recited below, is selected from $SO_2R^{3b}$, $C(O)R^{3b}$, and —CN;

$G_1$ is absent or is selected from $(CR^3R^{3a})_{1-5}$, $(CR^3R^{3a})_{0-2}$ $CR^3=CR^3(CR^3R^{3a})_{0-2}$, $(CR^3R^{3a})_{0-2}C\equiv C(CR^3R^{3a})_{0-2}$, $(CR^3R^{3a})_uC(O)(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uOC(O)NR^{3b}(CR^3R^{3a})_w$, $(CR^3R^{3a})_uNR^{3b}C(O)O(CR^3R^{3a})_w$, $(CR^3R^{3a})_uNR^{3b}C(O)NR^{3b}(CR^3R^{3a})_w$, $(CR^3R^{3a})_uNR^{3b}C(S)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, $(CR^3R^{3a})_uNR^{3b}S(O)_2NR^{3b}(CR^3R^{3a})_w$, $(CR^3R^{3a})_uNR^{3e}(CR^3R^{3a})_w$, $(CR^3R^{3a})_uC(O)(CR^3R^{3a})_uC(O)(CR^3R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(O)(CR^3R^{3a})_w$, $(CR^3R^{3a})_uC(O)(CR^3R^{3a})_uC(O)NR^{3b}(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(O)NR^{3b}C(O)(CR^3R^{3a})_w$, $(CR^3R^{3a})_uC(O)NR^{3b}S(O)_2(CR^3R^{3a})_w$, and $(CR^3R^{3a})_uS(O)_2NR^{3b}C(O)NR^{3b}CR^3R^{3a})_w$, wherein u+w or u+u+w total 0, 1, 2, 3, or 4, and the right side of $G_1$ is attached to G, provided that $G_1$ does not form a N—S, NCH$_2$N, NCH$_2$O, or NCH$_2$S bond with either group to which it is attached;

Z is selected from a bond, —$CR^3R^{3e})_{1-4}$—, $(CR^3R^{3e})_qO(CR^3R^{3e})_{q1}$, $(CR^3R^{3e})_qNR^{3b}(CR^3R^{3e})_{q1}$, $(CR^3R^{3e})_qC(O)(CR^3R^{3e})_{q1}$, $(CR^3R^{3e})_qC(O)O(CR^3R^{3e})_{q1}$, $(CR^3R^{3e})_qOC(O)(CR^3R^{3e})_{q1}$, $(CR^3R^{3e})_qC(O)NR^{3b}(CR^3R^{3e})_{q1}$, $(CR^3R^{3e})_qNR^{3b}C(O)(CR^3R^{3e})_{q1}$, $(CR^3R^{3e})_qOC(O)O(CR^3R^{3e})_{q1}$, $(CR^3R^{3e})_qOC(O)NR^{3b}(CR^3R^{3e})_{q1}$, $(CR^3R^{3e})_qNR^{3b}C(O)O(CR^3R^{3e})_{q1}$, $(CR^3R^{3e})_qNR^{3b}C(O)NR^{3b}(CR^3R^{3e})_{q1}$, $(CR^3R^{3e})_qC(O)(CR^3R^{3e})_qC(O)(CR^3R^{3e})_{q1}$, $(CR^3R^{3e})_qNR^{3b}(CR^3R^{3e})_qC(O)NR^{3b}(CR^3R^{3e})_{q1}$, $(CR^3R^{3e})_qNR^{3b}C(O)(CR^3R^{3e})_{q1}$, $(CR^3R^{3e})_qC(O)(CR^3R^{3e})_{q1}$, $(CR^3R^{3e})_qC(O)(CR^3R^{3e})_qC(O)NR^{3b}(CR^3R^{3e})_{q1}$, $(CR^3R^{3e})_qNR^{3b}C(O)(CR^3R^{3e})_qC(O)NR^{3b}(CR^3R^{3e})_{q1}$, $(CR^3R^{3e})_qS(CR^3R^{3e})_{q1}$, $(CR^3R^{3e})_qS(O)(CR^3R^{3e})_{q1}$, $(CR^3R^{3e})_qS(O)_2(CR^3R^{3e})_{q1}$, $(CR^3R^{3e})_qSO_2NR^{3b}(CR^3R^{3e})_{q1}$, $(CR^3R^{3e})_qNR^{3b}SO_2(CR^3R^{3e})_{q1}$, $(CR^3R^{3e})_qS(O)NR^{3b}C(O)(CR^3R^{3e})_{q1}$, $(CR^3R^{3e})_qC(O)NR^{3b}S(O)_2(CR^3R^{3e})_{q1}$, and $(CR^3R^{3e})_qNR^{3b}SO_2NR^{3b}(CR^3R^{3e})_{q1}$, wherein q+q1 or q+q+q1 total 0, 1, 2, 3, or 4, and the right side of Z is attached to A, provided that Z does not form a N—S, NCH$_2$N, NCH$_2$O, or NCH$_2$S bond with either group to which it is attached;

$Z^2$ is selected from H, $S(O)_2NHR^{3b}$, $C(O)R^{3b}$, $C(O)NHR^{3b}$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl$)$-$C_{3-10}$ carbocycle substituted with 0–3 $R^{1a}$, and —$(C_{0-4}$ alkyl$)$-5–10 membered heterocycle substituted with 0–3 $R^{1a}$ and consisting of: carbon atoms and 1–4 heteroatoms selected from the group consisting of N, O, and $S(O)_p$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—$O$—$(CR^3R^{3a})_r$—$R^{1b}$, —$(CR^3R^{3a})_r$—$NR^2$—$(CR^3R^{3a})_r$—$R^{1b}$, —$(CR^3R^{3a})_r$—$S(O)_p$—$(CR^3R^{3a})_r$—$R^{1b}$, —$(CR^3R^{3a})_r$—$CO_2$—$(CR^3R^{3a})_r$—$R^{1b}$, —$(CR^3R^{3a})_r$—$C(O)NR^2$—$(CR^3R^{3a})_r$—$R^{1b}$, —$(CR^3R^{3a})_r$—$C(O)$—$(CR^3R^{3a})_r$—$R^{1b}$, —$C_{2-6}$ alkenylene-$R^{1b}$, —$C_{2-6}$ alkynylene-$R^{1b}$, and —$(CR^3R^{3a})_r$—$C(=NR^{1b})NR^3R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $C_{1-3}$ alkyl, F, Cl, Br, I, —CN, —NO$_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $CH(CH_2OR^2)_2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NR^2R^{2a}$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond;

$R^2$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $C_{1-6}$ alkyl, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0–2 $R^{4b}$, and —$(CH_2)_r$-5–10 membered heterocycle containing from 1–4 heteroatoms selected from the group consisting of N, O, and $S(O)_p$ and substituted with 0–2 $R^{4b}$;

$R^{2d}$, at each occurrence, is selected from H, $CF_3$, $C_{1-4}$ alkoxy substituted with 0–2 $R^{4b}$, $C_{1-6}$ alkyl substituted with 0–2 $R^{4b}$, —$(CH_2)_r$—$C_{3-10}$ carbocycle substituted with 0–2 $R^{4b}$, and —$(CH_2)_r$-5–10 membered heterocycle consisting of: carbon atoms and 1–4 heteroatoms selected from the group consisting of N, O, and $S(O)_p$ and substituted with 0–2 $R^{4b}$;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $NR^3R^{3a}$ forms a 5 or 6 membered saturated, partially unsaturated, or unsaturated ring consisting of:

carbon atoms, the nitrogen atom to which $R^3$ and $R^{3a}$ are attached, and 0–1 additional heteroatoms selected from the group consisting of N, O, and $S(O)_p$;

$R^{3b}$, at each occurrence, is selected from H, $CF_3$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-5–10 membered carbocycle substituted with 0–3 $R^{1a}$, and —$(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-5–10 membered carbocycle substituted with 0–3 $R^{1a}$, and —$(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3f}$, at each occurrence, is selected from: $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-5–10 membered carbocycle substituted with 0–3 $R^{1a}$, and —$(C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^4$, at each occurrence, is selected from H, =O, $(CR^3R^{3a})_rOR^2$, F, Cl, Br, I, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rC(=NS(O)_2R^5)NR^2R^{2a}$, $(CR^3R^{3a})_rNHC(=NR^2)NR^2R^{2a}$, $(CR^3R^{3a})_rC(O)NHC(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2—C_{1-4}$ alkyl, $(CR^3R^{3a})_rNR^2SO_2R^5$, $(CR^3R^{3a})_rS(O)_pR^{5a}$, $(CR^3R^{3a})_r(CF_2)_rCF_3$, $NHCH_2R^{1b}$, $OCH_2R^{1b}$, $SCH_2R^{1b}$, $NH(CH_2)_2(CH_2)_rR^{1b}$, $O(CH_2)_2(CH_2)_rR^{1b}$, $S(CH_2)_2(CH_2)_tR^{1b}$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4a}$, at each occurrence, is selected from H, $(CR^3R^{3a})_rOR^2$, $(CR^3R^{3a})_rF$, $(CR^3R^{3a})_rBr$, $(CR^3R^{3a})_rCl$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NH(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNHC(=NR^2)NR^2R^{2a}$, $(CR^3R^{3a})_rSO_2NR^2R^{2a}$, $(CR^3R^{3a})_rNR^2SO_2NR^2R^{2a}$, $(CR_3R^{3a})_rNR^2SO_2—C_{1-4}$ alkyl, $(CR_3R^{3a})_rC(O)NHSO_2—C_{1-4}$ alkyl, $(CR^3R^{3a})NR^2SO_2R^5$, $(CR^3R^{3a})_rS(O)_pR^{5a}$, $(CR^3R^{3a})_r(CF_2)_rCF_3$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$ and substituted with 0–1 $R^5$;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_r—C(O)NR^3R^{3a}$, $(CH_2)_rNR^3C(O)NR^3R^{3a}$, $(CH_2)_r—C(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2—C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p—C_{1-4}$ alkyl, $(CH_2)_rS(O)_p$-phenyl, and $(CH_2)_r(CF_2)_rCF_3$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2—C_{1-4}$ alkyl, $NR^3SO_2CF_3$, $NR^3SO_2$-phenyl, $S(O)_pCF_3$, $S(O)_p—C_{1-4}$ alkyl, $S(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^{5a}$, at each occurrence, is selected from $C_{1-6}$ alkyl, $(CH_2)_rOR^3$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CF_2)_rCF_3$, phenyl substituted with 0–2 $R^6$, naphthyl substituted with 0–2 $R^6$, and benzyl substituted with 0–2 $R^6$, provided that $R^{5a}$ does not form a S—N or $S(O)_p$—C(O) bond;

$R^6$, at each occurrence, is selected from H, OH, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkyl-C(O)—, $C_{1-6}$ alkyl-O—, $(CH_2)_n$-phenyl, $C_{1-6}$ alkyl-S(O)$_2$—, $C(O)NH_2$, $C(O)NH—C_{1-4}$ alkyl, $C(O)N(C_{1-4}$ alkyl)$_2$, $C_{1-4}$ alkyl-OC(O)—, $C_{6-10}$ aryl-O—, $C_{6-10}$ aryl-OC(O)—, $C_{6-10}$ aryl-$CH_2C(O)$—, $C_{1-4}$ alkyl-C(O)O—$C_{1-4}$ alkyl-OC(O)—, $C_{6-10}$ aryl-C(O)O—$C_{1-4}$ alkyl-OC(O)—, $C_{1-6}$ alkyl-$NH_2$—C(O)—, phenyl-$NH_2$—C(O)—, and phenyl-$C_{1-4}$ alkyl-C(O)—;

$R^8$, at each occurrence, is selected from H, $C_{1-6}$ alkyl, and $(CH_2)_n$-phenyl;

alternatively, $NR^7R^8$ forms a 5–10 membered heterocyclic ring consisting of carbon atoms and 0–2 additional heteroatoms selected from the group consisting of N, O, and $S(O)_p$;

$R^9$, at each occurrence, is selected from H, $C_{1-6}$ alkyl, and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, 3, 4, 5, and 6;

r1, at each occurrence, is selected from 1, 2, 3, 4, 5, and 6; and t, at each occurrence, is selected from 0, 1, 2, and 3.

In a second aspect, the present invention provides a novel compound of Formula II:

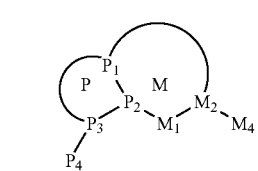

II or a stereoisomer or pharmaceutically acceptable salt thereof, wherein;

ring M, including P₁, P₂, M₁, and M₂, is a 5, 6, or 7 membered carbocycle or a 5, 6, or 7 membered heterocycle, consisting of: carbon atoms and 1–3 heteroatoms selected from O, S(O)$_p$, N, and NZ²;

ring M is substituted with 0–2 R$^{1a}$ and 0–2 carbonyl groups, and there are 0–3 ring double bonds;

ring P, including P₁, P₂, and P₃, is a 5 or 6 membered aromatic or dihydro-aromatic heterocycle, consisting of: carbon atoms and 1–3 heteroatoms selected from O, S(O)$_p$, and N;

ring P is substituted with 0–2 R$^{1a}$;

one of P₄ and M₄ is —Z-A-B and the other -G₁-G;

G is a group of formula IIa or IIb:

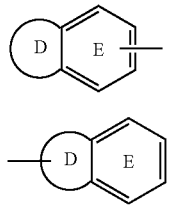

IIa

IIb ring D, including the two atoms of Ring E to which it is attached, is a 5–6 membered ring consisting of: carbon atoms and 0–2 heteroatoms selected from the group consisting of N, O, and S(O)$_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent, and ring E is selected from phenyl, pyridyl, pyrimidyl, and thienyl, and ring E is substituted with 1–3 R;

alternatively, ring D is absent, ring E is selected from phenyl, pyridyl, and thienyl, and ring E is substituted with 1 R and substituted with a 5–6 membered heterocycle consisting of: carbon atoms and 1–4 heteroatoms selected from the group consisting of N, O, and S(O)$_p$, wherein the 5–6 membered heterocycle is substituted with 0–2 carbonyl and 1–2 R and there are 0–3 ring double bonds;

R is selected from H, C$_{1-4}$ alkyl, F, Cl, OH, OCH₃, OCH₂CH₃, OCH(CH₃)₂, —CN, C(=NH)NH₂, C(=NH)NHOH, C(=NH)NHOCH₃, NH₂, NH(C$_{1-3}$ alkyl), N(C$_{1-3}$ alkyl)₂, CH₂NH₂, CH₂NH(C$_{1-3}$ alkyl), CH₂N(C$_{1-3}$ alkyl)₂, (CR⁸R⁹)$_r$NR⁷R⁸, C(O)NR⁷R⁸, CH₂C(O)NR⁷R⁸, S(O)$_p$NR⁷R⁸, CH₂S(O)$_p$NR⁷R⁸, SO₂R³, and OCF₃;

alternatively, when 2 R groups are attached to adjacent atoms, they combine to form methylenedioxy or ethylenedioxy;

A is selected from: C$_{5-10}$ carbocycle substituted with 0–2 R⁴, and 5–10 membered heterocycle consisting of: carbon atoms and 1–4 heteroatoms selected from the group consisting of N, O, and S(O)$_p$ and substituted with 0–2 R⁴;

B is selected from

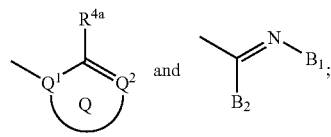

provided that Z and B are attached to different atoms on A and that the R$^{4a}$ shown is other than OH;

Q¹ and Q² are each N;

alternatively, one of Q¹ and Q² is CR³ and R$^{4a}$ is NR²R$^{2a}$ or NR$^{3a}$B₁, provided that when one of Q¹ and Q² is CR³, then this R³ group optionally forms a ring with the R² group of R$^{4a}$, this ring is a 5–6 membered ring consisting of, in addition to the C—C—N shown, carbon atoms and from 0–1 additional heteroatoms selected from N, O, and S(O)$_p$, and this ring is substituted with 0–1 R⁵;

ring Q is a 5–6 membered ring consisting of, in addition to the Q¹-CR$^{4a}$=Q² group shown, carbon atoms and 0–2 heteroatoms selected from N, O, and S(O)$_p$, and the ring is substituted with an additional 0–2 R$^{4a}$;

B₁ is selected from SO₂R$^{3b}$, C(O)R$^{3b}$, SO₂NR³R$^{3b}$, C(O)NR³R$^{3b}$, OR², and —CN;

B₂ is NR²R$^{2d}$ or CR³R²R$^{2d}$;

alternatively, CR³R²R$^{2d}$ forms a 5–6 membered ring consisting of: carbon atoms and 0–2 heteroatoms selected from N, O, and S(O)$_p$, and this ring is substituted with 0–2 R$^{4b}$;

alternatively, NR²R$^{2d}$ forms a 5–6 membered ring consisting of: carbon atoms and 0–2 additional heteroatoms selected from N, O, and S(O)$_p$, and this ring is substituted with 0–2 R$^{4b}$;

alternatively, when B₂ is NR²R$^{2d}$, B₁ and R$^{2d}$ combine to form a 5–6 membered ring consisting of: carbon atoms and 0–2 additional heteroatoms selected from N, O, and S(O)$_p$, and this ring is substituted with 0–2 R$^{4b}$ and the R² group of NR²R$^{2d}$, in addition to the groups recited below, is selected from SO₂R$^{3b}$ and C(O)R$^{3b}$;

Z is selected from a bond, CH₂, CH₂CH₂, CH₂O, OCH₂, C(O), NH, CH₂NH, NHCH₂, CH₂C(O), C(O)CH₂, C(O)NH, NHC(O), NHC(O)CH₂C(O)NH, S(O)₂, CH₂S(O)₂, S(O)₂(CH₂), SO₂NH, and NHSO₂, wherein the right side of Z is attached to A, provided that Z does not form a N—S, NCH₂N, NCH₂O, or NCH₂S bond with either group to which it is attached;

Z² is selected from H, C$_{1-4}$ alkyl, phenyl, benzyl, C(O)R$^{3b}$, S(O)R$^{3f}$, and S(O)₂R$^{3f}$;

R$^{1a}$, at each occurrence, is selected from H, —(CH₂)$_r$—R$^{1b}$, —(CH(CH₃))$_r$—R$^{1b}$, —(C(CH₃)₂)$_r$—R$^{1b}$, —O—(CR³R$^{3a}$)$_r$—R$^{1b}$, —NR²—(CR³R$^{3a}$)$_r$—R$^{1b}$, and —S—(CR³R$^{3a}$)$_r$—R$^{1b}$, provided that Ria forms other than an N-halo, N—S, O—O, or N—CN bond;

alternatively, when two R$^{1a}$ groups are attached to adjacent atoms, together with the atoms to which they are attached they form a 5–7 membered ring consisting of: carbon atoms and 0–2 heteroatoms selected from the group consisting of N, O, and S(O)$_p$, this ring being substituted with 0–2 R$^{4b}$ and 0–3 ring double bonds;

R$^{1b}$ is selected from H, CH₃, CH₂CH₃, CH₂CH₂CH₃, CH(CH₃)₂, F, Cl, Br, I, —CN, —CHO, CF₃, OR², NR²R$^{2a}$, C(O)R$^{2b}$, CO₂R$^{2b}$, OC(O)R², CO₂R$^{2a}$, S(O)$_p$R$^{2b}$, NR²(CH₂)$_r$OR², NR²C(O)R$^{2b}$, NR²C(O)NHR², NR²C(O)₂R$^{2a}$, OC(O)NR²R$^{2a}$, C(O)NR²R$^{2a}$, C(O)NR²(CH₂)$_r$OR², SO₂NR²R$^{2a}$, NR²SO₂R², C$_{5-6}$ carbocycle substituted with 0–2 R$^{4b}$, and 5–6 membered heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

R², at each occurrence, is selected from H, CF₃, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, C$_{5-6}$ carbocycle substituted with 0–2 R$^{4b}$, a —CH₂—C$_{5-6}$ carbocyclic group substituted with 0–2 R$^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $NR^3R^{3a}$ forms a 5 or 6 membered saturated, partially unsaturated, or unsaturated ring consisting of: carbon atoms and the nitrogen atom to which $R^3$ and $R^{3a}$ are attached;

$R^{3b}$, at each occurrence, is selected from H, $CF_3$, $CH_3$, $CH_2CH_3$, $CH_2CH_2CH_3$, $CH(CH_3)_2$, —$(C_{0-1}$ alkyl)-5–6 membered carbocycle substituted with 0–1 $R^{1a}$, and —$(C_{0-1}$ alkyl)-5–6 membered heterocycle substituted with 0–1 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^{4a}$, at each occurrence, is selected from H, $CH_2OR^2$, $OR^2$, $C_{1-4}$ alkyl, —CN, $CH_2CN$, $NO_2$, $CH_2NO_2$, $NR^2R^{2a}$, $CH_2NR^2R^{2a}$, $C(O)R^{2c}$, $CH_2C(O)R^{2c}$, $NR^2C(O)R^{2b}$, $(CH_2)_rC(O)NR^2R^{2a}$, $NR^2C(O)NR^2R^{2a}$, $(CH_2)_rSO_2NR^2R^{2a}$, $NR^2SO_2NR^2R^{2a}$, $NR^2SO_2R^5$, $(CH_2)_rS(O)_pR^{5a}$, $CH_2CF_3$, $CF_3$, 5–6 membered carbocycle substituted with 0–1 $R^5$, $CH_2$-5–6 membered carbocycle substituted with 0–1 $R^5$, a 5–6 membered heterocycle consisting of: carbon atoms and 1–4 heteroatoms selected from the group consisting of N, O, and $S(O)_p$ and substituted with 0–1 $R^5$, and a $CH_2$-5–6 membered heterocycle consisting of: carbon atoms and 1–4 heteroatoms selected from the group consisting of N, O, and $S(O)_p$ and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2CF_3$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

In a third aspect, the present invention provides a novel compound, wherein:

ring M is substituted with 0–2 $R^{1a}$ and is selected from the group:

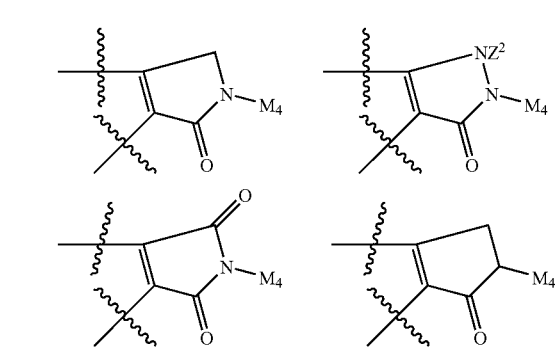

-continued
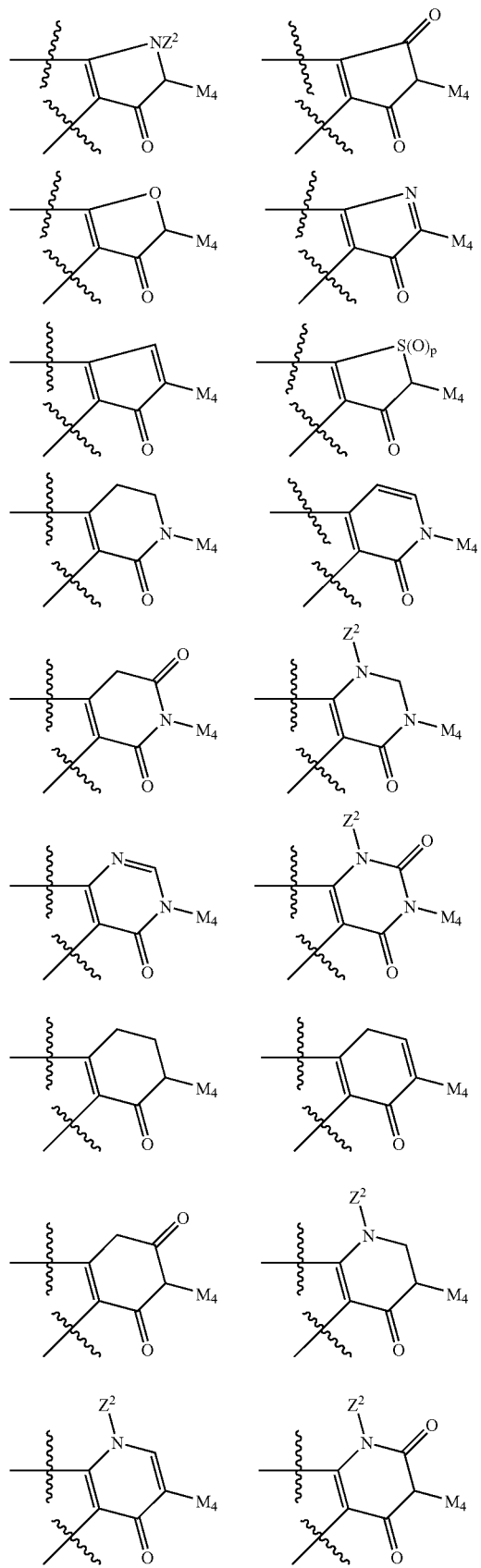
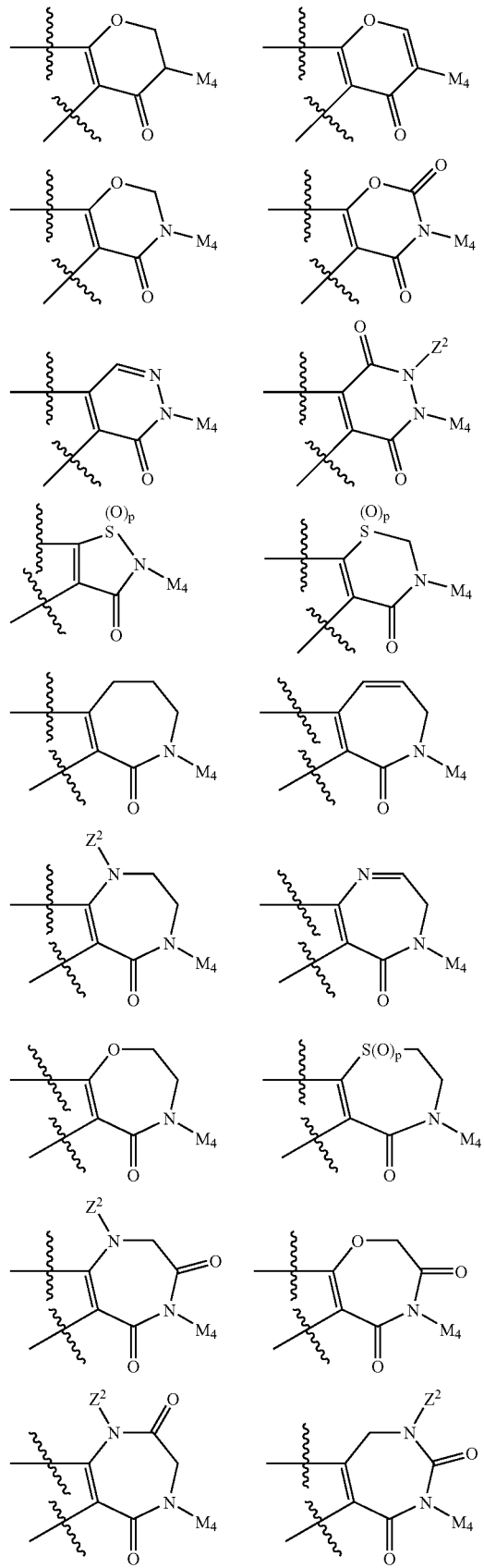

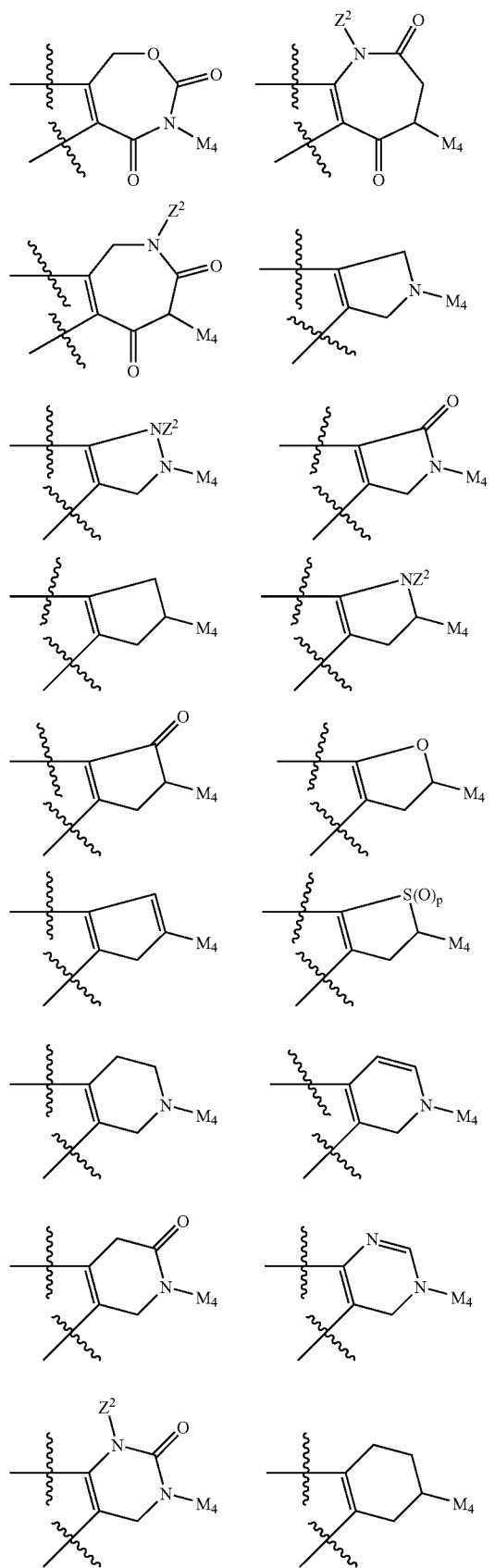
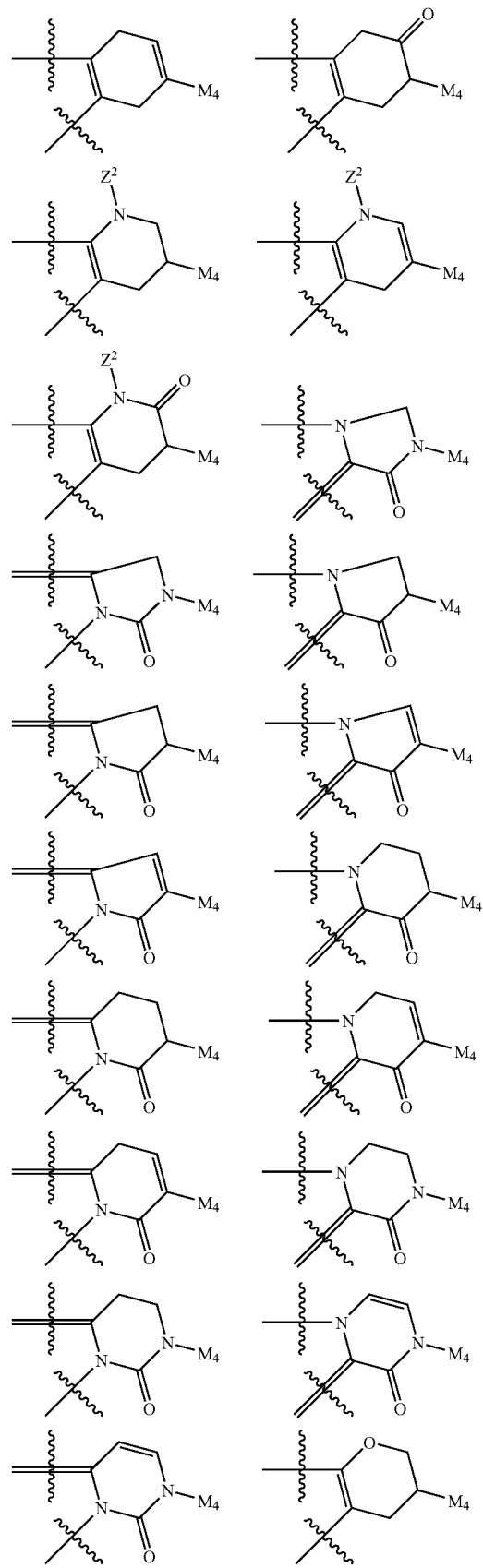

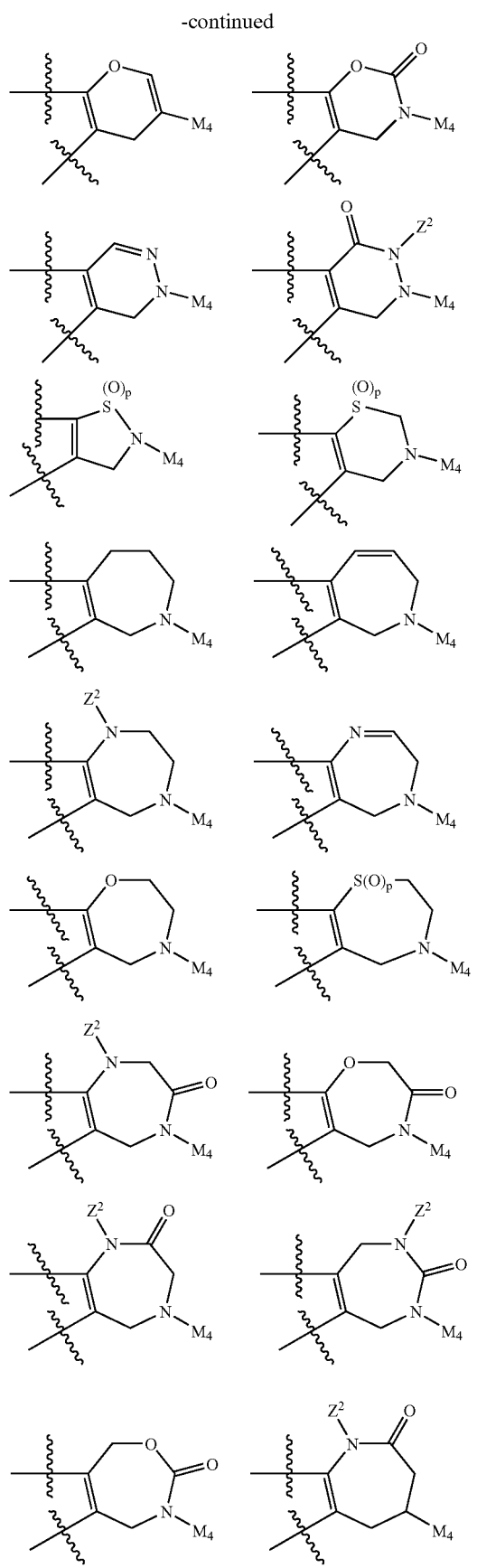
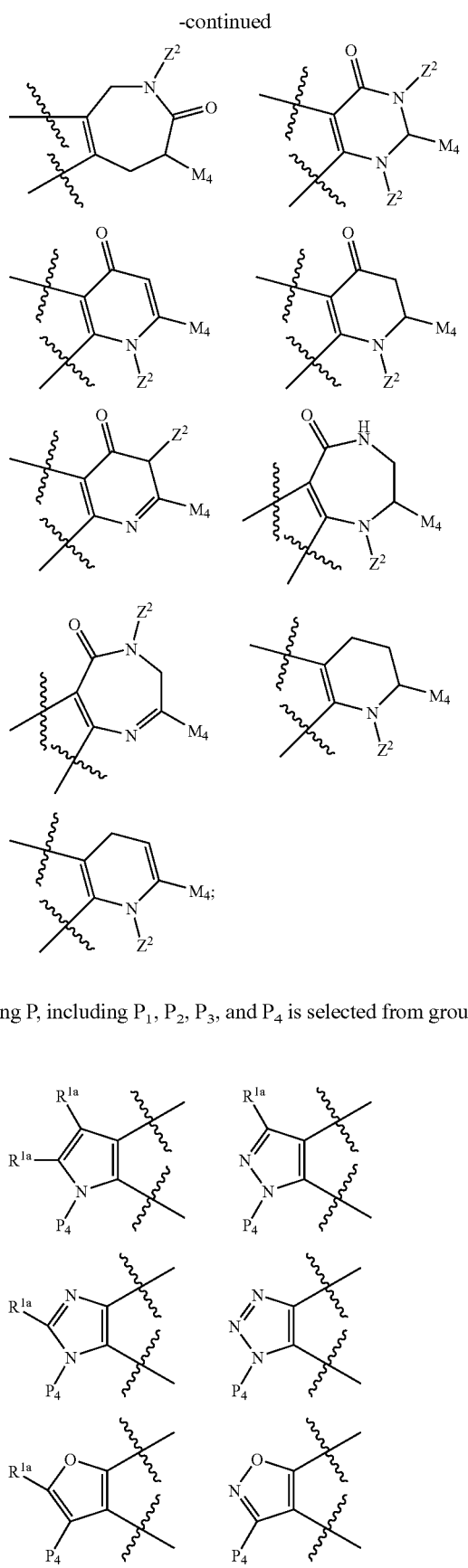
ring P, including $P_1$, $P_2$, $P_3$, and $P_4$ is selected from group:

-continued
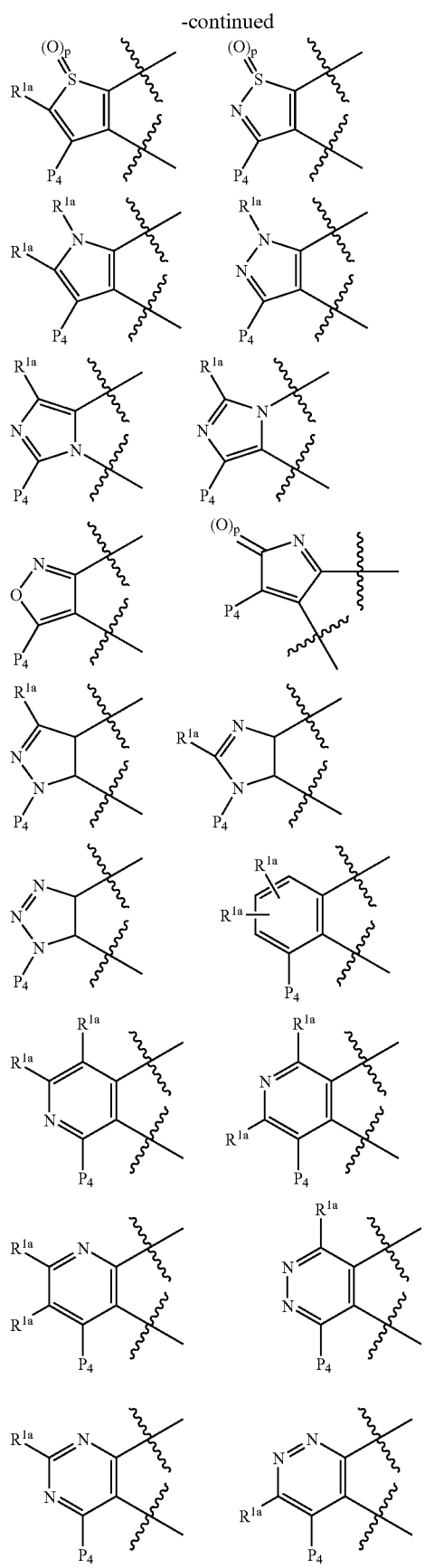
-continued
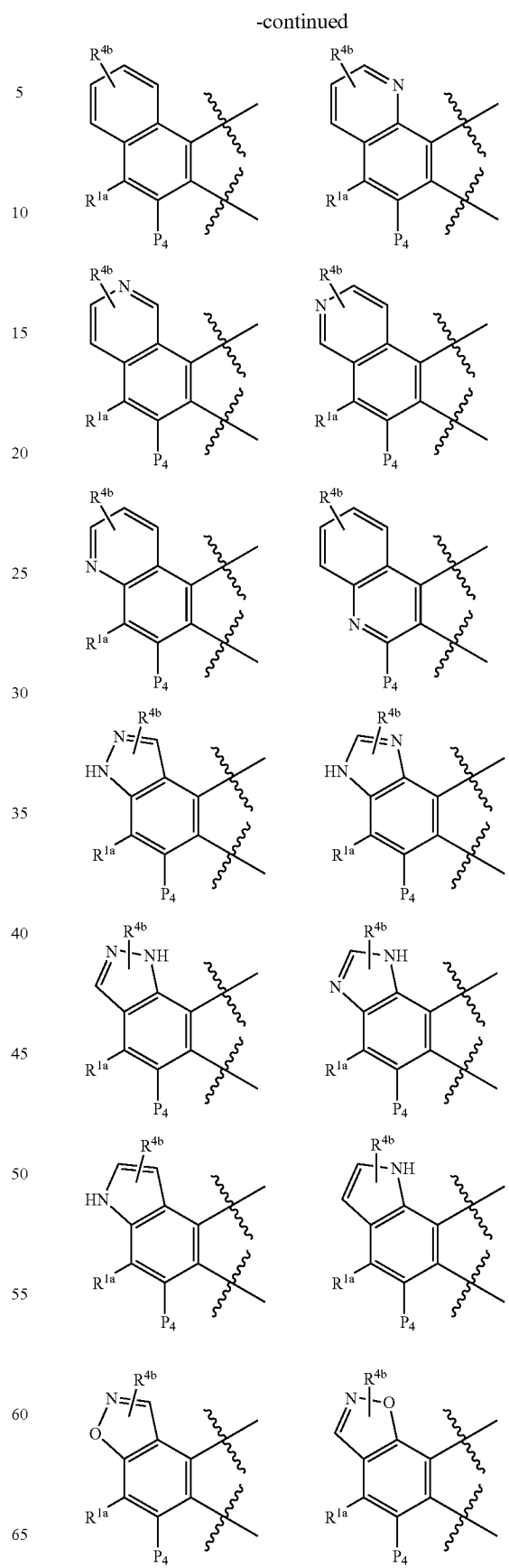

-continued

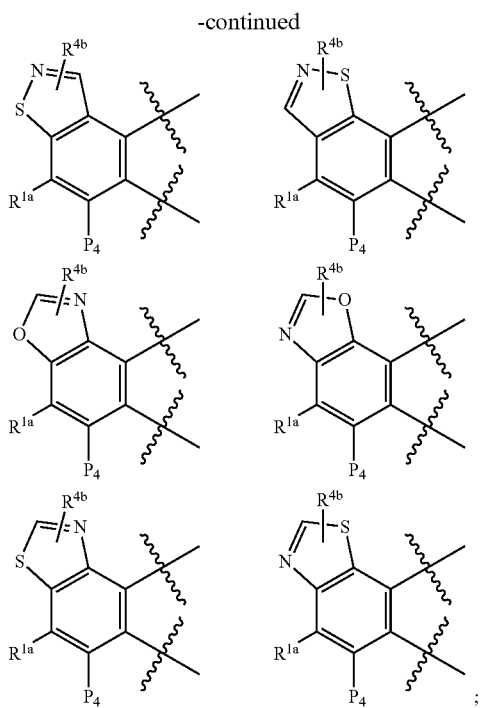

one of $P_4$ and $M_4$ is —Z-A-B and the other —$G_1$—G;

G is selected from the group: phenyl, 4-ethyl-phenyl, 2,5-bis-aminomethyl-phenyl, 2-amido-4-methoxy-phenyl, 2-amido-5-chloro-phenyl, 2-amido-phenyl, 2-aminomethyl-3-fluoro-phenyl, 2-aminomethyl-3-methoxy-phenyl, 2-aminomethyl-4-fluoro-phenyl, 2-aminomethyl-4-methoxy-phenyl, 2-aminomethyl-5-fluoro-phenyl 2-aminomethyl-5-methoxy-phenyl, 2-aminomethyl-6-fluoro-phenyl, 2-aminomethyl-phenyl, 2-amino-pyrid-4-yl, 2-aminosulfonyl-4-methoxy-phenyl, 2-aminosulfonyl-phenyl, 2-hydroxy-4-methoxy-phenyl, 2-methylsulfonyl-phenyl, 3-(N,N-dimethylamino)-4-chloro-phenyl, 3-(N,N-dimethylamino)-phenyl, 3-(N-hydroxy-amidino)-phenyl, 3-(N-methoxy-amidino)-phenyl, 3-(N-methylamino)-4-chloro-phenyl, 3-(N-methylamino)-phenyl, 3-amidino-phenyl, 3-amido-6-hydroxy-phenyl, 3-amido-phenyl, 3-amino-4-chloro-phenyl, 3-aminomethyl-phenyl, 3-amino-phenyl, 3-chloro-4-fluoro-phenyl, 3-chloro-phenyl, 3-hydroxy-4-methoxy-phenyl, 4-(N,N-dimethylamino)-5-chloro-thien-2-yl, 4-(N-methylamino)-5-chloro-thien-2-yl, 4-amino-5-chloro-thien-2-yl, 4-amino-pyrid-2-yl, 4-chloro-3-fluoro-phenyl, 4-chloro-phenyl, 4-chloro-pyrid-2-yl, 4-methoxy-2-methylsulfonyl-phenyl, 4-methoxy-phenyl, 2-methoxy-pyridyl-5-yl, 5-(N,N-dimethylamino)-4-chloro-thien-2-yl, 5-(N-methylamino)-4-chloro-thien-2-yl, 5-amino-4-chloro-thien-2-yl, 5-chloro-2-aminosulfonyl-phenyl, 5-chloro-2-methylsulfonyl-phenyl, 5-chloro-pyrid-2-yl, 5-chloro-thien-2-yl, 6-amino-5-chloro-pyrid-2-yl, 6-amino-pyrid-2-yl,

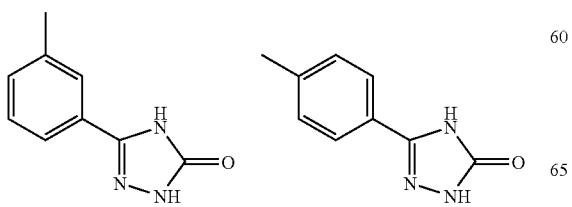

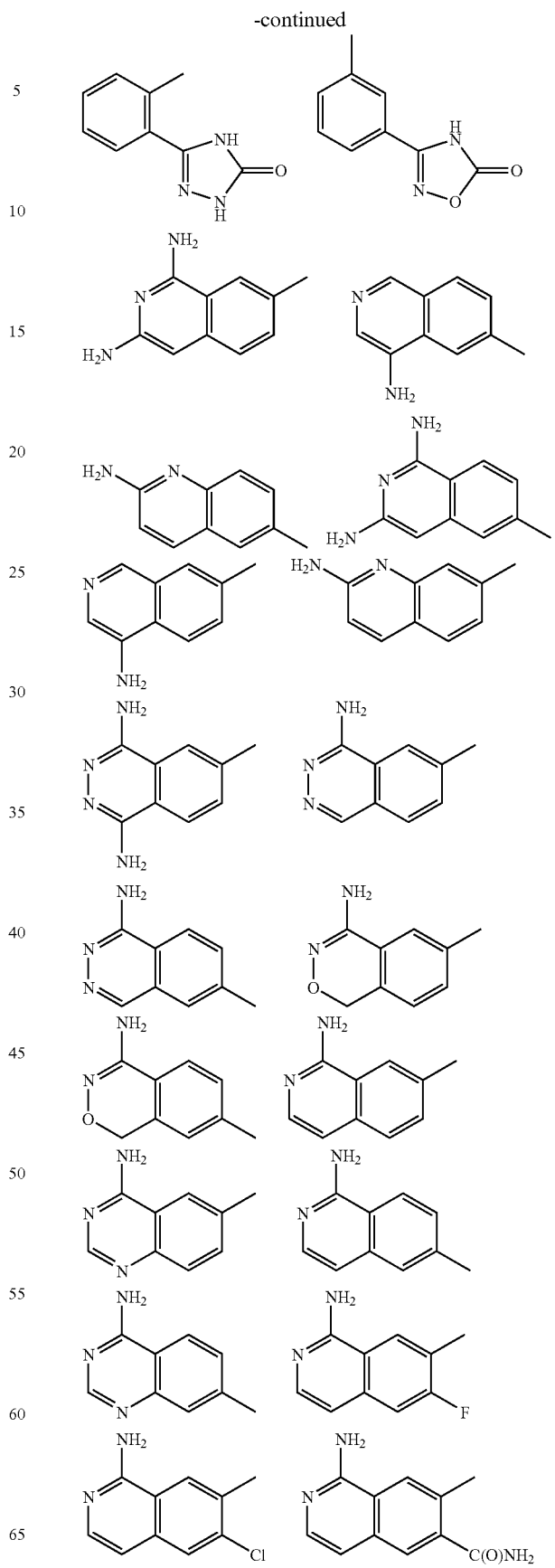

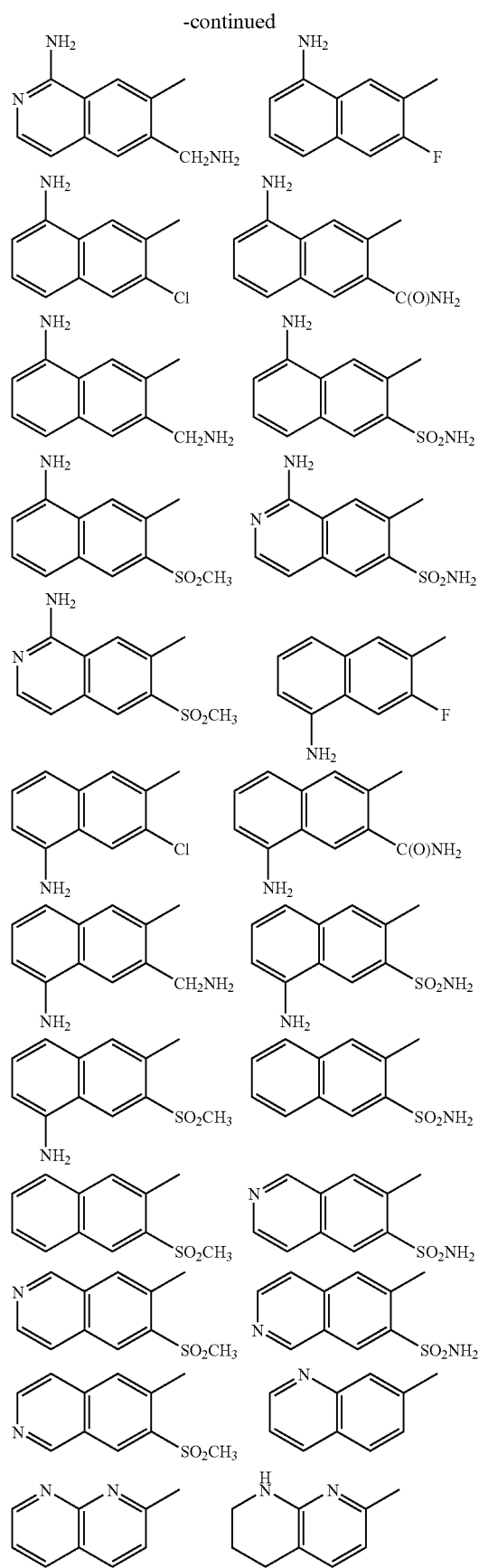
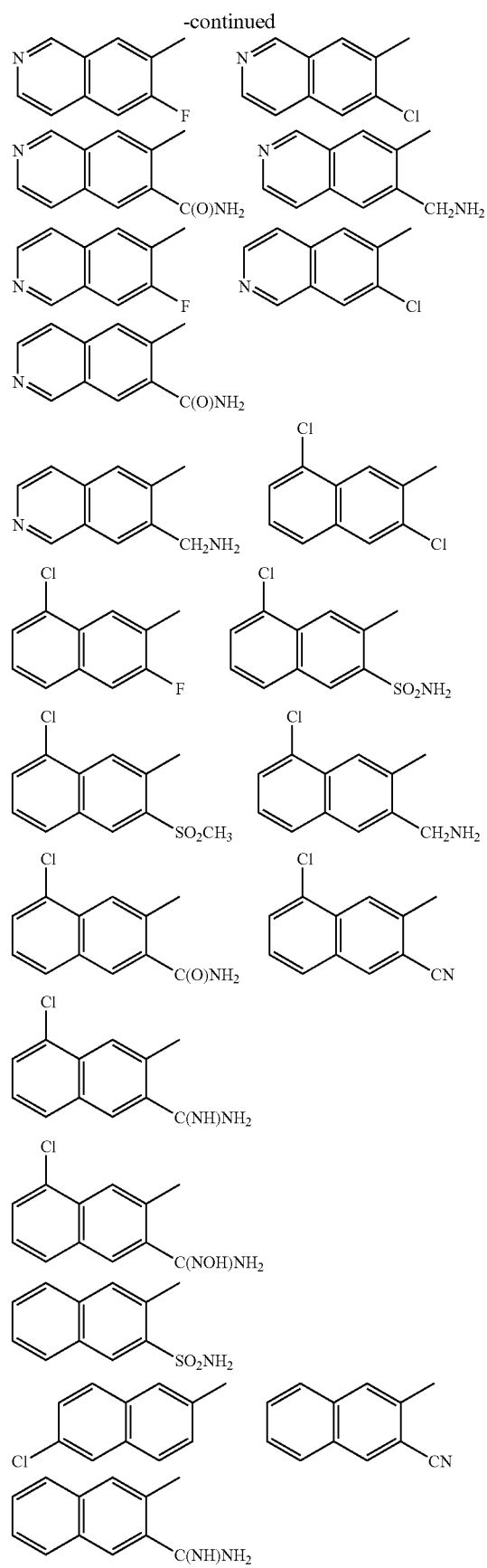

-continued
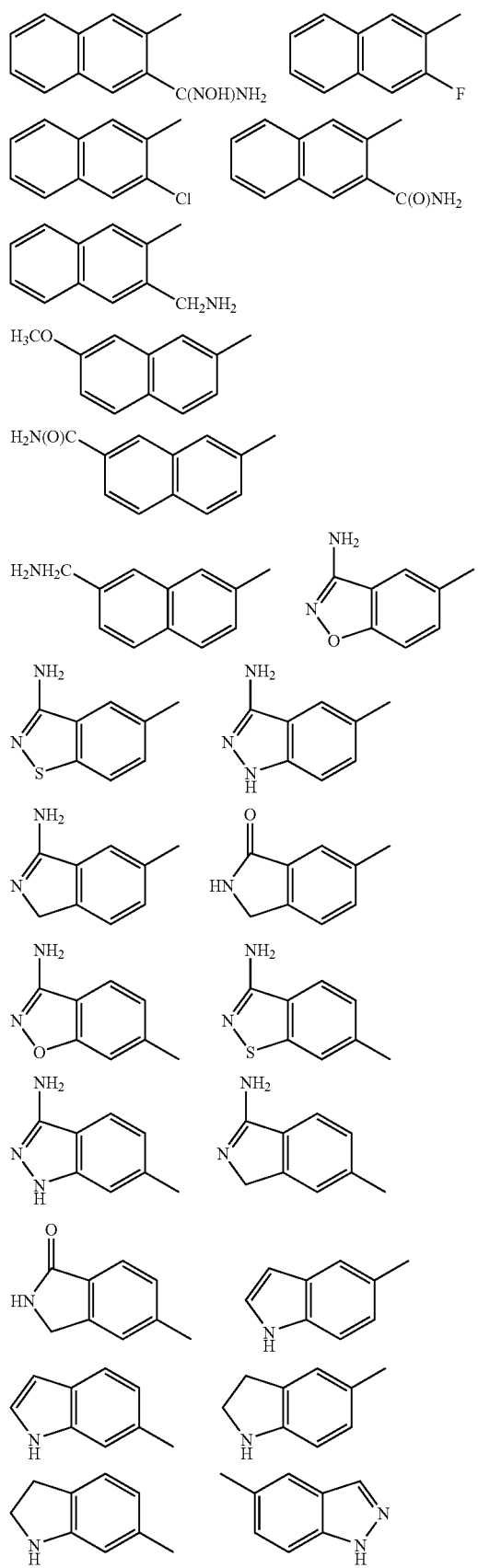
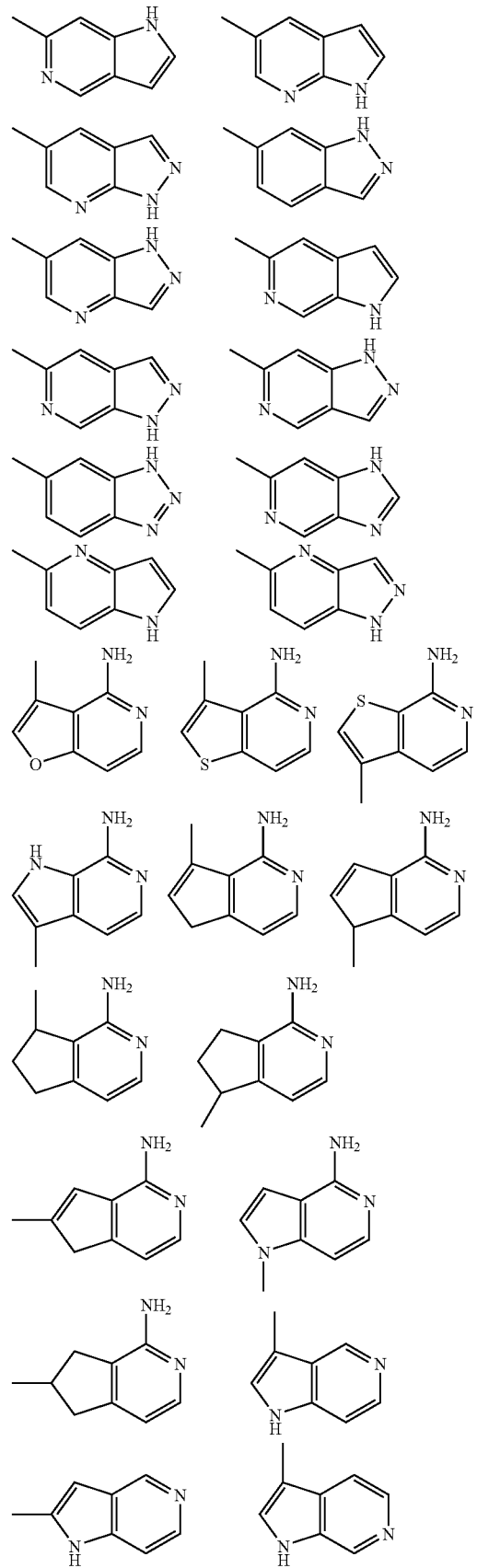

-continued

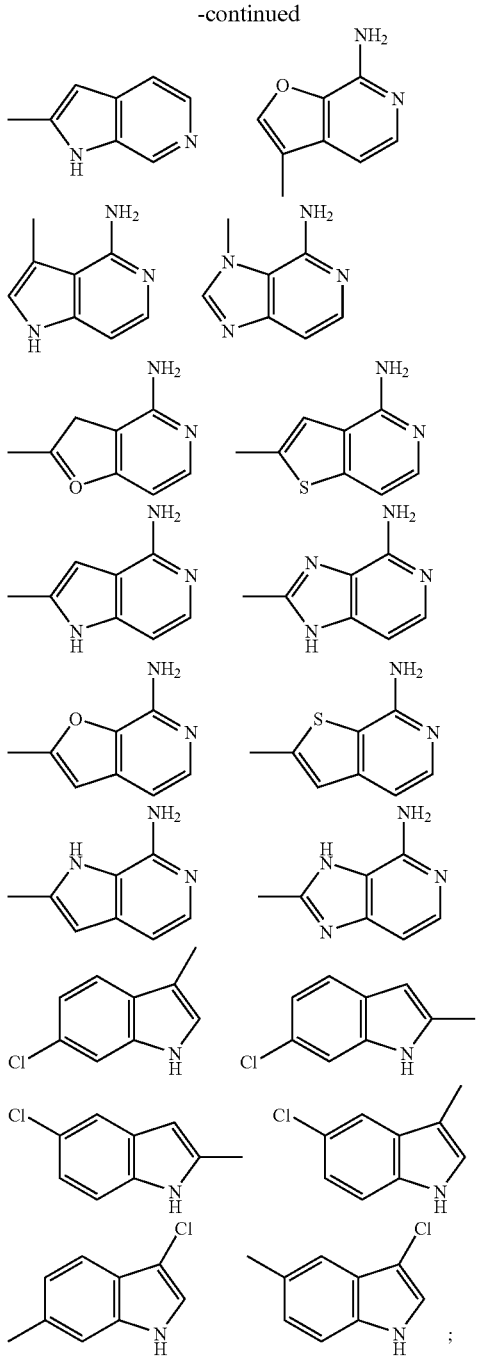

$G_1$ is absent or is selected from $(CR^3R^{3a})_{1-3}$, $CR^3$=$CR^3$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, and $(CR^3R^{3a})_uS(O)_2NR^{3b}(CR^3R^{3a})_w$, wherein u+w or u+u+w total 0, 1, or 2, wherein the right side of $G_1$ is attached to G, provided that $G_1$ does not form a N—S, NCH$_2$N, NCH$_2$O, or NCH$_2$S bond with either group to which it is attached;

A is selected from one of the following carbocyclic and heterocyclic groups which are substituted with 0–2 $R^4$: cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

B is selected from

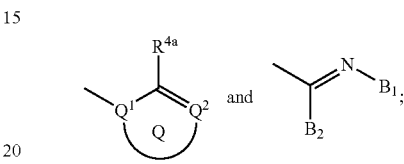

provided that Z and B are attached to different atoms on A and that the $R^{4a}$ shown is other than OH;

ring Q is a 5–6 membered ring consisting of, in addition to the N—$CR^{4a}$=N group shown, carbon atoms and 0–2 heteroatoms selected from N, O, and $S(O)_p$, and the ring is substituted with an additional 0–2 $R^{4a}$;

$B_1$ is selected from $SO_2R^{3b}$ and $OR^2$;

$B_2$ is $NR^2R^{2d}$;

alternatively, $NR^2R^{2d}$ forms a 5–6 membered ring consisting of: carbon atoms and 0–2 additional heteroatoms selected from N, O, and $S(O)_p$, and this ring is substituted with 0–2 $R^{4b}$;

alternatively, $B_1$ and $R^{2d}$ combine to form a 5–6 membered ring consisting of: carbon atoms and 0–1 additional heteroatoms selected from N, O, and $S(O)_p$, and this ring is substituted with 0–2 $R^{4b}$ and the $R^2$ group of $NR^2R^{2d}$, in addition to the groups recited below, can be $SO_2R^{3b}$;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^{2b}$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and a 5–6 membered aromatic heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and S(O)$_p$ and substituted with 0–2 R$^{4b}$;

alternatively, NR$^2$R$^{2a}$ forms a 5 or 6 membered saturated, partially saturated, or unsaturated ring substituted with 0–2 R$^{4b}$ and consisting of: carbon atoms, the nitrogen atom to which R$^2$ and R$^{2a}$ are attached, and 0–1 additional heteroatoms selected from the group consisting of N, O, and S(O)$_p$;

R$^{2b}$, at each occurrence, is selected from CF$_3$, C$_{1-4}$ alkoxy, CH$_3$, CH$_2$CH$_3$, CH$_2$CH$_2$CH$_3$, CH(CH$_3$)$_2$, benzyl substituted with 0–2 R$^{4b}$, phenyl substituted with 0–2 R$^{4b}$, and 5–6 membered aromatic heterocycle consisting of: carbon atoms and 1–4 heteroatoms selected from the group consisting of N, O, and S(O)$_p$ and substituted with 0–2 R$^{4b}$;

R$^{2c}$, at each occurrence, is selected from CF$_3$, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0–2 R$^{4b}$, phenyl substituted with 0–2 R$^{4b}$, and 5–6 membered aromatic heterocycle containing from 1–4 heteroatoms selected from the group consisting of N, O, and S(O)$_p$ and substituted with 0–2 R$^{4b}$;

R$^{2d}$, at each occurrence, is selected from H, CF$_3$, CH$_3$, CH$_2$CH$_3$, CH$_2$CH$_2$CH$_3$, CH(CH$_3$)$_2$, and OCH$_3$, benzyl;

R$^{3b}$, at each occurrence, is selected from H, CF$_3$, CH$_3$, CH$_2$CH$_3$, CH$_2$CH$_2$CH$_3$, and CH(CH$_3$)$_2$;

R$^4$, at each occurrence, is selected from H, CH$_2$OR$^2$, (CH$_2$)$_2$OR$^2$, OR$^2$, F, Cl, Br, I, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, (CH$_2$)$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, CF$_3$, and CF$_2$CF$_3$;

R$^{4a}$, at each occurrence, is selected from H, OR$^2$, CH$_2$OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, NR$^2$SO$_2$R$^5$, SO$_2$NR$^2$R$^{2a}$, 6 membered carbocycle substituted with 0–1 R$^5$, and a 5–6 membered heterocycle consisting of: carbon atoms and 1–2 heteroatoms selected from the group consisting of N, O, and S(O)$_p$ and substituted with 0–1 R$^5$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, CH$_2$NR$^3$C(O) R$^{3a}$, C(O)NR$^3$R$^{3a}$, CH$_2$C(O)NR$^3$R$^{3a}$, SO$_2$NR$^3$R$^{3a}$, CH$_2$SO$_2$NR$^3$R$^{3a}$, NR$^3$SO$_2$—C$_{1-4}$ alkyl, CH$_2$NR$^3$SO$_2$—C$_{1-4}$ alkyl, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, and CF$_3$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, SO$_2$NR$^3$R$^{3a}$, CF$_3$, phenyl substituted with 0–2 R$^6$, naphthyl substituted with 0–2 R$^6$, and benzyl substituted with 0–2 R$^6$; and, R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O) R$^{2b}$, SO$_2$NR$^2$R$^{2a}$, and NR$^2$SO$_2$C$_{1-4}$ alkyl.

In a fourth aspect, the present invention provides a novel compound, wherein:

ring M is substituted with 0–2 R$^{1a}$ and is selected from the group:

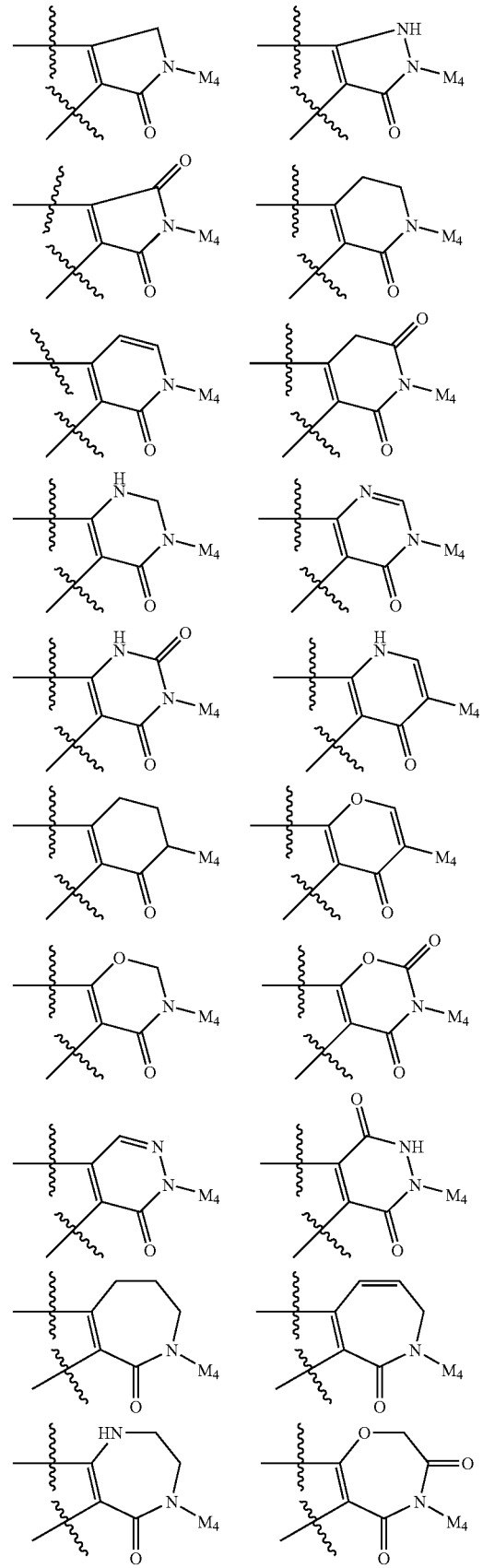

-continued
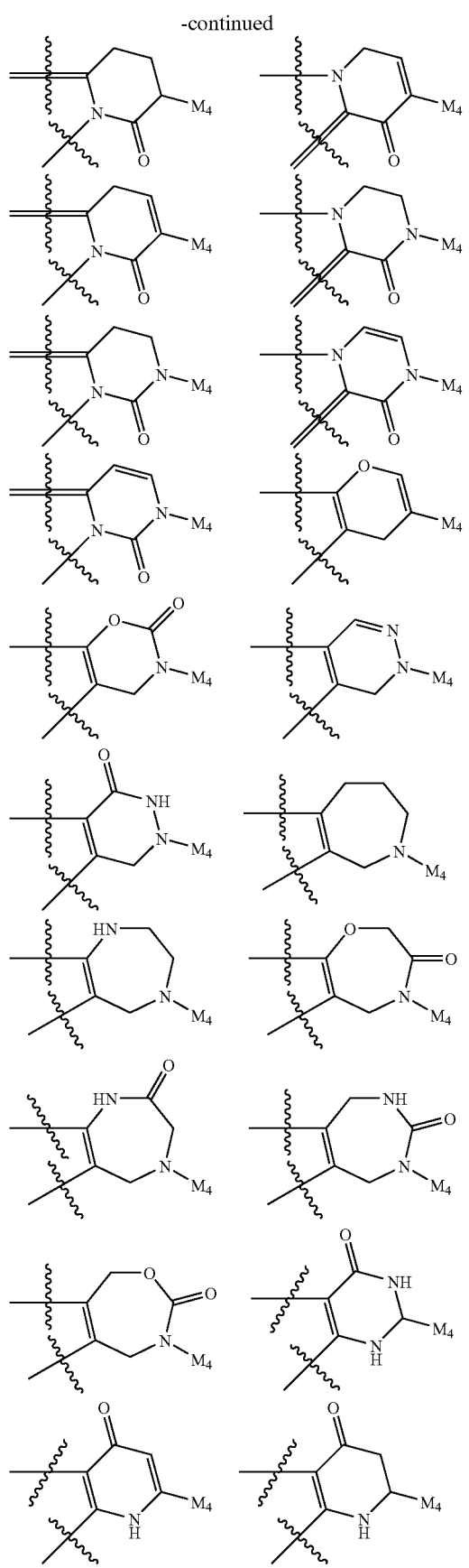
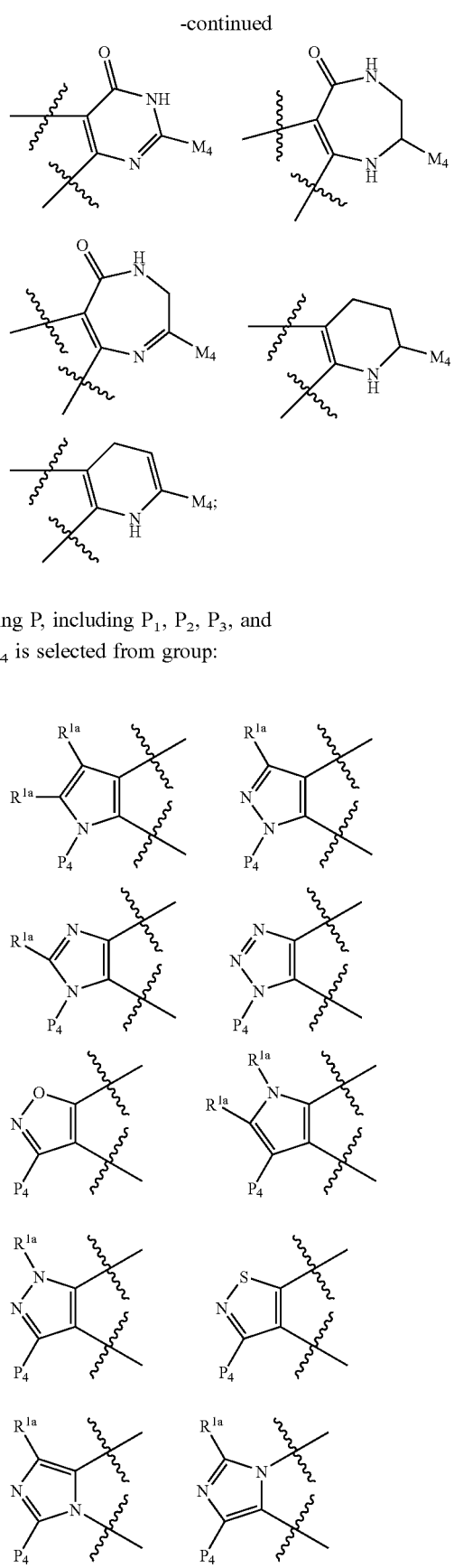
ring P, including $P_1$, $P_2$, $P_3$, and $P_4$ is selected from group:

-continued

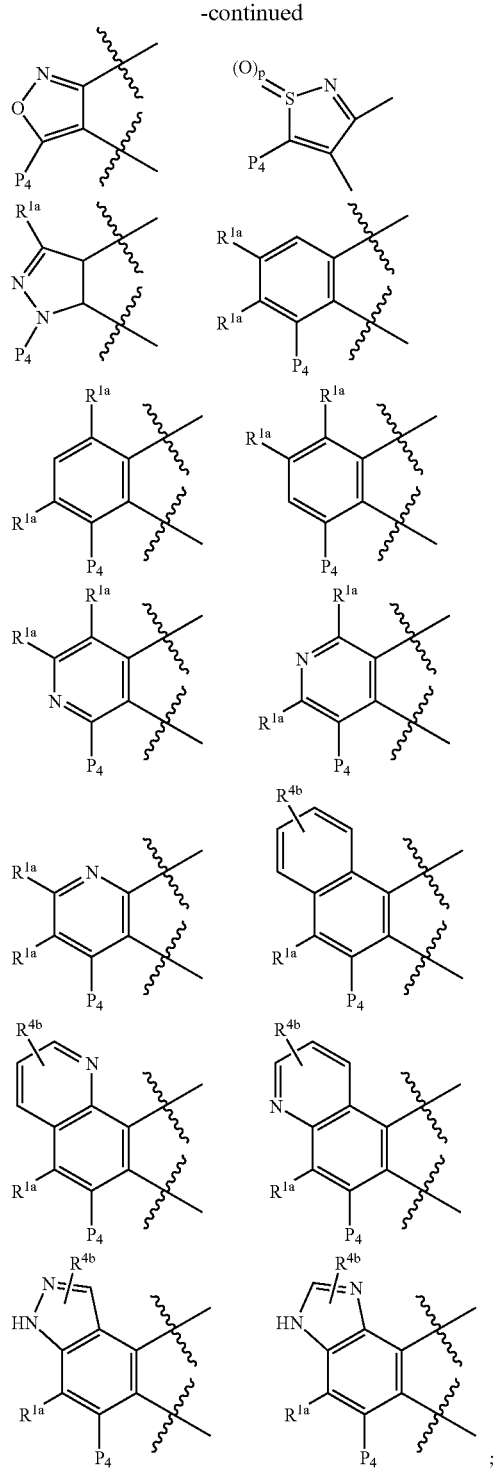

one of $P_4$ and $M_4$ is —A—B and the other -G;

G is selected from the group: 2-amido-4-methoxy-phenyl, 2-amido-phenyl, 2-aminomethyl-3-fluoro-phenyl, 2-aminomethyl-4-fluoro-phenyl, 2-aminomethyl-4-methoxy-phenyl, 2-aminomethyl-5-fluoro-phenyl, 2-aminomethyl-5-methoxy-phenyl, 2-aminomethyl-6-fluoro-phenyl, 2-aminomethyl-phenyl, 2-amino-pyrid-4-yl, 2-aminosulfonyl-4-methoxy-phenyl, 2-aminosulfonyl-phenyl, 2-methylsulfonyl-phenyl, 3-(N,N-dimethylamino)-4-chloro-phenyl, 3-(N,N-dimethylamino)-phenyl, 3-(N-nethylamino)-4-chloro-phenyl, 3-(N-methylamino)-phenyl, 3-amido-phenyl, 3-amino-4-chloro-phenyl, 3-aminomethyl-phenyl, 3-amino-phenyl, 3-chloro-phenyl, 4-(N,N-dimethylamino)-5-chloro-thien-2-yl, 4-(N-methylamino)-5-chloro-thien-2-yl, 4-amino-5-chloro-thien-2-yl, 4-chloro-phenyl, 4-methoxy-2-methylsulfonyl-phenyl, 4-methoxy-phenyl, 5-(N,N-dimethylamino)-4-chloro-thien-2-yl, 5-(N-methylamino)-4-chloro-thien-2-yl, 5-amino-4-chloro-thien-2-yl, 5-chloro-pyrid-2-yl, 5-chloro-thien-2-yl, 6-amino-5-chloro-pyrid-2-yl, 6-amino-pyrid-2-yl, 3-amidino-phenyl,

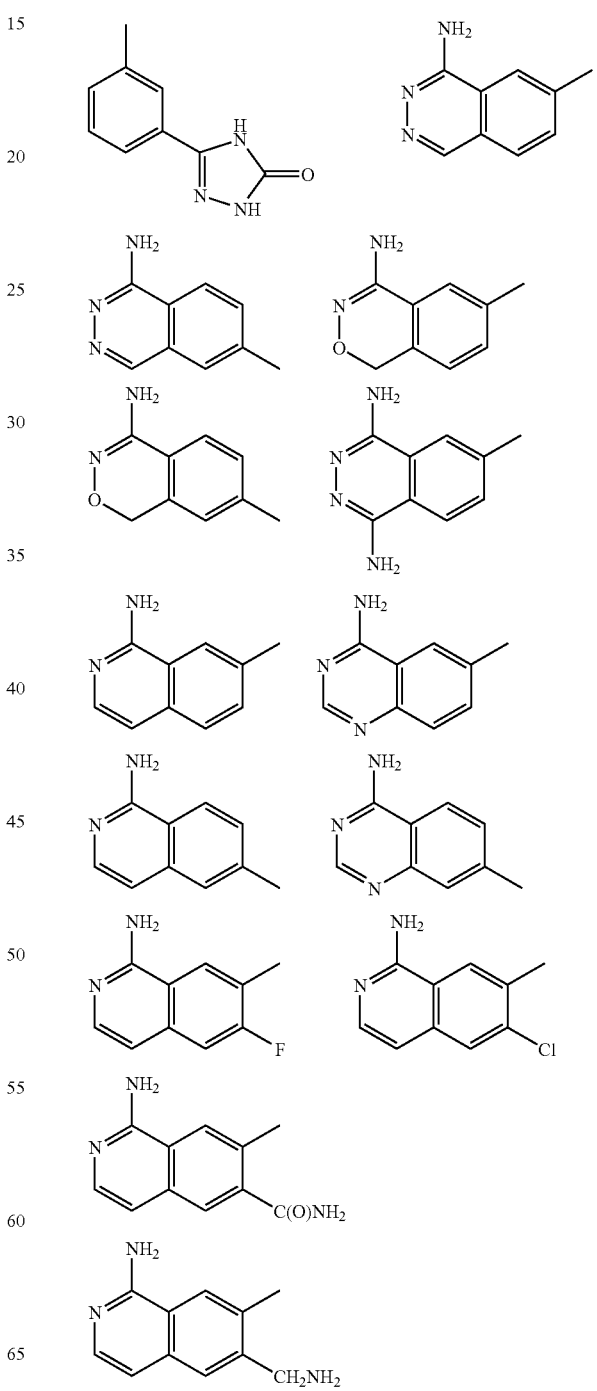

-continued
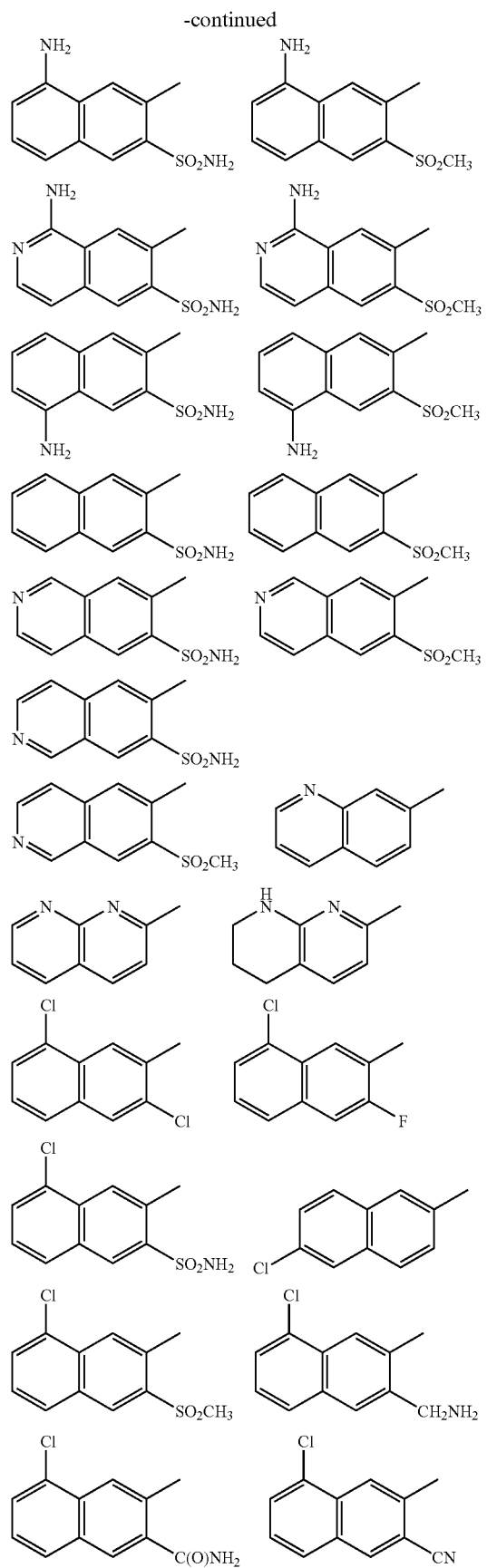
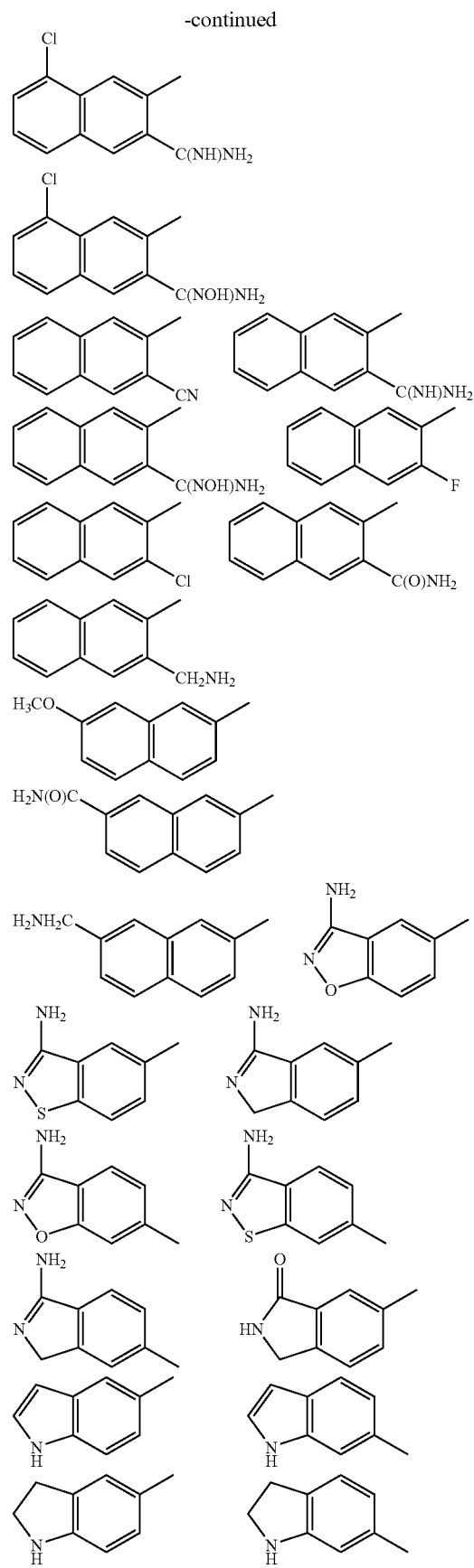

-continued

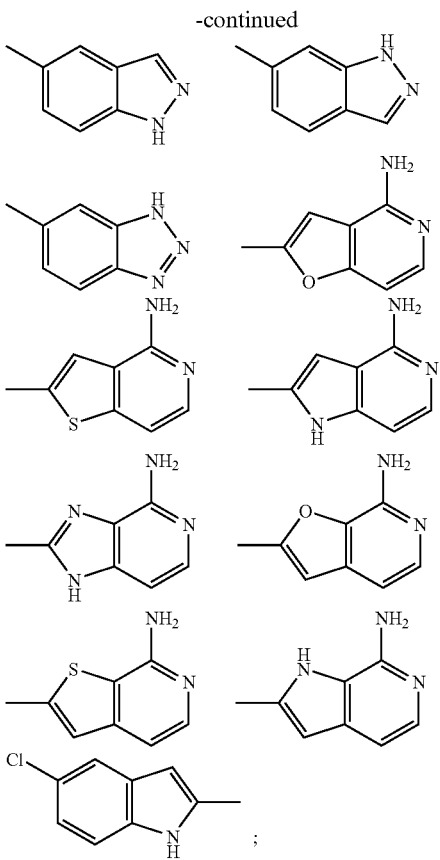

$G_1$ is absent or is selected from $CH_2$, $CH_2CH_2$, $CH_2O$, $OCH_2$, NH, $CH_2NH$, $NHCH_2$, $CH_2C(O)$, $C(O)CH_2$, $C(O)NH$, NHC(O), $CH_2S(O)_2$, $S(O)_2(CH_2)$, $SO_2NH$, and $NHSO_2$, wherein the right side of $G_1$ is attached to G, provided that $G_1$ does not form a N—S, $NCH_2N$, $NCH_2O$, or $NCH_2S$ bond with either group to which it is attached;

A is selected from cyclohexyl, phenyl, pyridyl, and pyrimidyl, and is substituted with 0–2 $R^4$;

B is selected from

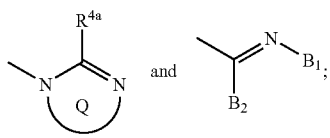

provided that Z and B are attached to different atoms on A and that the $R^{4a}$ shown is other than OH;

ring Q is a 5–6 membered ring consisting of, in addition to the $N-CR^{4a}=N$ group shown, carbon atoms and 0–1 heteroatoms selected from N, O, and $S(O)_p$, and the ring is substituted with an additional 0–2 $R^{4a}$;

$B_1$ is selected from $SO_2R^{3b}$ and $OR^2$;

$B_2$ is $NR^2R^{2d}$;

alternatively, $NR^2R^{2d}$ forms a 5–6 membered ring consisting of: carbon atoms and 0–1 additional heteroatoms selected from N, O, and $S(O)_p$, and this ring is substituted with 0–1 $R^{4b}$;

alternatively, $B_1$ and $R^{2d}$ combine to form a 5 membered ring consisting of: carbon atoms and 0–1 additional heteroatoms selected from N, O, and $S(O)_p$, and this ring is substituted with 0–2 $R^{4b}$ and the $R^2$ group of $NR^2R^{2d}$, in addition to the groups recited below, can be $SO_2R^{3b}$;

$R^{1a}$, at each occurrence, is selected from H, $R^{1b}$, $CH(CH_3)R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^{2b}$, $C(O)NR^2R^{2a}$, $SO_2NR^2R^{2a}$, $NR^2SO_2R^2$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

alternatively, $NR^2R^{2a}$ forms a 5 or 6 membered saturated, partially saturated, or unsaturated ring substituted with 0–1 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle consisting of: carbon atoms and 1–4 heteroatoms selected from the group consisting of N, O, and $S(O)_p$ and substituted with 0–1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–1 $R^{4b}$, phenyl substituted with 0–1 $R^{4b}$, and 5–6 membered aromatic heterocycle containing from 1–4 heteroatoms selected from the group consisting of N, O, and $S(O)_p$ and substituted with 0–1 $R^{4b}$;

$R^{2d}$, at each occurrence, is selected from H, $CH_3$, $CH_2CH_3$, $OCH_3$, and benzyl;

$R^{3b}$, at each occurrence, is selected from H and $CH_3$;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4a}$, at each occurrence, is selected from H, $OR^2$, $CH_2OR^2$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $C(O)R^{2c}$, $NR^2C(O)R^{2b}$, $C(O)NR^2R^{2a}$, $SO_2NR^2R^{2a}$, $NR^2SO_2R^5$, phenyl substituted with 0–1 $R^5$, and a 5–6 membered heterocycle consisting of: carbon atoms and 1 heteroatom selected from the group consisting of N, O, and $S(O)_p$ and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^5$, at each occurrence, is selected from H, =O, $CH_3$, $CH_2CH_3$, $CH_2CH_2CH_3$, $CH(CH_3)_2$, $OR^3$, $NR^3R^{3a}$, $C(O)R^3$, $NR^3C(O)R^{3a}$, $C(O)NR^3R^{3a}$, $SO_2NR^3R^{3a}$, and phenyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

In a fifth aspect, the present invention provides a novel compound, wherein:

ring M is substituted with 0–1 $R^{1a}$ and is selected from the group:

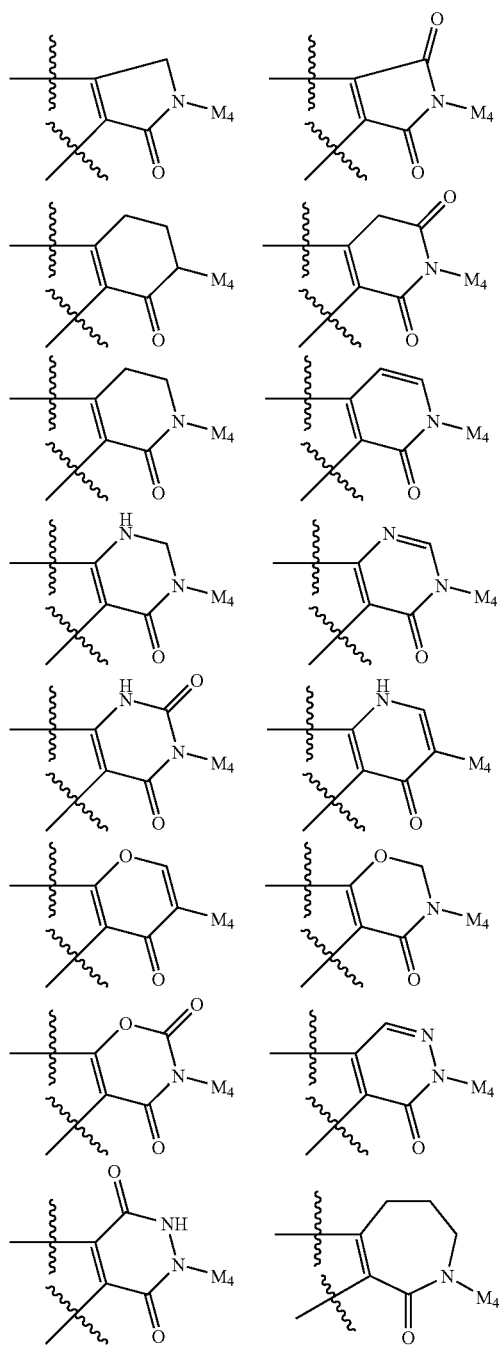

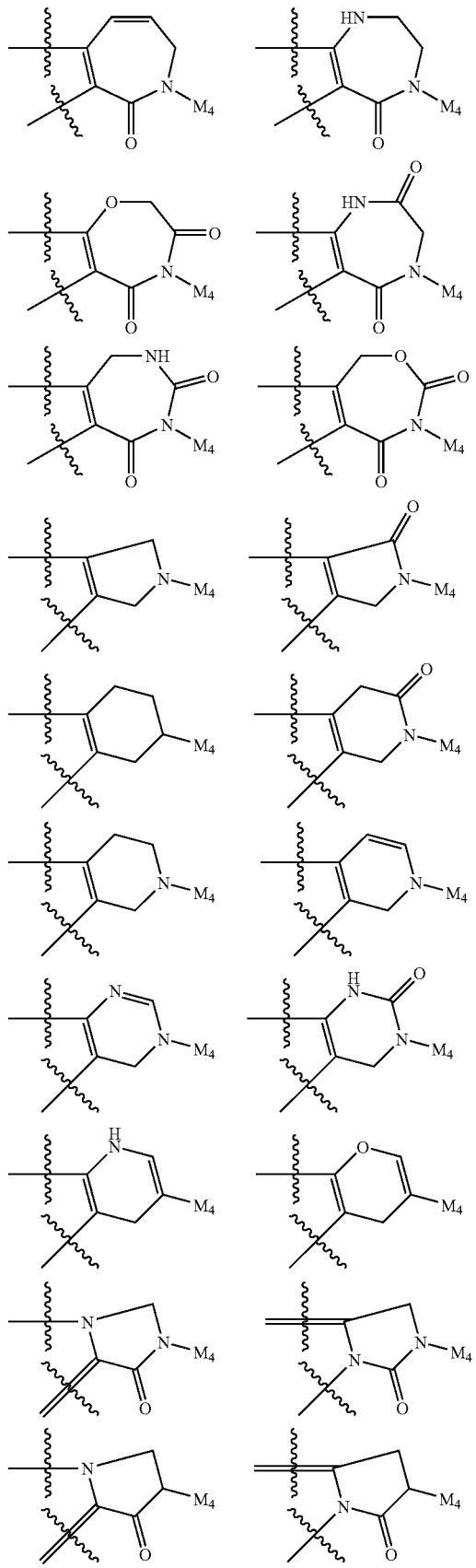

-continued

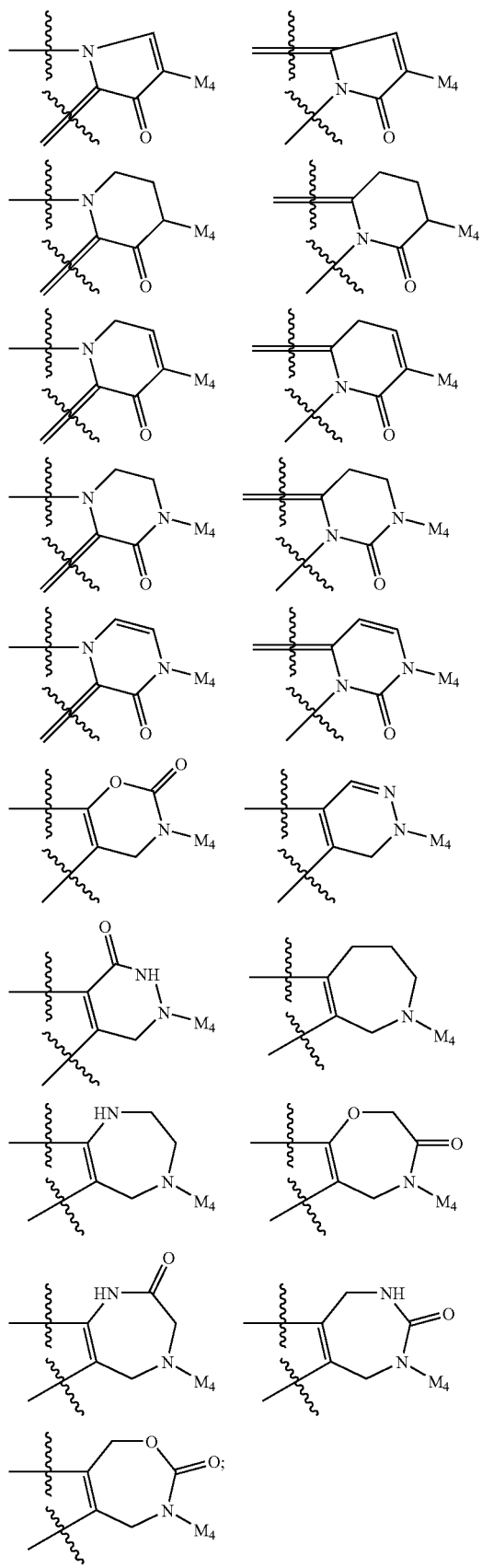

ring P, including $P_1$, $P_2$, $P_3$, and $P_4$ is selected from group:

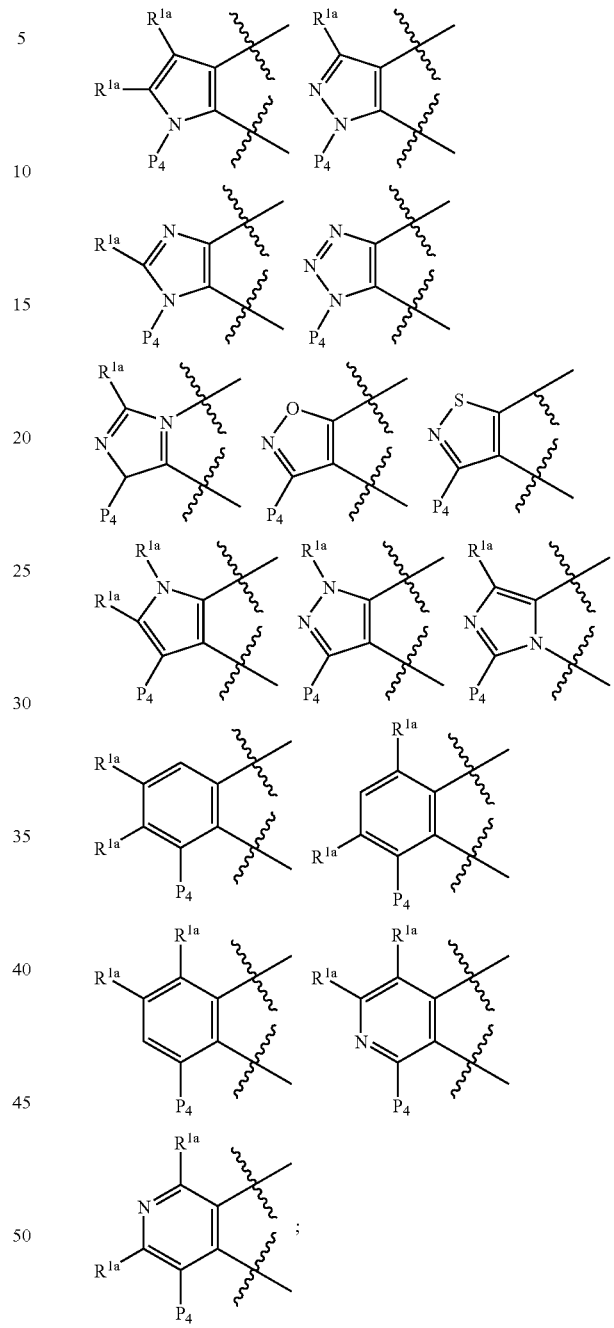

one of $P_4$ and $M_4$ is —A—B and the other —G;

G is selected from: 2-amido-4-methoxy-phenyl, 2-amido-phenyl, 2-aminomethyl-3-fluoro-phenyl, 2-aminomethyl-4-fluoro-phenyl, 2-aminomethyl-5-fluoro-phenyl, 2-aminomethyl-6-fluoro-phenyl, 2-aminomethyl-phenyl, 2-amino-pyrid-4-yl, 2-aminosulfonyl-4-methoxy-phenyl, 2-aminosulfonyl-phenyl, 3-amido-phenyl, 3-amino-4-chloro-phenyl, 3-aminomethyl-phenyl, 3-chloro-phenyl, 4-chloro-phenyl, 4-methoxy-phenyl, 5-chloro-pyrid-2-yl, 5-chloro-thien-2-yl, 6-amino-5-chloro-pyrid-2-yl, 6-amino-pyrid-2-yl, 3-amidino-phenyl,

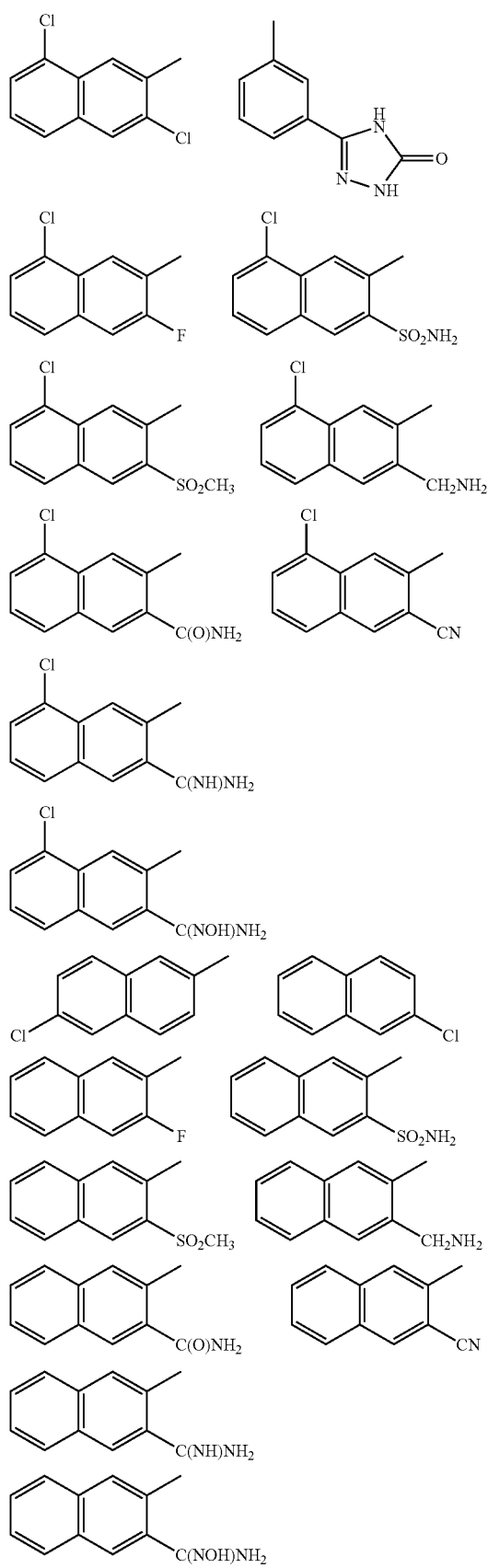
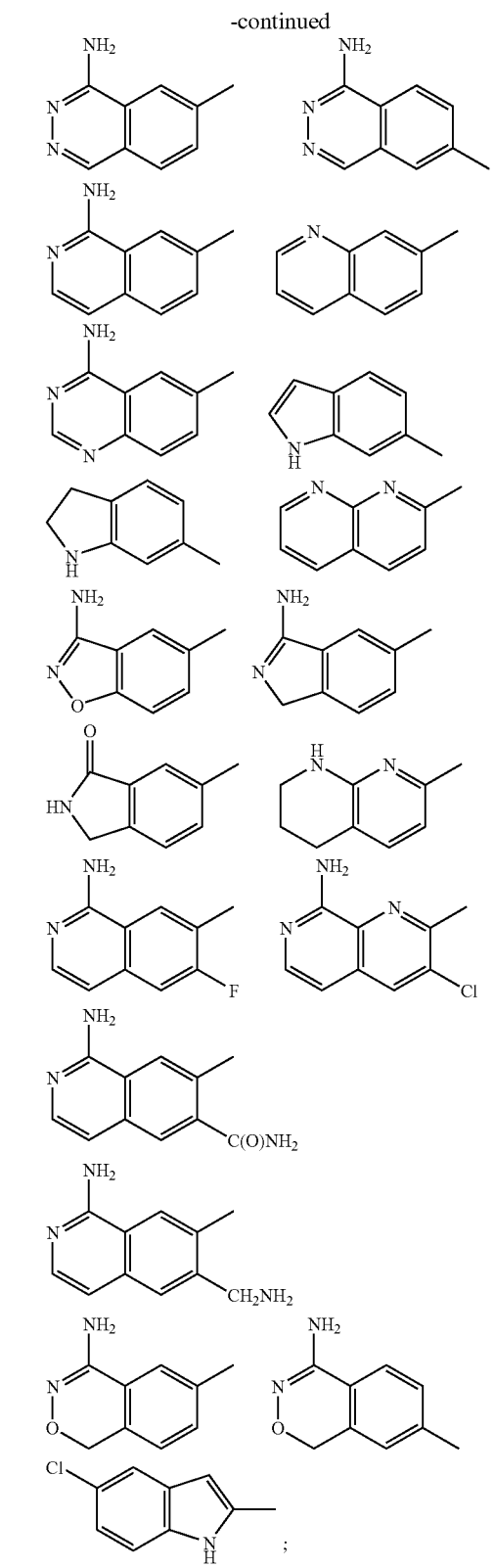
A is selected from the group: cyclohexyl, piperidinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B, provided that Z and B are attached to different atoms on A and that the $R^{4a}$ shown is other than OH, is selected from:

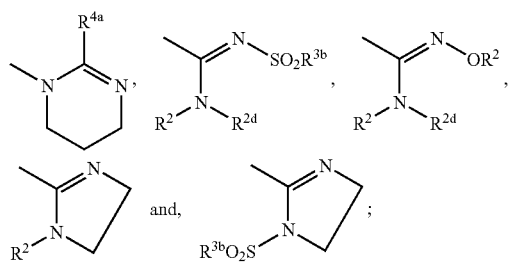

alternatively, $NR^2R^{2d}$ combines to form a ring selected from morpholine, piperaiine, piperidine, and pyrrolidine;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated, or unsaturated ring substituted with 0–1 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $CH_3$, $CH_2CH_3$, and $OCH_3$;

$R^{4a}$, at each occurrence, is selected from H, $OCH_3$, $CH_3$, $CH_2CH_3$, $CH_2CH_2CH_3$, $CH(CH_3)_2$, $NR^2R^{2a}$, $NR^2C(O)R^{2b}$, $NR^2SO_2R^5$, phenyl, 2-oxo-pyrrolidinyl, and 2-oxo-piperidinyl;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$; and $R^5$, at each occurrence, is selected from $CH_3$ and $CH_2CH_3$.

In a sixth aspect, the present invention provides a novel compound, wherein the compound is selected from:

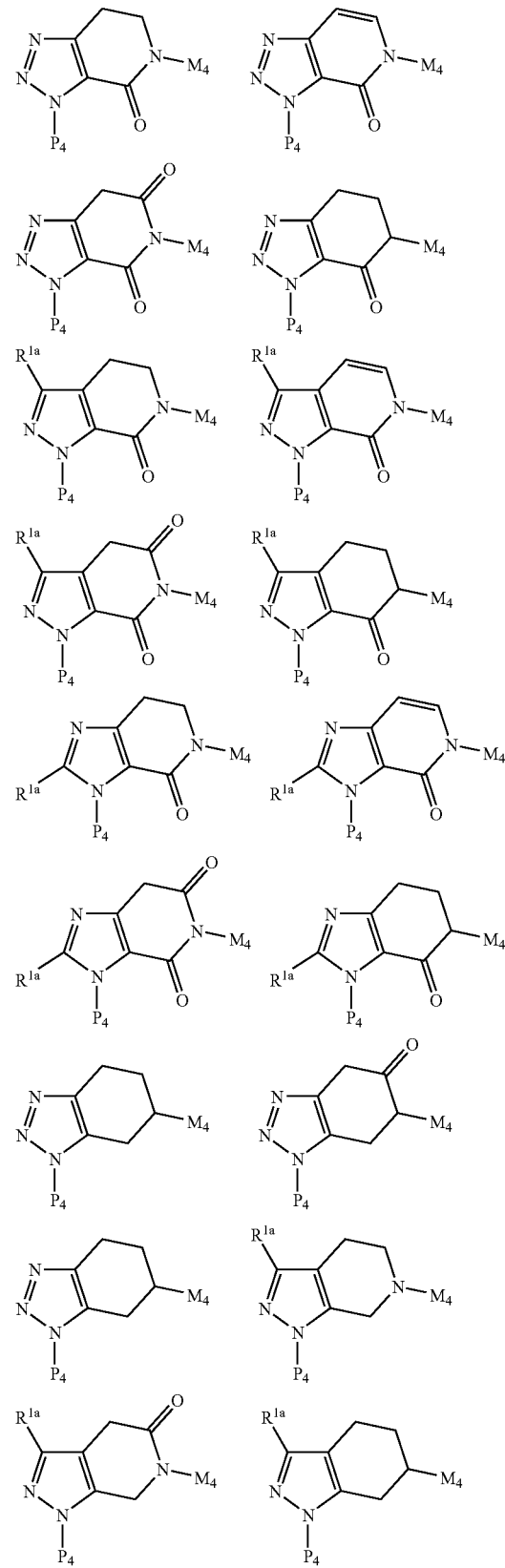

-continued
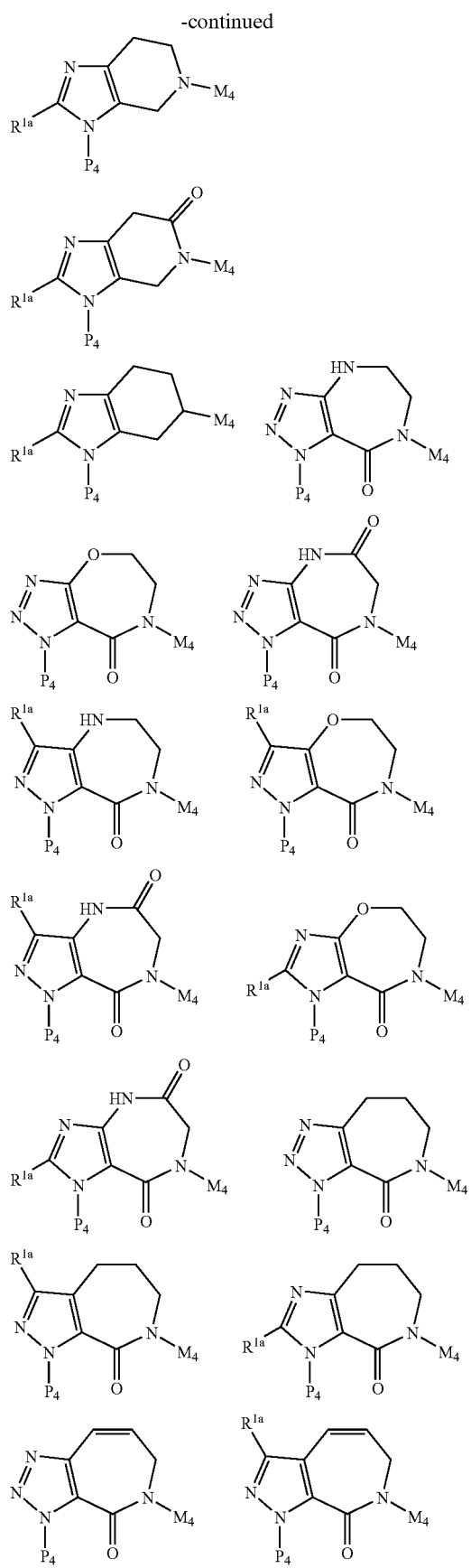
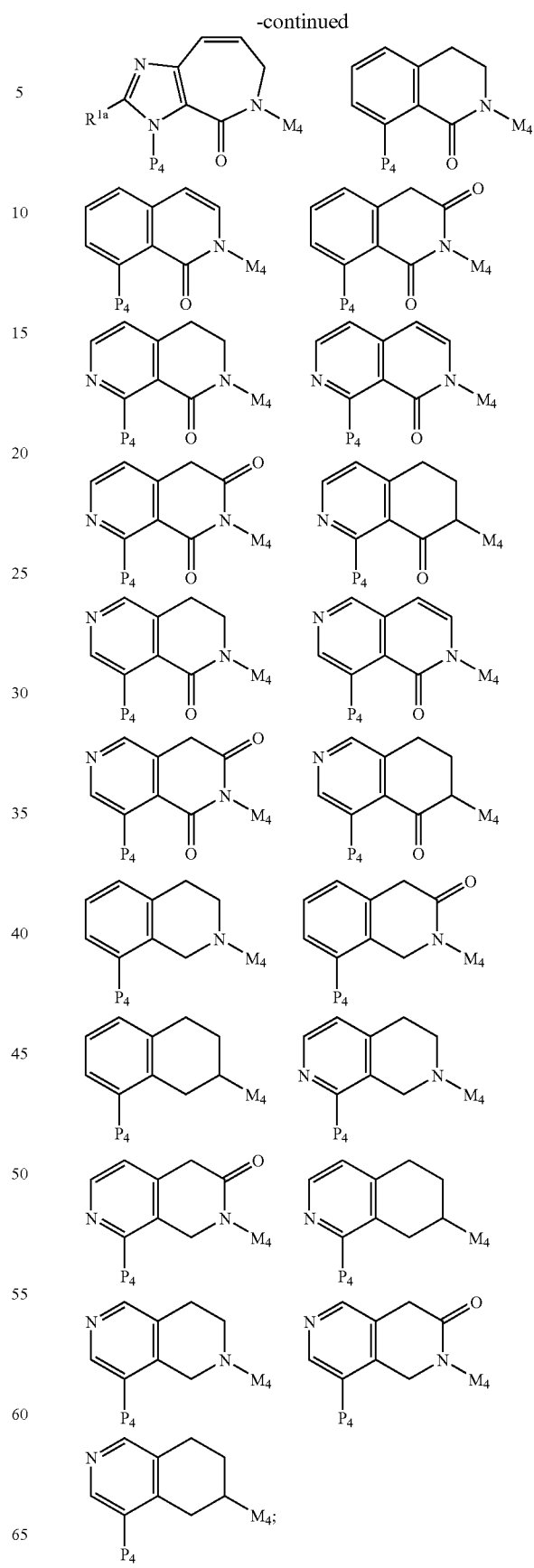

P4 is —G;
M4 is —A—B;
G is selected from:
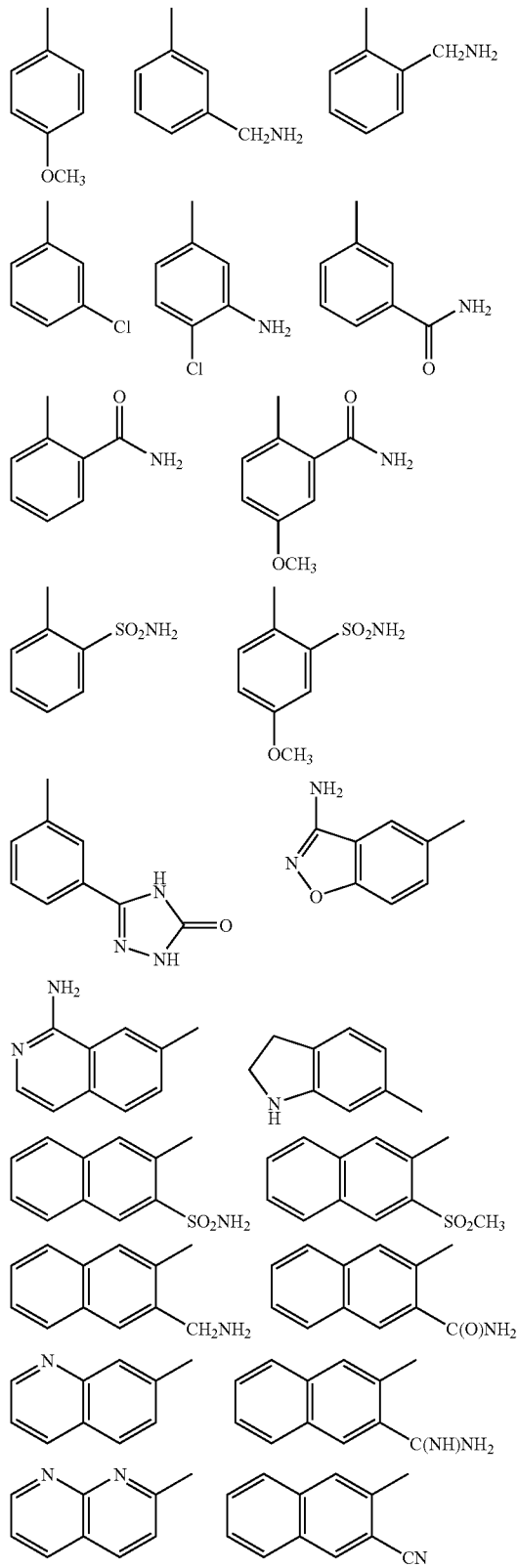
-continued
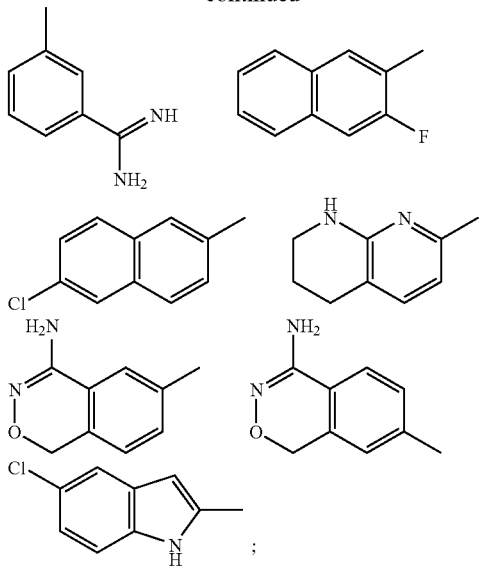
A is selected from:
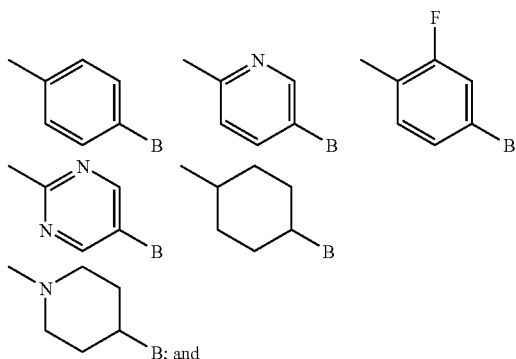
B is selected from:
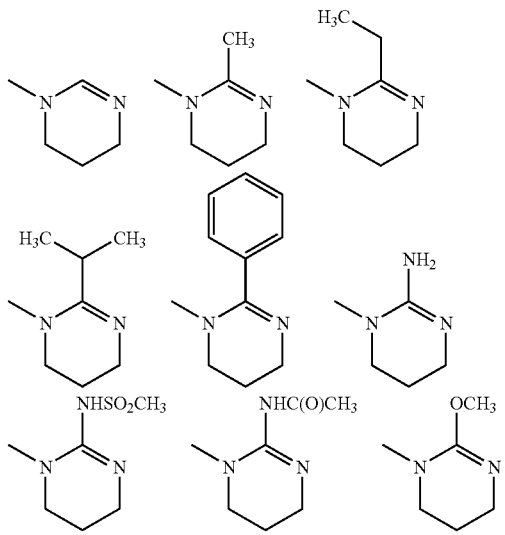

-continued
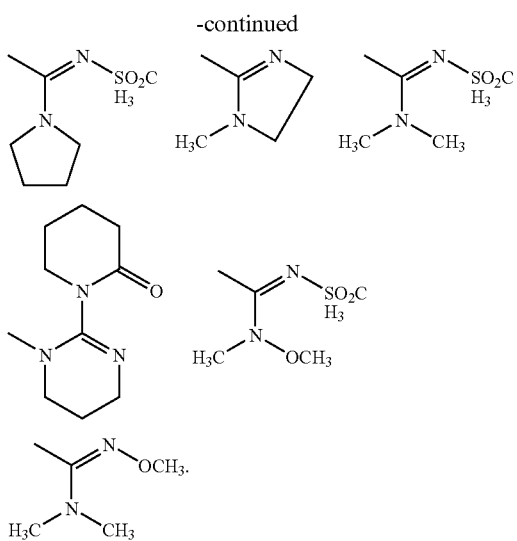
In a seventh aspect, the present invention provides a novel compound, wherein the compound is selected from:
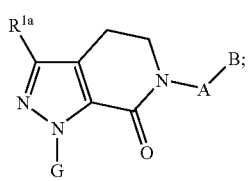
A—B is selected from:
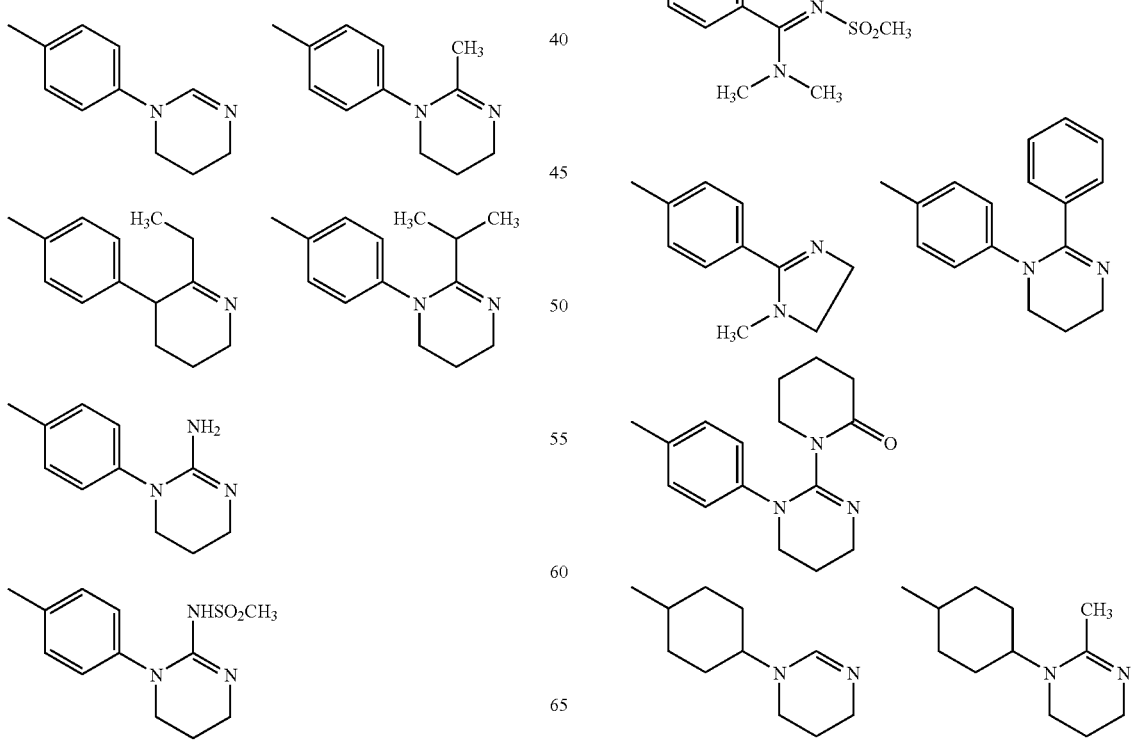
-continued
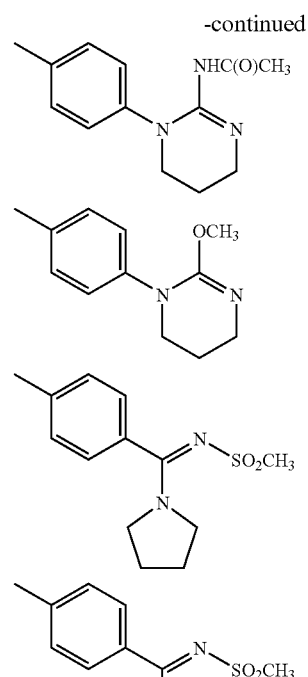

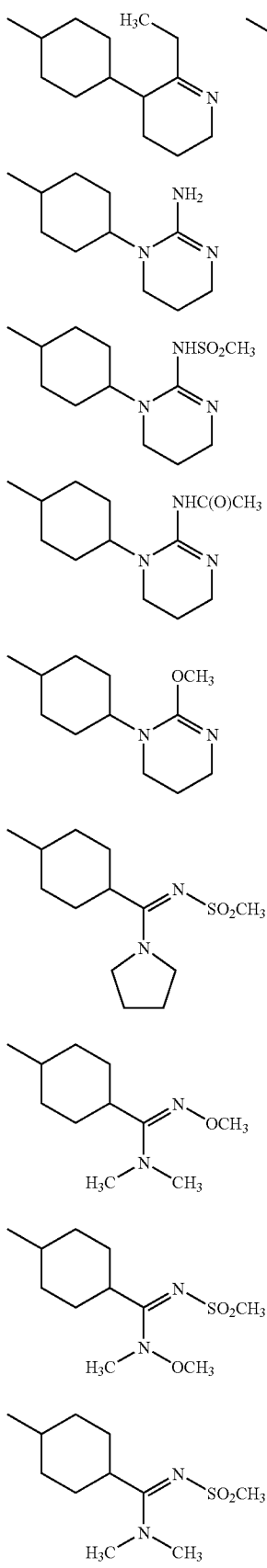

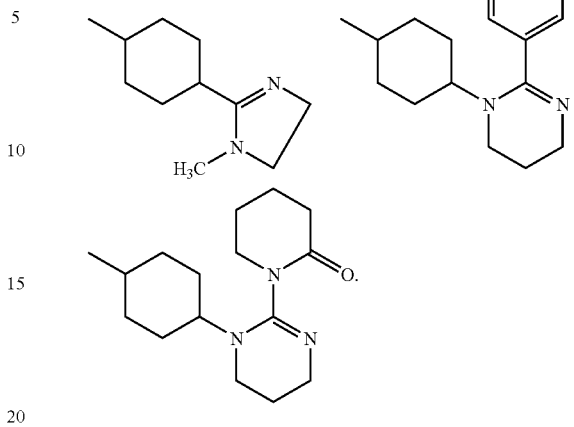

In an eighth aspect, the present invention provides a novel compound, wherein the compound is selected from the group:

6-[4-(5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one;

1-(4-methoxy-phenyl)-6-[4-(2-methyl-5,6-dihydro-4H-pyrimidin-1-yl)-phenyl]-3-trifluoromethyl-1,4,5,6-tetrahydro-pyrazolo[3,4-c]pyridin-7-one;

6-[4-(2-ethyl-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one;

6-[4-(2-isopropyl-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one;

1-(4-methoxy-phenyl)-6-[4-(2-phenyl-5,6-dihydro-4H-pyrimidin-1-yl)-phenyl]-3-trifluoromethyl-1,4,5,6-tetrahydro-pyrazolo[3,4-c]pyridin-7-one;

6-[4-(2-amino-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one;

N-({4-[1-(4-methoxy-phenyl)-7-oxo-3-trifluoromethyl-1,4,5,7-tetrahydro-pyrazolo[3,4-c]pyridin-6-yl]-phenyl}-methylamino-methylene)-methanesulfonamide;

N-(amino-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide;

N-(dimethylamino-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide;

N-((ethyl-methyl-amino)-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide;

N-({4-[1-(4-methoxy-phenyl)-7-oxo-3-trifluoromethyl-1,4,5,7-tetrahydro-pyrazolo[3,4-c]pyridin-6-yl]-phenyl}-piperidin-1-yl-methylene)-methanesulfonamide;

N-({4-[1-(4-methoxy-phenyl)-7-oxo-3-trifluoromethyl-1,4,5,7-tetrahydro-pyrazolo[3,4-c]pyridin-6-yl]-phenyl}-morpholin-4-yl-methylene)-methanesulfonamide;

N-((benzyl-methyl-amino)-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide;

6-[4-(dimethylamino-methanesulfonylimino-methyl)-phenyl]-1-(4-methoxy-phenyl)-7-oxo-4,5,6,7-tetrahydro-1H-pyrazolo[3,4-c]pyridine-3-carboxylic acid amide;

6-[4-(methanesulfonylimino-pyrrolidin-1-yl-methyl)-phenyl]-1-(4-methoxy-phenyl)-7-oxo-4,5,6,7-tetrahydro-1H-pyrazolo[3,4-c]pyridine-3-carboxylic acid amide;

N-({4-[3-cyano-1-(4-methoxy-phenyl)-7-oxo-1,4,5,7-tetrahydro-pyrazolo[3,4-c]pyridin-6-yl]-phenyl}-dimethylamino-methylene)-methanesulfonamide;

N-(dimethylamino-{4-[1-(4-methoxy-phenyl)-3-methyl-7-oxo-1,4,5,7-tetrahydro-pyrazolo[3,4-c]pyridin-6-yl]-phenyl}-methylene)-methanesulfonamide;

N-({4-[1-(4-methoxy-phenyl)-7-oxo-3-trifluoromethyl-1,4,5,7-tetrahydro-pyrazolo[3,4-c]pyridin-6-yl]-phenyl}-pyrrolidin-1-yl-methylene)-methanesulfonamide;

N-({4-[3-isopropenyl-1-(4-methoxy-phenyl)-7-oxo-1,4,5,7-tetrahydro-pyrazolo[3,4-c]pyridin-6-yl]-phenyl}-pyrrolidin-1-yl-methylene)-methanesulfonamide;

N-(1-{4-[1-(4-methoxy-phenyl)-7-oxo-3-trifluoromethyl-1,4,5,7-tetrhydro-pyrazolo[3,4-c]pyridin-6-yl]-phenyl}-1,4,5,6-tetrahydro-pyrimidin-2-yl)-methanesulfonamide;

(1-{4-[1-(4-methoxy-phenyl)-7-oxo-3-trifluoromethyl-1,4,5,7-tetrahydro-pyrazolo[3,4-c]pyridin-6-yl]-phenyl}-1,4,5,6-tetrahydro-pyrimidin-2-yl)-carbamic acid methyl ester;

N-(1-{4-[1-(4-methoxy-phenyl)-7-oxo-3-trifluoromethyl-1,4,5,7-tetrahydro-pyrazolo[3,4-c]pyridin-6-yl]-phenyl}-1,4,5,6-tetrahydro-pyrimidin-2-yl)-acetamide;

1-(4-methoxy-phenyl)-6-{4-[2-(2-oxo-piperidin-1-yl)-5,6-dihydro-pyrimidin-1-yl]-phenyl}-3-trifluoromethyl-1,4,5,6-tetrahydro-pyrazolo[3,4-c]pyridin-7-one;

1-(4-methoxy-phenyl)-6-{4-[2-(2-oxo-pyrrolidin-1-yl)-5,6-dihydro-pyrimidin-1-yl]-phenyl}-3-trifluoromethyl-1,4,5,6-tetrahydro-pyrazolo[3,4-c]pyridin-7-one;

1-(4-methoxy-phenyl)-6-[4-(2-methyl-5,6-dihydro-4H-pyrimidin-1-yl)-phenyl]-3-cyano-1,4,5,6-tetrahydro-pyrazolo[3,4-c]pyridin-7-one;

6-[4-(2-amino-5,6-dihydro-4H-pyrimidin-1-yl)-phenyl]-1-(4-methoxy-phenyl)-7-oxo-4,5,6,7-tetrahydro-1H-pyrazolo[3,4-c]pyridine-3-carbonitrile;

N-(1-{4-[3-cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-methanesulfonamide;

N-(1-{4-[3-cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-N-methyl-methanesulfonamide;

N-(1-{4-[3-cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-acetamide;

6-[4-(2-methoxy-5,6-dihydro-4H-pyrimidin-1-yl)-phenyl]-1-(4-methoxy-phenyl)-7-oxo-4,5,6,7-tetrahydro-1H-pyrazolo[3,4-c]pyridine-3-carbonitrile;

6-[4-(5,6-dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-[4-(2-methyl-5,6-dihydro-4H-pyrimidin-1-yl)-phenyl]-1,4,5,6-tetrahydro-pyrazolo[3,4-c]pyridin-7-one;

6-[4-(2-isopropyl-5,6-dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-[4-(2-phenyl-5,6-dihydro-4H-pyrimidin-1-yl)-phenyl]-1,4,5,6-tetrahydro-pyrazolo[3,4-c]pyridin-7-one;

6-[4-(2-amino-5,6-dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one;

3-methanesulfonyl-1-(4-methoxy-phenyl)-6-{4-[2-(2-oxo-piperidin-1-yl)-5,6-dihydro-4H-pyrimidin-1-yl]-phenyl}-1,4,5,6-tetrahydro-pyrazolo[3,4-c]pyridin-7-one;

6-[4-(5,6-dihydro-4H-pyrimidin-1-yl)-phenyl]-3-isopropoxy-1-(4-methoxy-phenyl)-1,4,5,6-tetrahydro-pyrazolo[3,4-c]pyridin-7-one;

3-{6-[4-(2-amino-5,6-dihydro-4H-pyrimidin-1-yl)-phenyl]-3-methanesulfonyl-7-oxo-4,5,6,7-tetrahydro-pyrazolo[3,4-c]pyridin-1-yl}-benzamide;

3-{3-methanesulfonyl-6-[4-(2-methyl-5,6-dihydro-4H-pyrimidin-1-yl)-phenyl]-7-oxo-4,5,6,7-tetrahydro-pyrazolo[3,4-c]pyridin-1-yl}-benzamide;

1-(3-chloro-phenyl)-6-[4-(2-methyl-5,6-dihydro-4H-pyrimidin-1-yl)-phenyl]-3-trifluoromethyl-1,4,5,6-tetrahydro-pyrazolo[3,4-c]pyridin-7-one;

N-(diethylamino-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide;

1-(4-methoxy-phenyl)-6-[4-(1-methyl-4,5-dihydro-1H-imidazol-2-yl)-phenyl]-3-trifluoromethyl-1,4,5,6-tetrahydro-pyrazolo[3,4-c]pyridin-7-one;

6-[4-(4,5-dihydro-1H-imidazol-2-yl)-phenyl]-1-(4-methoxy-phenyl)-3-trifluoromethyl-1,4,5,6-tetrahydro-pyrazolo[3,4-c]pyridin-7-one;

6-[4-(1-methanesulfonyl-4,5-dihydro-1H-imidazol-2-yl)-phenyl]-1-(4-methoxy-phenyl)-3-trifluoromethyl-1,4,5,6-tetrahydro-pyrazolo[3,4-c]pyridin-7-one; and 2-{4-[1-(4-methoxy-phenyl)-7-oxo-3-trifluoromethyl-1,4,5,7-tetrahydro-pyrazolo[3,4-c]pyridin-6-yl]-phenyl}-4,5-dihydro-imidazole-1-carboxylic acid ethyl ester; or a pharmaceutically acceptable salt form thereof.

In a ninth aspect, the present invention provides a novel compound, wherein the compound is of Formula IIIa, IIIb, or IIIc:

IIIa

IIIb

IIIc or a stereoisomer or pharmaceutically acceptable salt thereof, wherein;

ring M, including $M_1$, $M_2$, and, if present, $M_3$, is phenyl or a 3–10 membered carbocyclic or 4–10 membered heterocyclic ring consisting of: carbon atoms and 1–4 heteroatoms selected from O, $S(O)_p$, N, and $NZ^2$;

ring M is substituted with 0–3 $R^{1a}$ and 0–2 carbonyl groups, and there are 0–3 ring double bonds;

one of $P_4$ and $M_4$ is -Z-A-B and the other -$G_1$-G;

G is a group of formula IIa or IIb:

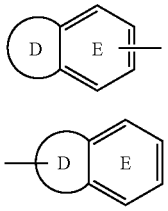

ring D, including the two atoms of Ring E to which it is attached, is a 5–6 membered ring consisting of: carbon atoms and 0–2 heteroatoms selected from the group consisting of N, O, and $S(O)_p$;

ring D is substituted with 0–2 R and there are 0–3 ring double bonds;

E is selected from phenyl, pyridyl, pyrimidyl, pyrazinyl, and pyridazinyl, and is substituted with 1–3 R;

alternatively, ring D is absent, and ring E is selected from phenyl, pyridyl, pyrimidyl, and thienyl, and ring E is substituted with 1–3 R;

alternatively, ring D is absent, ring E is selected from phenyl, pyridyl, and thienyl, and ring E is substituted with 1 R and substituted with a 5–6 membered heterocycle consisting of: carbon atoms and 1–4 heteroatoms selected from the group consisting of N, O, and $S(O)_p$, wherein the 5–6 membered heterocycle is substituted with 0–2 carbonyl and 1–2 R and there are 0–3 ring double bonds;

R is selected from H, $C_{1-4}$ alkyl, F, Cl, OH, $OCH_3$, $OCH_2CH_3$, $OCH(CH_3)_2$, —CN, $C(=NH)NH_2$, $C(=NH)NHOH$, $C(=NH)NHOCH_3$, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $(CR^8R^9)_rNR^7R^8$, $C(O)NR^7R^8$, $CH_2C(O)NR^7R^8$, $S(O)_pNR^7R^8$, $CH_2S(O)_pNR^7R^8$, $SO_2R^3$, and $OCF_3$;

alternatively, when 2 R groups are attached to adjacent atoms, they combine to form methylenedioxy or ethylenedioxy;

A is selected from: $C_{5-10}$ carbocycle substituted with 0–2 $R^4$, and 5–10 membered heterocycle consisting of: carbon atoms and 1–4 heteroatoms selected from the group consisting of N, O, and $S(O)_p$ and substituted with 0–2 $R^4$;

B is selected from

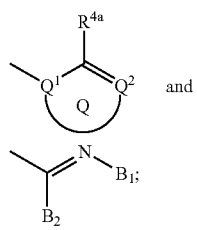

provided that Z and B are attached to different atoms on A and that the $R^{4a}$ shown is other than OH;

$Q^1$ and $Q^2$ are each N;

alternatively, one of $Q^1$ and $Q^2$ is $CR^3$ and $R^{4a}$ is $NR^2R^{2a}$ or $NR^{3a}B_1$, provided that when one of $Q^1$ and $Q^2$ is $CR^3$, then this $R^3$ group optionally forms a ring with the $R^2$ group of $R^{4a}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;

ring Q is a 5–6 membered ring consisting of, in addition to the $Q^1$—$CR^{4a}$=$Q^2$ group shown, carbon atoms and 0–2 heteroatoms selected from N, O, and $S(O)_p$, and the ring is substituted with an additional 0–2 $R^{4a}$;

$B_1$ is selected from $SO_2R^{3b}$, $C(O)R^{3b}$, $SO_2NR^3R^{3b}$, $C(O)NR^3R^{3b}$, $OR^2$, and —CN;

$B_2$ is $NR^2R^{2d}$ or $CR^3R^2R^{2d}$;

alternatively, $CR^3R^2R^{2d}$ forms a 5–6 membered ring consisting of: carbon atoms and 0–2 heteroatoms selected from N, O, and $S(O)_p$, and this ring is substituted with 0–2 $R^{4b}$;

alternatively, $NR^2R^{2d}$ forms a 5–6 membered ring consisting of: carbon atoms and 0–2 additional heteroatoms selected from N, O, and $S(O)_p$, and this ring is substituted with 0–2 $R^{4b}$;

alternatively, when $B_2$ is $NR^2R^{2d}$, $B_1$ and $R^{2d}$ combine to form a 5–6 membered ring consisting of: carbon atoms and 0–2 additional heteroatoms selected from N, O, and $S(O)_p$, and this ring is substituted with 0–2 $R^{4b}$ and the $R^2$ group of $NR^2R^{2d}$, in addition to the groups recited below, is selected from $SO_2R^{3b}$ and $C(O)R^{3b}$;

Z is selected from a bond, $CH_2$, $CH_2CH_2$, $CH_2O$, $OCH_2$, $C(O)$, NH, $CH_2NH$, $NHCH_2$, $CH_2C(O)$, $C(O)CH_2$, $C(O)NH$, $NHC(O)$, $NHC(O)CH_2C(O)NH$, $S(O)_2$, $CH_2S(O)_2$, $S(O)_2(CH_2)$, $SO_2NH$, and $NHSO_2$, wherein the right side of Z is attached to A, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^{3b}$, $S(O)R^{3f}$, and $S(O)_2R^{3f}$;

$R^{1a}$, at each occurrence, is selected from H, —$(CH_2)_r$—$R^{1b}$, —$(CH(CH_3))_r$—$R^{1b}$, —$(C(CH_3)_2)_r$—$R^{1b}$, —O—$(CR^3R^{3a})_r$—$R^{1b}$, —$NR^2$—$(CR^3R^{3a})_r$—$R^{1b}$, and —S—$(CR^3R^{3a})_r$—$R^{1b}$, provided that $R^{1a}$ forms other than an N-halo, N—S, O—O, or N—CN bond;

alternatively, when two $R^{1a}$ groups are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^{2b}$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0–2 $R^{4b}$, and 5–6 membered heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $C_{5-6}$ carbocycle substituted with 0–2 $R^{4b}$, a —$CH_2$—$C_{5-6}$ carbocyclic group substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^{2d}$, at each occurrence, is selected from H, $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl substituted with 0–2 $R^{4b}$, $C_{5-6}$ carbocycle substituted with 0–2 $R^{4b}$, and 5–6 membered heterocycle containing from 1–4 heteroatoms selected from the group consisting of N, O, and $S(O)_p$ and substituted with 0–2 $R^{4b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $NR^3R^{3a}$ forms a 5 or 6 membered saturated, partially unsaturated, or unsaturated ring consisting of: carbon atoms and the nitrogen atom to which $R^3$ and $R^{3a}$ are attached;

$R^{3b}$, at each occurrence, is selected from H, $CF_3$, $CH_3$, $CH_2CH_3$, $CH_2CH_2CH_3$, $CH(CH_3)_2$, —$(C_{0-1}$ alkyl)-5–6 membered carbocycle substituted with 0–1 $R^{1a}$, and —$(C_{0-1}$ alkyl)-5–6 membered heterocycle substituted with 0–1 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5–6 membered carbocycle substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^{4a}$, at each occurrence, is selected from H, $CH_2OR^2$, $OR^2$, $C_{1-4}$ alkyl, —CN, $CH_2CN$, $NO_2$, $CH_2NO_2$, $NR^2R^{2a}$, $CH_2NR^2R^{2a}$, $C(O)R^{2c}$, $CH_2C(O)R^{2c}$, $NR^2C(O)R^{2b}$, $(CH_2)_rC(O)NR^2R^{2a}$, $NR^2C(O)NR^2R^{2a}$, $(CH_2)_rSO_2NR^2R^{2a}$, $NR^2SO_2NR^2R^{2a}$, $NR^2SO_2R^5$, $(CH_2)_rS(O)_pR^{5a}$, $CF_3$, $CH_2CF_3$, $CH_2$-5–6 membered carbocycle substituted with 0–1 $R^5$, 5–6 membered carbocycle substituted with 0–1 $R^5$, a $CH_2$-5–6 membered heterocycle consisting of: carbon atoms and 1–4 heteroatoms selected from the group consisting of N, O, and $S(O)_p$ and substituted with 0–1 $R^5$, and a 5–6 membered heterocycle consisting of: carbon atoms and 1–4 heteroatoms selected from the group consisting of N, O, and $S(O)_p$ and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2CF_3$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

In a tenth aspect, the present invention provides a novel compound, wherein:

ring M, including $M_1$, $M_2$, and, if present, $M_3$, is selected from phenyl, pyrrole, furan, thiophene, pyrazole, imidazole, isoxazole, oxazole, isothiazole, thiazole, 1,2,3-triazole, 1,2,4-triazole, 1,3,4-triazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3,4-tetrazole, 1,2,3,5-tetrazole, pyran, thiopyran, thiopyran-1,1-dioxide, pyridine, pyrimidine, pyridazine, pyrazine, 1,2,3-triazine, 1,2,4-triazine, 1,2,3,4-tetrazine, dihydro-pyrrole, dihydro-furan, dihydro-thiophene, dihydro-pyrazole, dihydro-imidazole, dihydro-isoxazole, dihydro-oxazole, dihydro-isothiazole, dihydro-thiazole, dihydro-1,2,3-triazole, dihydro-1,2,4-triazole, dihydro-1,3,4-triazole, dihydro-1,2,3-oxadiazole, dihydro-1,2,4-oxadiazole, dihydro-1,3,4-oxadiazole, dihydro-1,2,3-thiadiazole, dihydro-1,2,4-thiadiazole, dihydro-1,3,4-thiadiazole, dihydro-1,2,3,4-tetrazole, dihydro-1,2,3,5-tetrazole, dihydro-pyran, dihydro-thiopyran, dihydro-thiopyran-1,1-dioxide, dihydro-pyridine, dihydro-pyrimidine, dihydro-pyridazine, dihydro-pyrazine, dihydro-1,2,3-triazine, dihydro-1,2,4-triazine, dihydro-1,2,3,4-tetrazine, cyclopropane, cyclobutane, cyclopentene, cyclopentane, cyclohexene, cyclohexane, cycloheptane, tetrahydro-pyrrole, tetrahydro-furan, tetrahydro-thiophene, tetrahydro-thiophene-1,1-dioxide, tetrahydro-pyrazole, tetrahydro-imidazole, tetrahydro-isoxazole, tetrahydro-oxazole, tetrahydro-isothiazole, tetrahydro-thiazole, tetrahydro-1,2,3-triazole, tetrahydro-1,2,4-triazole, tetrahydro-1,3,4-triazole, tetrahydro-1,2,3-oxadiazole, tetrahydro-1,2,4-oxadiazole, tetrahydro-1,3,4-oxadiazole, tetrahydro-1,2,3-thiadiazole, tetrahydro-1,2,4-thiadiazole, tetrahydro-1,3,4-thiadiazole, tetrahydro-1,2,3,4-tetrazole, tetrahydro-1,2,3,5-tetrazole, tetrahydro-pyran, tetrahydro-thiopyran, tetrahydro-thiopyran-1,1-dioxide, tetrahydro-pyridine, tetrahydro-pyrimidine, tetrahydro-pyridazine, tetrahydro-pyrazine, tetrahydro-1,2,3-triazine, tetrahydro-1,2,4-triazine, tetrahydro-1,2,3,4-tetrazine, piperidine, indan, 1,2,3,4-tetrahydro-naphthalene, 7,8-dimethyl-1-oxa-spiro[4.4]nonane, 6,7-dihydro-5H-[1]pyridine, 6,7-dihydro-5H-[2]pyridine, 5,6,7,8-tetrahydro-quinoline, 5,6,7,8-tetrahydro-isoquinoline, 5,6,7,8-tetrahydroquinoxaline, 6,7-dihydro-5H-cyclopentapyrazine, 4,5,6,7-tetrahydro-1H-benzoimidazole, 4,5,6,7-tetrahydrobenzothiazole, 4,5,6,7-tetrahydro-benzooxazole, 4,5,6,7-tetrahydro-benzo[c]isothiazole, 4,5,6,7-tetrahydro-benzo[c]isoxazole, 4,5,6,7-tetrahydro-2H-indazole, 4,5,6,7-tetrahydro-2H-isoindole, and 4,5,6,7-tetrahydro-1H-indole;

ring M is substituted with 0–3 $R^{1a}$ and 0–1 carbonyl group;

G is selected from the group: phenyl, 4-ethyl-phenyl, 2,5-bis-aminomethyl-phenyl, 2-amido-4-methoxy-phenyl, 2-amido-5-chloro-phenyl, 2-amido-phenyl, 2-aminomethyl-3-fluoro-phenyl, 2-aminomethyl-3-methoxy-phenyl, 2-aminomethyl-4-fluoro-phenyl, 2-aminomethyl-4-methoxy-phenyl, 2-aminomethyl-5-fluoro-phenyl, 2-aminomethyl-5-methoxy-phenyl, 2-aminomethyl-6-fluoro-phenyl, 2-aminomethyl-phenyl; 2-amino-pyrid-4-yl, 2-aminosulfonyl-4-methoxy-phenyl, 2-aminosulfonyl-phenyl, 2-hydroxy-4-methoxy-phenyl, 2-methyl sul fonyl-phenyl, 3-(N,N-dimethylamino)-4-chloro-phenyl, 3-(N,N-dimethylamino)-phenyl, 3-(N-hydroxy-amidino)-phenyl, 3-(N-methoxy-amidino)-phenyl, 3-(N-methylamino)-4-chloro-phenyl, 3-(N-methylamino)-phenyl, 3-amidino-phenyl, 3-amido-6-hydroxy-phenyl, 3-amido-phenyl, 3-amino-4-chloro-phenyl, 3-aminomethyl-phenyl, 3-amino-phenyl, 3-chloro-4-fluoro-phenyl, 3-chloro-phenyl, 3-hydroxy-4-methoxy-phenyl, 4-(N,N-dimethylamino)-5-chloro-thien-2-yl, 4-(N-methylamino)-5-chloro-thien-2-yl, 4-amino-5-chloro-thien-2-yl, 4-amino-pyrid-2-yl, 4-chloro-3-fluoro-phenyl, 4-chloro-phenyl, 4-chloro-pyrid-2-yl, 4-methoxy-2-methylsulfonyl-phenyl, 4-methoxy-phenyl, 5-(N,N-dimethylamino)-4-chloro-thien-2-yl, 5-(N-methylamino)-4-chloro-thien-2-yl, 5-amino-4-chloro-thien-2-yl, 5-chloro-2-aminosulfonyl-phenyl, 5-chloro-2-methylsulfonyl-phenyl, 5-chloro-pyrid-2-yl, 5-chloro-thien-2-yl, 6-amino-5-chloro-pyrid-2-yl, 6-amino-pyrid-2-yl,

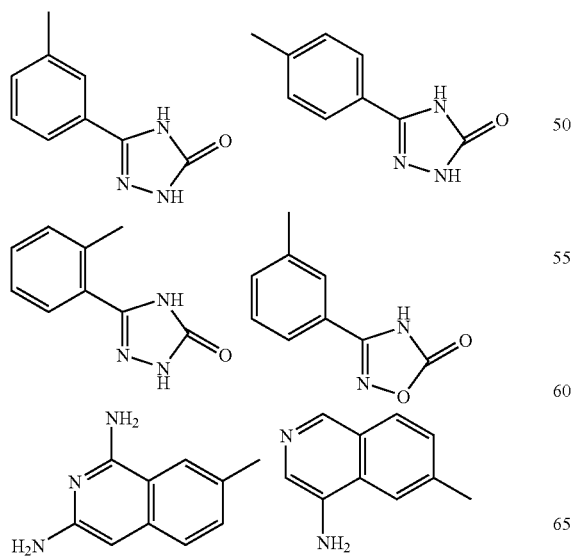

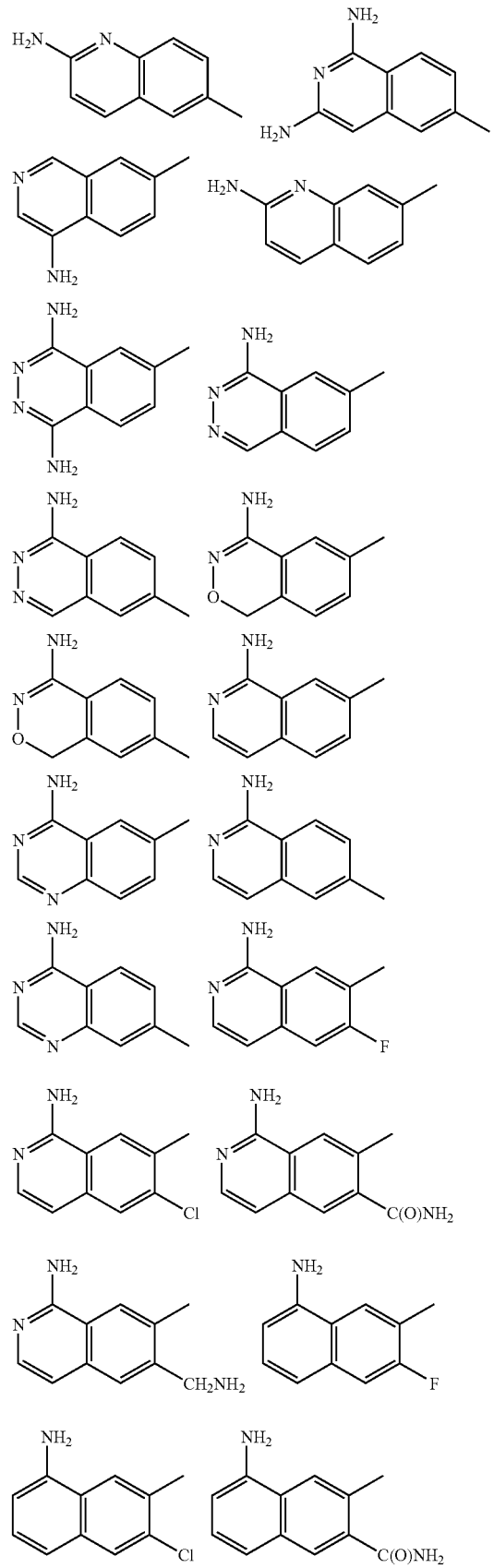

-continued
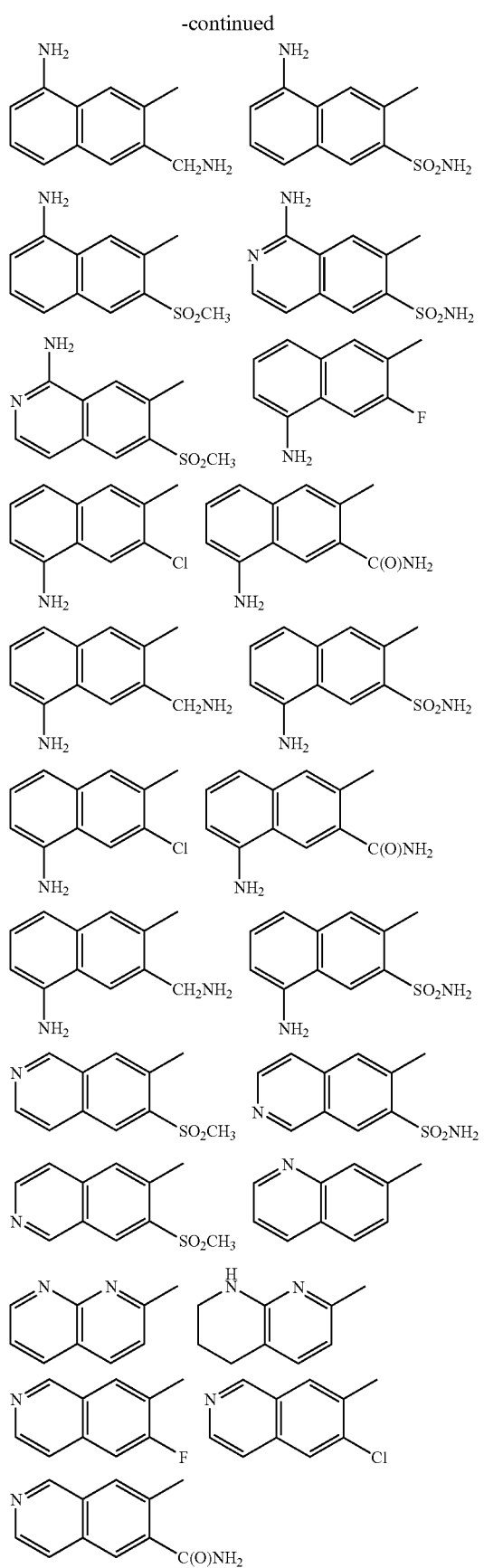
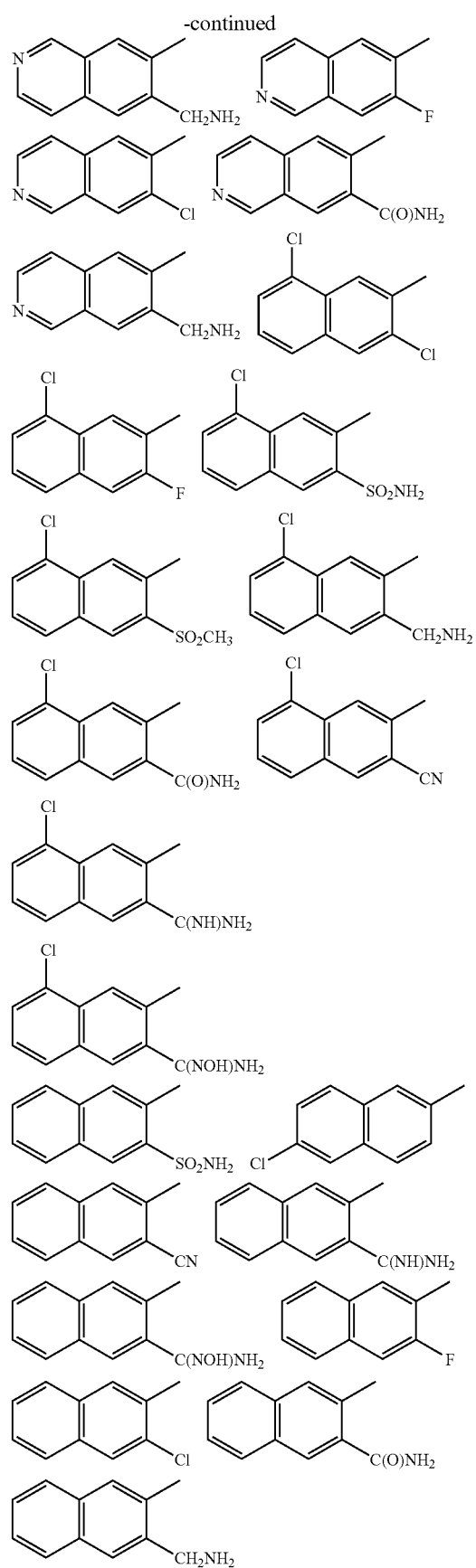

-continued
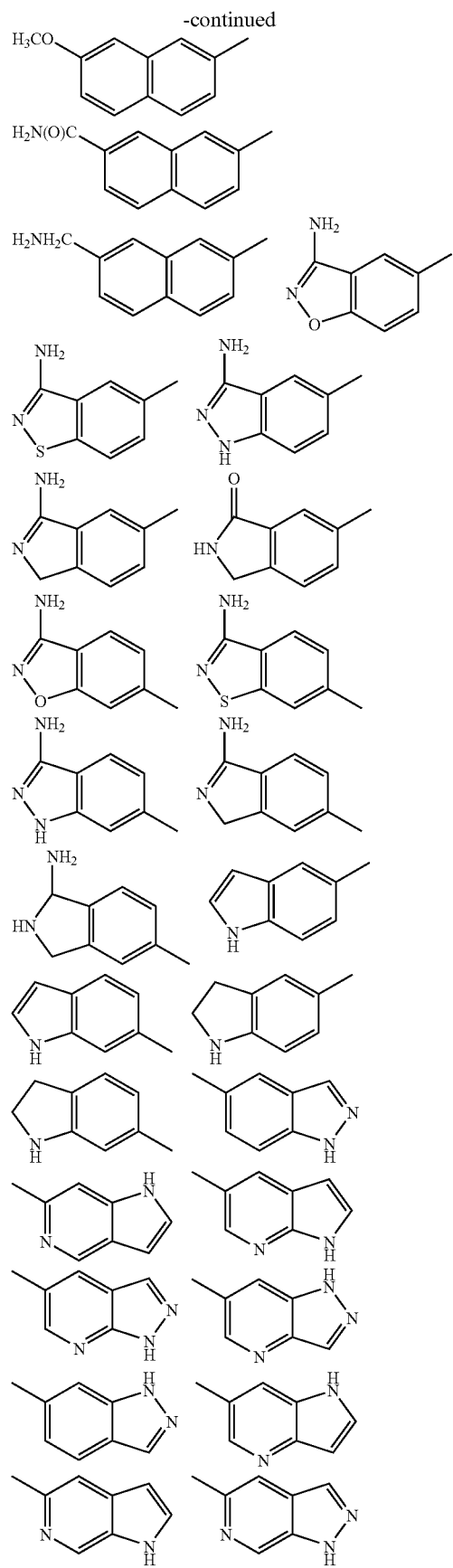
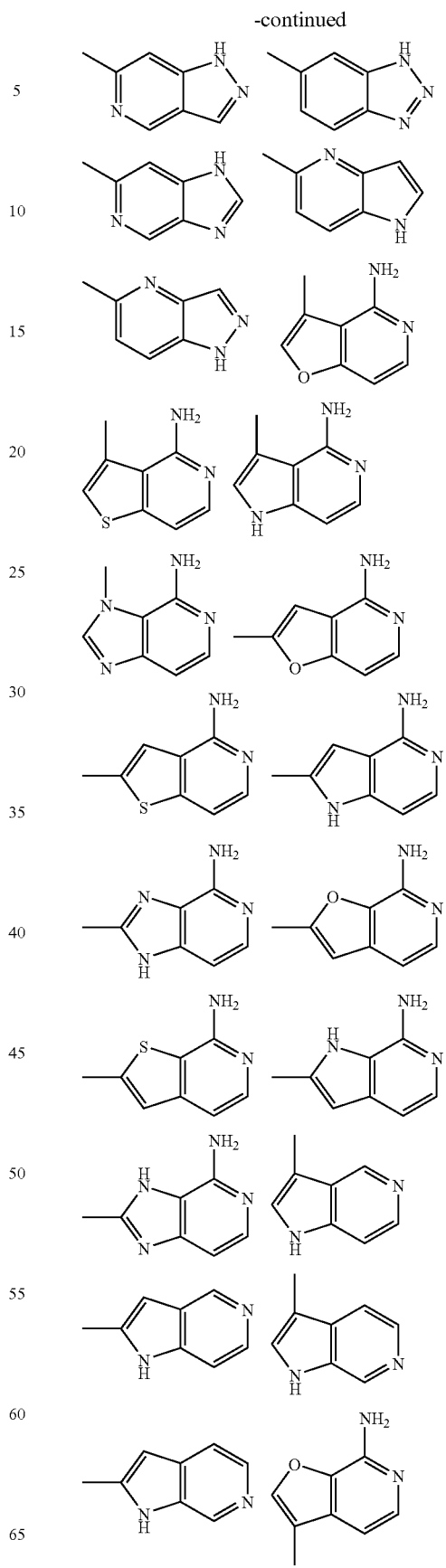

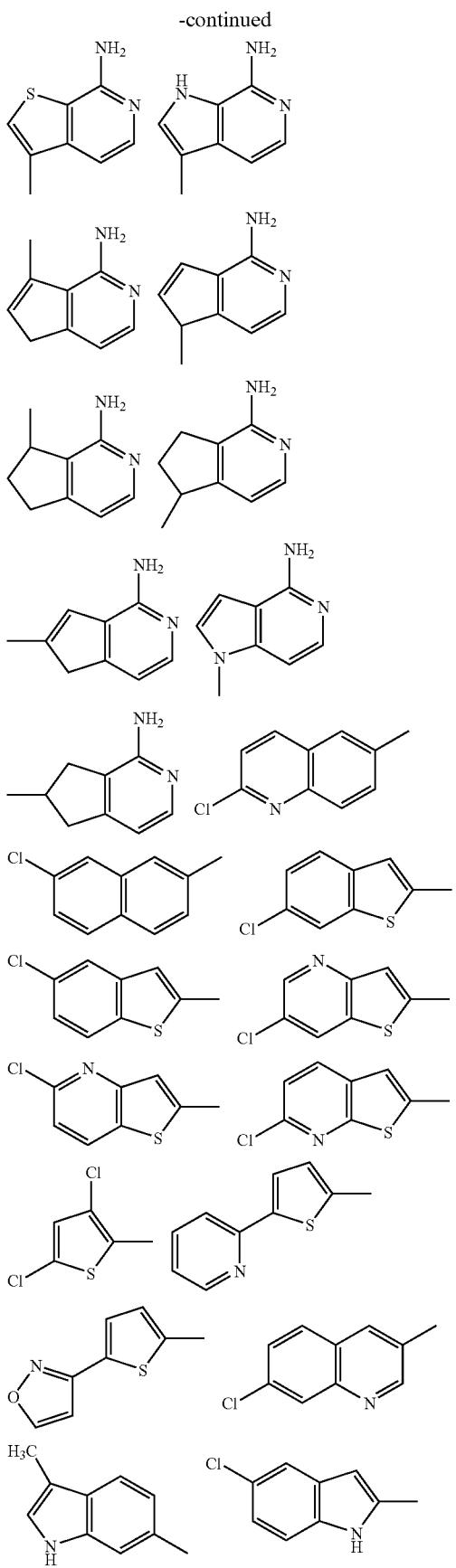

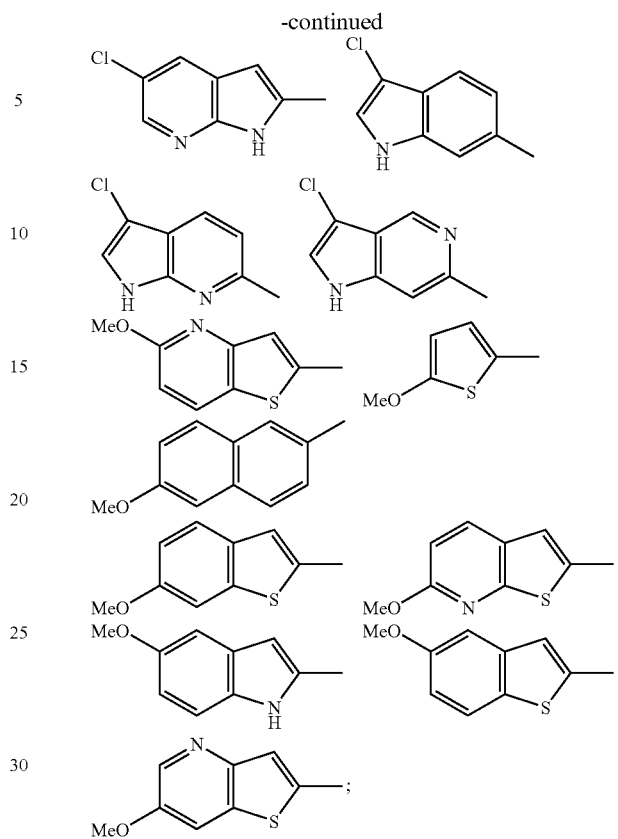

$G_1$ is absent or is selected from $(CR^3R^{3a})_{1-3}$, $CR^3=CR^3$, $(CR^3R^{3a})_uC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, and $(CR^3R^{3a})_uS(O)_2NR^{3b}(CR^3R^{3a})_w$, wherein u+w or u+u+w total 0, 1, or 2, wherein the right side of $G_1$ is attached to G, provided that $G_1$ does not form a N—S, $NCH_2N$, $NCH_2O$, or $NCH_2S$ bond with either group to which it is attached;

A is selected from one of the following carbocyclic and heterocyclic groups which are substituted with 0–2 $R^4$; cyclohexyl, phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

B is selected from

-continued

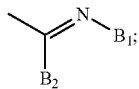

provided that Z and B are attached to different atoms on A and that the $R^{4a}$ shown is other than OH;

ring Q is a 5–6 membered ring consisting of, in addition to the N—$CR^{4a}$=N group shown, carbon atoms and 0–2 heteroatoms selected from N, O, and $S(O)_p$, and the ring is substituted with an additional 0–2 $R^{4a}$;

$B_1$ is selected from $SO_2R^{3b}$ and $OR^2$;

$B_2$ is $NR^2R^{2d}$;

alternatively, $NR^2R^{2d}$ forms a 5–6 membered ring consisting of: carbon atoms and 0–2 additional heteroatoms selected from N, O, and $S(O)_p$, and this ring is substituted with 0–2 $R^{4b}$;

alternatively, $B_1$ and $R^{2d}$ combine to form a 5–6 membered ring consisting of: carbon atoms and 0–1 additional heteroatoms selected from N, O, and $S(O)_p$, and this ring is substituted with 0–2 $R^{4b}$ and the $R^2$ group of $NR^2R^{2d}$, in addition to the groups recited below, can be $SO_2R^{3b}$;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5–6 membered ring consisting of: carbon atoms and 0–2 heteroatoms selected from the group consisting of N, O, and $S(O)_p$, this ring being substituted with 0–2 $R^{4b}$ and 0–3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_rR^{2b}$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0–2 $R^{4b}$, and 5–6 membered aromatic heterocycle consisting of carbon atoms and from 1–4 heteroatoms selected from the group consisting of N, O, and $S(O)_p$, and substituted with 0–2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0–2 $R^{4b}$, a benzyl substituted with 0–2 $R^{4b}$, and a 5–6 membered aromatic heterocycle consisting of: carbon atoms and 1–4 heteroatoms selected from the group consisting of N, O, and $S(O)_p$ and substituted with 0–2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

alternatively, $NR^2R^{2a}$ forms a 5 or 6 membered saturated, partially saturated, or unsaturated ring substituted with 0–2 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle consisting of: carbon atoms and 1–4 heteroatoms selected from the group consisting of N, O, and $S(O)_p$ and substituted with 0–2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl substituted with 0–2 $R^{4b}$, phenyl substituted with 0–2 $R^{4b}$, and 5–6 membered aromatic heterocycle containing from 1–4 heteroatoms selected from the group consisting of N, O, and $S(O)_p$ and substituted with 0–2 $R^{4b}$;

$R^{2d}$, at each occurrence, is selected from H, $CF_3$, $CH_3$, $CH_2CH_3$, $CH_2CH_2CH_3$, $CH(CH_3)_2$, $OCH_3$, and benzyl;

$R^{3b}$, at each occurrence, is selected from H, $CF_3$, $CH_3$, $CH_2CH_3$, $CH_2CH_2CH_3$, and $CH(CH_3)_2$;

$R^4$, at each occurrence, is selected from H, $OR^2$, $CH_2OR^2$, $(CH_2)_2OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$, at each occurrence, is selected from H, $OR^2$, $CH_2OR^2$, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2c}$, $NR^2C(O)R^{2b}$, $C(O)NR^2R^{2a}$, $NR^2C(O)NR^2R^{2a}$, $NR^2SO_2R^5$, $SO_2NR^2R^{2a}$, 6 membered carbocycle substituted with 0–1 $R^5$, and a 5–6 membered heterocycle consisting of: carbon atoms and 1–2 heteroatoms selected from the group consisting of N, O, and $S(O)_p$ and substituted with 0–1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $CF_3$, phenyl substituted with 0–2 $R^6$, naphthyl substituted with 0–2 $R^6$, and benzyl substituted with 0–2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

In an eleventh aspect, the present invention provides a novel compound, wherein the compound is selected from:

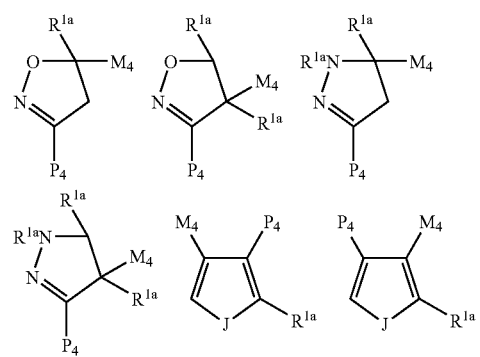

-continued
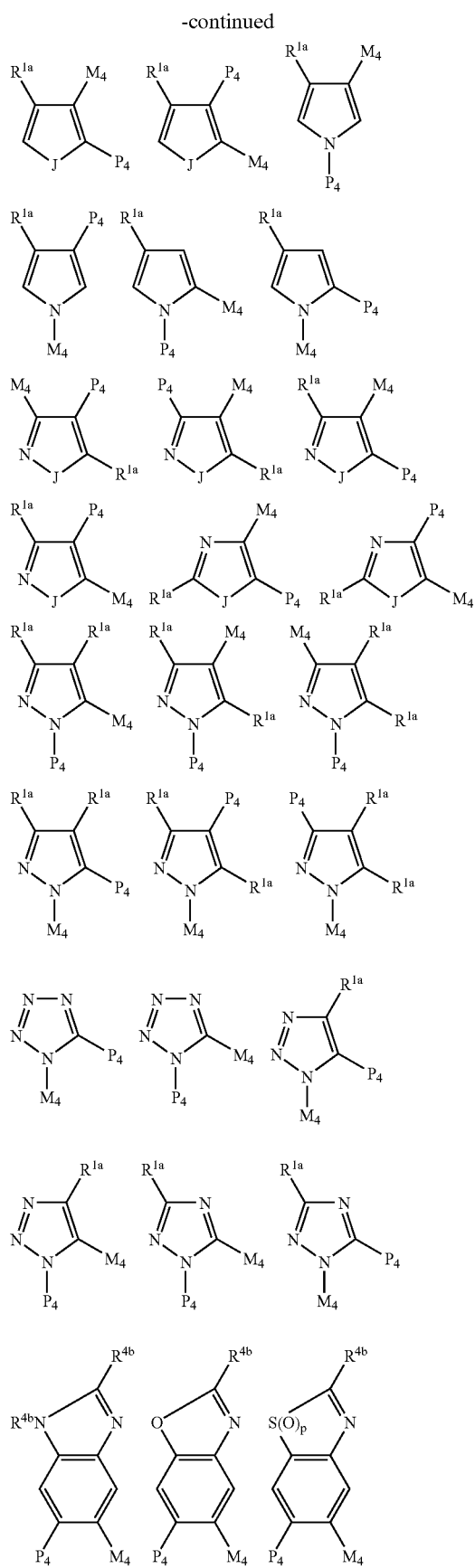
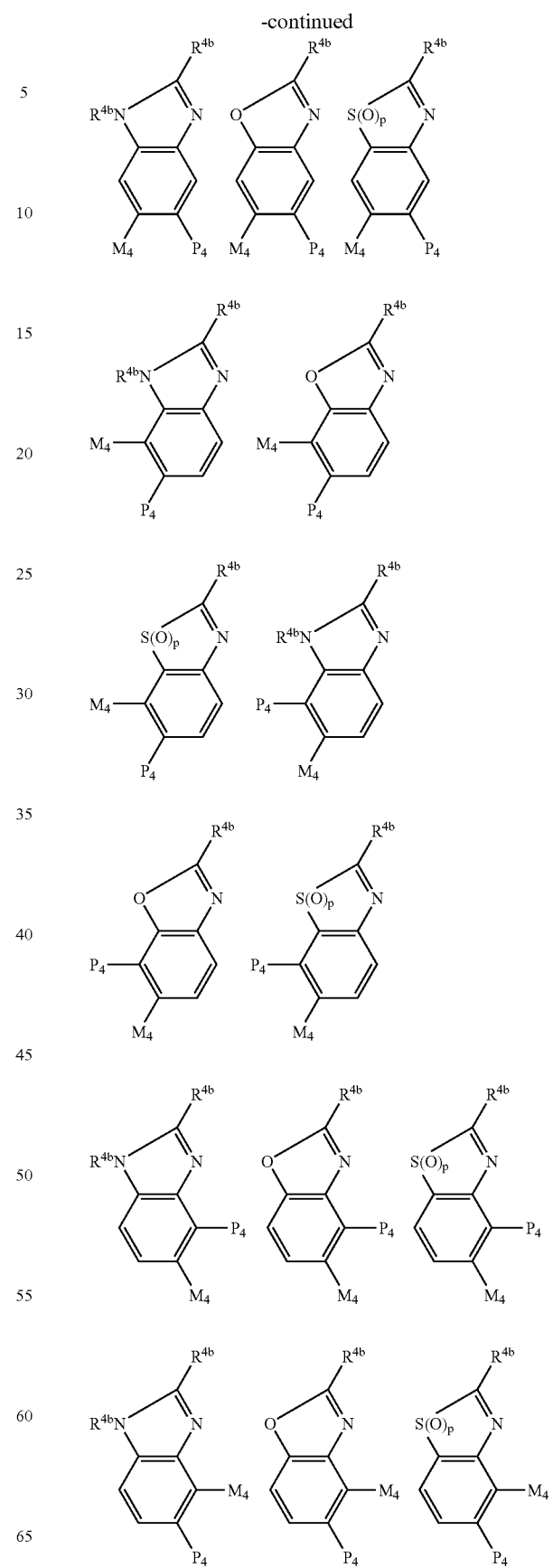

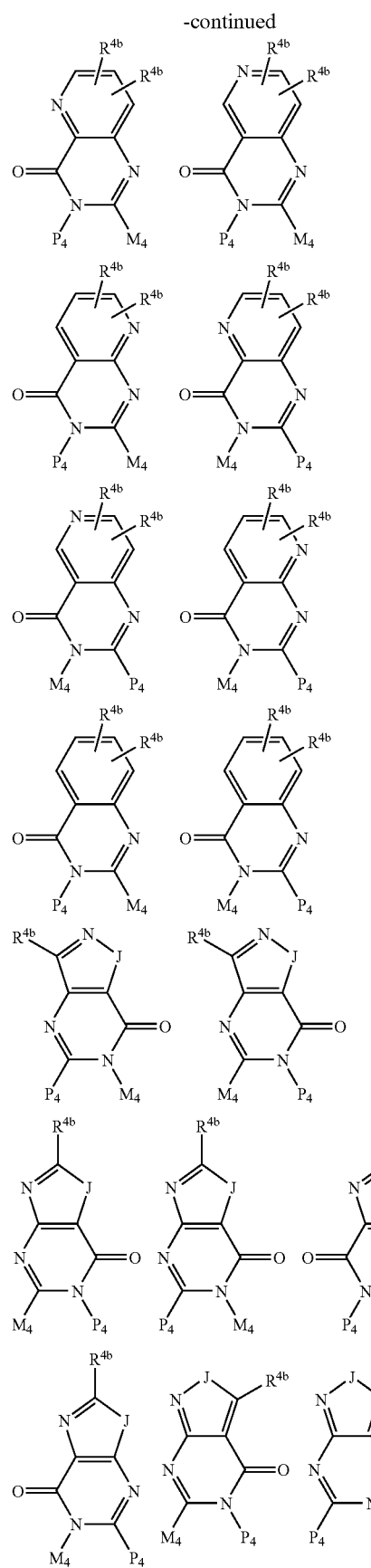
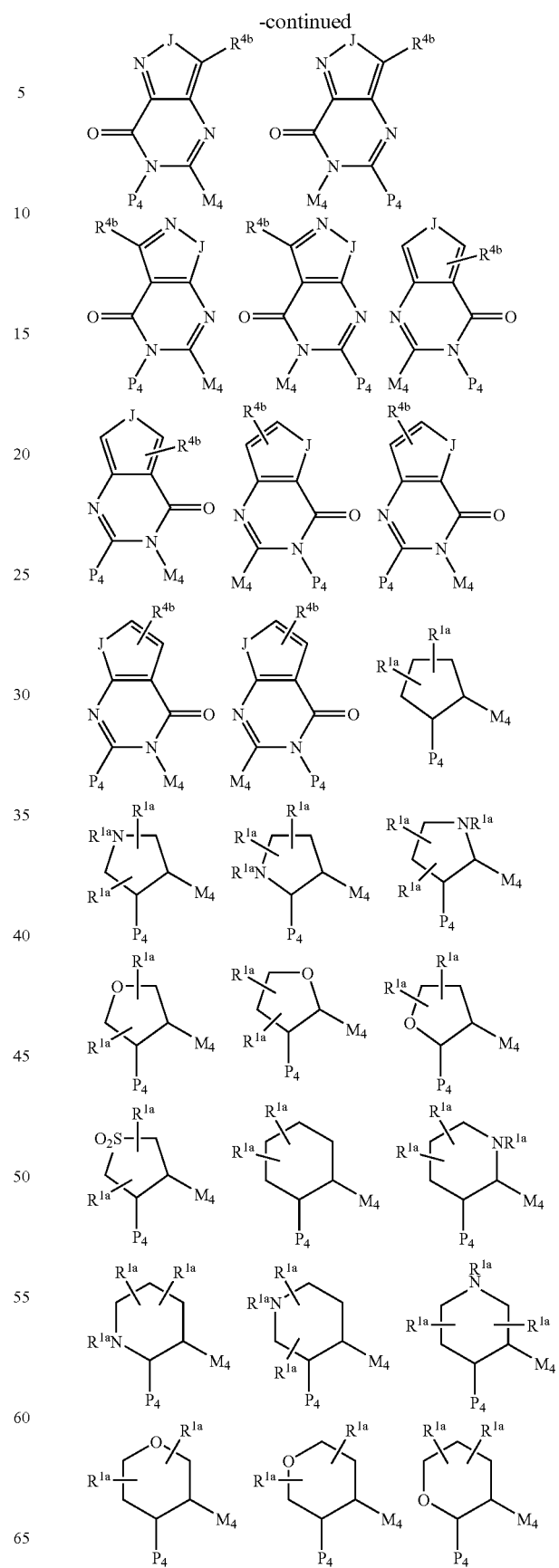

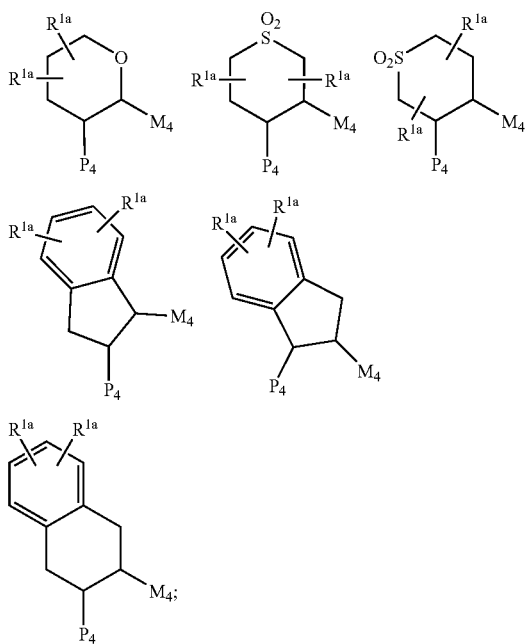

J is selected from O, S, NH, and $NR^{1a}$;

G is selected from: 2-amido-4-methoxy-phenyl, 2-amido-phenyl, 2-aminomethyl-3-fluoro-phenyl, 2-aminomethyl-4-fluoro-phenyl, 2-aminomethyl-4-methoxy-phenyl, 2-aminomethyl-5-fluoro-phenyl, 2-aminomethyl-5-methoxy-phenyl, 2-aminomethyl-6-fluoro-phenyl, 2-aminomethyl-phenyl, 2-amino-pyrid-4-yl, 2-aminosulfonyl-4-methoxy-phenyl, 2-aminosulfonyl-phenyl, 2-methylsulfonyl-phenyl, 3-(N,N-dimethylamino)-4-chloro-phenyl, 3-(N,N-dimethylamino)-phenyl, 3-(N-methylamino)-4-chloro-phenyl, 3-(N-methylamino)-phenyl, 3-amido-phenyl, 3-amino-4-chloro-phenyl, 3-aminomethyl-phenyl, 3-amino-phenyl, 3-chloro-phenyl, 4-(N,N-dimethylamino)-5-chloro-thien-2-yl, 4-(N-methylamino)-5-chloro-thien-2-yl, 4-amino-5-chloro-thien-2-yl, 4-chloro-phenyl, 4-methoxy-2-methylsulfonyl-phenyl, 4-methoxy-phenyl, 5-(N,N-dimethylamino)-4-chloro-thien-2-yl, 5-(N-methylamino)-4-chloro-thien-2-yl, 5-amino-4-chloro-thien-2-yl, 5-chloro-pyrid-2-yl, 5-chloro-thien-2-yl, 6-amino-5-chloro-pyrid-2-yl, 6-amino-pyrid-2-yl,

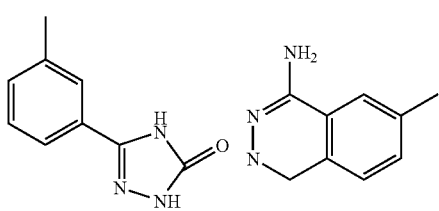

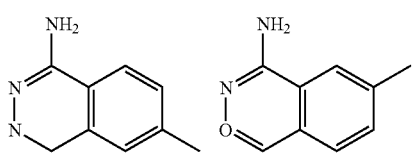

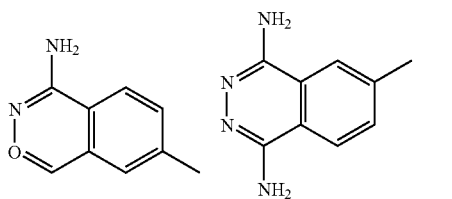

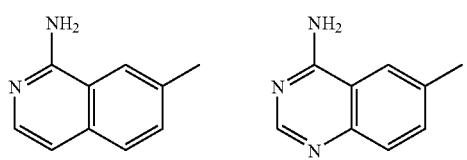

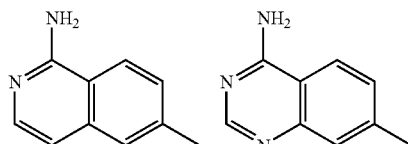

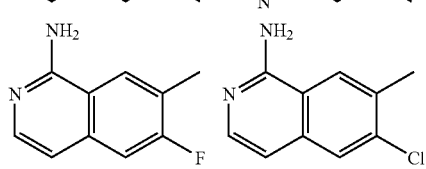

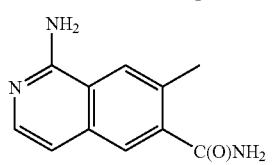

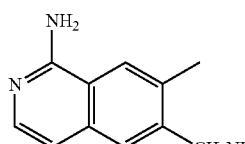

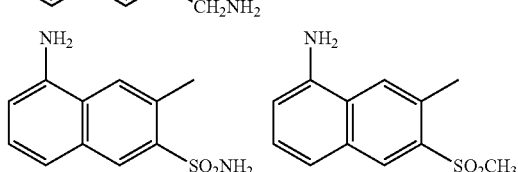

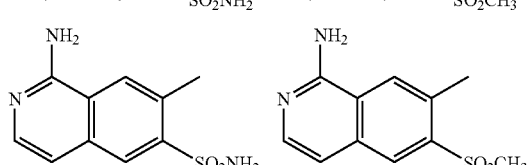

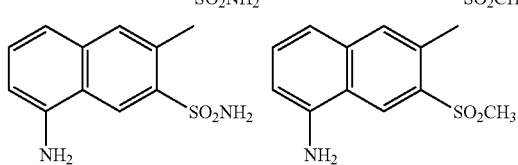

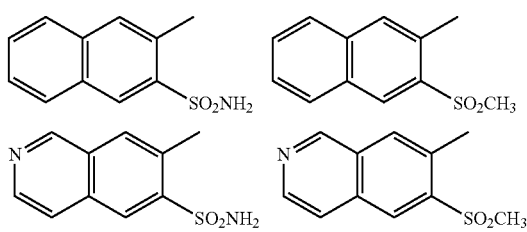

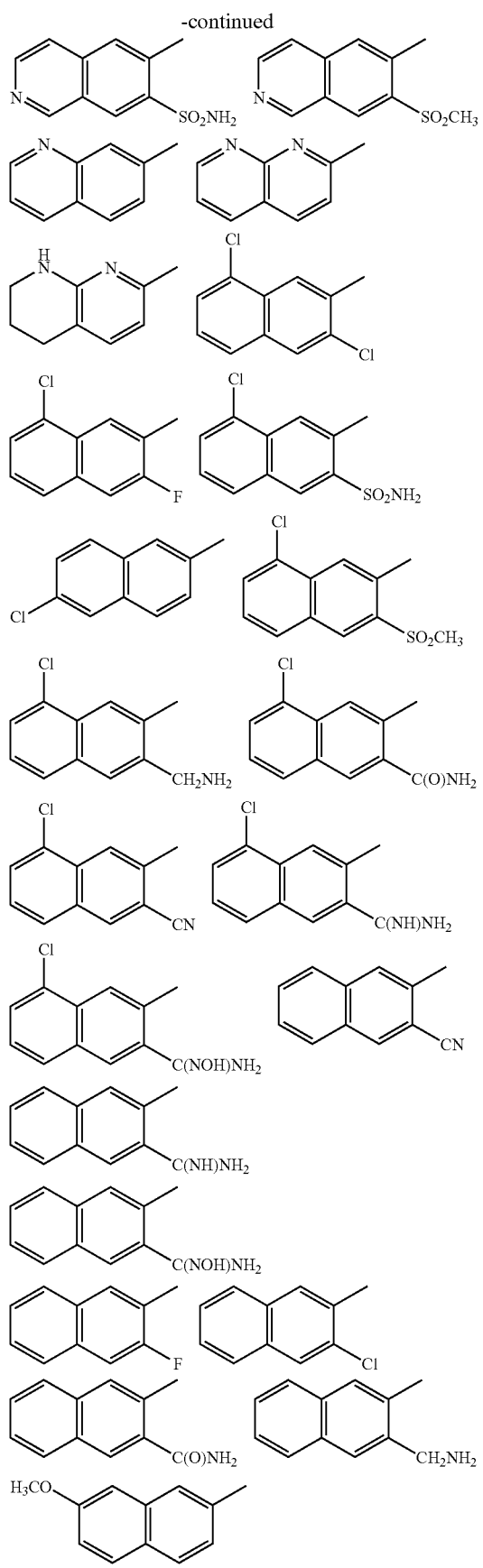
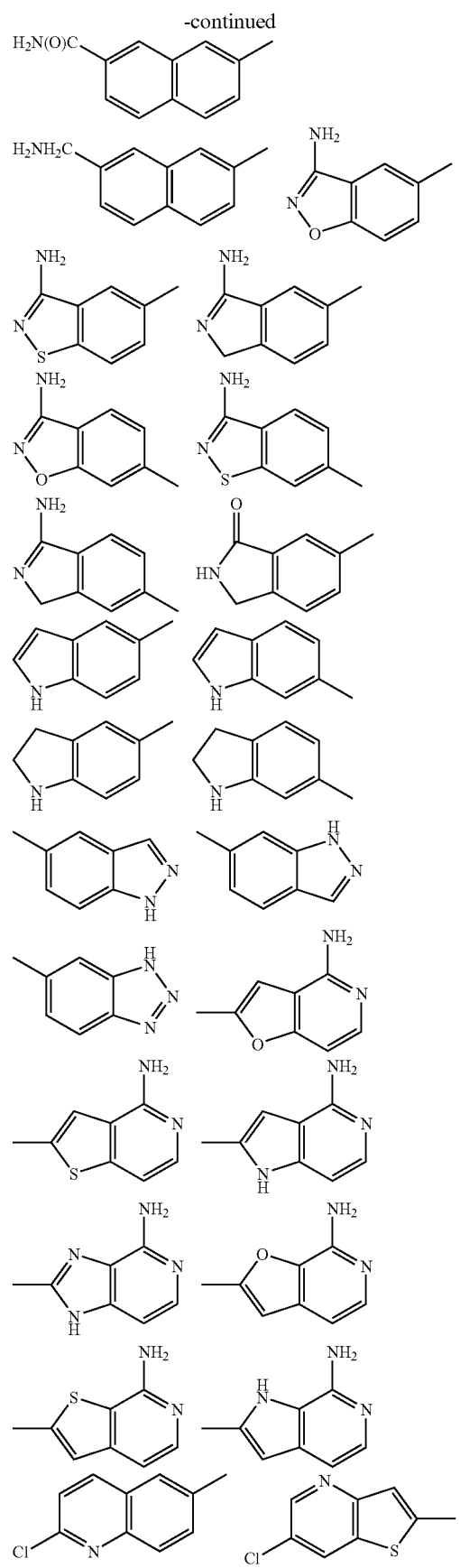

-continued

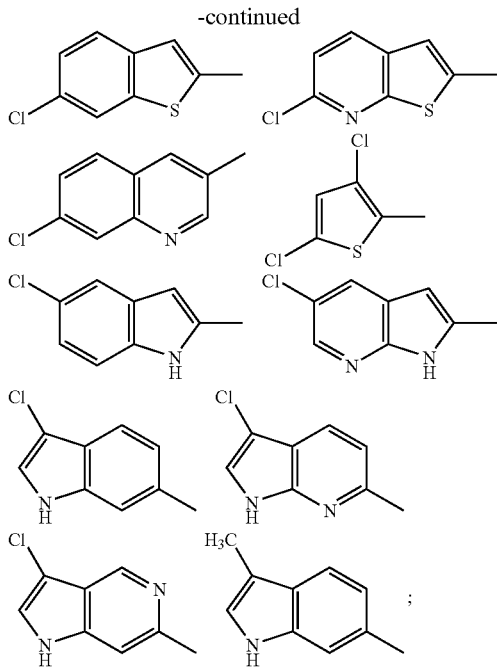

G₁ is absent or is selected from CH₂, CH₂CH₂, CH₂O, OCH₂, NH, CH₂NH, NHCH₂, CH₂C(O), C(O)CH₂, C(O)NH, NHC(O), CH₂S(O)₂, S(O)₂(CH₂), SO₂NH, and NHSO₂, wherein the right side of G₁ is attached to G, provided that G₁ does not form a N—S, NCH₂N, NCH₂O, or NCH₂S bond with either group to which it is attached;

A is selected from cyclohexyl, indolinyl, phenyl, pyridyl, and pyrimidyl, and is substituted with 0–2 R⁴;

B is selected from

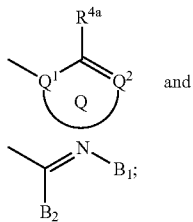

provided that Z and B are attached to different atoms on A and that the R⁴ᵃ shown is other than OH;

ring Q is a 5–6 membered ring consisting of, in addition to the N—CR⁴ᵃ=N group shown, carbon atoms and 0–1 heteroatoms selected from N, O, and S(O)ₚ, and the ring is substituted with an additional 0–2 R⁴ᵃ;

B₁ is selected from SO₂R³ᵇ and OR²;

B₂ is NR²R²ᵈ;

alternatively, NR²R²ᵈ forms a 5–6 membered ring consisting of: carbon atoms and 0–1 additional heteroatoms selected from N, O, and S(O)ₚ, and this ring is substituted with 0–1 R⁴ᵇ;

alternatively, B₁ and R²ᵈ combine to form a 5 membered ring consisting of: carbon atoms and 0–1 additional heteroatoms selected from N, O, and S(O)ₚ, and this ring is substituted with 0–2 R⁴ᵇ and the R² group of NR²R²ᵈ, in addition to the groups recited below, can be SO₂R³ᵇ;

R¹ᵃ, at each occurrence, is selected from H, R¹ᵇ, CH(CH₃)R¹ᵇ, C(CH₃)₂R¹ᵇ, and CH₂R¹ᵇ, provided that R¹ᵃ forms other than an N-halo, N—S, or N—CN bond;

R¹ᵇ is selected from CH₃, CH₂CH₃, F, Cl, Br, —CN, CF₃, OR², NR²R²ᵃ, C(O)R²ᵇ, CO₂R²ᵇ, CO₂R²ᵃ, S(O)ₚR²ᵇ, C(O)NR²R²ᵃ, SO₂NR²R²ᵃ, NR²SO₂R², and 5–6 membered aromatic heterocycle consisting of carbon atoms and from 1–4 heteroatoms selected from the group consisting of N, O, and S(O)ₚ, and substituted with 0–2 R⁴ᵇ, provided that R¹ᵇ forms other than an O—O, N-halo, N—S, or N—CN bond;

R², at each occurrence, is selected from H, CH₃, CH₂CH₃, CH₂CH₂CH₃, CH(CH₃)₂, phenyl substituted with 0–1 R⁴ᵇ, benzyl substituted with 0–1 R⁴ᵇ, and 5–6 membered aromatic heterocycle consisting of: carbon atoms and 1–4 heteroatoms selected from the group consisting of N, O, and S(O)ₚ and substituted with 0–1 R⁴ᵇ;

R²ᵃ, at each occurrence, is selected from H, CH₃, CH₂CH₃, CH₂CH₂CH₃, CH(CH₃)₂, benzyl substituted with 0–1 R⁴ᵇ, phenyl substituted with 0–1 R⁴ᵇ, and 5–6 membered aromatic heterocycle consisting of: carbon atoms and 1–4 heteroatoms selected from the group consisting of N, O, and S(O)ₚ and substituted with 0–1 R⁴ᵇ;

alternatively, NR²R²ᵈ forms a 5 or 6 membered saturated, partially saturated, or unsaturated ring substituted with 0–1 R⁴ᵇ and consisting of: carbon atoms, the nitrogen atom to which R² and R²ᵃ are attached, and 0–1 additional heteroatoms selected from the group consisting of N, O, and S(O)ₚ;

R²ᵇ, at each occurrence, is selected from OCH₃, OCH₂CH₃, OCH₂CH₂CH₃, OCH(CH₃)₂, CH₃, CH₂CH₃, CH₂CH₂CH₃, CH(CH₃)₂, benzyl substituted with 0–1 R⁴ᵇ, phenyl substituted with 0–1 R⁴ᵇ, and 5–6 membered aromatic heterocycle consisting of: carbon atoms and 1–4 heteroatoms selected from the group consisting of N, O, and S(O)ₚ and substituted with 0–1 R⁴ᵇ;

R²ᶜ, at each occurrence, is selected from OH, OCH₃, OCH₂CH₃, OCH₂CH₂CH₃, OCH(CH₃)₂, CH₃, CH₂CH₃, CH₂CH₂CH₃, CH(CH₃)₂, benzyl substituted with 0–1 R⁴ᵇ, phenyl substituted with 0–1 R⁴ᵇ, and 5–6 membered aromatic heterocycle containing from 1–4 heteroatoms selected from the group consisting of N, O, and S(O)ₚ and substituted with 0–1 R⁴ᵇ;

R²ᵈ, at each occurrence, is selected from H, CH₃, CH₂CH₃, OCH₃, and benzyl;

R³ᵇ, at each occurrence, is selected from H and CH₃;

R⁴, at each occurrence, is selected from OH, OR², CH₂OR², (CH₂)₂OR², F, Br, Cl, I, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, NR²R²ᵃ, CH₂NR²R²ᵃ, (CH₂)₂NR²R²ᵃ, CF₃, and CF₂CF₃;

R⁴ᵃ, at each occurrence, is selected from H, OR², CH₂OR², CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, NR²R²ᵃ, CH₂NR²R²ᵃ, C(O)R²ᶜ, NR²C(O)R²ᵇ, C(O)NR²R²ᵃ, SO₂NR²R²ᵃ, NR²SO₂R⁵, phenyl substituted with 0–1 R⁵, and a 5–6 membered heterocycle consisting of: carbon atoms and 1 heteroatom selected from the group consisting of N, O, and S(O)ₚ and substituted with 0–1 R⁵;

R⁴ᵇ, at each occurrence, is selected from H, =O, OR³, CH₂OR³, F, Cl, CH₃, CH₂CH₃, CH₂CH₂CH₃, CH(CH₃)₂, —CN, NO₂, NR³R³ᵃ, CH₂NR³R³ᵃ, C(O)R³, C(O)OR³ᶜ, NR³C(O)R³ᵃ, C(O)NR³R³ᵃ, SO₂NR³R³ᵃ, NR³SO₂—C₁₋₄ alkyl, NR³SO₂-phenyl, S(O)ₚ—C₁₋₄ alkyl, S(O)ₚ-phenyl, and CF₃;

R⁵, at each occurrence, is selected from H, =O, CH₃, CH₂CH₃, CH₂CH₂CH₃, CH(CH₃)₂, OR³, NR³R³ᵃ, C(O)R³, NR³C(O)R³ᵃ, C(O)NR³R³ᵃ, SO₂NR³R³ᵃ, and phenyl substituted with 0–2 R⁶; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.
In a twelfth aspect, the present invention provides a novel compound, wherein the compound is selected from:
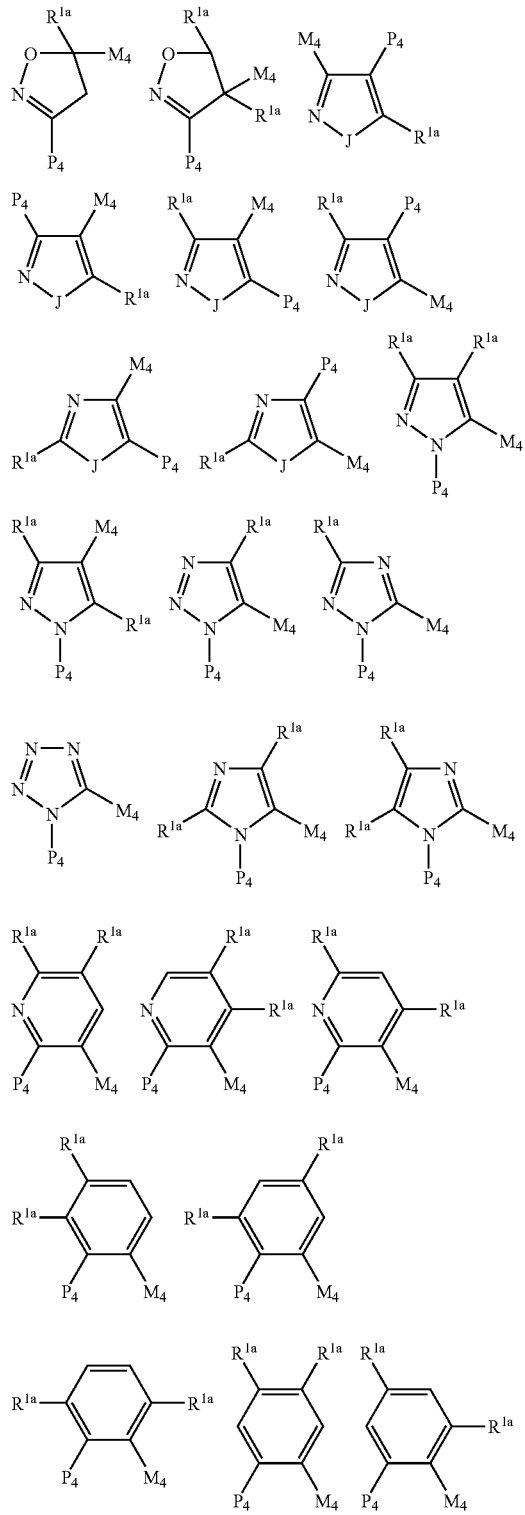
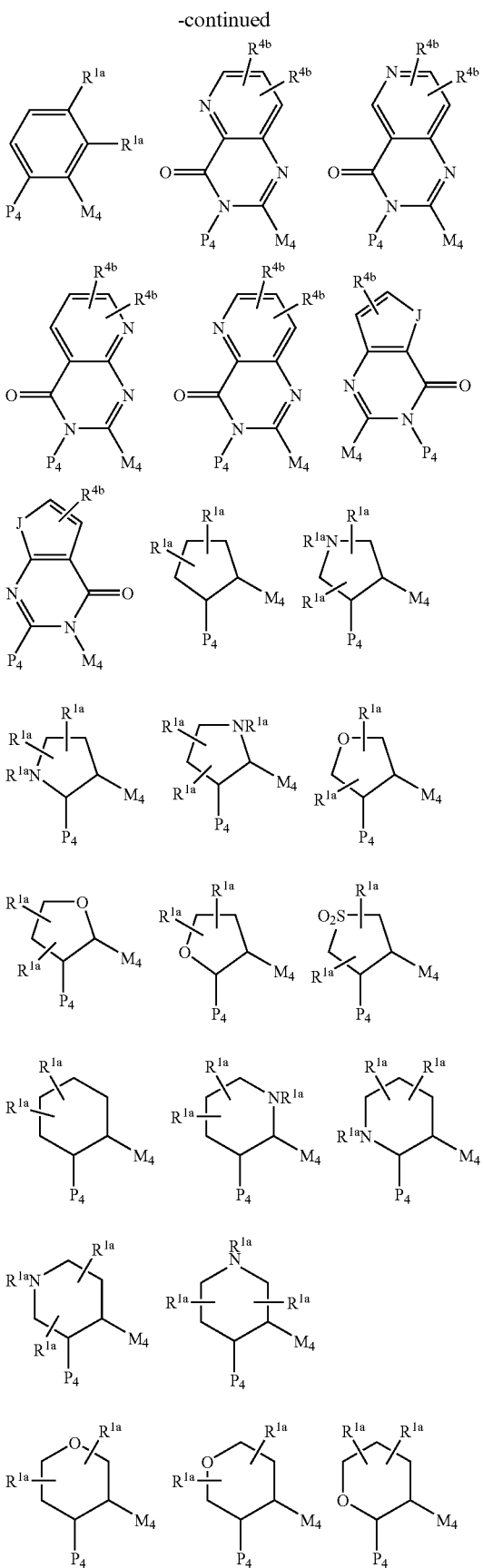
-continued

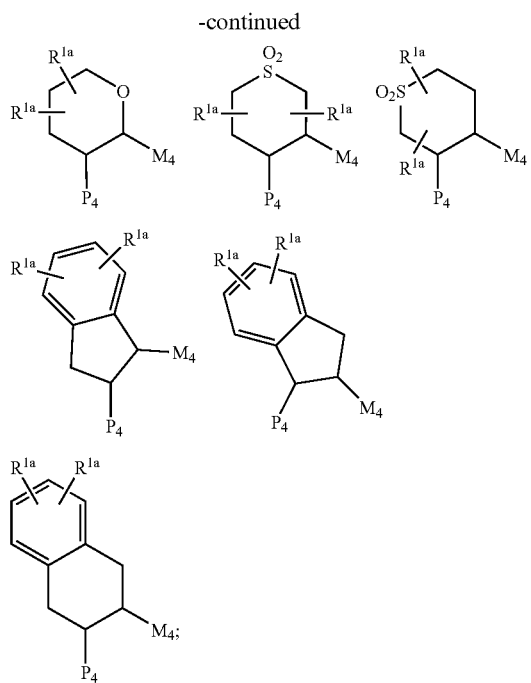

J is selected from O, S, NH, and $NR^{1a}$;

$P_4$ is -G;

$M_4$ is -Z-A-B;

G is selected from: 2-amido-4-methoxy-phenyl, 2-amido-phenyl, 2-aminomethyl-3-fluoro-phenyl, 2-aminomethyl-4-fluoro-phenyl, 2-aminomethyl-5-fluoro-phenyl, 2-aminomethyl-6-fluoro-phenyl, 2-aminomethyl-phenyl, 2-amino-pyrid-4-yl, 2-aminosulfonyl-4-methoxy-pheny, 2-aminosulfonyl-phenyl, 3-amido-phenyl, 3-amino-4-chloro-phenyl, 3-aminomethyl-phenyl, 3-chloro-phenyl, 4-chloro-phenyl, 4-methoxy-phenyl, 5-chloro-pyrid-2-yl, 5-chloro-thien-2-yl, 6-amino-5-chloro-pyrid-2-yl, 6-amino-pyrid-2-yl,

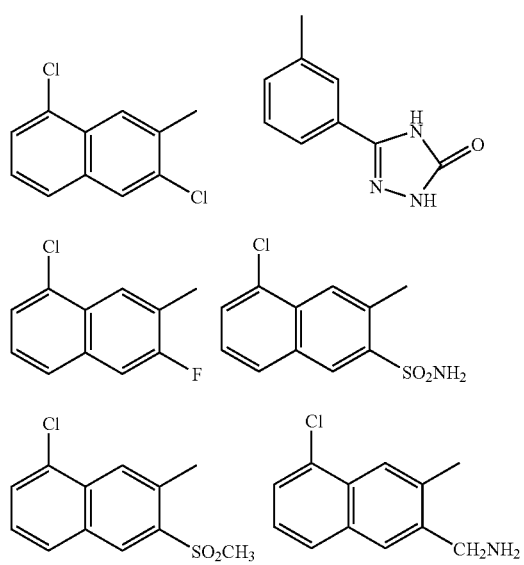

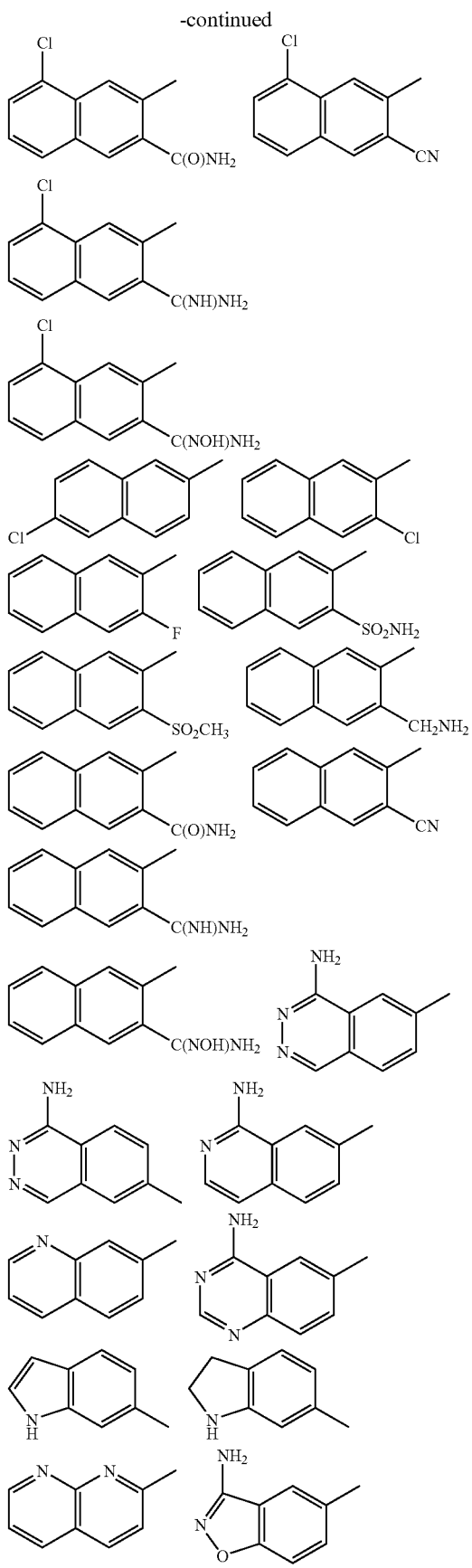

-continued

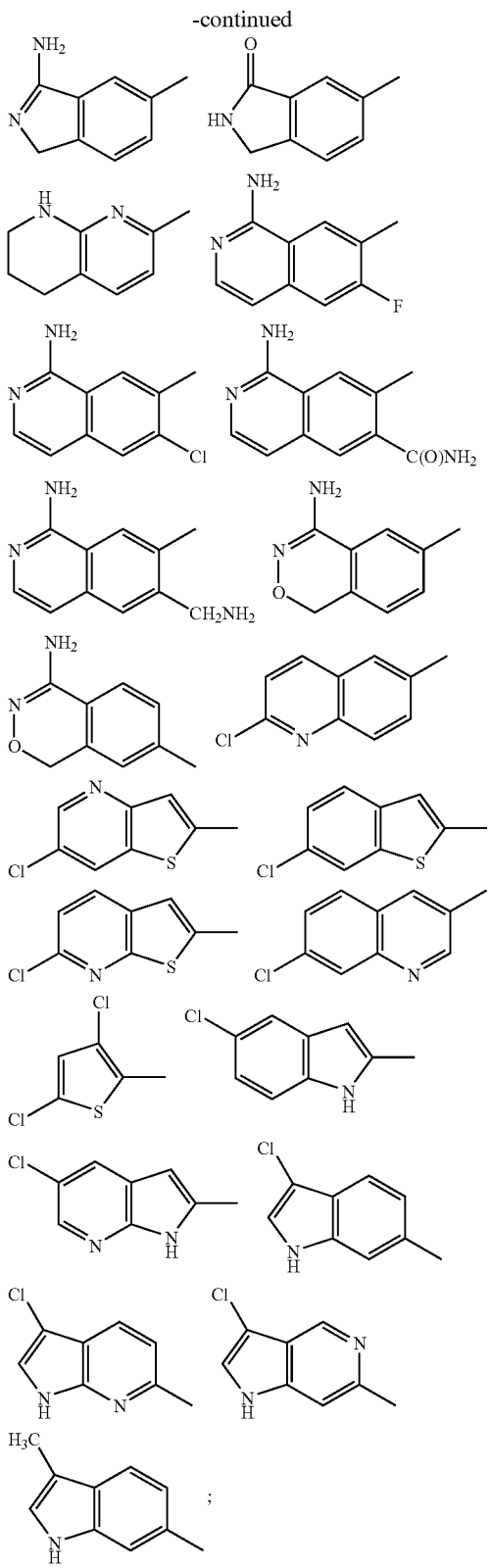

A is selected from the group: cyclohexyl, piperidinyl indolinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B, provided that Z and B are attached to different atoms on A and that the $R^{4a}$ shown is other than OH, is selected from:

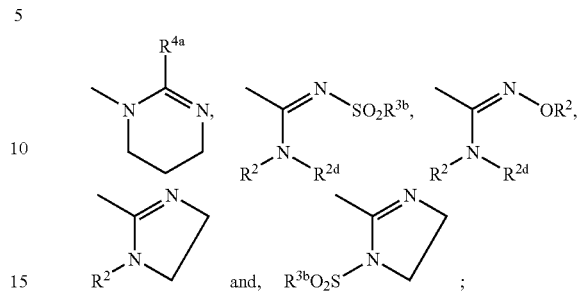

alternatively, $NR^2R^{2d}$ combines to form a ring selected from morpholine, piperazine, piperidine, and pyrrolidine;

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated, or unsaturated ring substituted with 0–1 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{2d}$, at each occurrence, is selected from H, $CH_3$, $CH_2CH_3$, $OCH_3$;

$R^{4a}$, at each occurrence, is selected from H, $OCH_3$, $CH_3$, $CH_2CH_3$, $CH_2CH_2CH_3$, $CH(CH_3)_2$, $NR^2R^{2a}$, $NR^2C(O)R^{2b}$, $NR^2SO_2R^5$, phenyl, 2-oxo-pyrrolidinyl, and 2-oxo-piperidinyl;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$; and $R^5$, at each occurrence, is selected from $CH_3$ and $CH_2CH_3$.

In a thirteenth aspect, the present invention provides a novel compound, wherein the compound is selected from:

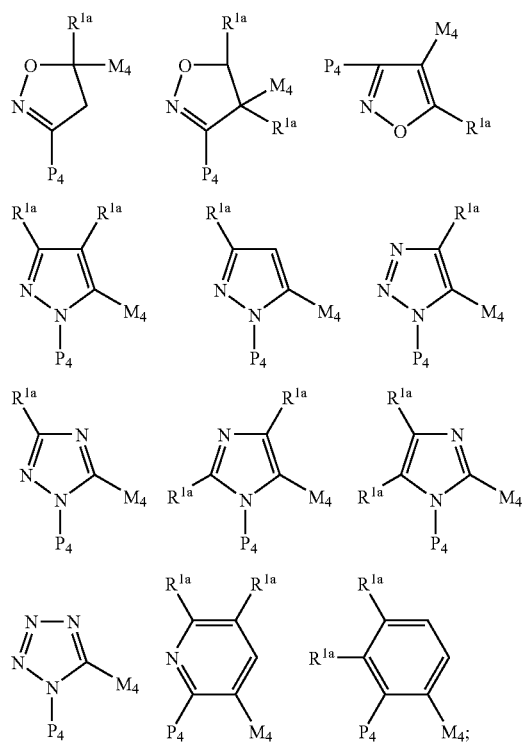
G is selected from:
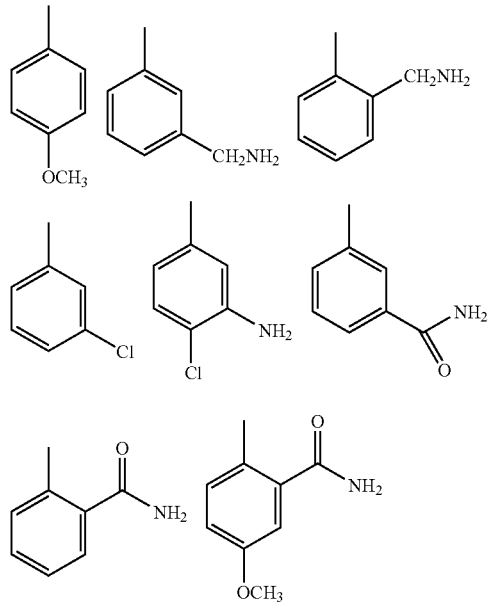
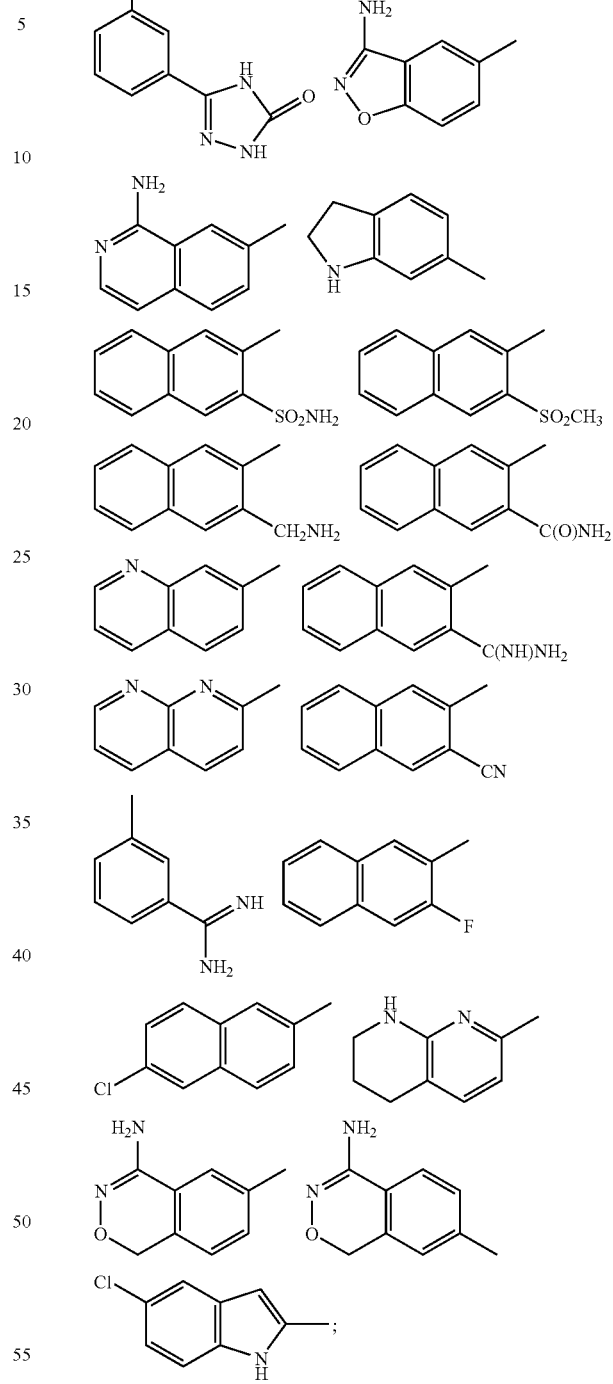
A is selected from:
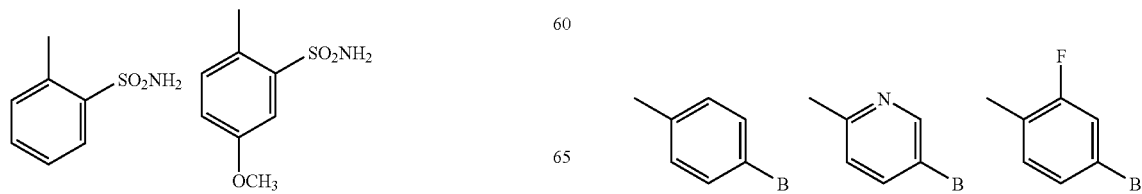

-continued
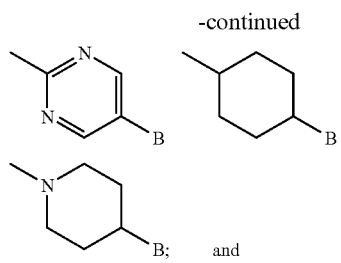
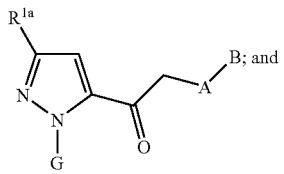
A-B is selected from:
B is selected from:
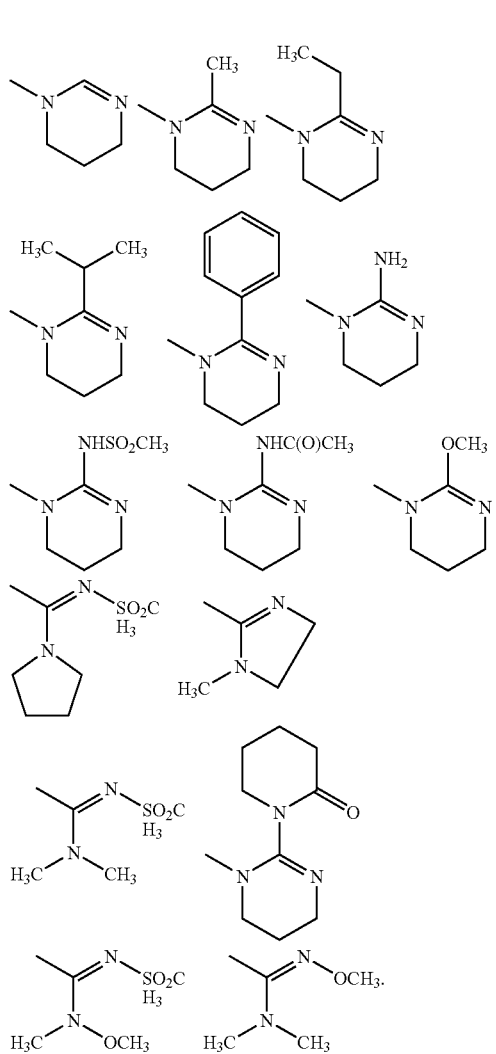
In a fourteenth aspect, the present invention provides a novel compound, wherein the compound is selected from:
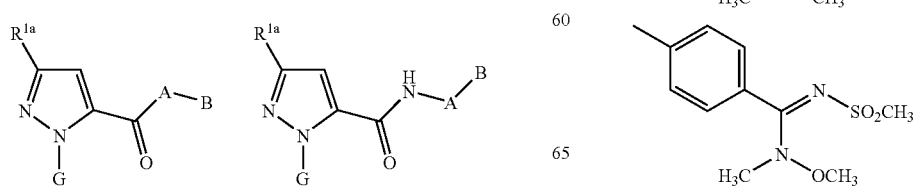
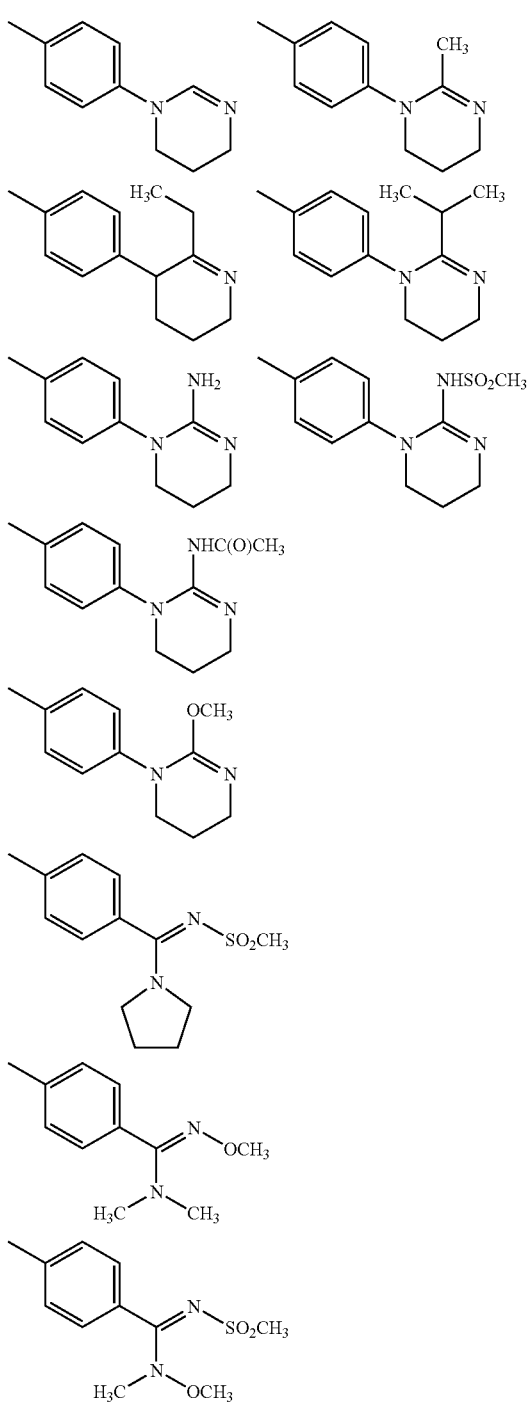

-continued

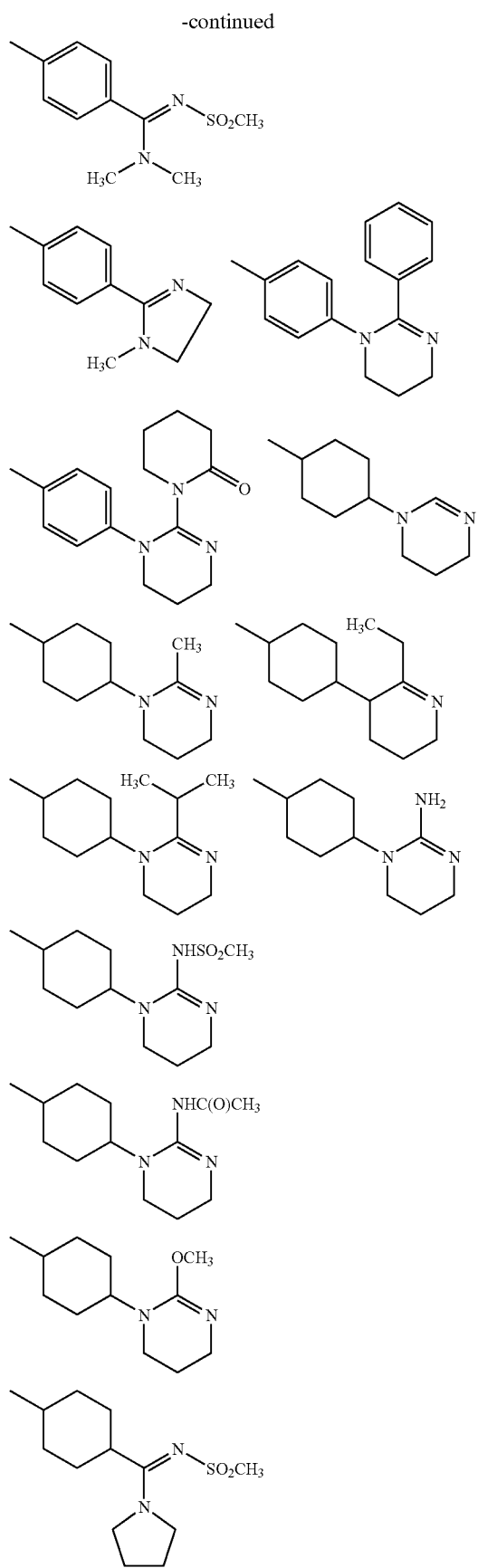
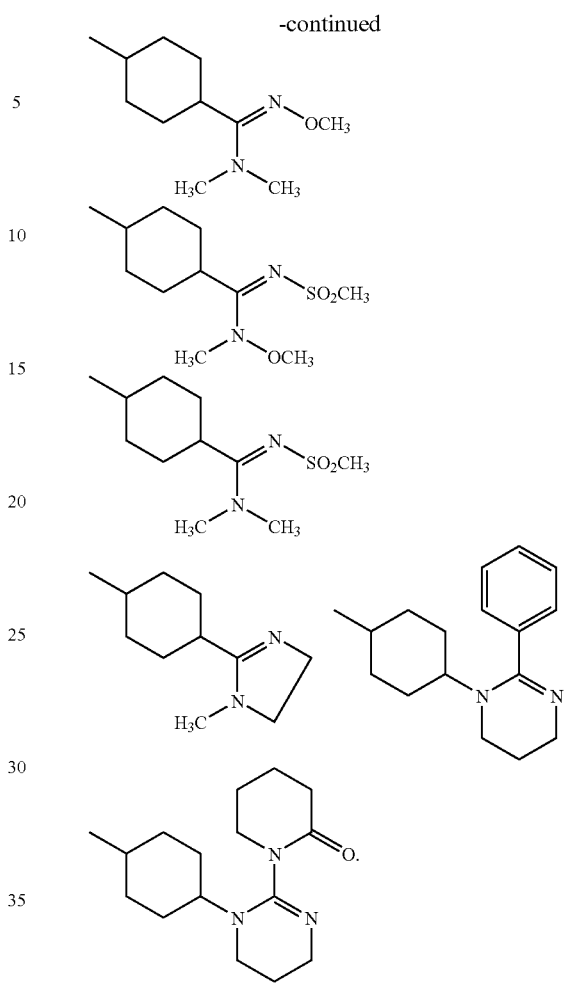

In a fifteenth aspect, the present invention provides a novel compound, wherein the compound is selected from the group:

5-chloro-N-(5-chloropyridin-2-yl)-2-[(4-{(Z)-(dimethylamino)[(methylsulfonyl)imino]methyl}benzoyl)amino]benzamide;

N-(5-chloropyridin-2-yl)-2-[(4-{(Z)-(dimethylamino)[(methylsulfonyl)imino]methyl}benzoyl)amino]-5-methoxybenzamide;

(1R, 2S)-3-chloro-1H-indole-6-carboxylic acid {2-[4-(N,N-dimethyl-N'-(methylsulfonyl)carbamimidoyl)-benzoylamino]-cyclohexyl}-amide;

pyrrolidine-1,2-dicarboxylic acid 1-[(4-chloro-phenyl)-amide]2-{[4-(methanesulfonylimino-pyrrolidin-1-yl-methyl)-phenyl]-amide};

(R)-N2-(4-(N,N-dimethyl-N'-(methylsulfonyl)carbamimidoyl)phenyl)-N1-(4-chlorophenyl)pyrrolidine-1,2-dicarboxamide;

(R)-pyrrolidine-1,2-dicarboxylic acid 1-[(3-chloro-1H-indol-6-yl)-amide]2-{[4-(dimethylamino-methanesulfonylimino-methyl)-phenyl]-amide};

(R)-pyrrolidine-1,2-dicarboxylic acid 1-[(5-chloro-thiophen-2-yl)-amide]2-{[4-(dimethylamino-methanesulfonylimino-methyl)-phenyl]-amide};

(R)-pyrrolidine-1,2-dicarboxylic acid 1-[(6-chloro-pyridin-3-yl)-amide]2-{[4-(dimethylamino -methanesulfonylimino-methyl)-phenyl]-amide};

(Z)-5-chloro-thiophene-2-carboxylic acid {3-[4-(methanesulfonylimino-pyrrolidin-1-yl-methyl)-phenyl]-2-oxo-oxazolidin-5-ylmethyl}-amide;

N-((3-(4-(N,N-dimethyl-N'-(methylsulfonyl)carbamimidoyl)phenyl)-2-oxooxazolidin-5-yl)methyl)-5-chlorothiophene-2-carboxamide;

N-((3-(4-(N,N-dimethyl-N'-(methylsulfonyl)carbamimidoyl)phenyl)-2-oxooxazolidin-5-yl)methyl)-3-chloro-1H-indole-5-carboxamide;

N-((3-(4-(N,N-dimethyl-N'-(methylsulfonyl)carbamimidoyl)phenyl)-2-oxooxazolidin-5-yl)methyl)-6-chloro-1H-indole-2-carboxamide;

N-((3-(4-(N,N-dimethyl-N'-(methylsulfonyl)carbamimidoyl)phenyl)-2-oxooxazolidin-5-yl)methyl)-4-chlorobenzamide;

N-((3-(4-(N,N-dimethyl-N'-(methylsulfonyl)carbamimidoyl)phenyl)-2-oxooxazolidin-5-yl)methyl)-3-chloro-1H-indole-6-carboxamide;

N-((3-(4-(N,N-dimethyl-N'-(methylsulfonyl)carbamimidoyl)phenyl)-2-oxooxazolidin-5-yl)methyl)-6-chloro-2-naphthamide;

N-((3-(4-(N,N-dimethyl-N'-(methylsulfonyl)carbamimidoyl)phenyl)-2-oxooxazolidin-5-yl)methyl)-6-chlorobenzo[b]thiophene-2-carboxamide;

N-((3-(4-(N,N-dimethyl-N'-(methylsulfonyl)carbamimidoyl)phenyl)-2-oxooxazolidin-5-yl)methyl)-5-chlorobenzo[b]thiophene-2-carboxamide;

N-((3-(4-(N,N-dimethyl-N'-(methylsulfonyl)carbamimidoyl)phenyl)-2-oxooxazolidin-5-yl)methyl)-5-chlorothieno[3,2-b]pyridine-2-carboxamide;

2-(3-amino-benzo[d]isoxazol-5-yl)-5-trifluoromethyl-2H-pyrazole-3-carboxylic acid [4-(methanesulfonylimino-pyrrolidin-1-yl-methyl)-phenyl]-amide;

2-(4-methoxy-phenyl)-5-trifluoromethyl-2H-pyrazole-3-carboxylic acid [4-(methanesulfonylimino-pyrrolidin-1-yl-methyl)-phenyl]-amide;

2-(3-aminomethyl-phenyl)-5-trifluoromethyl-2H-pyrazole-3-carboxylic acid [4-(methanesulfonylimino-pyrrolidin-1-yl-methyl)-phenyl]-amide; and 2-(3-aminomethyl-4-fluoro-phenyl)-5-trifluoromethyl-2H-pyrazole-3-carboxylic acid [4-(methanesulfonylimino-pyrrolidin-1-yl-methyl)-phenyl]-amide; or a pharmaceutically acceptable salt form thereof.

In a sixteenth aspect, the present invention provides a novel compound, wherein the compound is selected from the group:

N-hydroxy-4-[1-(4-methoxy-phenyl)-7-oxo-3-trifluoromethyl-1,4,5,7-tetrahydro-pyrazolo[3,4-c]pyridin-6-yl]-N-methyl-benzamidine;

N-hydroxy-4-[1-(4-methoxy-phenyl)-7-oxo-3-trifluoromethyl-1,4,5,7-tetrahydro-pyrazolo[3,4-c]pyridin-6-yl]-benzamidine;

N-methoxy-4-[1-(4-methoxy-phenyl)-7-oxo-3-trifluoromethyl-1,4,5,7-tetrahydro-pyrazolo[3,4-c]pyridin-6-yl]-benzamidine;

N-methoxy-4-[1-(4-methoxy-phenyl)-7-oxo-3-trifluoromethyl-1,4,5,7-tetrahydro-pyrazolo[3,4-c]pyridin-6-yl]-N-methyl-benzamidine;

4-[1-(4-methoxy-phenyl)-7-oxo-3-trifluoromethyl-1,4,5,7-tetrahydro-pyrazolo[3,4-c]pyridin-6-yl]-N-methyl-benzamidine;

4-[1-(4-methoxy-phenyl)-7-oxo-3-trifluoromethyl-1,4,5,7-tetrahydro-pyrazolo[3,4-c]pyridin-6-yl]-N,N-dimethyl-benzamidine;

6-[4-(imino-pyrrolidin-1-yl-methyl)-phenyl]-1-(4-methoxy-phenyl)-3-trifluoromethyl-1,4,5,6-tetrahydro-pyrazolo[3,4-c]pyridin-7-one;

6-[4-(imino-piperidin-1-yl-methyl)-phenyl]-1-(4-methoxy-phenyl)-3-trifluoromethyl-1,4,5,6-tetrahydro-pyrazolo[3,4-c]pyridin-7-one;

6-[4-(imino-morpholin-4-yl-methyl)-phenyl]-1-(4-methoxy-phenyl)-3-trifluoromethyl-1,4,5,6-tetrahydro-pyrazolo[3,4-c]pyridin-7-one;

4-[1-(4-methoxy-phenyl)-7-oxo-3-trifluoromethyl-1,4,5,7-tetrahydro-pyrazolo[3,4-c]pyridin-6-yl]-benzamidine;

N-ethyl-4-[1-(4-methoxy-phenyl)-7-oxo-3-trifluoromethyl-1,4,5,7-tetrahydro-pyrazolo[3,4-c]pyridin-6-yl]-N-methyl-benzamidine;

N,N-diethyl-4-[1-(4-methoxy-phenyl)-7-oxo-3-trifluoromethyl-1,4,5,7-tetrahydro-pyrazolo[3,4-c]pyridin-6-yl]-benzamidine;

N-benzyl-4-[1-(4-methoxy-phenyl)-7-oxo-3-trifluoromethyl-1,4,5,7-tetrahydro-pyrazolo[3,4-c]pyridin-6-yl]-N-methyl-benzamidine;

6-[4-(N,N-dimethyl-carbamimidoyl)-phenyl]-1-(4-methoxy-phenyl)-7-oxo-4,5,6,7-tetrahydro-1H-pyrazolo[3,4-c]pyridine-3-carboxylic acid amide;

6-[4-(imino-pyrrolidin-1-yl-methyl)-phenyl]-1-(4-methoxy-phenyl)-7-oxo-4,5,6,7-tetrahydro-1H-pyrazolo[3,4-c]pyridine-3-carboxylic acid amide;

4-[1-(4-methoxy-phenyl)-3-methyl-7-oxo-1,4,5,7-tetrahydro-pyrazolo[3,4-c]pyridin-6-yl]-N,N-dimethyl-benzamidine;

6-[4-(imino-pyrrolidin-1-yl-methyl)-phenyl]-1-(4-methoxy-phenyl)-3-methyl-1,4,5,6-tetrahydro-pyrazolo[3,4-c]pyridin-7-one;

4-[3-cyano-1-(4-methoxy-phenyl)-7-oxo-1,4,5,7-tetrahydro-pyrazolo[3,4-c]pyridin-6-yl]-N,N-dimethyl-benzamidine;

6-[4-(imino-pyrrolidin-1-yl-methyl)-phenyl]-1-(4-methoxy-phenyl)-7-oxo-4,5,6,7-tetrahydro-1H-pyrazolo[3,4-c]pyridine-3-carbonitrile;

6-[4-(imino-pyrrolidin-1-yl-methyl)-phenyl]-3-isopropenyl-1-(4-methoxy-phenyl)-1,4,5,6-tetrahydro-pyrazolo[3,4-c]pyridin-7-one;

4-[3-isopropenyl-1-(4-methoxy-phenyl)-7-oxo-1,4,5,7-tetrahydro-pyrazolo[3,4-c]pyridin-6-yl]-N,N-dimethyl-benzamidine;

4-[1-(3-aminomethyl-phenyl)-7-oxo-3-trifluoromethyl-1,4,5,7-tetrahydro-pyrazolo[3,4-c]pyridin-6-yl]-N,N-dimethyl-benzamidine;

4-[1-(3-aminomethyl-4-fluoro-phenyl)-7-oxo-3-trifluoromethyl-1,4,5,7-tetrahydro-pyrazolo[3,4-c]pyridin-6-yl]-N,N-dimethyl-benzamidine;

2-(3-amino-benzo[d]isoxazol-5-yl)-5-trifluoromethyl-2H-pyrazole-3-carboxylic acid [4-(N,N-dimethyl-carbamimidoyl)-phenyl]-amide;

2-(3-amino-benzo[d]isoxazol-5-yl)-5-trifluoromethyl-2H-pyrazole-3-carboxylic acid [4-(imino-pyrrolidin-1-yl-methyl)-phenyl]-amide;

2-(3-amino-benzo[d]isoxazol-5-yl)-5-methyl-2H-pyrazole-3-carboxylic acid [4-(N,N-dimethyl-carbamimidoyl)-phenyl]-amide;

2-(3-amino-benzo[d]isoxazol-5-yl)-5-methyl-2H-pyrazole-3-carboxylic acid [4-(imino-pyrrolidin-1-yl-methyl)-phenyl]-amide;

6-[4-(imino-isoxazolidin-2-yl-methyl)-phenyl]-1-(4-methoxy-phenyl)-3-methyl-1,4,5,6-tetrahydro-pyrazolo[3,4-c]pyridin-7-one; and 6-[4-(imino-isoxazolidin-2-yl-methyl)-phenyl]-1-(4-methoxy-phenyl)-3-trifluoromethyl-1,4,5,6-tetrahydro-pyrazolo[3,4-c]pyridin-7-one; or a pharmaceutically acceptable salt form thereof.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof, and,
(c) a package insert stating that the pharmaceutical composition can be used for the treatment of a thromboembolic disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt form thereof; and,
(c) a package insert stating that the pharmaceutical composition can be used in combination with a second therapeutic agent to treat a thromboembolic disorder.

In another preferred embodiment, the present invention provides a novel article of manufacture, further comprising:
(d) a second container;

wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2 v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocycle" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and S(O)$_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, S(O)₂H, or S(O)H group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

All references cited herein are hereby incorporated in their entirety herein by reference.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. Also, the functionality present on the molecule should be consistent with the transformations proposed. This will sometimes require a judgment to modify the order of the synthetic steps or to select one particular process scheme over another in order to obtain a desired compound of the invention.

Another major consideration in the planning of any synthetic route in this field is the judicious choice of the protecting group. An authoritative account describing the many alternatives to the trained practitioner is Greene and Wuts (*Protective Groups In Organic Synthesis*, Wiley and Sons, 1991).

The synthesis of compounds of the present invention involving intermediate A-B can be accomplished via standard methods known to those skilled in the art. A general route that involves this type of methodology is outlined in Scheme 1. Construction of compounds with general structure G-G₁-M-Z-A-B can be performed in two directions: 1) from G (or G-G₁) to G-G₁-M then to G-G₁-M-Z-A-B or 2) From A-B (or Z-A-B) to M-Z-A-B then to G-G₁-M-Z-A-B. During the synthesis of these compounds, it may be useful or necessary to use protecting groups to prevent cross-reaction during the coupling conditions. Examples of suitable protecting groups and their uses are described in "The Peptides: analysis, Synthesis, Biology", Academic Press, Vol.3 (Groii et al, Eds., 1981). Functional group transformations and coupling reactions that can be used to prepare compounds of the present invention are described in "Advanced Organic Chemistry: Reaction, Mechanism, and Structure" (March et al, 4th Ed.) and "Comprehensive Organic Transformations" (Larock, 2nd Ed.).

Scheme 1

1) P—M—M₁ ≡ G—G₁—M—Z—A—B

Formula I

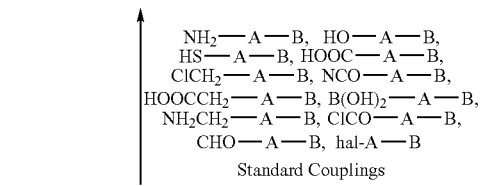

Standard Couplings

G—G₁—M—(acid chloride, acid, sulfonylchloride, amino, isocyanate, alkylhalide, aldehyde, alcohol, sulfonamide, etc)

Formula A or

2) P—M—M₁ ≡ G—G₁—M—Z—A—B

Formula I

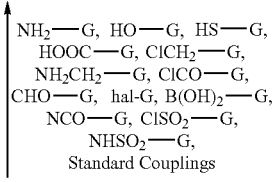

Standard Couplings

B—A—Z—M—(acid chloride, acid, sulfonylchloride, amino, isocyanate, alkylhalide, aldehyde, alcohol, sulfonamide, etc)

Formula B

Non-linker compounds such as G-M-A-B can be obtained by first preparing the G-M portion, followed by coupling to the A-B group. As an example, for pyrazoles this involves the cyclization of an appropriate hydrazine with a dione (Scheme 2). Alternatively, the G-M group can be prepared by a [3+2] cycloaddition of an appropriately substituted chlorohydrazone with 3-morpholin-4-yl-5,6-dihydro-1H-pyridin-2-one. The resultant pyrazolopiperidinone-NH intermediate can then be condensed with a variety of I-A-B substituents under standard conditions known to those in the art to afford compounds of the present invention.

Scheme 2

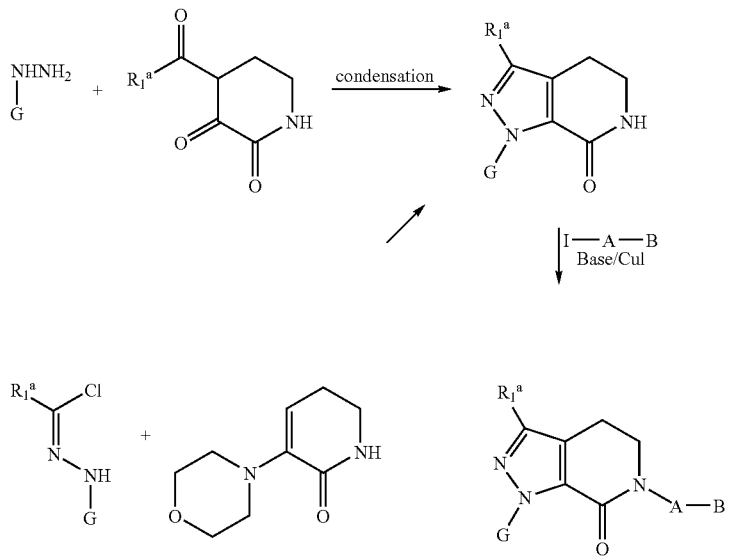

Once the preparation of key intermediates bearing a p-nitro- and or a p-cyano-phenyl substituent have been established, elaboration to compounds of the present invention can be carried out as outlined below or via other methods known to those skilled in the art.

Cyclic phenyl amidino compounds of the present invention can be prepared following the general procedure outlined in Scheme 3. It should be noted that this methodology could also be successfully applied to a P-M-Z-A-NH$_2$ intermediate to afford compounds of the present invention.

The diamino intermediate from Scheme 3 can also be cyclized with carbonyldiimidazole followed by treatment with POCl$_3$ or an alkylating agent or converted to its triflate. These are versatile intermediates to those skilled in the art for further manipulations to compounds of the present invention, as shown in Scheme 4. This methodology could be successfully applied to a P-M-Z-A-NH$_2$ intermediate as well to afford compounds of the present invention.

Scheme 3

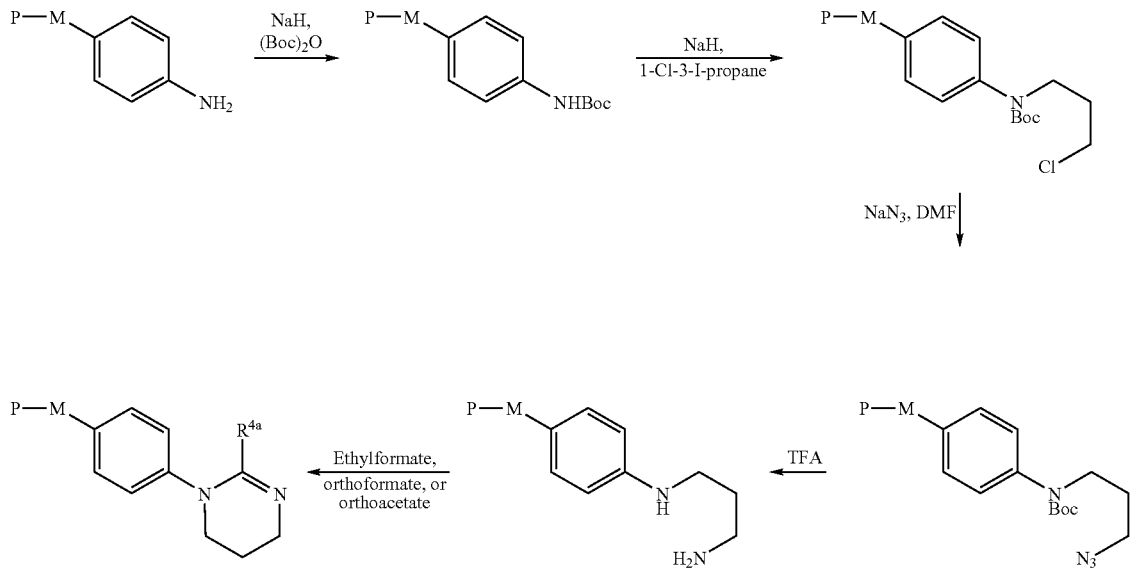

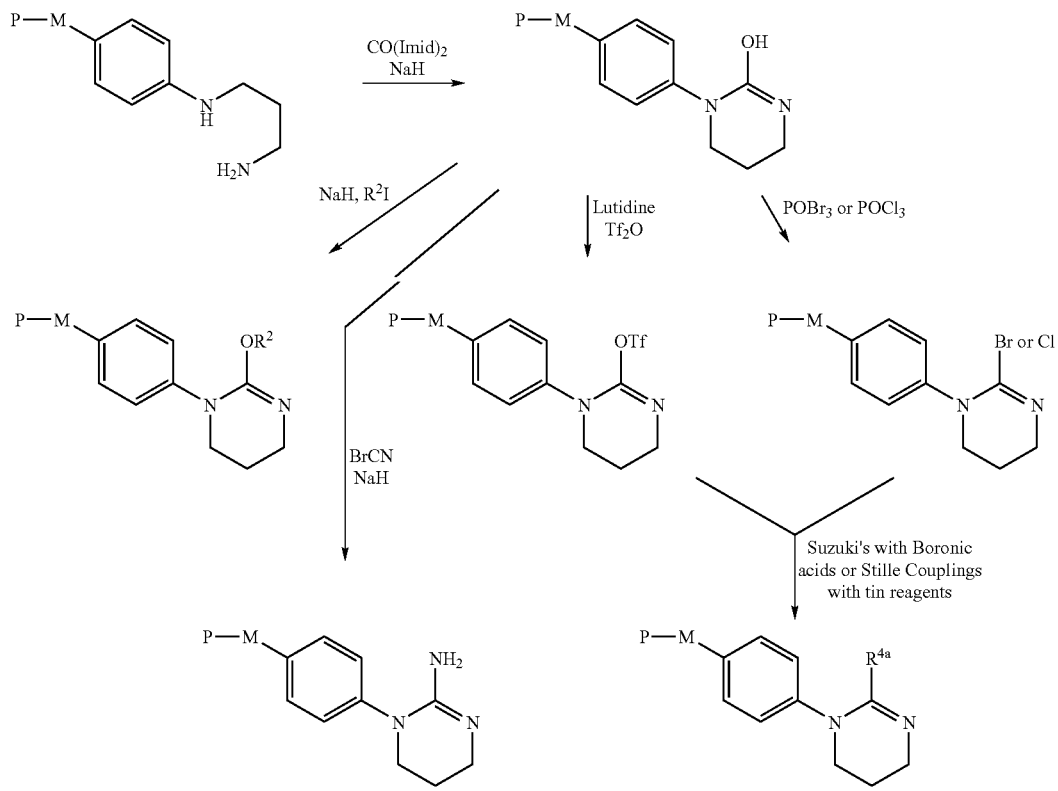
Scheme 4
The guanidino derivative from Scheme 4 can be converted to a number of compounds of the present invention by known techniques, as outlined in Scheme 5. This methodology could also be successfully applied to the P-M-Z-A-NH$_2$ intermediate to afford compounds of the present invention.
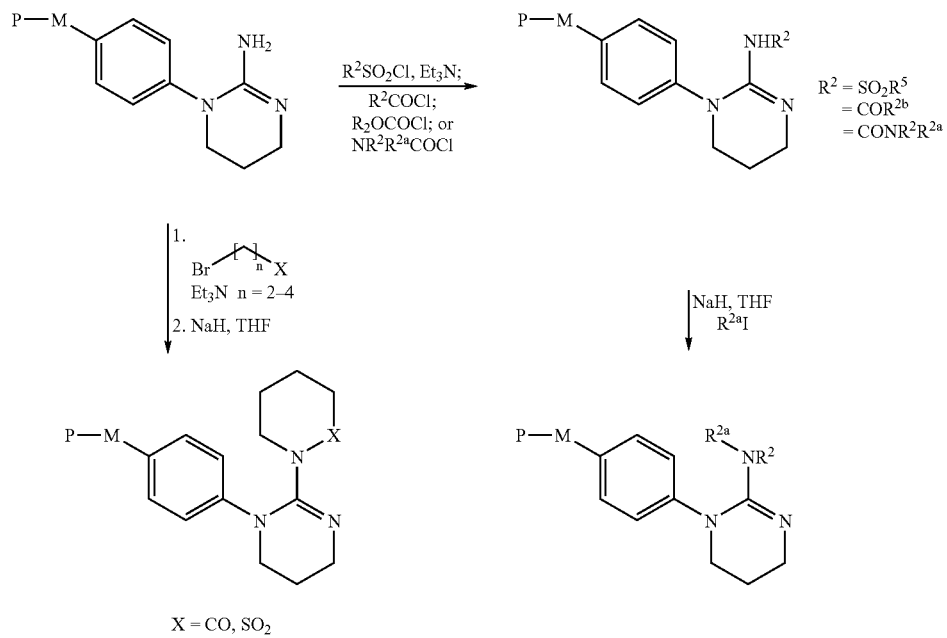
Scheme 5

The methodologies of Scheme 5 can be used to obtain additional compounds of the present invention as shown in Scheme 6.

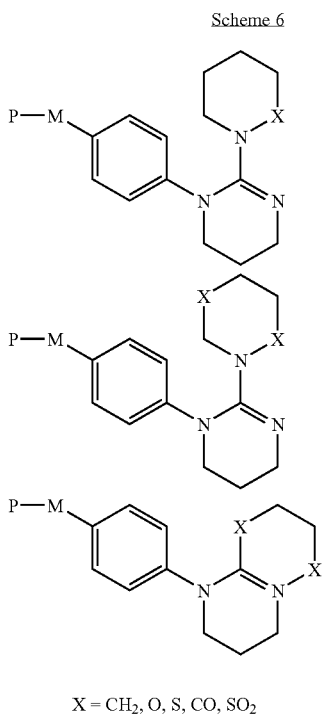

X = $CH_2$, O, S, CO, $SO_2$

Phenylamidino-sulfonyl and -carbonyl compounds of the present invention can be obtained from the readily available amidino-compounds shown in Scheme 7.

the art can prepare various sulfonyl, carbonylamidino, or suitably protected cyclic amidino intermediates and couple them via known techniques to the various templates described herein to afford compounds of the present invention.

Schemes 3–7 describe how to make and couple the present A-B moieties to prepare compounds of the present invention. The remaining portions of the compounds of the present invention, $G-G_1-P-M-Z$, $G-G_1-M-P-Z$, $G-G_1-P-M$, $G-G_1-M-P$, $G-G_1-M-Z$, and $G-G_1-M$, can be prepared using methods known to those of ordinary skill in the art. All of the following patents and publications are incorporated herein by reference. For compounds wherein ring P is absent and ring M is a 5-, 6-, or 7-membered ring, one of ordinary skill in the art can look to U.S. Pat. Nos. 5,939,418, 5,925,635, 6,057,342, 6,187,797, 6,020,357, 6,060,491, 5,998,424, 6,191,159, WO98/57951, WO99/32454, WO00/039108, WO00/059902, WO01/32628, WO01/005785, WO02/00651, WO02/102380, and WO02/00647 for starting materials and intermediates to which the present B and/or A-B groups can be coupled. For compounds wherein ring P is fused to ring M (i.e., a bicyclic moiety), one of ordinary skill in the art can look to WO00/39131, WO02/94197, U.S. Ser. Nos. 10/104,467, 10/105,477 and WO02/00655 for starting materials and intermediates to which the present B and/or A-B groups can be coupled.

For compounds wherein G is a ring substituted with a basic moiety, one of ordinary skill in the art can look to U.S. Pat. Nos. 5,939,418, 5,925,635, 6,057,342, 6,187,797, 6,020,357, 6,060,491, 6,191,159, WO98/57951, WO99/32454 WO00/059902, WO01/32628, WO00/39131, WO02/00651, WO02/102380, WO02/94197, U.S. Ser. Nos. 10/104,467, and 10/105,477 for starting materials and intermediates to which the present B and/or A-B groups can be coupled. For compounds wherein G is a ring substituted with a non-basic group, one of ordinary skill in the art can look to

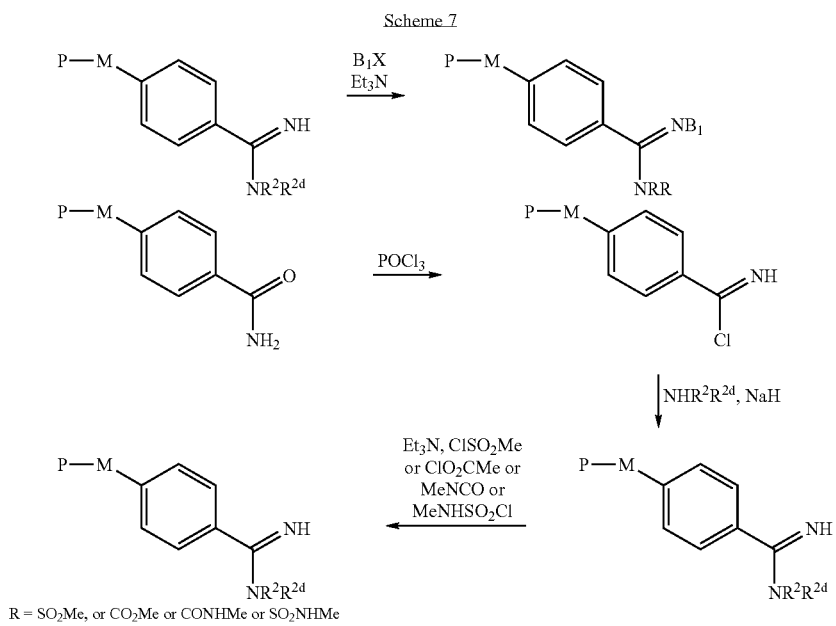

The chemistry described above can be implemented at any stage of the synthetic process. Those knowledgeable in U.S. Pat. No. 5,998,424, WO00/39131, WO00/059902, WO01/32628, WO02/00651, WO02/102380, WO02/94197, U.S. Ser. Nos. 10/104,467, and 10/105,477 for starting materials and intermediates which the present B and/or A-B groups can be coupled. For compounds wherein G is a bicyclic moiety, one of ordinary skill in the art can look to WO98/57951 WO00/039108, WO00/39131, WO02/00651, WO02/102380, WO02/94197, U.S. Ser. Nos. 10/104,467, and 10/105,477 for starting materials and intermediates to form the present G-G$_1$-P-M-Z, G-G$_1$-M-P-Z, G-G$_1$-P-M-Z-A, and/or G-G$_1$-M-P-Z-A groups to which the present B and/or A-B groups can be coupled. For compounds wherein A is an indoline or similar bicycle, one of ordinary skill in the art can look to WO01/005785 for starting materials and intermediates to which the present B group can be coupled or from which the present A-B groups can be formed. Scheme 8 illustrates some of the numerous pyrrole intermediates that can be used to prepare compounds of the present invention (RZ is the point of attachment for Z-A-B and can be H, a protecting group, Z, Z-A, A, or a group modifiable to Z or Z-A). These intermediates are described in the above-noted patents and publications.

-continued

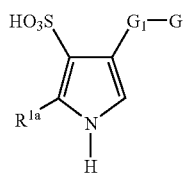

Scheme 9 illustrates some of the numerous imidazole, triazole, and tetrazole intermediates that can be used to prepare compounds of the present invention. These intermediates are described in the above-noted patents and publications. In Scheme 9, V is nitro, amino, thio, hydroxy, sulfonic acid, sulfonic ester, sulfonyl chloride, ester, acid, or halide. U is aldehyde, ester, acid, amide, amino, thiol, hydroxy, sulfonic acid, sulfonic ester, sulfonyl chloride, or methylene halide.

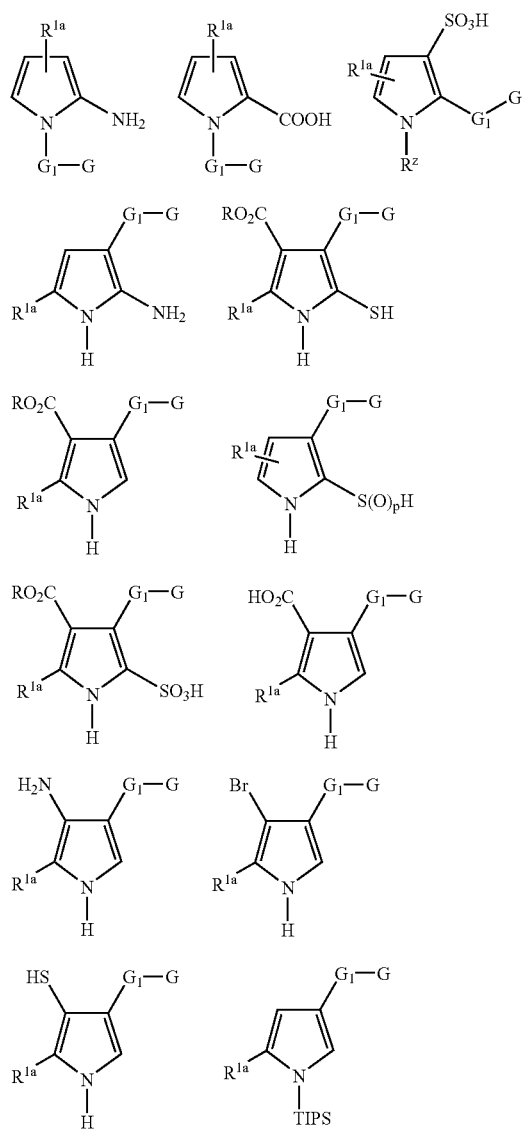

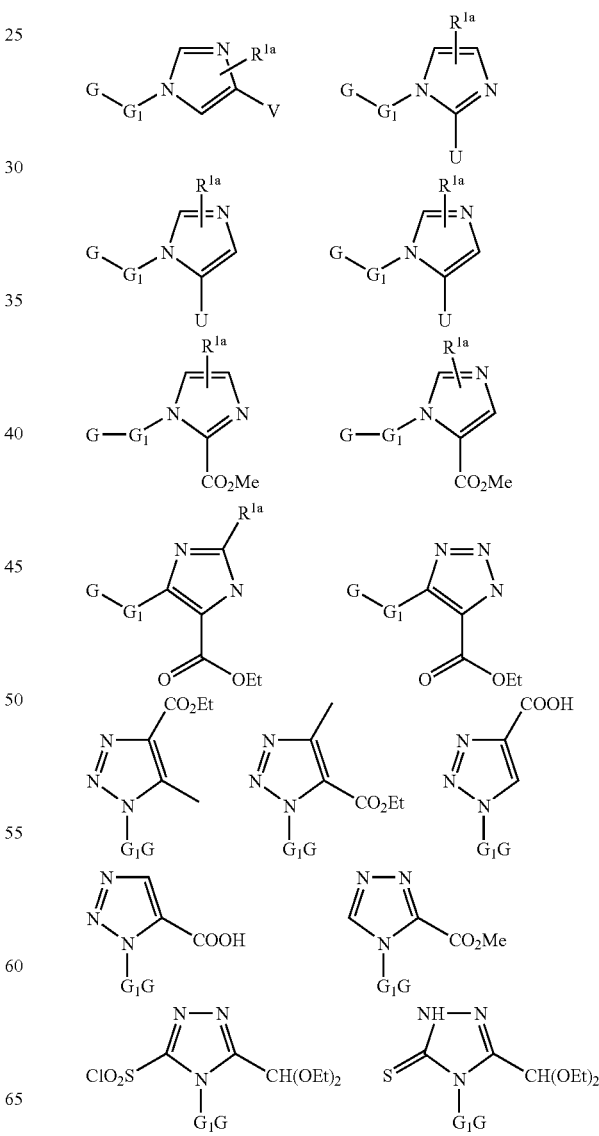

Scheme 9

-continued

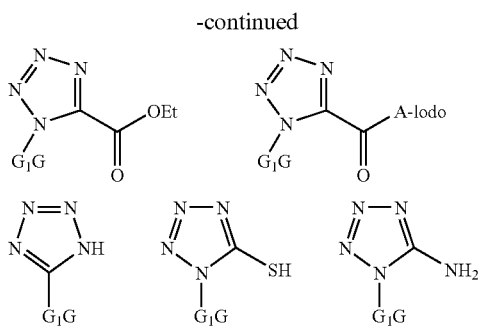

Scheme 10 shows some of the numerous pyrazole intermediates that can be used to prepare compounds of the present invention. These intermediates are described in the above-noted patents and publications.

Scheme 10

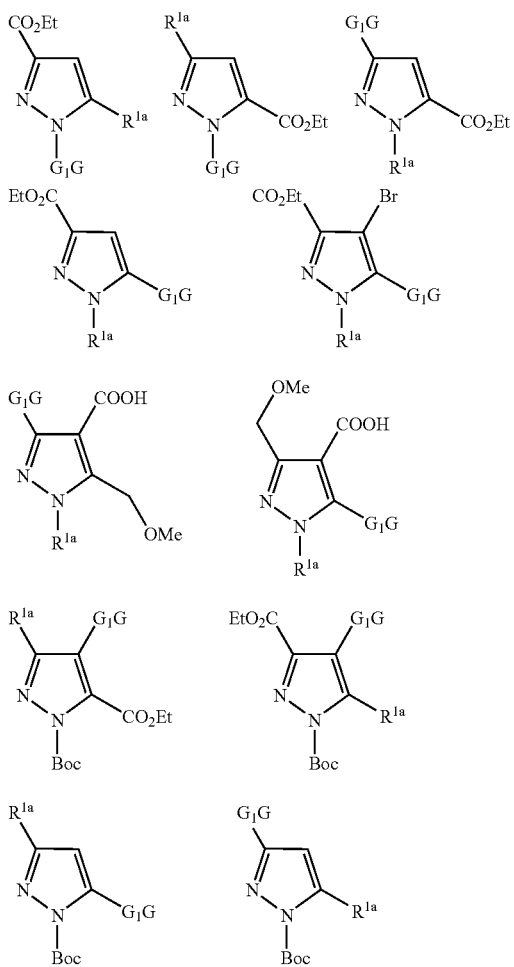

Scheme 11 depicts some of the numerous oxazole, thiazole, isoxazole, oxadiazole, and thiadiazole intermediates that can be used to prepare compounds of the present invention. These intermediates are described in the above-noted patents and publications. In Scheme 11, V is nitro, amino, ester, or acid.

Scheme 11

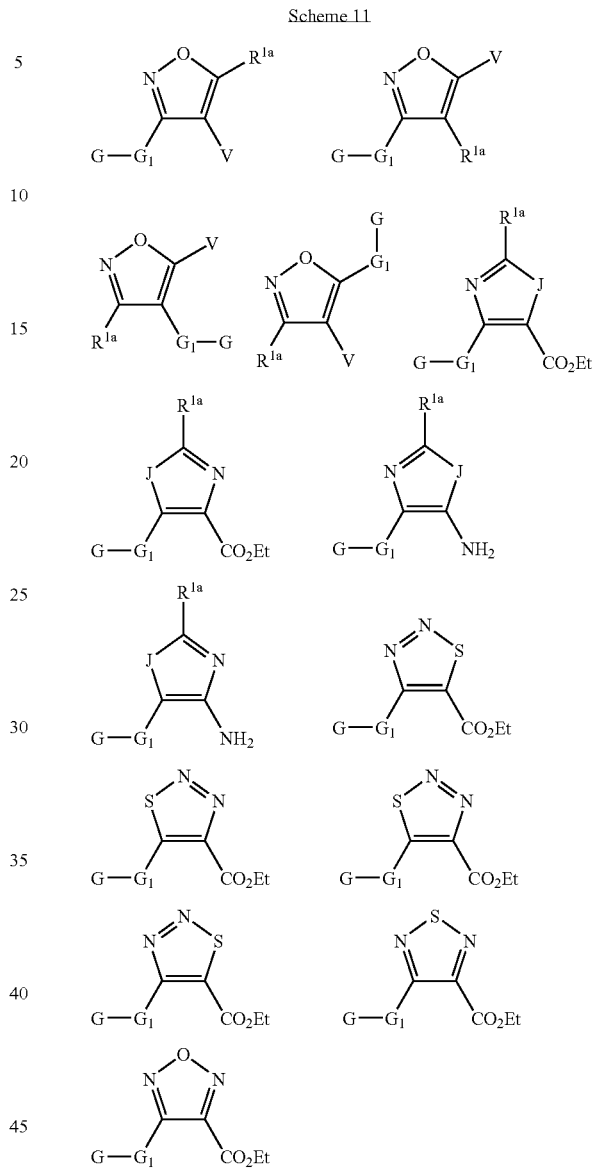

Scheme 12 illustrates two intermediates useful for making a compound of the present invention wherein ring P is fused to ring M. Scheme 12 also illustrates a number of bicyclic compounds that can be made from these intermediates or derivatives thereof. These intermediates and their modification are described in the above-noted patents and publications.

Scheme 12

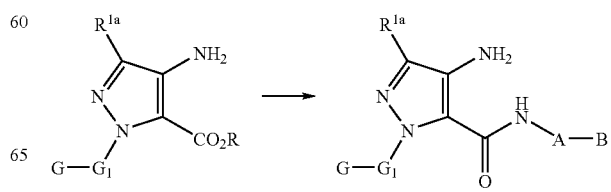

-continued

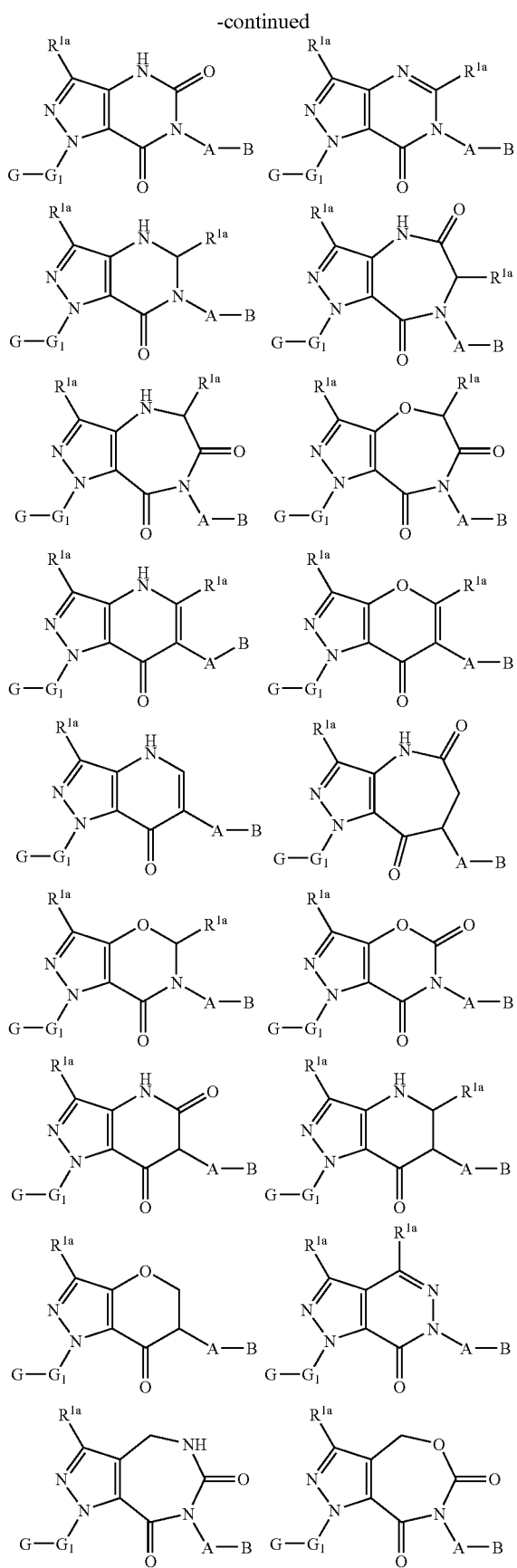

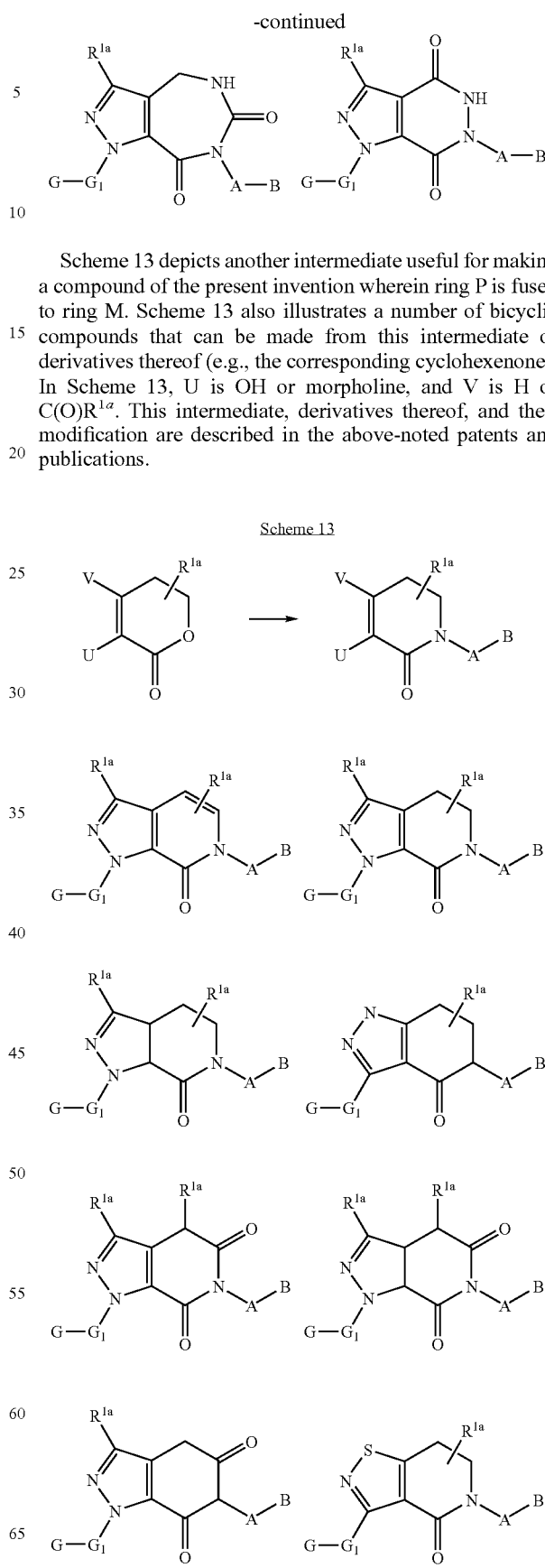

Scheme 13 depicts another intermediate useful for making a compound of the present invention wherein ring P is fused to ring M. Scheme 13 also illustrates a number of bicyclic compounds that can be made from this intermediate or derivatives thereof (e.g., the corresponding cyclohexenone). In Scheme 13, U is OH or morpholine, and V is H or $C(O)R^{1a}$. This intermediate, derivatives thereof, and their modification are described in the above-noted patents and publications.

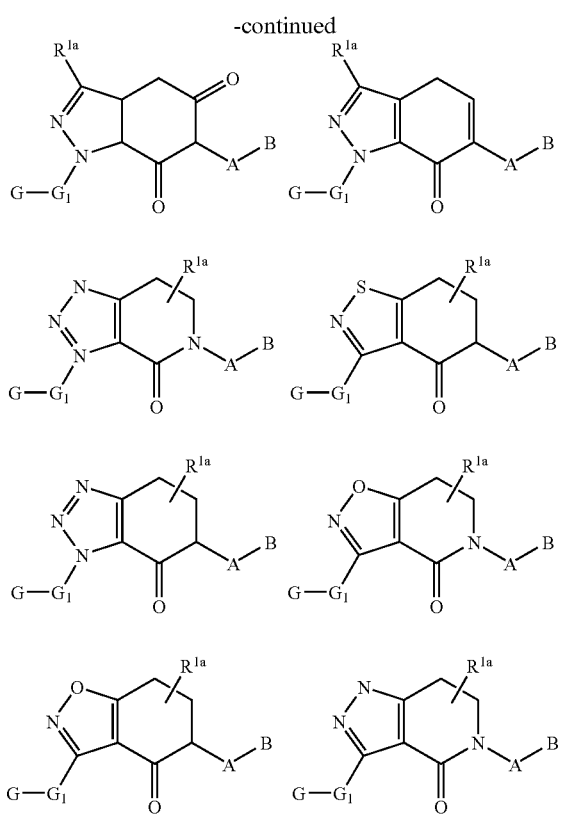

Scheme 14 shows another intermediate useful for making a compound of the present invention wherein ring P is fused to ring M and a number of bicyclic compounds that can be made from this intermediate or derivatives thereof. This intermediate, derivatives thereof, and their modification are described in the above-noted patents and publications.

Scheme 15 illustrates a number of other bicyclic rings that are part of the present invention, i.e., rings P-M. Scheme 15 also describes a method of converting the shown rings to compounds of the present invention. This method is also applicable to heterobicyclics not shown.

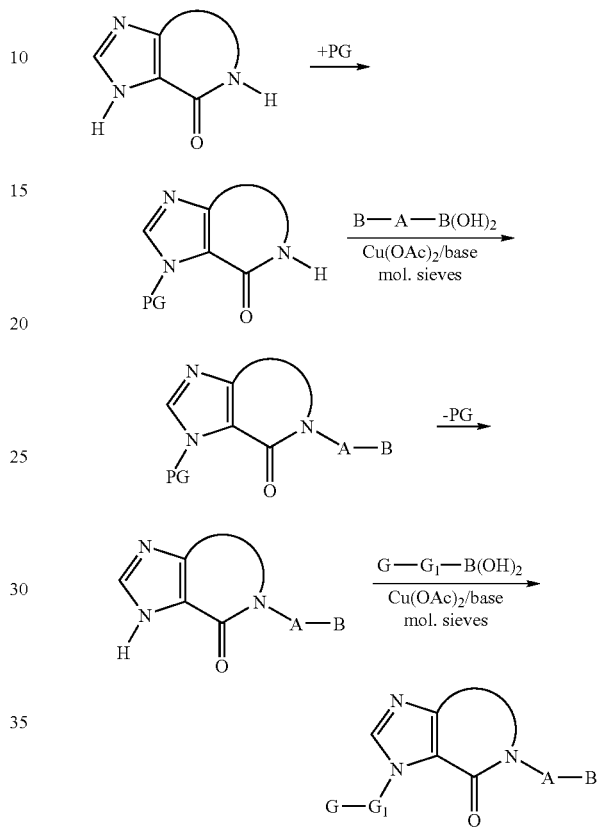

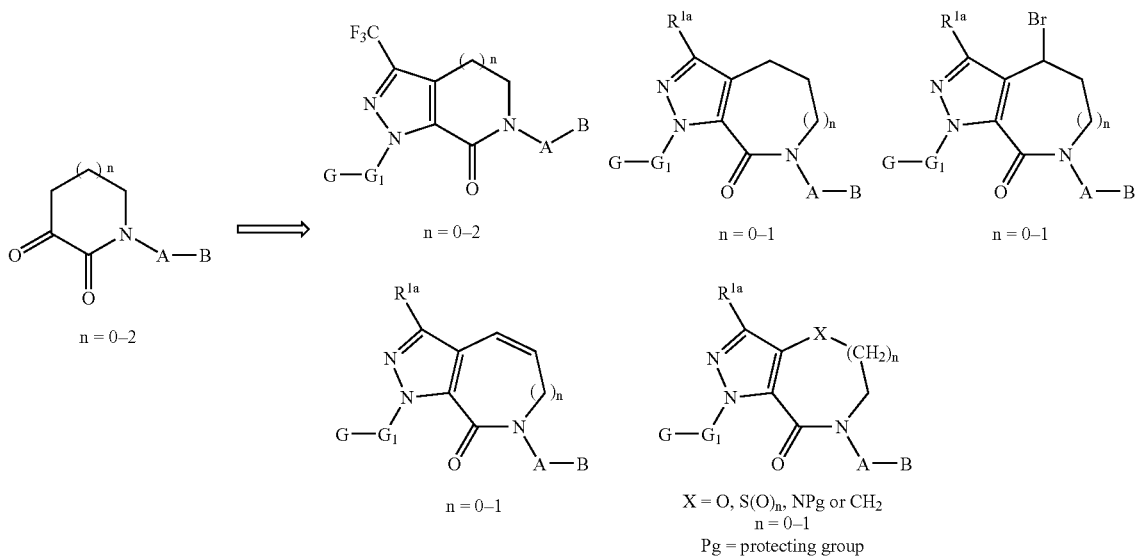

-continued
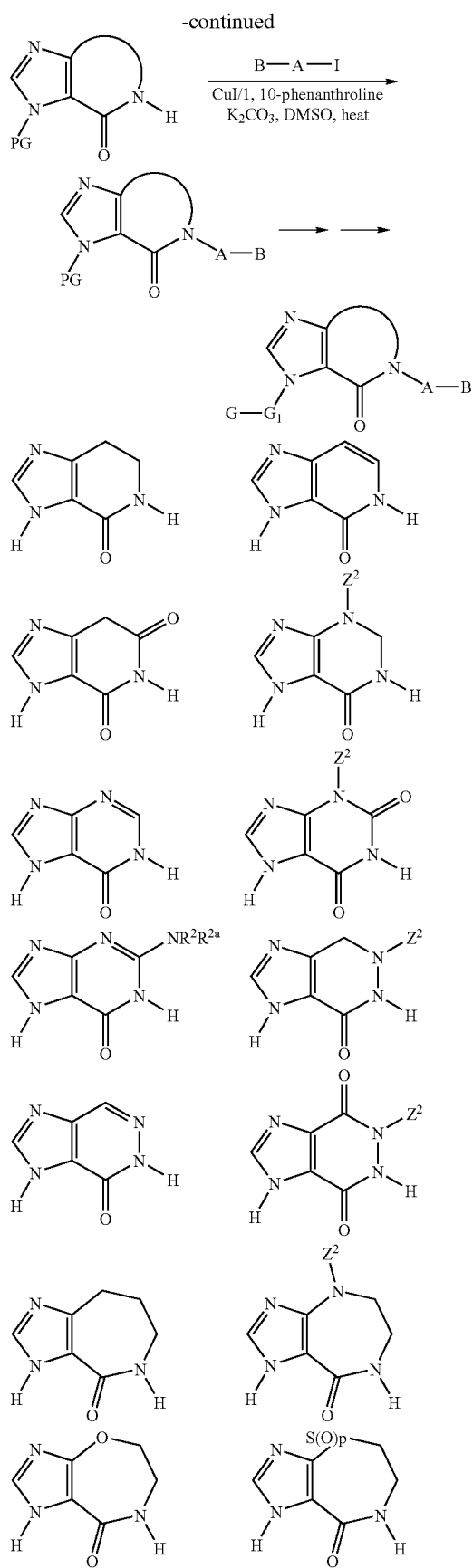
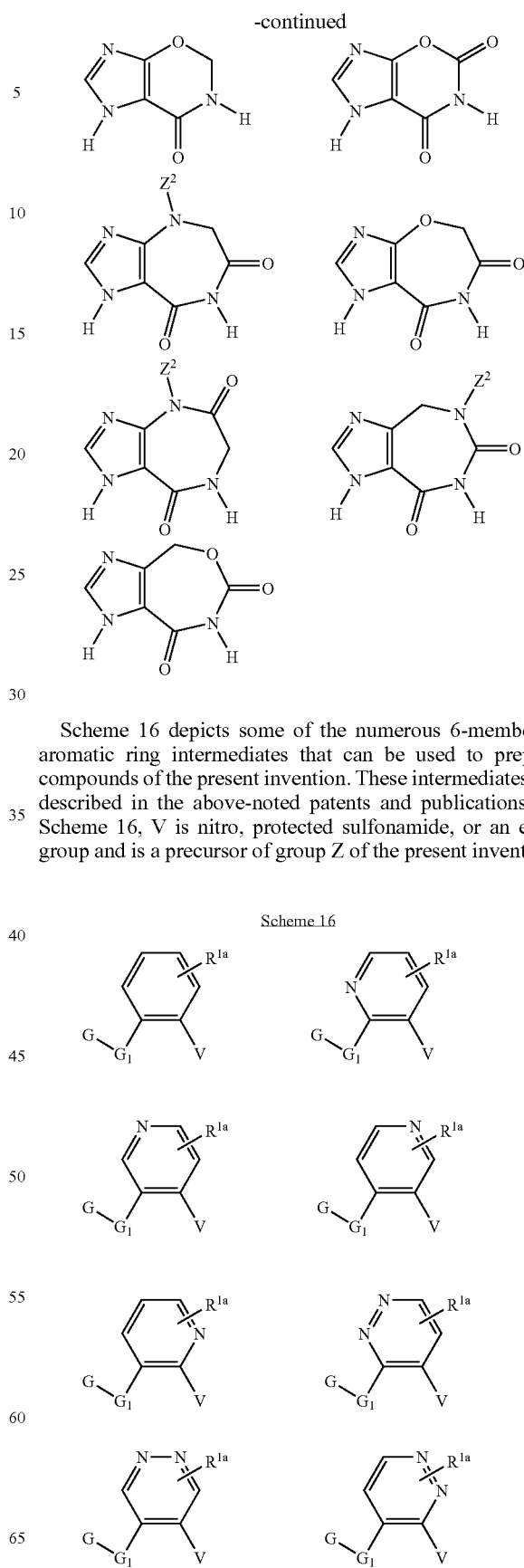
Scheme 16 depicts some of the numerous 6-membered aromatic ring intermediates that can be used to prepare compounds of the present invention. These intermediates are described in the above-noted patents and publications. In Scheme 16, V is nitro, protected sulfonamide, or an ester group and is a precursor of group Z of the present invention.
Scheme 16
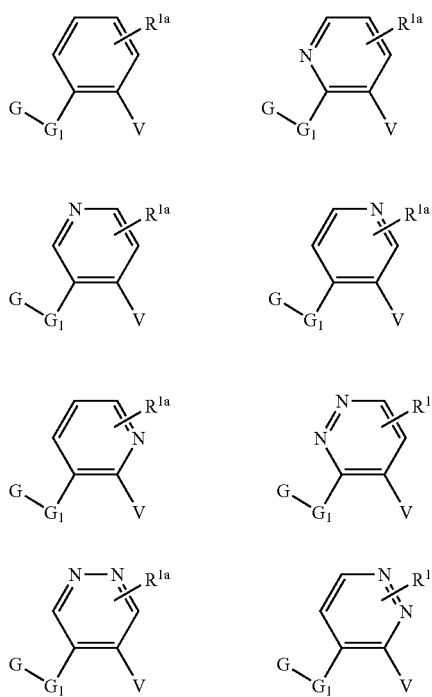

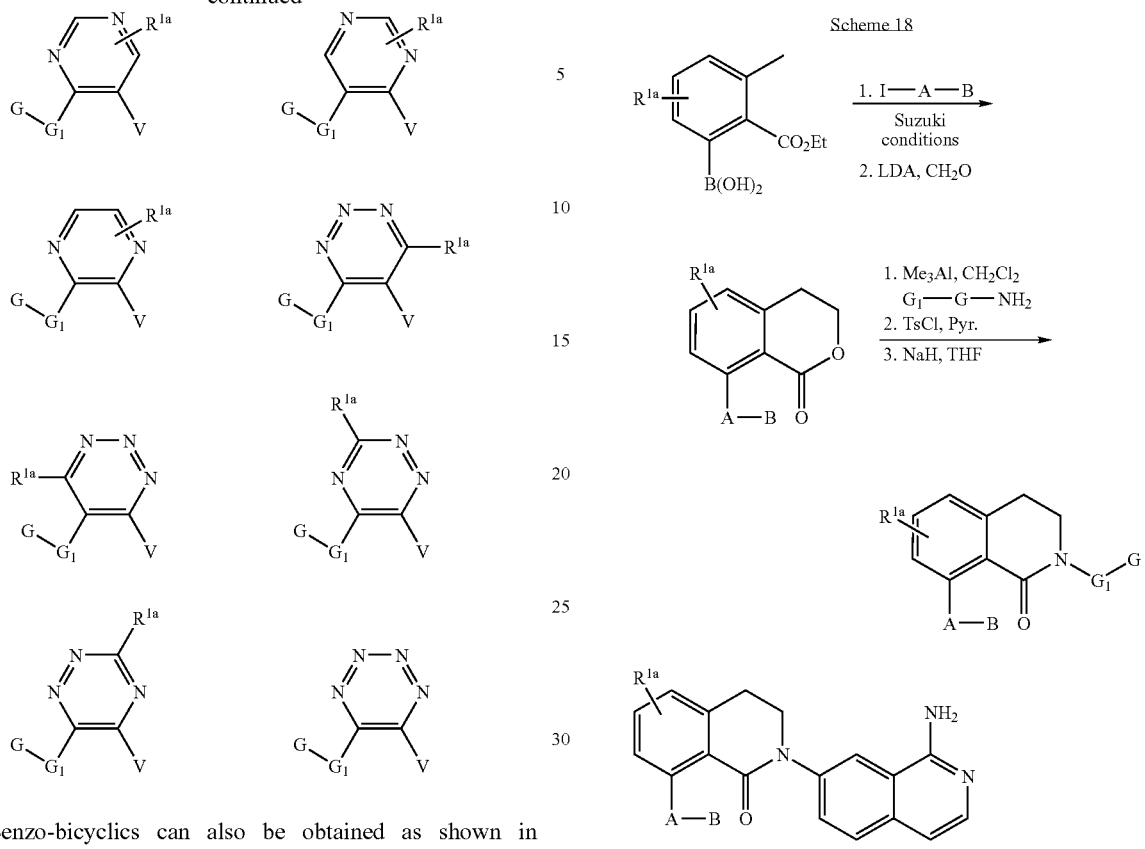
Benzo-bicyclics can also be obtained as shown in Schemes 17 and 18.
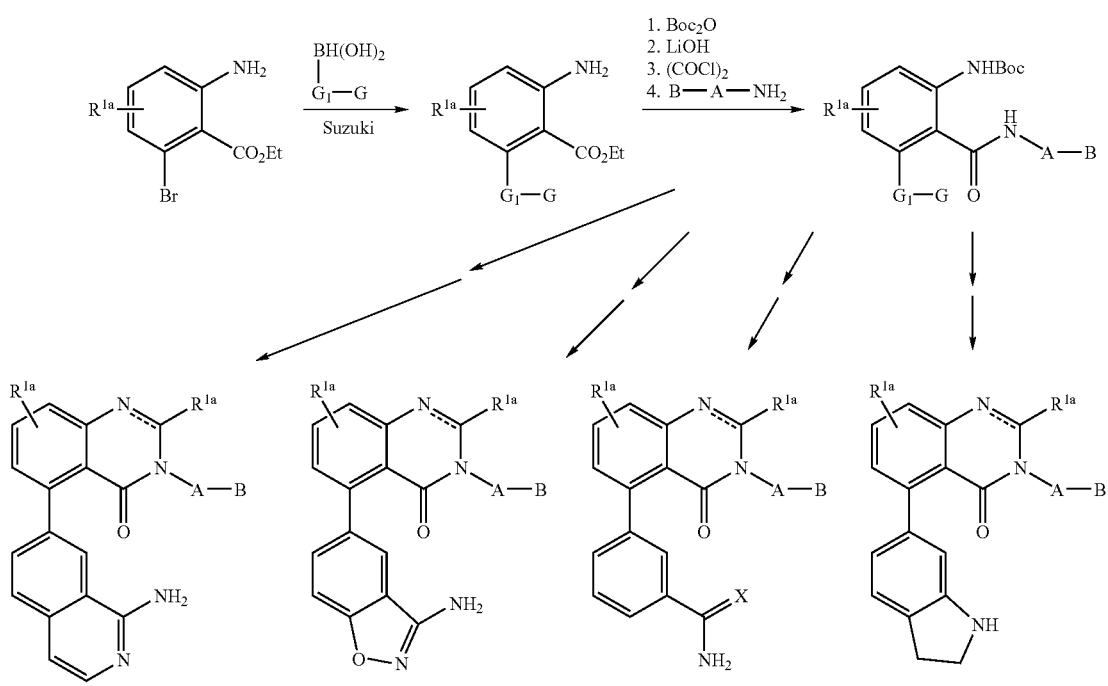

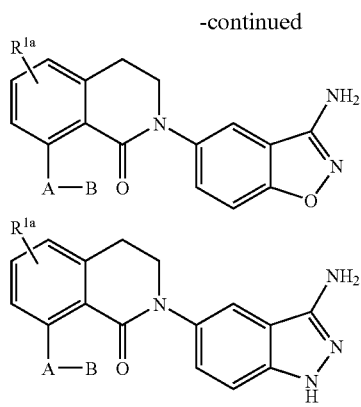

Compounds of the present invention wherein ring P is absent and ring M is a six-membered ring can be obtained as shown in Scheme 19. These types of compounds can be obtained from commercially available anthranilic acids or their anthranilates. Anthranilic acids or their nitro precursors can be coupled with a suitable B-A-NH$_2$ in presence of a base such as triethyl amine, pyridine, or DMAP. Subsequent coupling with an appropriate acid chloride, aniline, or aminopyridyl should afford compounds of the present invention.

Scheme 19

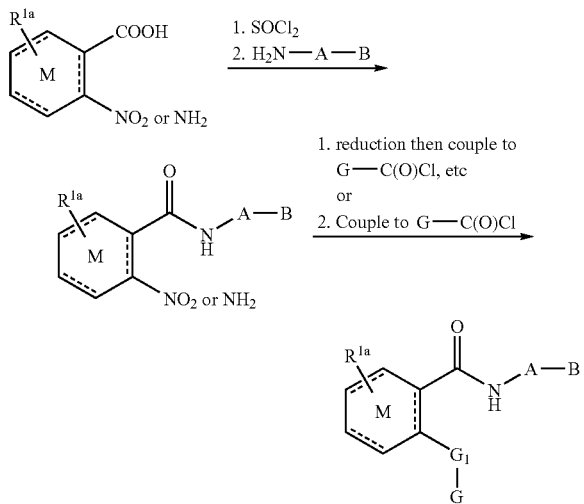

In an analogous fashion the anthranilates can be coupled with a suitable amine, aniline, or aminopyrimidyl to afford the corresponding benzamide. The benzamides can then be coupled with an appropriate B-A-V (wherein V is a acid chloride derivative, an alkyl halide, or a sulfonyl chloride) to afford additional compounds of the present invention (see Scheme 20).

Scheme 20

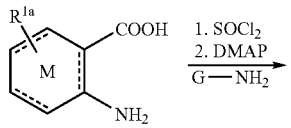

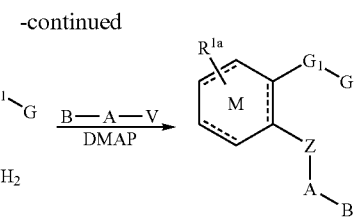

Commercially available ring M derivatives bearing a nitro and amino functionality can also be derivatized as shown below to afford bisamide analogs. In this case, coupling of the aniline with B-A-V (wherein V is an acid chloride, a sulfonyl chloride, or an alkylhalide) affords an intermediate that can be subjected to treatment with an appropriate G-U (wherein U is either an acid chloride or an alkyl halide) in the presence of a suitable base such as DMAP. It should be noted that the order of addition of B-A-V and G-U can be reversed to obtain other compounds of the present invention (see Scheme 21).

Scheme 21

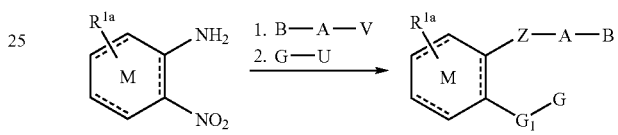

The syntheses shown above could be modified to use coupling intermediates such as Iodo-A-V, wherein V is an acid chloride, amino, alkylhalide, or sulfonyl chloride. These in turn could be coupled to a G-U group. The iodo-intermediate could then be subjected to Ullman or Buchwald coupling as described previously to afford compounds of the present invention. The iodo-intermediate could also be converted to an amine via standard Buchwald conditions to afford the corresponding anilino intermediate. This in turn could be coupled as previously described to afford compounds of the present invention.

The syntheses of the bisamide compounds shown in Schemes 19–21 can also be applied to the syntheses of compounds wherein ring M is a 5-membered heterocycle. The bisamides can also be further converted into bicyclic pyrimidin-4-ones under acidic conditions as shown in Scheme 22.

Scheme 22

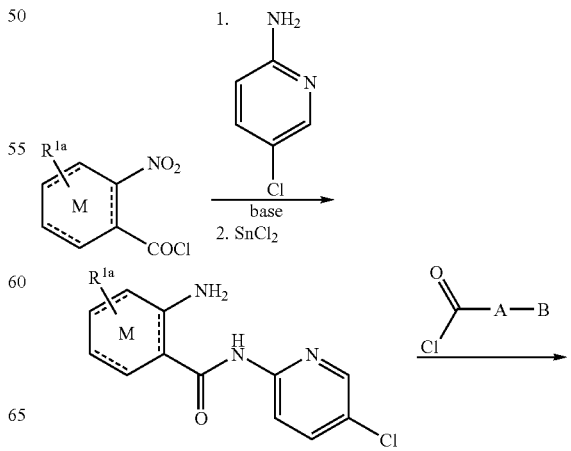

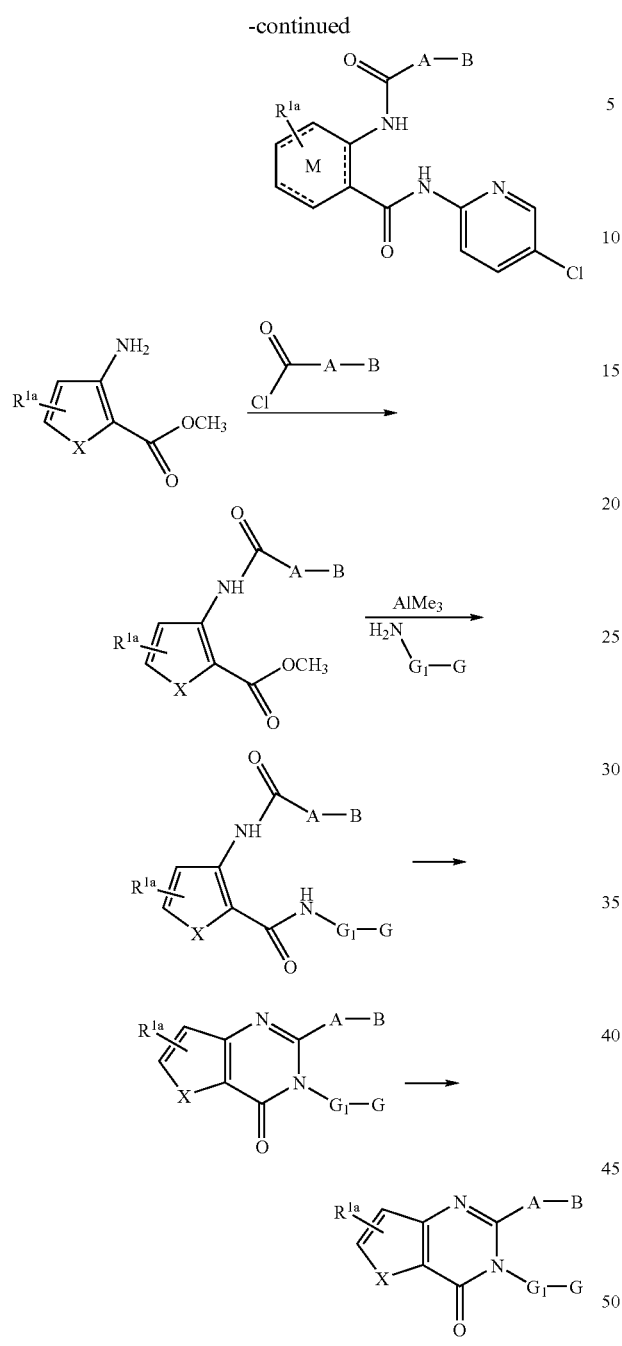
Scheme 23 illustrates the synthesis of piperidine derivatives by using the methods described above and known to those skilled in the art.
Scheme 23
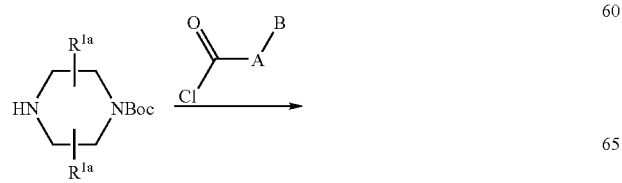
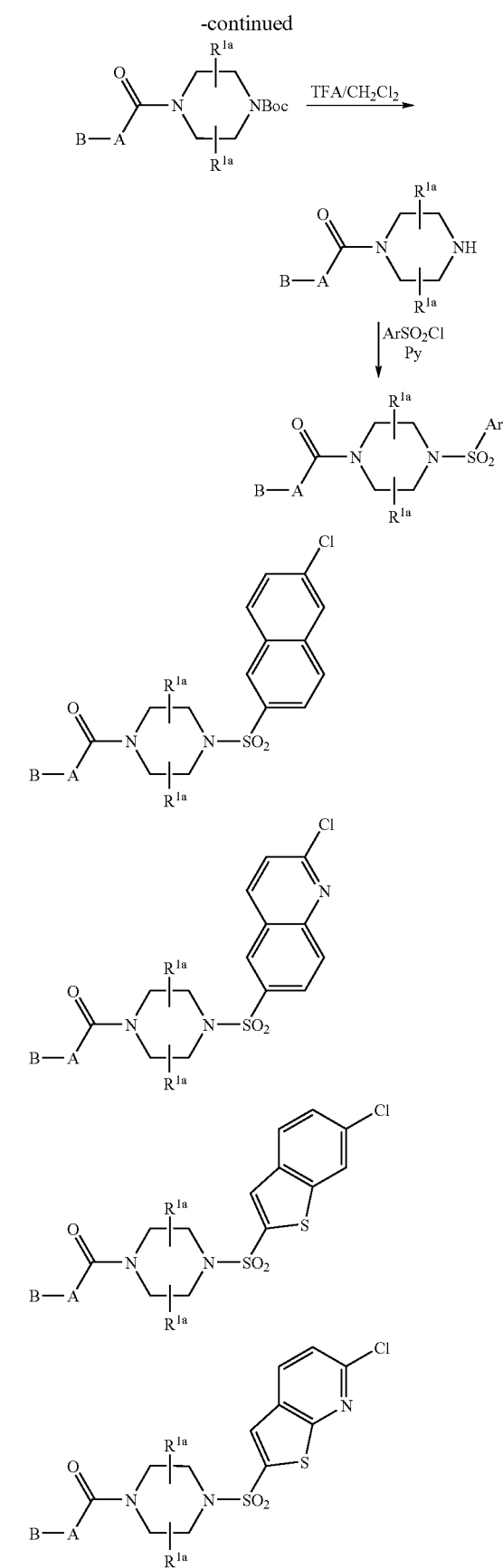

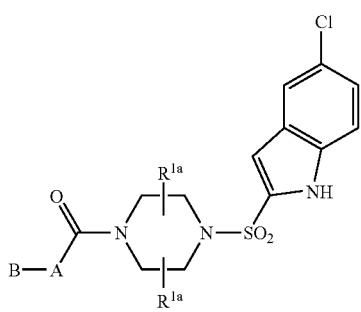

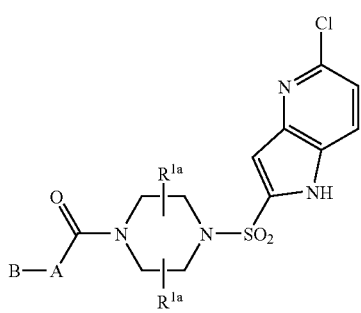

Compounds of the present invention wherein ring P is absent and ring M is a 3–10 membered non-aromatic carbocycle or heterocycle can also be prepared by using the methods described previously and known to those skilled in the art. Scheme 24 illustrates a number of non-aromatic M rings that are considered to be part of the present invention. Scheme 24 also describes general methods of converting these rings to compounds of the present invention. As one of ordinary skill in the art would recognize, this method would be applicable to other non-aromatic rings not shown.

Scheme 24

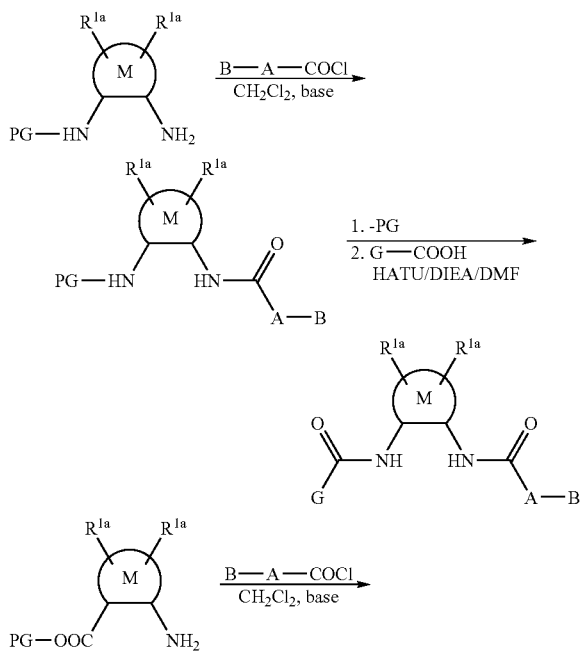

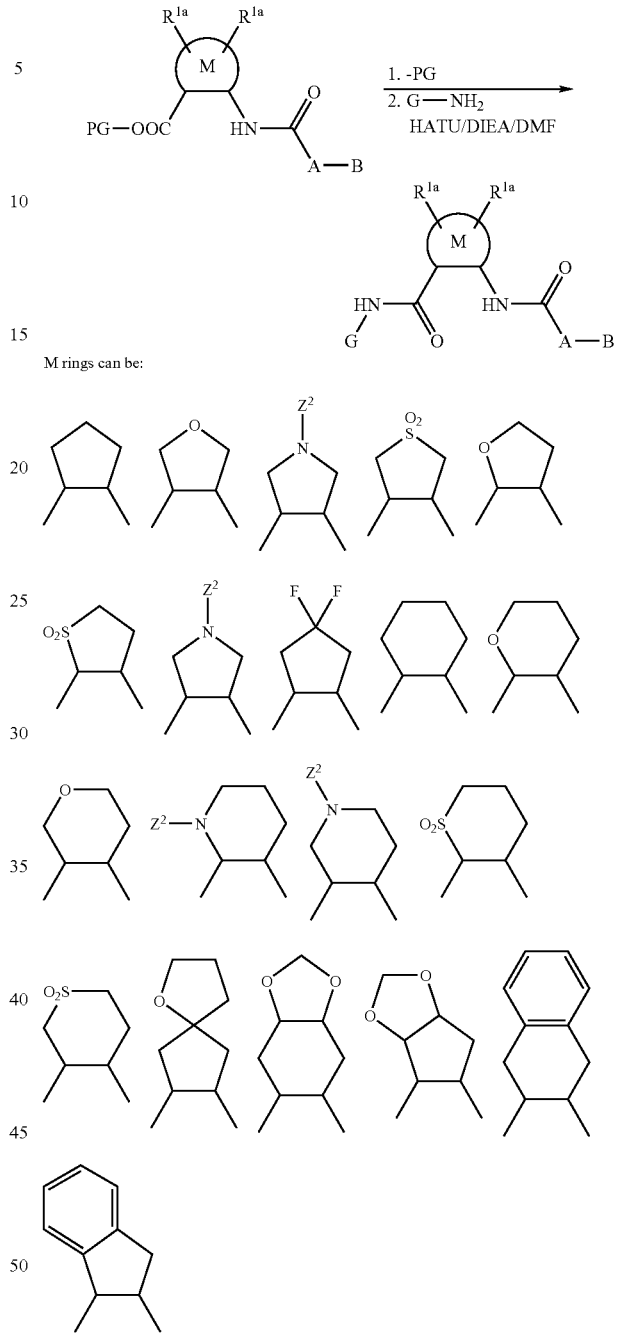

M rings can be:

The properly protected, enantiomerically pure cyclic amino acid cores can be obtained via Davies' protocol (*J. Chem. Soc. Perkin Trans I*, 1994, 1411) or via the reduction of enamines (*J. Org. Chem.* 1996, 61, 5557). The corresponding diamino compounds can be obtained via saponification of the ester of the cyclic amino acids followed by Curtius rearrangement. On the other hand, the cyclic diamines can be prepared via literature methods. (See, for example, *Tetrahedron: Assymmetry*, 1997, 8, 1861 and *Tetrahedron Lett*. 1998, 39, 6921).

A series of compounds of formula I wherein $G_1$ is 1,1-dioxo-sulfonylmethyl is prepared following the sequence outlined in Scheme 25.

Scheme 25
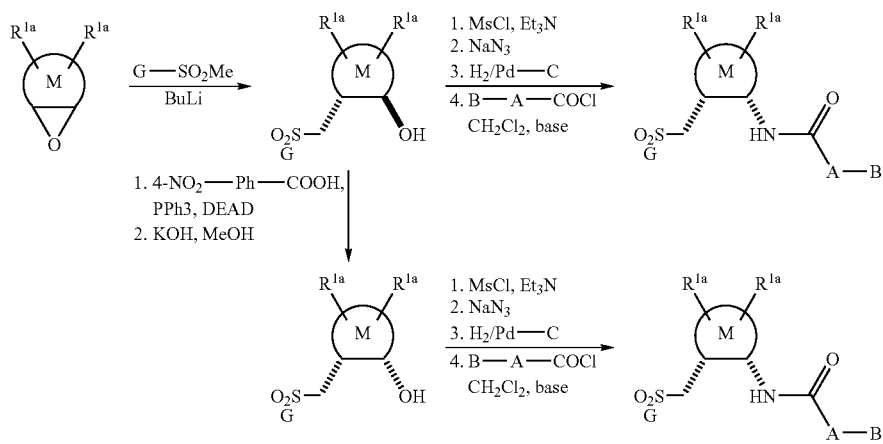
One diastereomer of a compound of Formula I may be more potent against factor Xa than the others. Thus, the following stereochemistries are considered to be a part of the present invention.
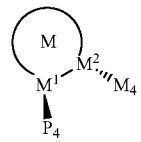
Ic
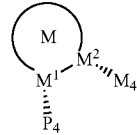
Id
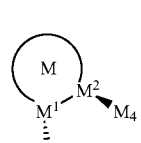
Ie
[image: If]
[image: Ig]
[image: Ih]
-continued
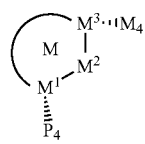
Ii
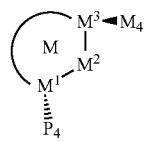
Ij
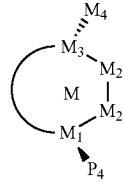
Ik
[image: Il]
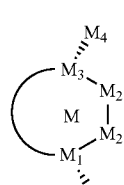
Im
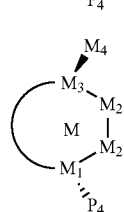
In When required, separation of the racemic material can be achieved by HPLC using a chiral column or by a resolution using a resolving agent such as camphonic chloride (*Antimicrobial Agents and Chemotheraphy*, 1995, 2602–2605). A chiral compound of Formula I may also be directly synthesized using a chiral catalyst or a chiral ligand (See, for example, *Tetrahedron Lett.* 1995, 36, 8937–8940).

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 um. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 min and the velocities (rate of absorbance change vs. time) were measured in the time frame of 25–30 min. The following relationship was used to calculate $K_i$ values:

$$(v_o - v_s)/v_s = I/(K_i(1 + S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Compounds tested in the above assay are considered to be active if they exhibit a $K_i$ of $\leq 10$ µM. Preferred compounds of the present invention have $K_i$'s of $\leq 1$ µM. More preferred compounds of the present invention have $K_i$'s of $\leq 0.1$ µM. Even more preferred compounds of the present invention have $K_i$'s of $\leq 0.01$ µM. Still more preferred compounds of the present invention have $K_i$'s of $\leq 0.001$ µM. Using the methodology described above, a number of compounds of the present invention were found to exhibit $K_i$'s of <10 µM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After 40 min, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 min of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 µm, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrythmic agents, anti-hypertensive agents, calcium channel blockers (L-type and T-type), cardiac glycosides, diruetics, mineralocorticoid receptor antagonists, phospodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, antitumor agents, anti-ulcer and gastroesophageal reflux disease agents, growth hormone and/or growth hormone secretagogues, thyroid mimetics (including thyroid receptor antagonist), anti-infective agents, anti-viral agents, antibacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin, for example LOVENOX™), synthetic pentasaccharide, direct acting thrombin inhibitors including hirudin and argatrobanas, factor VIIa, IXa, XIa inhibitors, well as other factor Xa inhibitors such as those described in the publications identified above under Background of the Invention.

The term anti-platelet agents (or platelet inhibitory agents), as used herein, denotes agents that inhibit platelet finction, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal (α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV ($DP_4$) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/min during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of The present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of The present invention and about 50 to 150 milligrams of the anti-platelet agent, preferably about 0.1 to 1 milligrams of the compound of The present invention and about 1 to 3 milligrams of antiplatelet agents, per kilogram of patient body weight.

Where the compounds of The present invention are administered in combination with thrombolytic agent, typically a daily dosage may be about 0.1 to 1 milligrams of the compound of The present invention, per kilogram of patient body weight and, in the case of the thrombolytic agents, the usual dosage of the thrombolyic agent when administered alone may be reduced by about 70–80% when administered with a compound of The present invention.

Where two or more of the foregoing second therapeutic agents are administered with the compound of The present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of The present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

5-chloro-N-(5-chloropyridin-2-yl)-2-[(4-{(Z)-(dimethylamino)[(methylsulfonyl)imino]methyl}benzoyl)amino]benzamide

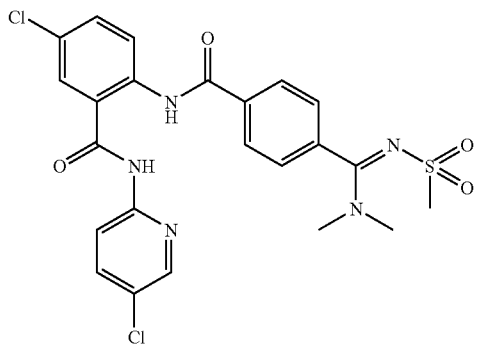

Part A: To a solution of 2-amino-4-chloropyridine (129 mg, 1.0 mmol) in anhydrous THF at 78° C. was added KHMDS (4.0 mL, 0.5 M solution in toluene). The mixture was stirred at this temperature under $N_2$ for 30 min and a solution of 5-chloro-isatoic anhydride (198.0 mg, 1.0 mmol) in THF was added to the above mixture. The resulting mixture was warmed to rt gradually and stirred for 10 hr. The reaction mixture was quenched with sat. $NH_4Cl$ solution, most of the solvent was evaporated, and the residue was diluted with ethyl acetate, washed with brine, and dried over $MgSO_4$. Removal of the solvent and chromatography on silica gel (20% ethyl acetate in hexane) yielded the desired product A as light brown solid. LC-MS found: $(M+1)^+$ =282.2.

Part B: To a solution of methyl 4-cyanobezoate (1.0 g, 6.2 mmol) in MeOH at 0° C. was added HCl in dioxane (30 mL, 4.0 N in dioxane). The reaction mixture was stirred at rt for 16 hr. The solvent was removed and the resulting white residue was dissolved in 15 mL of 2.0 M dimethylamine in MeOH. The resulting mixture was stirred at rt for 24 hr. Removal of the solvent provided the desired amidine as a white solid. LC-MS found: $(2M+1)^+$=413.4.

Part C: To a solution of the product obtained above.(1.28 g, 6.2 mmol) in $CH_2Cl_2$ at 0° C. was added TEA slowly followed by MsCl (0.72 mL, 9.32 mmol). The mixture was stirred at 0° C. for 4 hr. Water was the added. The organic layer was separated and washed with brine and dried over $MgSO_4$. Reverse phase HPLC purification (20% $CH_3CN$ in $H_2O$) provided the desired sulfonylamidine as a white solid. LC-MS found: $(M+1)^+$=285.1.

Part D: To a solution of the product obtained above (0.18 g, 0.63 mmol) in THF (4.0 mL) at 0° C. was added 1.0 N LiOH (1.0 mL). The resulted mixture was stirred at 0° C. for 2 hr. The reaction mixture was acidified with 1.0 N HCl (1.0 mL) to pH 3. Removal of the solvent and reverse phase HPLC purification (15% $CH_3CN$ in $H_2O$) gave the desired 4-(dimethylamino-methanesulfonylimino-methyl)-benzoic acid as a white solid. LC-MS found: $(M+1)^+$=271.1.

Part E: To a mixture of the product obtained above (90.0 mg, 0.33 mmol) and the product obtained from Step a (A) (45.0 mg, 0.15 mmol) in DMF was added BOP (150.0 mg, 0.34 mmol), DIEA (0.2 mL), and DMAP (8.0 mg). The resulting mixture was stirred at rt for 3 days. Most of the solvent was removed, and the residue was purified by reverse phase HPLC (20% $CH_3CN$ in $H_2O$). The desired product was obtained as a white solid. LC-MS found: $(M+1)^+$=534.1.

Example 2

N-(5-chloropyridin-2-yl)-2-[(4-{(Z)-(dimethylamino)[(methylsulfonyl)imino]methyl}benzoyl)amino]-5-methoxybenzamide

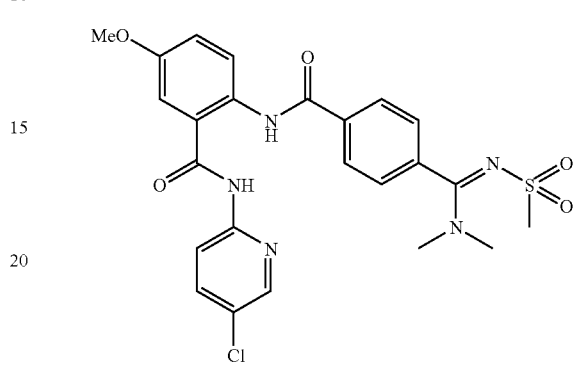

Following a procedure analogous to that described in Example 1, N-(5-chloropyridin-2-yl)-2-[(4-{(Z)-(dimethylamino)[(methylsulfonyl)imino]methyl}benzoyl)amino]-5-methoxybenzamide was obtained as a white solid. LC-MS found: $(M+1)^+$=530.1.

Example 3

6-[4-(5,6-Dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one

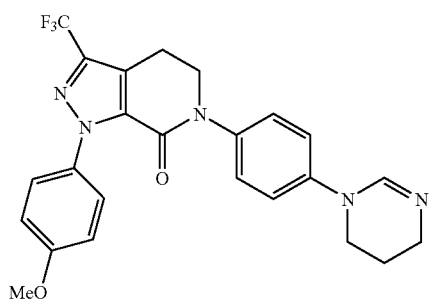

Part A: To a solution of 5.0 g (9.96 mmol) of {4-[1-(4-methoxy-phenyl)-7-oxo-3-trifluoromethyl-1,4,5,7-tetrahydro-pyrazolo[3,4-c]pyridin-6-yl]-phenyl}-carbamic acid tert-butyl ester in 50 mL of DMF was added NaH (797 mg, 19.92 mmol, 60% in oil) at 0° C. After being stirred at rt for 30 min, 1-chloro-3-iodopropane (2.14 mL, 19.92 mmol) was added to the mixture. The reaction was stirred at rt overnight, then quenched with aq. $NH_4Cl$. The resulting mixture was extracted with ether. The combined organic layers were washed with water, brine, and dried ($Na_2SO_4$). The crude material was used directly in the next step.

Part B: A mixture of the crude chloride product from Part A in 50 mL of DMF was treated overnight with sodium azide at 60° C. The reaction mixture was diluted with water and extracted with ether. The combined organic layers were washed with water, brine, dried ($Na_2SO_4$), and concentrated to dryness under reduced pressure. The resulting residue was purified by column chromatography to yield 5.25 g (90% in 2 steps) of (3-azido-propyl)-{4-[1-(4-methoxy-phenyl)-7-oxo-3-trifluoromethyl-1,4,5,7-tetrahydro-pyrazolo[3,4-c]pyridin-6-yl]-phenyl}-carbamic acid tert-butyl ester. APCI MS m/z: 586 (M⁺+1).

Part C: A mixture of the above azide (5.25 g, 8.97 mmol) in 200 mL of methanol was hydrogenated overnight in the presence of 600 mg of 10% Pd/C, under 1 atmosphere of hydrogen. The reaction mixture was filtered through a pad of Celite®. The filtrate was concentrated to dryness under reduced pressure and then used directly in next step.

Part D: The crude material made above was treated with 20 mL of TFA at rt for 30 min. After evaporation of the TFA, the residue was diluted with methylene chloride, washed with aq. Na₂CO₃, and dried (Na₂SO₄) to give of 6-[4-(3-amino-propylamino)-phenyl]-1-(4-methoxy-phenyl)-3-trifluoromethyl-1,4,5,6-tetrahydro-pyrazolo[3,4-c]pyridin-7-one (3.79 g, 92% in 2 steps). APCI MS m/z: 460 (M⁺+1).

Part E: A mixture of the above diamine (110 mg, 0.24 mmol) and 5 mL of triethylorthoformate was heated at 110° C. overnight. The excess orthoformate was stripped off under reduced pressure. The resulting residue was purified via RP-HPLC to generate the title compound as a TFA salt (106 mg, 76%). APCI MS m/z: 470 (M⁺+1).

Example 4

1-(4-Methoxy-phenyl)-6-[4-(2-methyl-5,6-dihydro-4H-pyrimidin-1-yl)-phenyl]-3-trifluoromethyl-1,4,5,6-tetrahydro-pyrazolo[3,4-c]pyridin-7-one

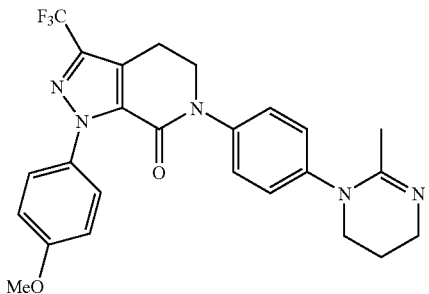

The title compound was prepared using a procedure similar to that described for Example 3: APCI MS m/z 484 (M+H)⁺.

Example 5

6-[4-(2-Ethyl-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one

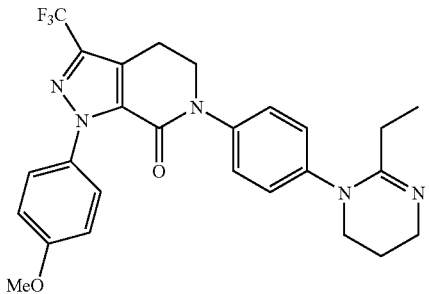

The title compound was prepared using a procedure similar to that described for Example 3: APCI MS m/z 498 (M+H)⁺.

Example 6

6-[4-(2-Isopropyl-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one

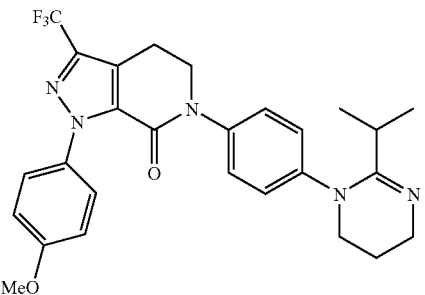

The title compound was prepared using a procedure similar to that described for Example 3: APCI MS m/z 512 (M+H)⁺.

Example 7

1-(4-Methoxy-phenyl)-6-[4-(2-phenyl-5,6-dihydro-4H-pyrimidin-1-yl)-phenyl]-3-trifluoromethyl-1,4,5,6-tetrahydro-pyrazolo[3,4-c]pyridin-7-one

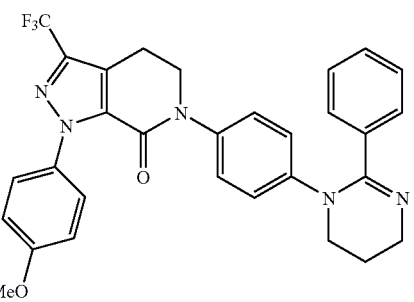

The title compound was prepared using a procedure similar to that described for Example 3: APCI MS m/z 546 (M+H)⁺.

Example 8

6-[4-(2-Amino-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one

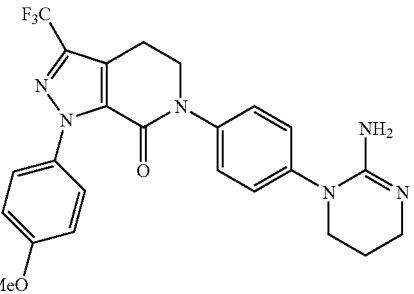

The title compound was prepared using a procedure similar to that described for Example 3: APCI MS m/z 485 (M+H)⁺.

Example 9

N-({4-[1-(4-Methoxy-phenyl)-7-oxo-3-trifluoromethyl-1,4,5,7-tetrahydro-pyrazolo[3,4-c]pyridin-6-yl]-phenyl}-methylamino-methylene)-methanesulfonamide

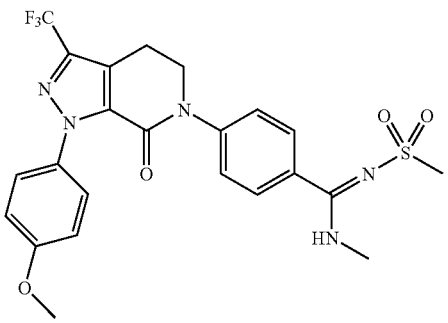

Part A. 2-Piperidone (9.00 g, 90.79 mmol), 4-iodobenzonitrile (24.95 g, 108.95 mmol), cesium carbonate (44.37 g, 136.18 mmol), palladium (II) acetate (4.08 g, 18.16 mmol), and 9,9-dimethyl-4,5-bis(diphenylphosphino)xanthene (15.76 g, 27.24 mmol) were charged to a round bottom flask and flushed with $N_2$. Degassed 1,4-dioxane (100 mL) was added to the flask, and the flask was flushed again with $N_2$. The reaction was heated to 80° C. for 5hr. The reaction was cooled to rt and concentrated to dryness. The crude material was dissolved in water (250 mL) and ethyl acetate (250 mL), extracted with ethyl acetate (3×200 mL), washed with brine (1×250 mL), dried with $MgSO_4$, and concentrated. Purification by flash chromatography using 0–100% ethyl acetate/hexanes gradient as the eluent afforded 16.84 g (93%): $^1$H NMR ($CDCl_3$) δ 7.67 (d, j=8.8 Hz, 2H), 7.43 (d, j=8.8 Hz, 2H), 2.59 (t, j=6.2 Hz, 2H), 1.98–1.92 (m, 4H) ppm.

Part B. 4-(2-Oxo-piperidin-1-yl)-benzonitrile (32.05 g, 160.1 mmol) was dissolved in chloroform (500 mL). Phosphorus pentachloride (100 g, 480.2 mmol) was added, and the reaction was heated at reflux for 4 hr. The reaction was cooled and poured over wet ice, extracted with chloroform (3×500 mL), washed with brine (1×250 mL), dried with $MgSO_4$, and concentrated. The di-chloro intermediate was dissolved in morpholine (150 mL) and refluxed for 1.5 hr. The reaction was concentrated, quenched with water (250 mL), extracted into ethyl acetate (3×200 mL), washed with brine (1×200 mL), dried with $MgSO_4$, and concentrated. Purification by flash chromatography using 0–100% ethyl acetate/hexanes afforded the desired product (33.04 g, 73%).

Part C. The products from parts A and B were subjected to a [3+2] cyclization in refluxing toluene to afford 4-[1-(4-methoxy-phenyl)-7-oxo-3-trifluoromethyl-1,4,5,7-tetrahydro-pyrazolo[3,4-c]pyridin-6-yl]-benzonitrile.

Part D. The product from part C (0.200 g, 0.485 mmol) was dissolved in 1:1 MeOH/$CHCl_3$. Hydrogen chloride gas was bubbled through the solution for 15 min, and it was then tightly capped and sealed. The reaction was stirred overnight at rt and then concentrated to dryness. The crude intermediate was dissolved in methanol (100 mL) and 2M methylamine (1.21 mL, 2.43 mmol) was added. The reaction was tightly capped and sealed and stirred overnight at rt. The reaction was concentrated and purified by reverse phase HPLC and freeze-dried to yield 4-[1-(4-methoxy-phenyl)-7-oxo-3-trifluoromethyl-1,4,5,7-tetrahydro-pyrazolo[3,4-c]pyridin-6-yl]-N-methyl-benzamidine (0.147 g, 68%): $^1$H NMR ($CD_3OD$) δ 7.76(d, j=8.8 Hz, 2H), 7.61(d, j=8.8 Hz, 2H), 7.47(d, j=9.1 Hz, 2H), 7.00(d, j=9.2 Hz, 2H), 4.22(t, j=6.6 Hz, 2H), 3.84(s, 3H), 3.20(t, j=6.4 Hz, 2H), 3.10(s, 3H) ppm; Mass Spec 444.4 (M+H)$^+$.

Part E. The amidine from part D (0.138 g, 0.311 mmol) was dissolved in methylene chloride (10 mL). Methanesulfonyl chloride (0.036 mL, 0.467 mmol) and triethylamine (0.065 mL, 0.467 mmol) were added to the reaction. The reaction was stirred at rt overnight. The reaction was concentrated and purified by flash chromatography using 0–100% ethyl acetate/hexanes as the eluent followed by a methanol flush. Further purification by reverse phase HPLC and freeze-dried yielded the final product (0.120 g, 74%): $^1$H NMR ($CHCl_3$) δ 7.62 (d, j=8.8 Hz, 1H), 7.52 (d, j=8.4 Hz, 1H), 7.47–7.37 (m, 4H), 6.96–6.91 (m, 2H), 4.18 (q, j=7.1 Hz, 2H), 3.82 (d, j=1.5 Hz, 3H), 3.21–3.14 (m, 2H), 3.06 (s, 3H), 3.03 (s, 3H) ppm; Mass Spec 522.3 (M+H)$^+$.

Example 10

N-(Amino-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide

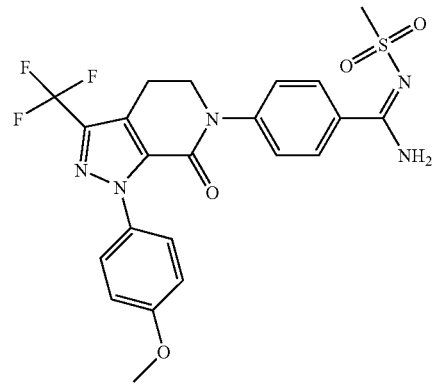

The title compound was prepared using a procedure similar to that described for Example 9. ESI mass spectrum 508.3 (M+H).

Example 11

N-(Dimethylamino-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide

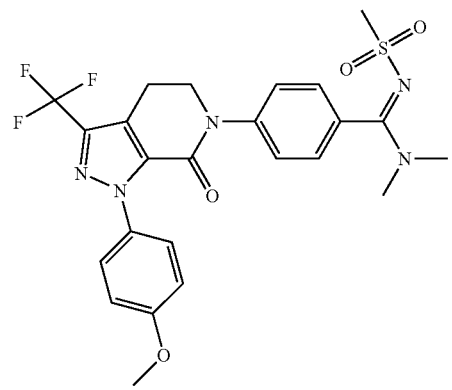

The title compound was prepared using a procedure similar to that described for Example 9. ESI Mass Spec 536.3(M+H)$^+$.

Example 12

N-((Ethyl-methyl-amino)-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide

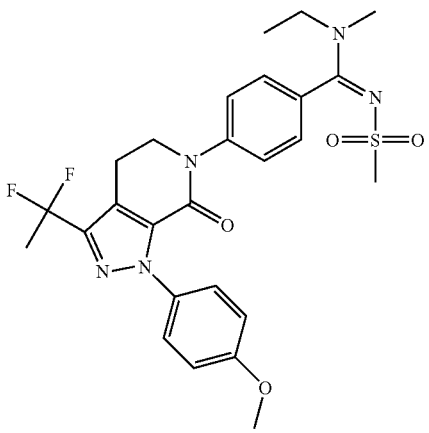

The title compound was prepared following the procedure similar to example 9. ESI Mass Spec 572.4 (M+H+Na)⁺.

Example 13

N-({4-[1-(4-Methoxy-phenyl)-7-oxo-3-trifluoromethyl-1,4,5,7-tetrahydro-pyrazolo[3,4-c]pyridin-6-yl]-phenyl}-piperidin-1-yl-methylene)-methanesulfonamide

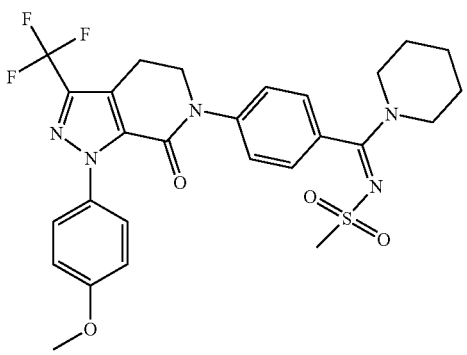

The title compound was prepared using a procedure similar to that described for Example 9. Mass Spec 576.4 (M+H)⁺.

Example 14

N-({4-[1-(4-Methoxy-phenyl)-7-oxo-3-trifluoromethyl-1,4,5,7-tetrahydro-pyrazolo[3,4-c]pyridin-6-yl]-phenyl}-morpholin-4-yl-methylene)-methanesulfonamide

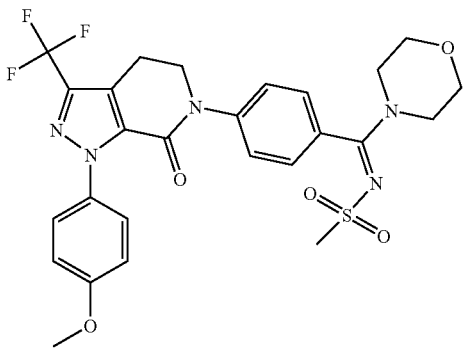

The title compound was prepared using a procedure similar to that described for Example 9. ESI Mass Spec 600.3 (M+H+Na)⁺.

Example 15

N-((Benzyl-methyl-amino)-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide

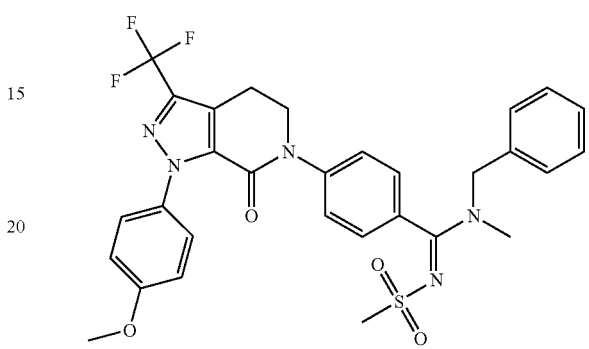

The title compound was prepared using a procedure similar to that described for Example 9. ESI Mass Spec 612.3 (M+H)⁺.

Example 16

6-[4-(Dimethylamino-methanesulfonylimino-methyl)-phenyl]-1-(4-methoxy-phenyl)-7-oxo-4,5,6,7-tetrahydro-1H-pyrazolo[3,4-c]pyridine-3-carboxylic acid amide

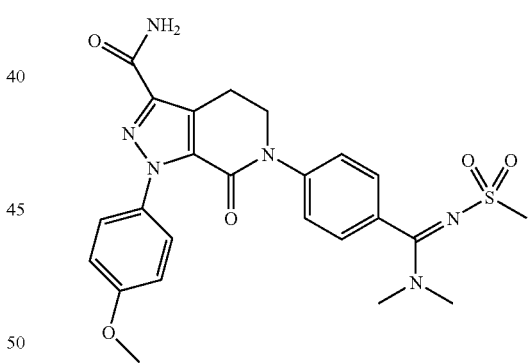

6-(4-Cyano-phenyl)-1-(4-methoxy-phenyl)-7-oxo-4,5,6,7-tetrahydro-1H-pyrazolo[3,4-c]pyridine-3-carboxylic acid ethyl ester (0.100 g, 0.240 mmol) was dissolved in 1:1 methanol/chloroform (20 mL), and hydrogen chloride gas was bubbled through the solution for 15 min, and it was then tightly capped and sealed. The reaction was stirred overnight at rt and then concentrated to dryness. The crude intermediate was dissolved in methanol (10 mL), and 2M dimethylamine (0.012 mL, 2.40 mmol) was added. The reaction was tightly capped and sealed and stirred overnight at rt. The reaction was concentrated and redissolved in methylene chloride (6 mL). Methanesulfonylchloride (0.03 mL, 0.360 mmol) and triethylamine (0.08 mL, 0.600 mmol) were added to the reaction. The reaction was stirred at rt overnight. The reaction was then concentrated and purified by flash chromatography using 0–100% ethyl acetate/hexanes as the eluent followed by methanol. The methanesulfonamide intermediate was dissolved in 5% ammonia/ethylene glycol and heated at 80° C. in a sealed tube for 2 hr. The reaction was quenched with water (50 mnL), extracted with ethyl acetate (3×50 mL), washed with brine (50 mL), dried with MgSO₄, and concentrated. Purification by reverse phase HPLC and freeze-drying afforded the title compound (0.032 g, 26%): ¹H NMR (CHCl₃) δ 7.83–7.35 (m, 6H), 6.99–6.93 (m, 3H), 6.36 (bs, 1H), 4.18 (t, j=6.6 Hz, 2H), 3.83 (s, 3H), 3.37 (t, j=6.8 Hz, 2H), 3.19 (s, 3H), 2.93 (s, 3H), 2.81 (s, 3H) ppm; Mass Spec 511.3 (M+H)⁺.

Example 17

6-[4-(Methanesulfonylimino-pyrrolidin-1-yl-methyl)-phenyl]-1-(4-methoxy-phenyl)-7-oxo-4,5,6,7-tetrahydro-1H-pyrazolo[3,4-c]pyridine-3-carboxylic acid amide

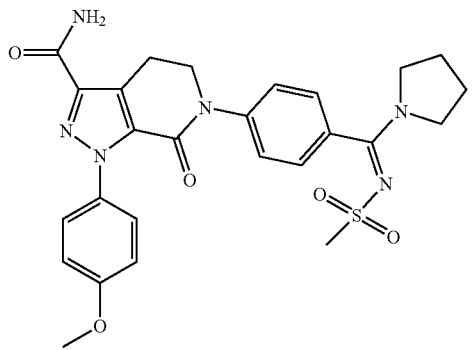

The title compound was prepared using a procedure similar to that described for Example 16. ESI Mass Spec 559.3 (M+H+Na)⁺.

Example 18

N-({4-[3-Cyano-1-(4-methoxy-phenyl)-7-oxo-1,4,5,7-tetrahydro-pyrazolo[3,4-c]pyridin-6-yl]-phenyl}-dimethylamino-methylene)-methanesulfonamide

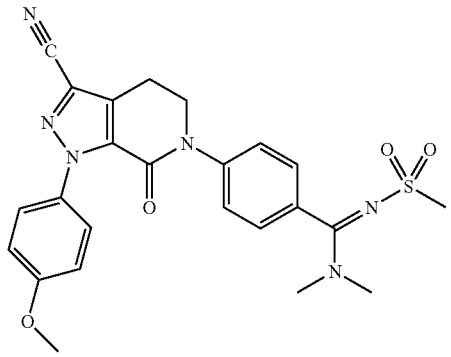

N,N-Dimethylformamide (0.1 mL) was added to acetonitrile (10 mL) and cooled to 0° C. Oxalyl chloride (0.113 mL, 1.29 mmol) was added to the reaction. Once gas evolution stopped, 6-[4-(dimethylamino-methanesulfonylimino-methyl)-phenyl]-1-(4-methoxy-phenyl)-7-oxo-4,5,6,7-tetrahydro-1H-pyrazolo[3,4-c]pyridine-3-carboxylic acid amide (0.020 g, 0.039 mmol) was dissolved in acetonitrile (2 mL) and added to the reaction and stirred at 0° C. for 20 min. Pyridine (1 mL) was then added to the reaction, and it was warmed to rt and stirred overnight. The reaction was quenched with 1N hydrogen chloride (50 mL), extracted with ether 3×50 mL), washed with brine (1×50 mL), dried with MgSO₄, and concentrated. Purification by reverse phase HPLC and freeze-dried to afford the title compound (0.014 g, 72%): ¹H NMR (CHCl₃) δ 7.45 (d, j=8.8 Hz, 2H), 7.40 (d, j=1.1 Hz, 4H), 6.95 (d, j=8.7 Hz, 2H), 4.21 (t, j=6.6 Hz, 2H), 3.83 (s, 3H), 3.19 (s, 3H), 3.17 (t, j=6.1 Hz, 2H), 2.94 (s, 3H), 2.81 (s, 3H) ppm; Mass Spec 493.5 (M+H)⁺.

Example 19

N-(Dimethylamino-{4-[1-(4-methoxy-phenyl)-3-methyl-7-oxo-1,4,5,7-tetrahydro-pyrazolo[3,4-c]pyridin-6-yl]-phenyl}-methylene)-methanesulfonamide

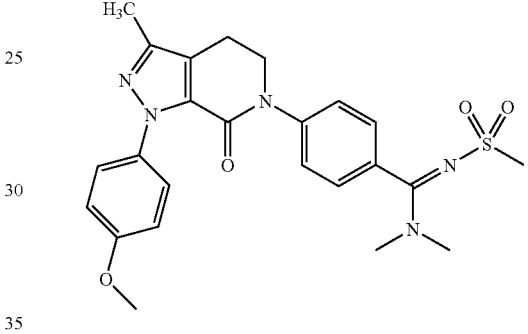

Part A. 4-[1-(4-Methoxy-phenyl)-3-methyl-7-oxo-1,4,5,7-tetrahydro-pyrazolo[3,4-c]pyridin-6-yl]-benzonitrile (0.250 g, 0.98 mmol) was dissolved in 1:1 MeOH/CHCl₃ (30 mL). Hydrogen chloride gas was bubbled through the solution for 15 min, and it was then tightly capped and sealed. The reaction was stirred overnight at rt and then concentrated to dryness. The crude intermediate was dissolved in methanol (30 mL) and 2M dimethylamine (5.23 mL, 10.5 mmol) was added. The reaction was tightly capped and sealed and stirred overnight at rt. The reaction was concentrated and purified by reverse phase HPLC and freeze-dried to yield 4-[1-(4-methoxy-phenyl)-3-methyl-7-oxo-1,4,5,7-tetrahydro-pyrazolo[3,4-c]pyridin-6-yl]-N,N-dimethyl-benzamidine (0.255 g, 71%): ¹H NMR (CHCl₃) δ 9.66 (s, 0.5H), 8.73 (s, 0.5H), 7.51–7.38 (m, 6H), 6.91 (d, j=8.8 Hz, 2H), 4.13(t, j=6.6 Hz, 2H), 3.80 (s, 3H), 3.33 (s, 3H), 3.06 (s, 3H), 2.96 (t,j=6.4 Hz, 2H), 2.35 (s, 3H) ppm; Mass Spec 404.3 (M+H)⁺.

Part B. The amidine from part A (0.220 g, 0.425 mmol) was dissolved in methylene chloride (20 mL). Methanesulfonyl chloride (0.07 mL, 0.637 mmol) and triethylamine (0.207, 0.1.49 mmol) were added to the reaction. The reaction was stirred at rt overnight. The reaction was concentrated and purified by flash chromatography using 0–100% ethyl acetate/hexanes as the eluent followed by a methanol flush. Further purification by reverse phase HPLC and freeze-drying yielded the title compound (0.137 g, 67%): ¹H NMR (CHCl₃) δ 7.44–7.34 (m, 6H), 6.91 (d, j=8.8 Hz, 2H), 4.15 (t, j=6.6 Hz, 2H), 3.80 (s, 3H), 3.19 (s, 3H), 2.93 (s, 3H), 2.93 (t, j=6.4 Hz, 2H), 2.81 (s, 3H), 2.35(s, 3H) ppm; ESI Mass Spectra 482 (M+H)⁺.

Example 20

N-({4-[1-(4-Methoxy-phenyl)-7-oxo-3-trifluoromethyl-1,4,5,7-tetrahydro-pyrazolo[3,4-c]pyridin-6-yl]-phenyl}-pyrrolidin-1-yl-methylene)-methanesulfonamide

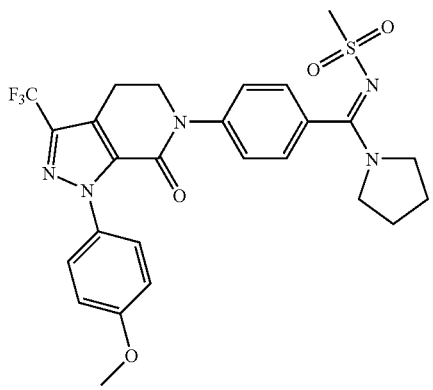

The title compound was prepared using a procedure similar to that described for Example 9. ESI mass spectra 562 (M+H)⁺.

Example 21

N-({4-[3-Isopropenyl-1-(4-methoxy-phenyl)-7-oxo-1,4,5,7-tetrahydro-pyrazolo[3,4-c]pyridin-6-yl]-phenyl}-pyrrolidin-1-yl-methylene)-methanesulfonamide

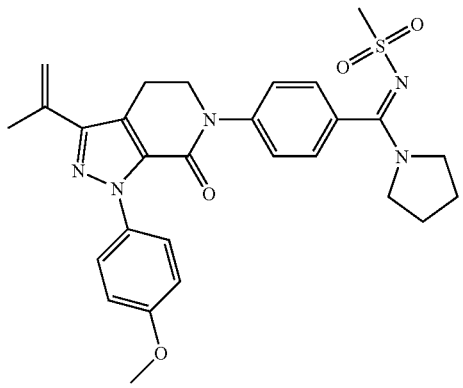

The title compound was prepared using a procedure similar to that described for Example 9. ESI mass spectra 508.3 (M+H)⁺.

Example 22

N-(1-{4-[1-(4-Methoxy-phenyl)-7-oxo-3-trifluoromethyl-1,4,5,7-tetrahydro-pyrazolo[3,4-c]pyridin-6-yl]-phenyl}-1,4,5,6-tetrahydro-pyrimidin-2-yl)-methanesulfonamide

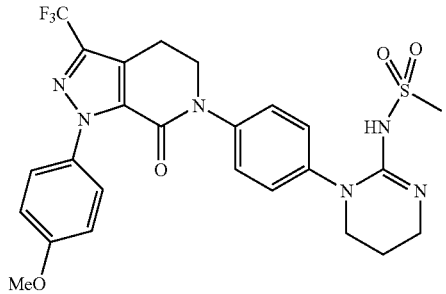

The title compound was prepared from Example 8 by treatment with triethylamine and methanesulfonylchloride. ESI mass spectrum 563.3 (M+H)⁺.

Example 23

(1-{4-[1-(4-Methoxy-phenyl)-7-oxo-3-trifluoromethyl-1,4,5,7-tetrahydro-pyrazolo[3,4-c]pyridin-6yl]-phenyl}-1,4,5,6-tetrahydro-pyrimidin-2yl)-carbamic acid methyl ester

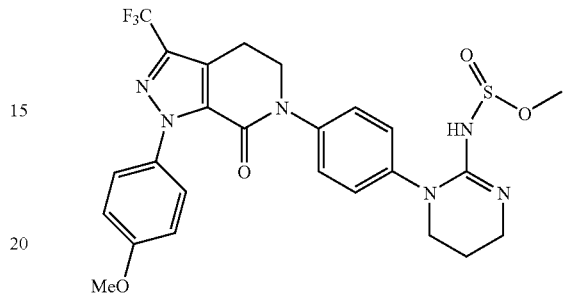

The title compound was prepared from Example 8 by treatment with triethylamine and methylchloroformate. ESI mass spectrum 543.3 (M+H)⁺.

Example 24

N-(1-{4-[1-(4-Methoxy-phenyl)-7-oxo-3-trifluoromethyl-1,4,5,7-tetrahydro-pyrazolo[3,4-c]pyridin-6-yl]-phenyl}-1,4,5,6-tetrahydro-pyrimidin-2-yl)-acetamide

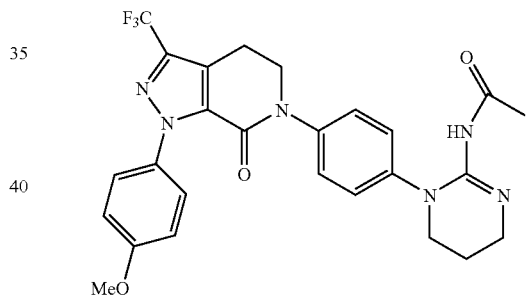

The title compound was prepared from Example 8 by treatment with triethylamine and acetic anhydride. ESI mass spectrum 527.3 (M+H)⁺.

Example 25

1-(4-Methoxy-phenyl)-6-{4-[2-(2-oxo-piperidin-1-yl)-5,6-dihydro-4H-pyrimidin-1-yl]-phenyl}-3-trifluoromethyl-1,4,5,6-tetrahydro-pyrazolo[3,4-c]pyridin-7-one

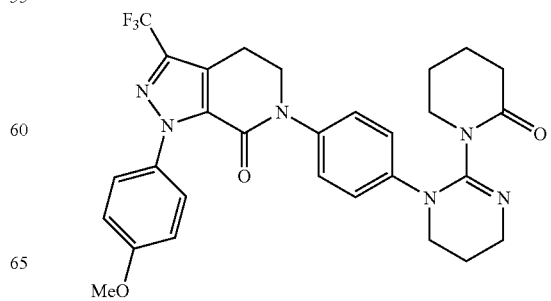

The title compound was prepared from Example 8 by treatment with excess sodium hydride and bromo valerylchloride. ESI mass spectrum 567.3 (M+H)+.

Example 26

1-(4-Methoxy-phenyl)-6-{4-[2-(2-oxo-pyrrolidin-1-yl)-5,6-dihydro-4H-pyrimidin-1-yl]-phenyl}-3-trifluoromethyl-1,4,5,6-tetrahydro-pyrazolo[3,4-c]pyridin-7-one

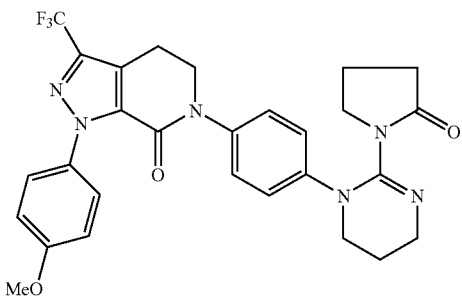

The title compound was prepared from Example 8 by treatment with excess sodium hydride and bromo butyrylchloride. ESI mass spectrum 553.3 (M+H)+.

Example 27

1-(4-Methoxy-phenyl)-6-[4-(2-methyl-5,6-dihydro-4H-pyrimidin-1-yl)-phenyl]-3-cyano-1,4,5,6-tetrahydro-pyrazolo[3,4-c]pyridin-7-one

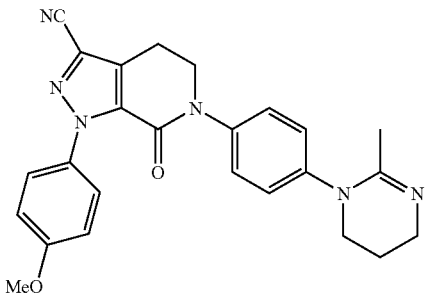

The title compound was prepared following the procedure outlined for Example 3. ESI mass spectrum 441.3 (M+H)+.

Example 28

6-[4-(2-Amino-5,6-dihydro-4H-pyrimidin-1-yl)-phenyl]-1-(4-methoxy-phenyl)-7-oxo-4,5,6,7-tetrahydro-1H-pyrazolo[3,4-c]pyridine-3-carbonitrile

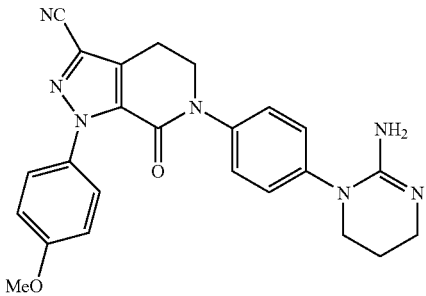

The title compound was prepared following the procedure outlined for Examples 3 and 18. ESI mass spectrum 442 (M+H).

Example 29

N-(1-{4-[3-Cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-methanesulfonamide

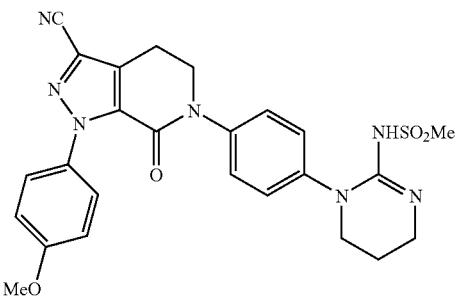

The title compound was prepared following the procedure outlined for Examples 3, 18, and 22. ESI mass spectrum 520.3 (M+H)+.

Example 30

N-(1-{4-[3-Cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-N-methyl-methanesulfonamide

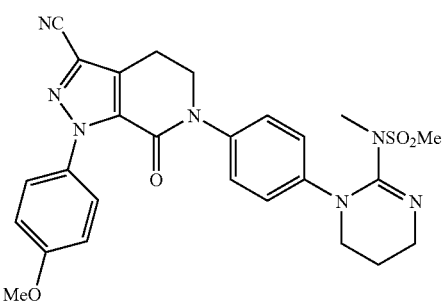

The title compound was prepared following the procedure outlined for Examples 3, 18, and 22. ESI mass spectrum 534 (M+H)+.

Example 31

N-(1-{4-[3-Cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-acetamide

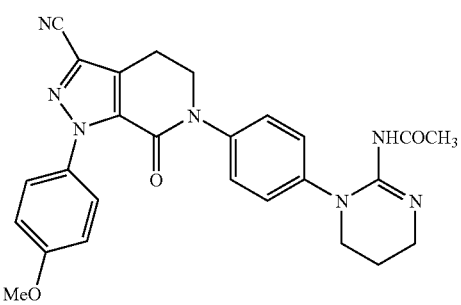

The title compound was prepared following the procedure outlined for Examples 3, 18, and 24. ESI mass spectrum 484.3 (M+H)+.

Example 32

6-[4-(2-Methoxy-5,6-dihydro-4H-pyrimidin-1-yl)-phenyl]-1-(4-methoxy-phenyl)-7-oxo-4,5,6,7-tetrahydro-1H-pyrazolo[3,4-c]pyridine-3-carbonitrile

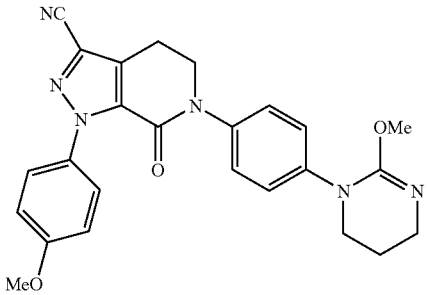

The title compound was prepared following the procedure outlined for Examples 3 and 18. ESI mass spectrum 457 (M+H).

Example 33

6-[4-(5,6-Dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one

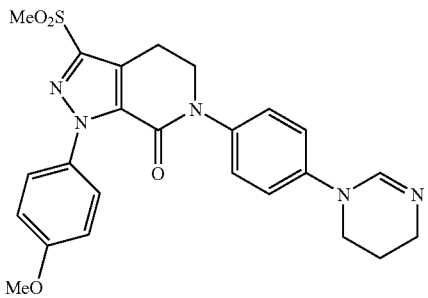

The title compound was prepared following the procedure outlined for Example 3. In this case the hydrazone used in the [3+2] cycloaddition was N-(1-methanesulfonyl-chloro)-N'-(4-methoxy-phenyl)-hydrazine. ESI mass spectrum 480 (M+H).

Example 34

3-Methanesulfonyl-1-(4-methoxy-phenyl)-6-[4-(2-methyl-5,6-dihydro-4H-pyrimidin-1-yl)-phenyl]-1,4,5,6-tetrahydro-pyrazolo[3,4-c]pyridin-7-one

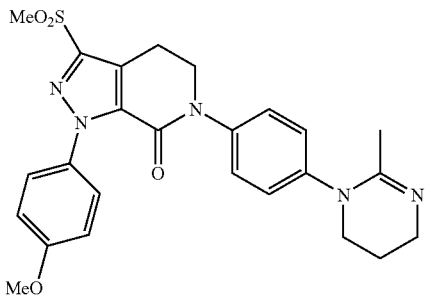

The title compound was prepared following the procedure outlined for Examples 3 and 33. ESI mass spectrum 494.3 (M+H)$^+$.

Example 35

6-[4-(2-Isopropyl-5,6-dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one

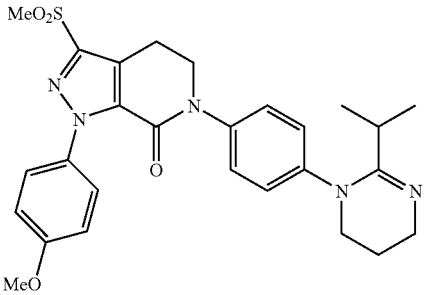

The title compound was prepared following the procedure outlined for Examples 3 and 33. ESI mass spectrum 522.3 (M+H)$^+$.

Example 36

3-Methanesulfonyl-1-(4-methoxy-phenyl)-6-[4-(2-phenyl-5,6-dihydro-4H-pyrimidin-1-yl)-phenyl]-1,4,5,6-tetrahydro-pyrazolo[3,4-c]pyridin-7-one

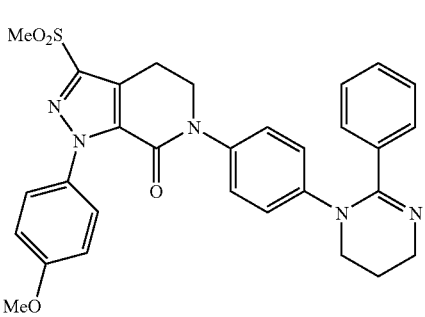

The title compound was prepared following the procedure outlined for Examples 3 and 33. ESI mass spectrum 556.3 (M+H)$^+$.

Example 37

6-[4-(2-Amino-5,6-dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one

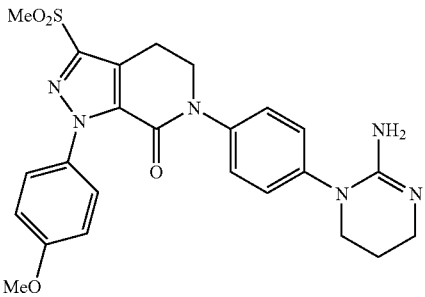

The title compound was prepared following the procedure outlined for Examples 3 and 33. ESI mass spectrum 495.3 (M+H)$^+$.

Example 38

3-Methanesulfonyl-1-(4-methoxy-phenyl)-6-{4-[2-(2-oxo-piperidin-1-yl)-5,6-dihydro-4H-pyrimidin-1-yl]-phenyl}-1,4,5,6-tetrahydro-pyrazolo[3,4-c]pyridin-7-one

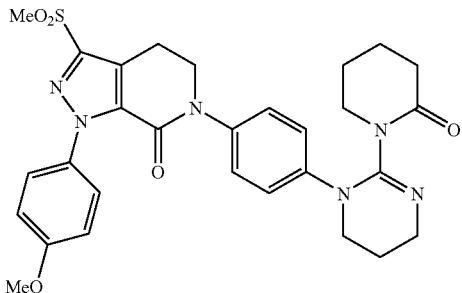

The title compound was prepared following the procedure outlined for Examples 3, 33, and 25. ESI mass spectrum 577 (M+H).

Example 39

6-[4-(5,6-Dihydro-4H-pyrimidin-1-yl)-phenyl]-3-isopropoxy-1-(4-methoxy-phenyl)-1,4,5,6-tetrahydro-pyrazolo[3,4-c]pyridin-7-one

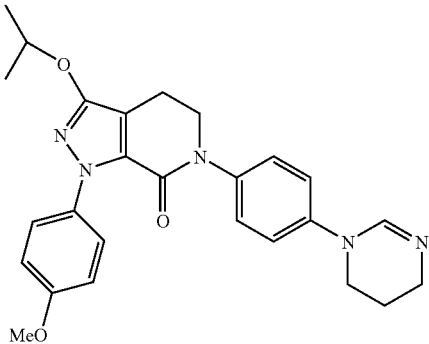

Condensation of 4-methoxyphenylhydrazine with 1-(4-nitro-phenyl)-4-(2,2,2-trichloro-acetyl)-piperidine-2,3-dione in refluxing methanol-acetic acid media afforded 3-hydroxy-1-(4-methoxy-phenyl)-6-(4-nitro-phenyl)-1,4,5,6-tetrahydro-pyrazolo[3,4-c]pyridin-7-one. Treatment of this intermediate with NaH and isopropyliodide afforded the corresponding 3-isopropoxy pyrazolo intermediate which was subjected to the same experimental protocol as described for Example 3 to afford the title compound. ESI mass spectrum 460 (M+H)$^+$.

Example 40

3-{6-[4-(2-Amino-5,6-dihydro-4H-pyrimidin-1-yl)-phenyl]-3-methanesulfonyl-7-oxo-4,5,6,7-tetrahydro-pyrazolo[3,4-c]pyridin-1-yl}-benzamide

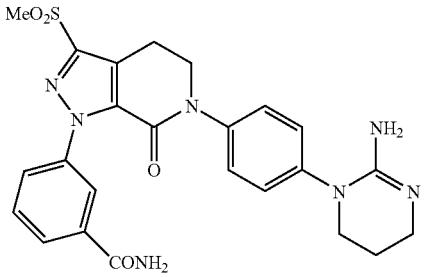

The title compound was prepared following a procedure similar to that outlined for Examples 3 and 33. In this particular case the hydrazine was used to prepare the chlorosulfoyl hydrazone 3-hyrazinobenzoic acid. The pyrazole that was formed was esterified and the sequence outlined for Example 3 was then carried out. Final conversion to the 3-carboxamidophenyl title compound was carried out with ammonia. ESI mass spectrum 508.3 (M+H)$^+$.

Example 41

3-{3-Methanesulfonyl-6-[4-(2-methyl-5,6-dihydro-4H-pyrimidin-1-yl)-phenyl]-7-oxo-4,5,6,7-tetrahydro-pyrazolo[3,4-c]pyridin-1-yl}-benzamide

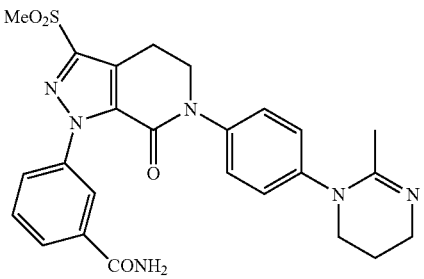

The title compound was prepared following a procedure similar to that outlined for Example 41. ESI mass spectrum 507.3 (M+H)$^+$.

Example 42

1-(3-Chloro-phenyl)-6-[4-(2-methyl-5,6-dihydro-4H-pyrimidin-1-yl)-phenyl]-3-trifluoromethyl-1,4,5,6-tetrahydro-pyrazolo[3,4-c]pyridin-7-one

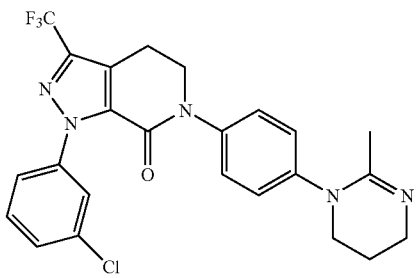

Using 3-chlorophenylhydrazine the title compound was prepared following the procedure outlined for Example 3. ESI mass spectrum 488 (M+H).

Example 43

2-(3-Amino-benzo[d]isoxazol-5-yl)-5-trifluoromethyl-2H-pyrazole-3-carboxylic acid [4-(methanesulfonylimino-pyrrolidin-1-yl-methyl)-phenyl]-amide

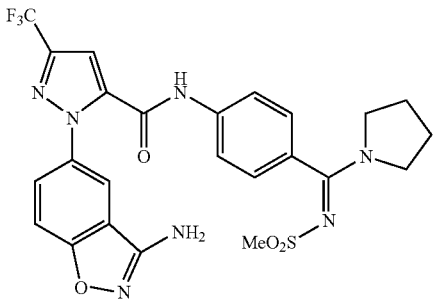

Part A. 4-Amino benzonitrile (1 g) was saturated with anhydrous HCl in methanol. The reaction mixture was capped and stirred at rt for 18 h, concentrated, and redissolved in methanol. To this solution was added excess pyrrolidine. It was then stirred for 24 h. The solvents were evaporated, and the crude was treated with methanesulfonyl chloride and excess triethylamine. The reaction mixture was stirred at rt for 24 h and purified via flash chromatography (Hexane/ethylacetate 1:1) to afford pure compound.

Part B. The product from part A was dissolved in ethylacetate (20 mL) and three equiv. of tin chloride were added. The reaction mixture was stirred at rt for 24 h, quenched with water, and washed with sat. ammonia solution. Pure product was extracted with ethyl acetate.

Part C. The product from part B was treated with 2-(3-cyano-4-fluoro-phenyl)-5-trifluoromethyl-2H-pyrazole-3-carbonyl chloride in methylene chloride and 4-dimethylaminopyridine as base. Pure coupled product was obtained by silica gel flash chromatography.

Part D. The product from part C was than treated with acetylhydroxylamine in DMF and potassium carbonate to obtain the title compound as colorless crystals. ESI mass spectrum 562 (M+H).

Example 44

2-(4-Methoxy-phenyl)-5-trifluoromethyl-2H-pyrazole-3-carboxylic acid [4-(methanesulfonylimino-pyrrolidin-1-yl-methyl)-phenyl]-amide

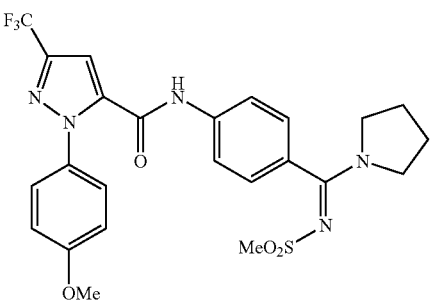

Prepared as previously discussed from the coupling of the product from part B (Example 43) and the acid chloride obtained from 2-(4-methoxy-phenyl)-5-trifluoromethyl-2H-pyrazole-3-carboxylic acid. ESI mass spectrum 536 (M+H)$^+$.

Example 45

2-(3-Aminomethyl-phenyl)-5-trifluoromethyl-2H-pyrazole-3-carboxylic acid [4-(methanesulfonylimino -pyrrolidin-1-yl-methyl)-phenyl]-amide

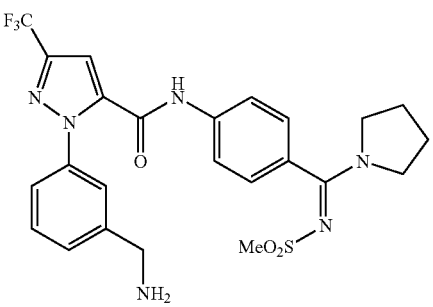

Prepared as previously discussed from the peptide coupling of the product from part B (Example 43) and the acid chloride obtained from 2-[3-(tert-butoxycarbonylamino-methyl)-phenyl]-5-trifluoromethyl-2H-pyrazole-3-carboxylic acid. Removal of the Boc protecting group afforded the title compound. ESI mass spectrum 535 (M+H)$^+$.

Example 46

2-(3-Aminomethyl-4-fluoro-phenyl)-5-trifluoromethyl-2H-pyrazole-3-carboxylic acid [4-(methanesulfonylimino-pyrrolidin-1-yl-methyl)-phenyl]-amide

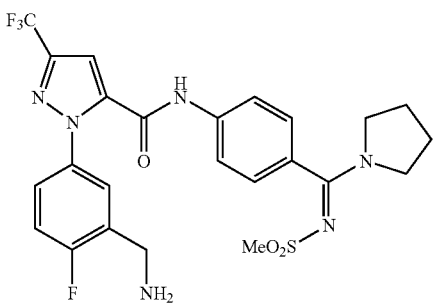

2-(3-Cyano-4-fluoro-phenyl)-5-trifluoromethyl-2H-pyrazole-3-carboxylic acid [4-(methanesulfonylimino-pyrrolidin-1-yl-methyl)-phenyl]-amide, prepared as outlined in Example 41, was subjected to catalytic reduction to afford the title compound. ESI mass spectrum 553.3 (M+H)$^+$.

Example 47

N-(Diethylamino-{4-[1-(4-methoxy-phenyl)-7-oxo-3-trifluoromethyl-1,4,5,7-tetrahydro-pyrazolo[3,4-c]pyridin-6-yl]-phenyl}-methylene)-methanesulfonamide

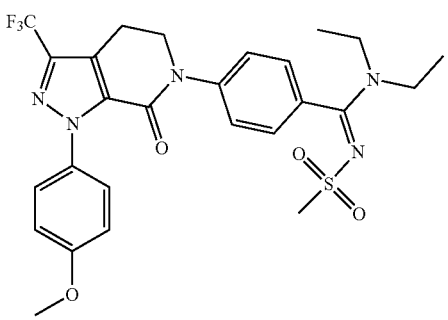

The title compound was prepared using a procedure similar to that described for Example 9. ESI Mass Spec (M+H)$^+$564.3.

Example 48

1-(4-Methoxy-phenyl)-6-[4-(1-methyl-4,5-dihydro-1H-imidazol-2-yl)-phenyl]-3-trifluoromethyl-1,4,5,6-tetrahydro-pyrazolo[3,4-c]pyridin-7-one

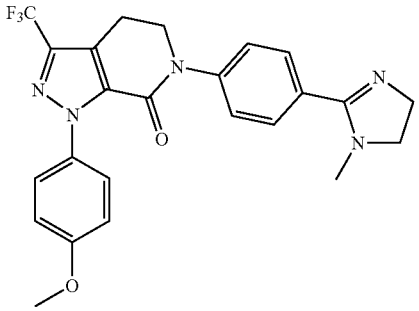

Condensation of 4-methoxyphenylhydrazine with 4-[2,3-dioxo-4-(2,2,2-trifluoro-acetyl)-piperidin-1-yl]-benzonitrile afforded the desired intermediate 4-[1-(4-methoxy-phenyl)-7-oxo-3-trifluoromethyl-1,4,5,7-tetrahydro-pyrazolo[3,4-c]pyridin-6-yl]-benzonitrile. This intermediate was dissolved in anhydrous methanol and HCl gas was bubbled through for 15 min. The reaction mixture was stirred at room temperature for 18 h and concentrated. The residue was re-dissolved in methanol and 2 equivalents of N-methyl-ethylenediamine were added. The reaction mixture was stirred at room temperature for 18 h and concentrated. Pure product was obtained via reverse phase HPLC. ESI mass spectrum 470 (M+H)+.

Example 49

6-[4-(4,5-Dihydro-1H-imidazol-2-yl)-phenyl]-1-(4-methoxy-phenyl)-3-trifluoromethyl-1,4,5,6-tetrahydro-pyrazolo[3,4-c]pyridin-7-one

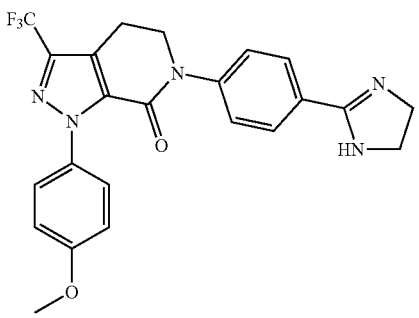

The title compound can be prepared in a similar fashion to that described for Example 48. In this case ethylenediamine can be used in the condensation step with the Pinner imidate described in Example 48. ESI mass spectrum 456 (M+H)+.

Example 50

6-[4-(1-Methanesulfonyl-4,5-dihydro-1H-imidazol-2-yl)-phenyl]-1-(4-methoxy-phenyl)-3-trifluoromethyl-1,4,5,6-tetrahydro-pyrazolo[3,4-c]pyridin-7-one

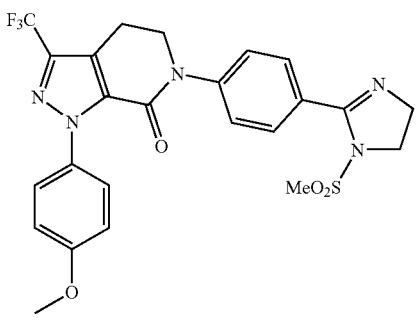

The title compound can be prepared by treating Example 49 with methane sulfonylchloride in excess triethylamine. Pure product can be obtained by reverse phase HPLC. ESI mass spectrum 534 (M+H)+.

Example 51

2-{4-[1-(4-Methoxy-phenyl)-7-oxo-3-trifluoromethyl-1,4,5,7-tetrahydro-pyrazolo[3,4-c]pyridin-6-yl]-phenyl}-4,5-dihydro-imidazole-1-carboxylic acid ethyl ester

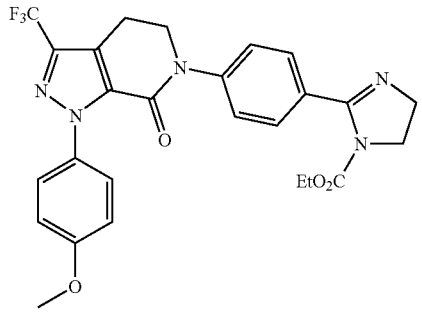

The title compound can be prepared by treating Example 49 with ethyl chloroformate in excess triethylamine. Pure product can beobtained by reverse phase HPLC. ESI mass spectrum 528 (M+H)+.

Other amidine containing compounds of this invention that were obtained via the experimental protocols outlined above include Example 52

N-Hydroxy-4-[1-(4-methoxy-phenyl)-7-oxo-3-trifluoromethyl-1,4,5,7-tetrahydro-pyrazolo[3,4-c]pyridin-6-yl]-N-methyl-benzamidine

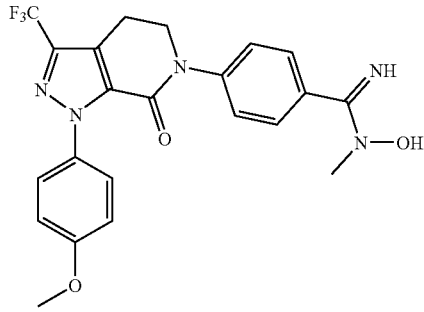

ESI mass spectrum 460 (M+H).

Example 53

N-Hydroxy-4-[1-(4-methoxy-phenyl)-7-oxo-3-trifluoromethyl-1,4,5,7-tetrahydro-pyrazolo[3,4-c]pyridin-6-yl]-benzamidine

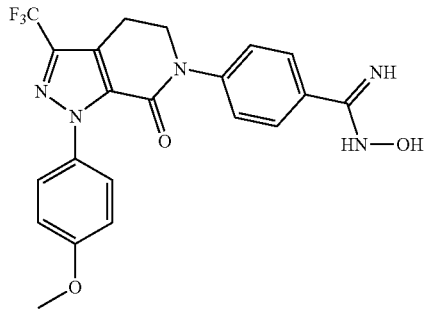

ESI mass spectrum 446 (M+H).

Example 54

N-Methoxy-4-[1-(4-methoxy-phenyl)-7-oxo-3-trifluoromethyl-1,4,5,7-tetrahydro-pyrazolo[3,4-c]pyridin-6-yl]-benzamidine

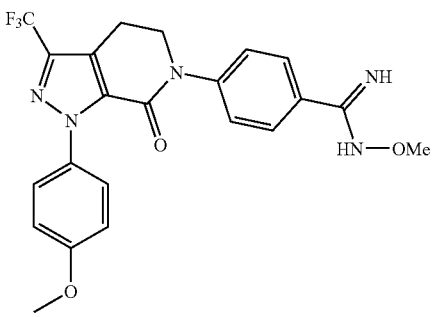

ESI mass spectrum 460 (M+H).

Example 55

N-Methoxy-4-[1-(4-methoxy-phenyl)-7-oxo-3-trifluoromethyl-1,4,5,7-tetrahydro-pyrazolo[3,4-c]pyridin-6-yl]-N-methyl-benzamidine

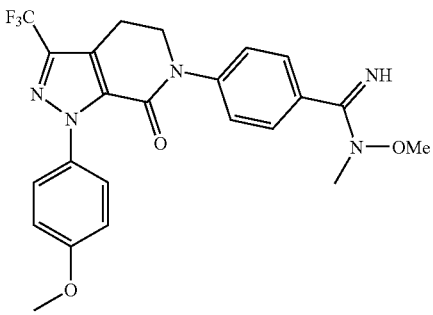

ESI mass spectrum 474 (M+H).

Example 56

(1R, 2S)-3-chloro-1H-indole-6-carboxylic acid {2-[4-(N,N-dimethyl-N'-(methylsulfonyl)carbamimidoyl)-benzoylamino]-cyclohexyl}-amide

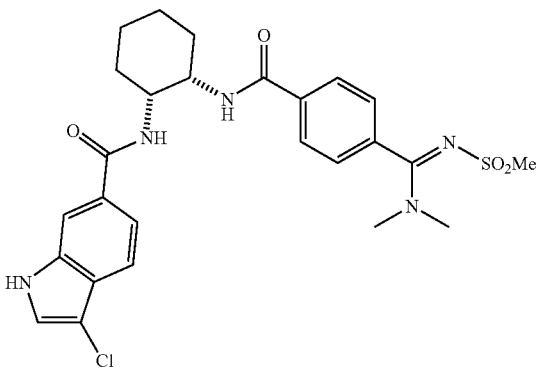

Part A. To a solution of (1S, 2S)-2-benzyloxyhexyl-amine (10.0 g, 38.78 mmol) in THF (100 mL) were added Et$_3$N (20.0 mL, 0.14 mol) and (Boc)$_2$O (12.50 g, 7.3 mmol) sequentially at 0° C. The reaction mixture was stirred overnight at room temperature and evaporated. It was diluted with EtOAc (200 mL). The organic phase was washed with H$_2$O, brine, and dried (Na$_2$SO$_4$). The solvent was evaporated to afford (1S, 2S)-2-benzyloxy-cyclohexyl-carbamic acid tert-butyl ester (14.8 g, 100%) as a white solid. MS m/z 306.2 ([M+H]$^+$).

Part B. The product from Part A (8.0 g, 26.2 mmol) was dissolved in cyclohexene (100 mL) and ethanol (150 mL), and Pd/C (2.0 g) was added. The reaction mixture was refluxed for 6 h and filtered through a pad of Celite®. The filtrate was evaporated to afford (1S, 2S)-2-hydroxy-cyclohexyl-carbamic acid tert-butyl ester (5.7 g, 100%) as a white solid. MS m/z 216.2 ([M+H]$^+$).

Part C. To a solution of the product from Part B (3.10 g, 14.4 mmol) in CH$_2$Cl$_2$ (50 mL) were added pyridine (1.34 mL, 16.58 mmol) and methane sulfonic anhydride (2.81 g, 16.13 mmol) sequentially at 0° C. The reaction mixture was stirred for 1.5 h at 0° C., then quenched with H$_2$O, and extracted with EtOAc (3×50 mL). The organic phase was washed with H$_2$O, brine, and dried (Na$_2$SO$_4$). The solvent was evaporated to afford (1S, 2S)-methanesulfonic acid 2-tert-butoxycarbonylamino-cyclohexyl ester (4.0 g, 95%) as a white solid. MS m/z 294.2 ([M+H]$^+$).

Part D. NaN$_3$ (4.0 g, 61.53 mmol) was added to a solution of the product from Part C (4.0 g, 13.65 mmol) in DMSO (14 mL). The reaction mixture was heated at 80° C. to 85° C. for 1.5 day with vigorous stirring. The reaction was cooled to room temperature, poured into water, and extracted with EtOAc (4×100 mL). The extracts were combined and washed with H$_2$O, aqueous LiCl (10%), brine, and dried (Na$_2$SO$_4$). The solvent was evaporated, and the residue was taken to next step without purification. The residue (2.7 g) was dissolved in THF (50 mL), and PPh$_3$ (3.26 g, 12.44 mmol) was added followed by the addition of H$_2$O (10 mL). The reaction mixture was heated at 70° C. for 24 h. It was evaporated, and EtOAc was added. It was washed with 1N HCl (2×50 mL), and the acidic layer was basified with solid Na$_2$CO$_3$, and extracted with EtOAc (3×) to afford crude (1S, 2R)-2-amino-cyclohexyl-carbamic acid tert-butyl ester (1.8 g, 62% for 2 steps) as a white solid. MS m/z 215.2 ([M+H]$^+$).

Part E. 3-Chloro-1H-indole-6-carboxylic acid (0.11 g, 0.56 mmol) and was dissolved in DMF (1.5 mL). To this solution was added the product from Part D (0.081 g, 0.38 mmol) followed by the addition of HATU (0.231 g, 0.605 mmol) and DIEA (0.20 mL, 1.15 mmol). The mixture was stirred at rt for 4 h. It was diluted with ethyl acetate; washed with water, aqueous LiCl (10%), and brine; and dried (Na$_2$SO$_4$). After evaporation of the solvent, the residue was purified on silica gel to afford (1S, 2R)-{2-[(3-chloro-1H-indole-6-carbonyl)-amino]-cyclohexyl}-carbamic acid tert-butyl ester (140 mg, 95%) as a white solid. MS m/z 392.2 ([M+H]$^+$).

Part F. The product from Part E (140 mg, 0.36 mmol) was suspended in CH$_2$Cl$_2$ (15 mL), and TFA (5 mL) was added. A clear solution was obtained and stirred for 1 h at ambient temperature. The resulting solution was concentrated. The residue was partitioned between EtOAc and aqueous Na$_2$CO$_3$. The aqueous solution was extracted with EtOAc (3×10 mL), and the extracts were combined and washed with brine and dried (Na$_2$SO$_4$). Evaporation of the solvent afforded (1R, 2S)-3-chloro-1H-indole-6-carboxylic acid (2-amino-cyclohexyl)-amide (104 mg, 99%) as a white solid that was taken to next step without purification. MS m/z 292.2 ([M+H]$^+$).

Part G. The product from Part F (40 mg, 0.14 mmol), 4-(N,N-dimethyl-N'-(methylsulfonyl)carbamimidoyl)benzoic acid (30 mg, 0.11 mmol), BOP (63 mg, 0.14 mmol), and N-methylmorpholine (0.020 mL) were stirred in DMF (0.5mL) at room temperature for 1 h. The reaction mixture was diluted with ethyl acetate, washed with water, aqueous LiCl (10%), brine, and dried (MgSO$_4$). After evaporation of the solvent, the residue was purified on RP HPLC using gradient CH$_3$OH—H$_2$O-TFA to afford (1R, 2S)-3-chloro-1H-indole-6-carboxylic acid {2-[4-(N,N-dimethyl-N'-(methylsulfonyl)carbamimidoyl)-benzoylamino]-cyclohexyl}-amide as white solids.

Example 57

Pyrrolidine-1,2-dicarboxylic acid 1-[(4-chloro-phenyl)-amide]2-{[4-(methanesulfonylimino-pyrrolidin-1-yl-methyl)-phenyl]-amide}

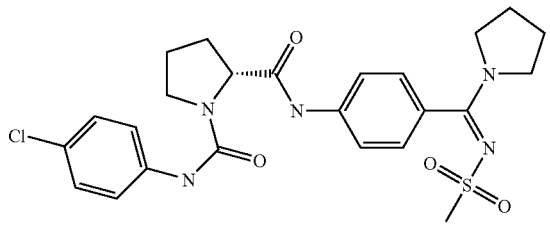

Part A: 4-Nitrobenzonitrile (5.4 g, 36.5 mmol) was dissolved in 200 mL of anhydrous methyl acetate and 20 mL of MeOH. The whole mixture was cooled to 0° C. and bubbled with dry HCL gas for 1 hour. The resulting mixture was placed at 5° C. for 12 hours, the solvent was removed to obtain 5.8 g of methyl 4-nitrobenzimidate as its HCl salt.

Part B: The product from Part A (2.5 g, 11.5 mmol) was dissolved in 80 mL of anhydrous MeOH. To this mixture was added 1.64 g (23 mmol, 2 eq) of pyrrolidine and the resulting mixture stirred overnight at room temperature. Volatiles were evaporated and 80 mL of 1N HCl solution was added. The insoluble material was removed by filtration and the mother liquors evaporated to dryness, dissolved in 120 mL of 1N NaOH solution and extracted with CH$_2$Cl$_2$ (4×25 mL). Organic phases were combined, dried over MgSO$_4$ and concentrated to yield 1.32 g (38%) of the expected (4-nitrophenyl)(pyrrolidin-1-yl)methanimine as a yellow oil.

Part C: The product from Part B (1.32 g, 6.02 mmol) was dissolved in 40 mL of CH$_2$Cl$_2$, and the solution was cooled to 0° C. DMAP (892 mg, 7.22 mmol, 1.2 eq) was added followed by 0.56 mL (7.22 mmol, 1.2 eq) of methanesulfonyl chloride in 15 mL of CH$_2$Cl$_2$. The resulting mixture was stirred overnight at room temperature then washed successively with 1N HCl (2×20 mL), 1N NaOH (2×15 mL), and brine (2×20 mL); dried over MgSO$_4$; and concentrated to yield an oil. This was purified by ISCO system flash chromatograpy (eluting with Hexane-AcOEt 30%) to yield 980 mg of (E)-N-((4-nitrophenyl)(pyrrolidin-1-yl)methylene)methanesulfonamide as a white solid.

Part D: 0.98 g (3.296 mmol) of the compound prepared as above were mixed with 2.23 g (9.888 mmol, 3 eq) of SnCl$_2$, 2H$_2$O and 45 mL of ethanol and refluxed for 2 h. Volatiles were evaporated, 80 mL of 1N NaOH added and the mixture extracted with CH$_2$Cl$_2$ (3×30 mL). The organic phase was dried over MgSO$_4$ and concentrated to yield 890 mg of N-((4-aminophenyl)(pyrrolidin-1-yl)methylene)methanesulfonamide as a yellow solid.

Part E: 89.5 mg (0.416 mmol) of commercial Boc-D-proline were mixed with 2 eq of EDC (158.3 mg, 0.831 mmol), 3 eq of HOBT, H$_2$O (168.7 mg, 1.25 mmol), 3 eq of TEA (126.5 mg, 174 μL) and 3 mL of DMF under N$_2$ atmosphere. 100 mg (0.374 mmol) of the aniline from part D were added together with 1.5 mL of additional DMF. The mixture was allowed to stir overnight at room temperature. 10 mL of AcOEt were added and the mixture was washed with water (3×3 mL). The organic phase was dried over MgSO$_4$ and concentrated to yield a crude mixture of (R)-2-[4-(methanesulfonylimino-pyrrolidin-1-yl-methyl)-phenylcarbamoyl]-pyrrolidine-1-carboxylic acid tert-butyl ester, which was purified by ISCO system flash chromatography (Eluted with gradient AcOEt/ Hexane 30%).

Part F: The product from Part E (23 mg, 0.05 mmol) was mixed with 1 mL of 1,4 dioxane/HCl 4N solution and stirred at room temperature overnight. The volatiles were evaporated to yield (R)-pyrrolidine-2-carboxylic acid [4-(methanesulfonylimino-pyrrolidin-1-yl-methyl)-phenyl]-amide HCl salt, which was used in the next step without further purification.

Part G: The product from Part F (0.05 mmol) was mixed with 3 mL of anhydrous CH$_2$Cl$_2$, 0.1 mmol (2 eq) of TEA. Next, 0.05 mmol (1 eq) of p-chlorophenylisocyanate were added, and the reaction mixture stirred at room temperature overnight. Volatiles were evaporated and the crude compound obtained was purified by preparative HPLC (Shimadzu Phenomenex Luna 5u 21.2×100; flow rate 20 ml/min; detection at 220 nM; Gradient elution 0% to 100% B over 20 min; (A=10% MeOH, 90% H$_2$O, 0.1% TFA&B=90% MeOH, 10% H$_2$O, 0.1% TFA) to yield the title compound. $^1$H NMR (500 MHz, CDCl$_3$) δ 9.76 (s, 1H), 7.64 (d, J=10 Hz, 2H), 7.39–7.24 (m, 6H), 6.49 (s, 1H), 4.72 (d, J=5 Hz, 1H), 3.65 (t, 2H), 3.56 (m, 1H), 3.42 (m, 1H), 3.14 (m, 2H), 2.88 (s, 3H), 2.65 (m, 1H), 2.15 (m, 1H), 1.98–1.85 (m, 6H), ppm. LC-MS (ESI) 518.27 [M+H]$^+$, t$_R$=5.362 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{24}$H$_{29}$N$_5$O$_4$SCl [M+H]$^+$518.1629, found 518.1614.

Example 58

(R)-N2-(4-(N,N-dimethyl-N'-(methylsulfonyl)carbamimidoyl)phenyl)-N1-(4-chlorophenyl)pyrrolidine-1,2-dicarboxamide

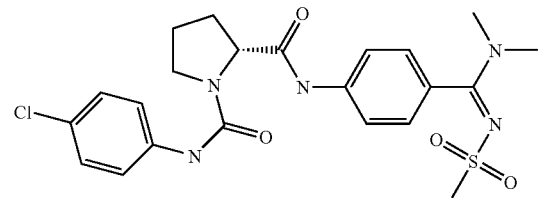

Part A: The product from Example 57, Part A, (3.3 g, 15.2 mmol) was dissolved in 80 mL of anhydrous CH$_3$OH. 15.2 mL (30.5 mmol) of dimethylamine (2.0 M solution in MeOH) was added and the mixture stirred overnight. Volatiles were evaporated and 100 mL of 1N HCl solution was added. The insoluble material was removed by filtration and the mother liquors evaporated to dryness, dissolved in 120 mL of 1N NaOH solution and extracted with CHCl$_3$ (3×30 mL). Organic phases were combined, dried over MgSO$_4$ and concentrated to yield 1.14 g of N,N-dimethyl-4-nitrobenzamidine as a yellow oil.

Part B: According to the procedure described Example 57, part C, 1.14 g (5.9 mmol) of (4-nitrophenyl)(pyrrolidin-1-yl)methanimine were reacted with methane sulfonyl chloride to yield N,N-dimethyl-N'-(methylsulfonyl)-4-nitrobenzamidine (890 mg).

Part C: 0.89 g (3.28 mmol) of the compound from Part B were mixed with 2.22 g (9.84 mmol, 3 eq) of SnCl$_2$-2H$_2$O and 40 mL of ethanol and refluxed for 2.5 h. The volatiles were evaporated, 80 mL of 1N NaOH added, and the mixture extracted with CH$_2$Cl$_2$ (3×30 mL). The organic phase was dried over MgSO$_4$ and concentrated to yield 495 mg of 4-amino-N,N-dimethyl-N'-(methylsulfonyl)benzamidine as a white solid after ISCO system flash chromatography purification.(Eluting AcOEt/Hexane gradient 0% to 10%).

Part D: 25 mg (0.116 mmol) of Boc D proline were mixed with 2 mL of DMF, 2 equivalents (0.23 mmol, 44.5 mg) of EDC, 3 equivalents of HOBT (47 mg; 0.348 mmol) and 3 equivalents of TEA (935 mg, 48.5 µL). To this mixture under N$_2$ atmosphere were added 25 mg (0.104 mmol, 0.9 eq) of the product from Part C. The mixture was stirred overnight at room temperature and under N$_2$ atmosphere. 10 mL of AcOEt were added and the mixture was washed with water (3×3 mL). The organic phase was dried over MgSO$_4$, filtered, and concentrated to yield a crude oil. This was further purified by ISCO system flash chromatography (12 g cartridge loading with CH$_2$Cl$_2$ Gradient elution 0% to 100% B over 41 min; (A=Hexane, B=AcOEt)) to yield 18.7 mg of (R)-tert-butyl 2-((4-(N,N-dimethyl-N'-(methylsulfonyl)carbamimidoyl)phenyl)carbamoyl)pyrrolidine-1-carboxylate as a solid. LC-MS (ESI) 439.31 [M+H]$^+$, t$_R$=2.363 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$ & B=90% MeOH, 10% H$_2$O, 0.2% H$_3$PO$_4$).

Part E: The product from Part D (18.7 mg, 0.043 mmol) was mixed with 1 mL of 1,4 dioxane/HCl 4N solution. The suspension was stirred overnight then volatiles evaporated to yield (R)—N-(4-(N,N-dimethyl-N'-(methylsulfonyl)carbamimidoyl)phenyl)pyrrolidine-2-carboxamide HCl salt (26.6 mg) as a slurry, which was used without purification in the next step.

Part F: 10.6 mg (0.028 mmol) of the hydrochloride were dissolved in 2 mL of anhydrous CH$_2$Cl$_2$. 2 eq of TEA and 1 eq of p-chlorophenyl isocyanate were added, and the mixture was stirred under N$_2$ atmosphere for 8 h. Volatiles were evaporated. 3 mL of CH$_2$Cl$_2$ were added and the mixture was washed twice with 1 mL of water, dried over MgSO$_4$, and concentrated. The crude product was purified by prep HPLC to give the title compound. $^1$H NMR (500 MHz, CDCl$_3$) δ 9.76 (s, 1H), 7.45–7.24 (m, 8H), 6.4 (s, 1H), 4.72 (d, J=5 Hz, 1H), 3.6 (m, 1H), 3.45 (m, 1H), 3.25 (s, 3H) 2.93 (s, 3H), 2.84 (s, 3H), 2.65 (m, 1H), 2.3–1.9 (m, 3H), ppm. LC-MS (ESI) 492.15 [M+H]$^+$, t$_R$=4.928 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). HRMS (ESI) m/z calcd for C$_{22}$H$_{27}$N$_5$O$_4$SCl [M+H]$^+$ 492.14724, found 492.1506.

Using the procedures described above, Examples 59–61 could be prepared:

Example 59

(R)-Pyrrolidine-1,2-dicarboxylic acid 1-[(3-chloro-1H-indol-6-yl)-amide]2-{[4-(dimethylamino-methanesulfonylimino-methyl)-phenyl]-amide}

Example 60

(R)-Pyrrolidine-1,2-dicarboxylic acid 1-[(5-chloro-thiophen-2-yl)-amide]2-{[4-(dimethylamino-methanesulfonylimino-methyl)-phenyl]-amide}

Example 61

(R)-Pyrrolidine-1,2-dicarboxylic acid 1-[(6-chloro-pyridin-3-yl)-amide]2-{[4-(dimethylamino-methanesulfonylimino-methyl)-phenyl]-amide}

Example 62

(Z)-5-Chloro-thiophene-2-carboxylic acid {3-[4-(methanesulfonylimino-pyrrolidin-1-yl-methyl)-phenyl]-2-oxo-oxazolidin-5-ylmethyl}-amide

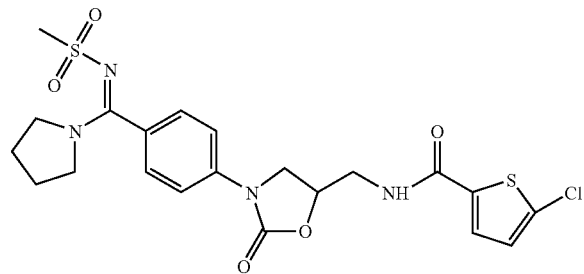

Part A: To a cooled (–30° C.) solution of 16.26 g (0.1 mol) of 5-chlorothiophene-2-carboxylic acid in 75 ml of CH$_2$Cl$_2$ were added 0.15 mol (75 mL, 1.5 eq) of oxalyl chloride 2M solution in CH$_2$Cl$_2$ followed by 4 drops of DMF. The mixture was stirred for 1.5 h. Volatiles were evaporated to yiled the acid chloride as a yellow oil. The crude acid chloride obtained (0.1 mol) was mixed with 41 mL of pyridine and 41 mL of THF. The mixture was cooled to –20° C. and 7.5 mL (0.1 mol) of allylamine was added. The temperature was allowed to increase to ambient and stirring continued for 3 h. Volatiles were evaporated and 300 mL of water added. The yellow precipitate was collected and washed with water. Purified by ISCO system flash chromatography (120 g cartridge loading with CH$_2$Cl$_2$ gradient elution 0% to 100% B over 30 min; (A=CH$_2$Cl$_2$, B=10% MeOH)) to yield 15.7 mg of the N-allyl-5-chlorothiophene-2-carboxamide as a solid. T$_R$=2.67 min (Shimadzu Phenomenex S5 ODS 4.6×50 mm Luna flow rate 2.5 ml/mn; detection at 220 nM; gradient elution 0% to 100% B over 4 min; (A=10% MeOH, 90% H$_2$O, 0.2% H$_3$PO$_4$ & B=90% MeOH, 10% H$_2$O, 0.2% H$_3$PO$_4$).

Part B: 5.315 g (0.026 mol) of the N-allyl derivative prepared as above, were dissolved in 35 mL of CH$_2$Cl$_2$. The solution was cooled to 0° C. and 10.18 g (70% purity, 0.041 mol) of m-CPBA was added portion-wise. The temperature was kept at 0° C. and the mixture stirred overnight. 50 mL of CH$_2$Cl$_2$ were added, the mixture was washed with 10% NaHSO$_4$ (3×20 mL) solution. The organic phase was next washed with saturated NaHCO$_3$ (2×20 mL), NaCl (2×20 mL), dried over MgSO$_4$ and concentrated to yield a crude oil purified by ISCO system flash chromatography (120 g cartridge. Gradient elution 0% to 100% B over 30 min; (A=Hexane, B=AcOt)) to yield 1.1 g of 5-chloro-N-(oxiran-2-ylmethyl)thiophene-2-carboxamide as a solid. T$_R$=2.313 min (Shimadzu Phenomenex S5 ODS 4.6×50 mm Luna flow rate 2.5 ml/mn; detection at 220 nM; Gradient elution 0% to 100% B over 4 min; (A=10% MeOH, 90% H$_2$O, 0.2% H$_3$PO$_4$ & B=90% MeOH, 10% H$_2$O, 0.2% H$_3$PO$_4$).

Part C: 179 mg (0.670 mmol) of the aniline from Example 57, Part D was dissolved in 1 mL of EtOH and few drops of water. To this mixture was added 50 mg of the epoxide prepared in part B as above and the mixture was heated to 100° C. for 4 hours. Additional 2×50 mg of the epoxide were introduced and the reaction stirred at 100° C. for another 2×3 hours. The solvent was evaporated to yield a reddish oil purified by ISCO System flash chromatography (Gradient elution 0% to 100% B over 30 min; (A=Hexane, B=AcOEt) then 0% to 100% B over 30 min; (A=AcOEt, B=10% MeOH and 0.1% NH$_4$OH)) to yield 160 mg of 5-Chloro-thiophene-2-carboxylic acid {2-hydroxy-3-[4-(methanesulfonylimino-pyrrolidin-1-yl-methyl)-phenylamino]-propyl}-amide as a yellow solid. Further purification by prep HPLC yielded an analytically pure sample. Tt$_R$=5.268 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). $^1$H NMR (500 MHz, CDCl$_3$) δ 7.52 (d, J=4.05 Hz, 1H), 7.26 (d, J=8.05 Hz, 2H), 7.02 (d, J=4.05 Hz, 1H), 6.9 (d, J=8.05 Hz, 2H), 3.98 (m, 1H), 3.62 (t, 2H), 3.5 (m, 1H). 3.4 (m, 1H), 3.3 (m, 1H), 3.2 (m, 3H), 2.79 (s, 3H), 2.0 (m, 2H), 1.88 (m, 2H), ppm. LC-MS (ESI) 485.23 [M+H]$^+$. HRMS (ESI) m/z calcd for C$_{20}$H$_{26}$N$_4$O$_4$S$_2$Cl [M+H]$^+$ 485.1084, found 485.1068.

Part D: 120 mg (0.247 mmol) of the product from Part C were mixed with 60 mg (0.371 mmol)of CDI and 2 mL of anhydrous THF and heated at 80° C. for 3 h. The volatiles were evaporated and the residue was purified first by ISCO system flash chromatography (gradient elution 0% to 100% B over 30 min; (A=Hexane, B=AcOEt)) then by preparative HPLC to yield the target derivative. T$_R$=5.178 min (Shimadzu Phenomenex S5 ODS 4.6×50 mm Luna flow rate 2.5 ml/mn; detection at 220 nM; Gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). $^1$H NMR (400 MHz, DMSO-d6) δ 9.1 (t, 1H) 7.81 (d, J=4.05 Hz, 1H), 7.74 (d, J=8.8 Hz, 2H), 7.52 (d, J=8.05 Hz, 2H), 7.31 (d, J=4.05 Hz, 1H), 4.98 (m, 1H), 4.34 (t, J=9.0 Hz 1H), 4.005 (q, J=6.1 Hz and J=9.3 Hz, 1H), 3.74 (m, 2H), 3.64 (m, 2H), 3.49 (bs, 2H), 3.19 (m, 2H), 2.85 (s, 3H), 2.02 (m, 2H), 1.93 (m, 2H), ppm. LC-MS (ESI) 511.18 [M+H]$^+$. HRMS (ESI) m/z calcd for C$_{21}$H$_{24}$N$_4$O$_5$S$_2$Cl [M+H]$^+$ 511.08767, found 511.0867.

Example 63

N-((3-(4-(N,N-dimethyl-N'-(methylsulfonyl)carbamimidoyl)phenyl)-2-oxooxazolidin-5-yl)methyl)-5-chlorothiophene-2-carboxamide

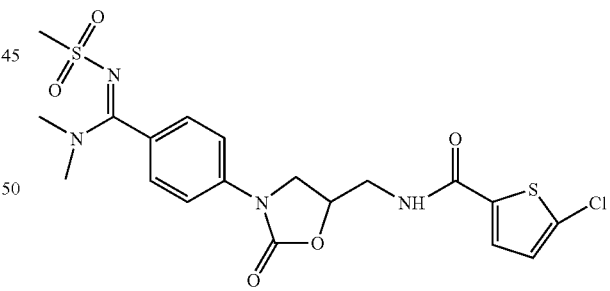

Part A: To mixture of 345 mg (1.43 mmol) of 4-amino-N,N-dimethyl-N'-(methylsulfonyl)benzamidine, 1.5 mL of EtOH, and 0.5 mL of H$_2$O heated at 100° C. was added portion-wise 311 mg (1.43 mmol) of 5-chloro-N-(oxiran-2-ylmethyl)thiophene-2-carboxamide. After 8 hours, the volatiles were evaporated and the compound purified by purified by ISCO System flash chromatography (Gradient elution 0% to 100% B over 40 min; (A=Hexane, B=AcOEt) then 0% to 100% B over 30 min; (A=AcOEt, B=5% MeOH and 1% NH$_4$OH)) to yield 320 mg of N-(3-(4-(N,N-dimethyl -N'-(methylsulfonyl)carbamimidoyl)phenylamino)-2-hydroxypropyl)-5-chlorothiophene-2-carboxamide as a yellow oil.

Further purification by prep HPLC yield an analytically pure sample. $T_R$=4.758 min (Shimadzu Phenomenex S5 ODS 4.6×50 mm Luna flow rate 2.5 ml/mn; detection at 220 nM; gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). $^1$H NMR (500 MHz, CDCl$_3$) δ 7.52 (d, J=4.05 Hz, 1H), 7.26 (d, J=8.05 Hz, 2H), 7.02 (d, J=4.05 Hz, 1H), 6.9 (d, J=8.05 Hz, 2H), 3.98 (m, 1H), 3.62 (t, 2H), 3.5 (m, 1H). 3.4 (m, 1H), 3.3 (m, 1H), 3.2 (m, 3H), 2.79 (s, 3H), 2.0 (m, 2H), 1.88 (m, 2H), ppm. LC-MS (ESI) 459.21 [M+H]$^+$. HRMS (ESI) m/z calcd for C$_{18}$H$_{24}$N$_4$O$_4$S$_2$Cl [M+H]$^+$ 459.09276, found 459.0917.

Part B: A mixture of 320 mg (0.697 mmol) of the compound from part A, 170 mg (1.046 mmol, 1.5 eq) of CDI and 5 mL of anhydrous THF was refluxed for 8 h. After the introduction of additional 50 mg of CDI, the reflux was continued for 22 more hours. Volatiles were evaporated, and the residue was purified first by ISCO system flash chromatography (gradient elution 0% to 100% B over 60 min; (A=Hexane, B=AcOEt)) then by preparative HPLC to yield the title compound. $T_R$=4.722 min (Shimadzu Phenomenex S5 ODS 4.6×50 mm Luna flow rate 2.5 ml/mn; detection at 220 nM; gradient elution 0% to 100% B over 8 min; (A=10% MeOH, 90% H$_2$O, 0.2% H$_3$PO$_4$ & B=90% MeOH, 10% H$_2$O, 0.2% H$_3$PO$_4$). $^1$H NMR (400 MHz, DMSO-d6) δ 9.08 (t, 1H) 7.75 (d, J=4.07 Hz, 1H), 7.69 (d, J=8.8 Hz, 2H), 7.40 (d, J=8.8 Hz, 2H), 7.25 (d, J=4.05 Hz, 1H), 4.95 (m, 1H), 4.28 (t, 1H), 3.95 (q, 1H), 3.67 (m, 2H), 3.19 (m, 3H), 2.81 (s, 3H), 2.8 (s, 3H) ppm. LC-MS (ESI) 485.12 [M+H]$^+$. HRMS (ESI) m/z calcd for C$_{19}$H$_{22}$N$_4$O$_5$S$_2$Cl [M+H]$^+$ 485.07202, found 485.0722.

By using the procedures described above, the following compounds can also be prepared:

N-((3-(4-(N,N-dimethyl-N'-(methylsulfonyl)carbamimidoyl)phenyl)-2-oxooxazolidin-5-yl)methyl)-3-chloro-1H-indole-5-carboxamide;

N-((3-(4-(N,N-dimethyl-N'-(methylsulfonyl)carbamimidoyl)phenyl)-2-oxooxazolidin-5-yl)methyl)-6-chloro-1H-indole-2-carboxamide;

N-((3-(4-(N,N-dimethyl-N'-(methylsulfonyl)carbamimidoyl)phenyl)-2-oxooxazolidin-5-yl)methyl)-4-chlorobenzamide;

N-((3-(4-(N,N-dimethyl-N'-(methylsulfonyl)carbamimidoyl)phenyl)-2-oxooxazolidin-5-yl)methyl)-3-chloro-1H-indole-6-carboxamide;

N-((3-(4-(N,N-dimethyl-N'-(methylsulfonyl)carbamimidoyl)phenyl)-2-oxooxazolidin-5-yl)methyl)-6-chloro-2-naphthamide;

N-((3-(4-(N,N-dimethyl-N'-(methylsulfonyl)carbamimidoyl)phenyl)-2-oxooxazolidin-5-yl)methyl)-6-chlorobenzo[b]thiophene-2-carboxamide;

N-((3-(4-(N,N-dimethyl-N'-(methylsulfonyl)carbamimidoyl)phenyl)-2-oxooxazolidin-5-yl)methyl)-5-chlorobenzo[b]thiophene-2-carboxamide; and N-((3-(4-(N,N-dimethyl-N'-(methylsulfonyl)carbamimidoyl)phenyl)-2-oxooxazolidin-5-yl)methyl)-5-chlorothieno[3,2-b]pyridine-2-carboxamide.

The preparation of the compounds of this invention, in general, utilizes amidine starting materials. The penultimate amidine starting materials can be obtained via the Pinner reactions followed by treatment with appropriate amine reagents (see Examples 9 and 19). Intermediates that can be prepared this way include the following.

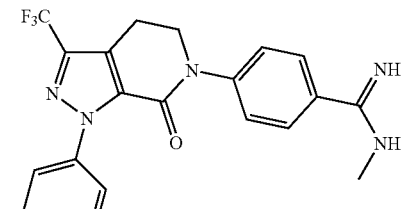

MS 444 (M + H)

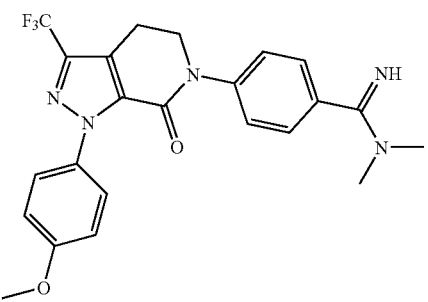

MS 458 (M + H)

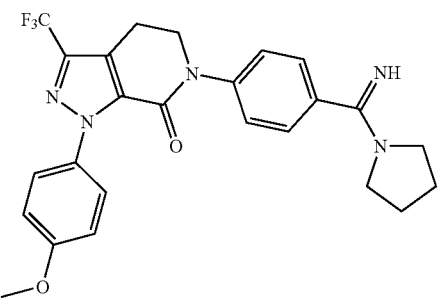

MS 484 (M + H)

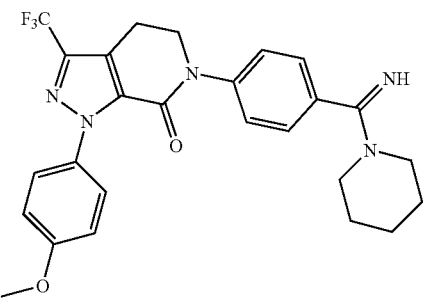

MS 498 (M + H)

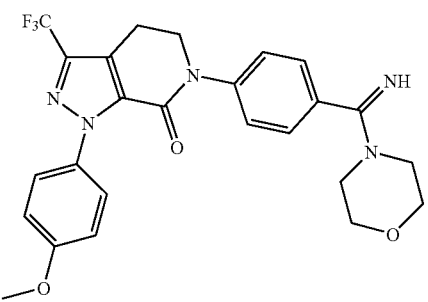

MS 500 (M + H)

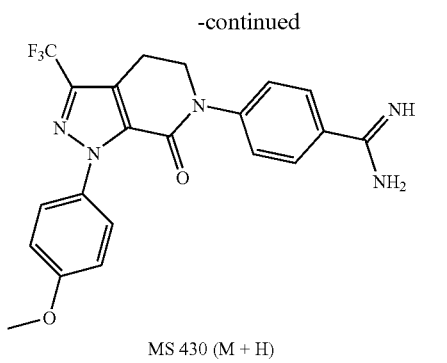
MS 430 (M + H)
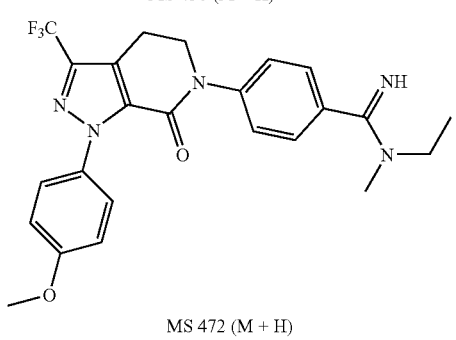
MS 472 (M + H)
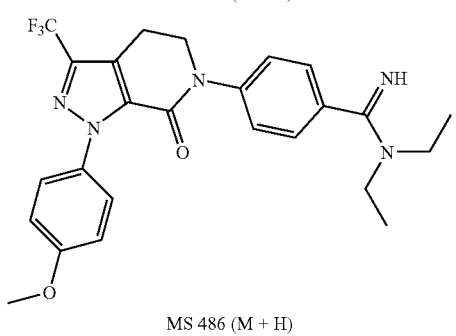
MS 486 (M + H)
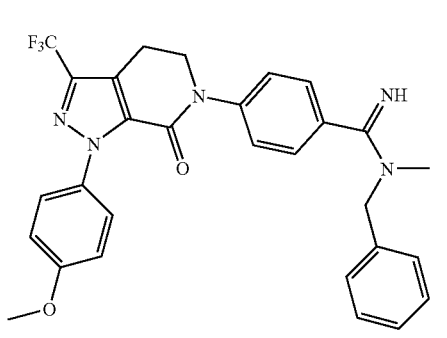
MS 534 (M + H)
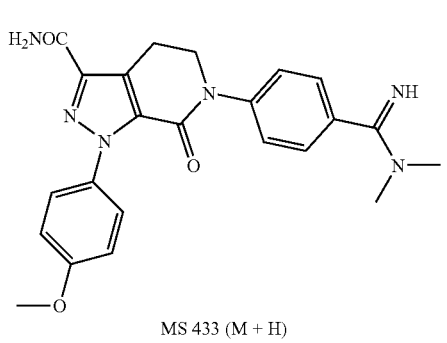
MS 433 (M + H)
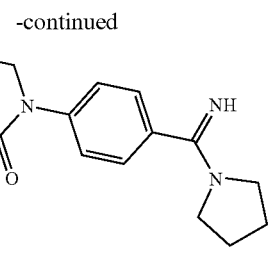
MS 459 (M + H)
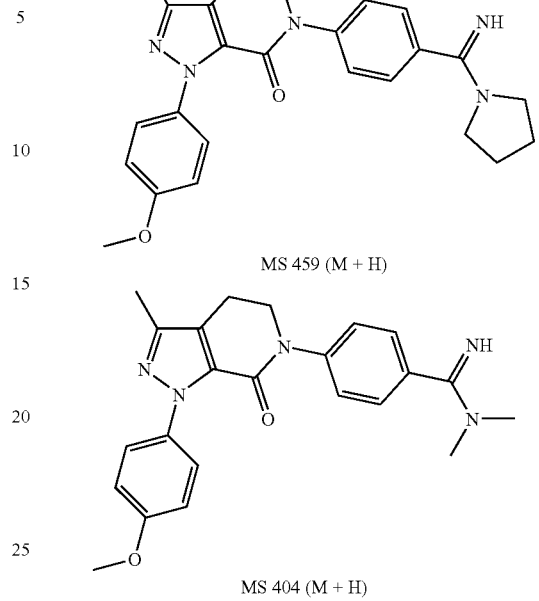
MS 404 (M + H)
MS 430 (M + H)
MS 415 (M + H)
MS 441 (M + H)

-continued
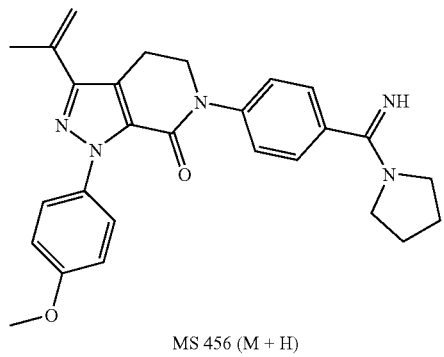
MS 456 (M + H)
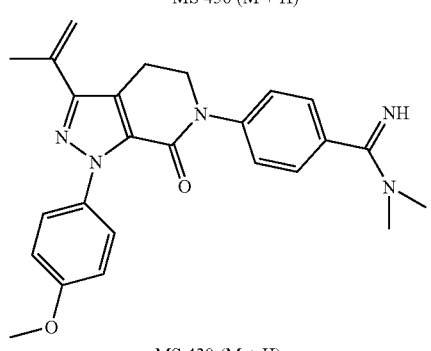
MS 430 (M + H)
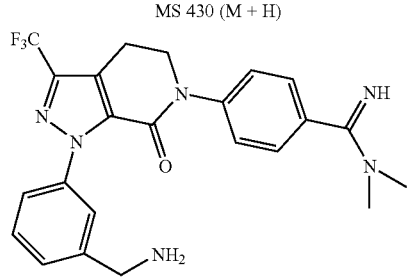
MS 457 (M + H)
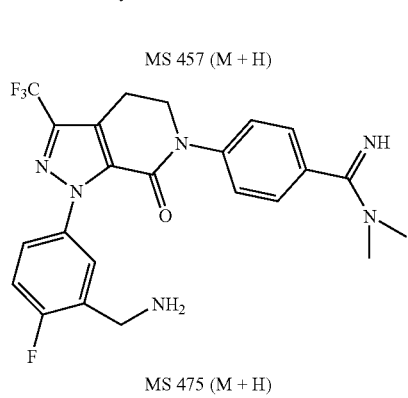
MS 475 (M + H)
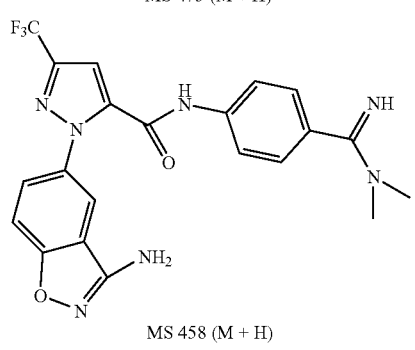
MS 458 (M + H)
-continued
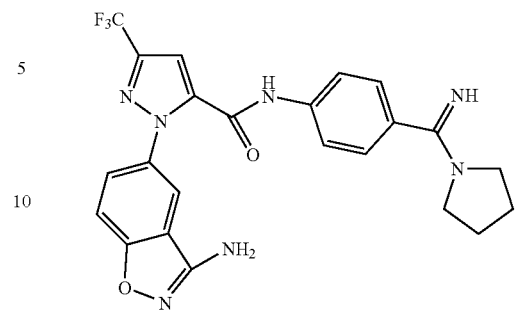
MS 484 (M + H)
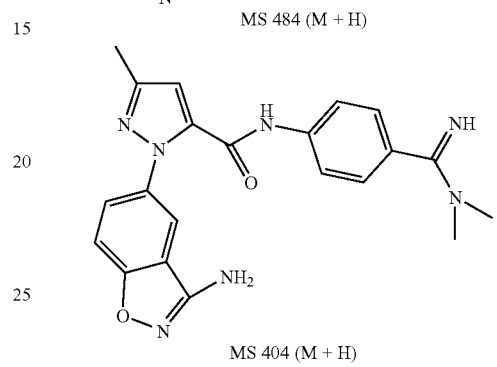
MS 404 (M + H)
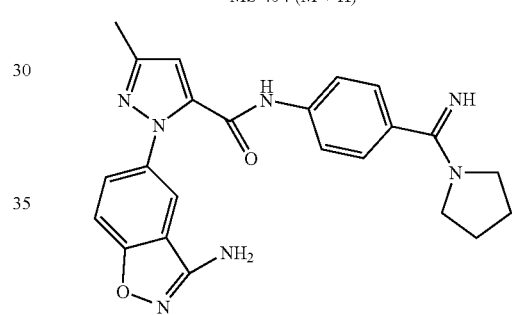
MS 430 (M + H)
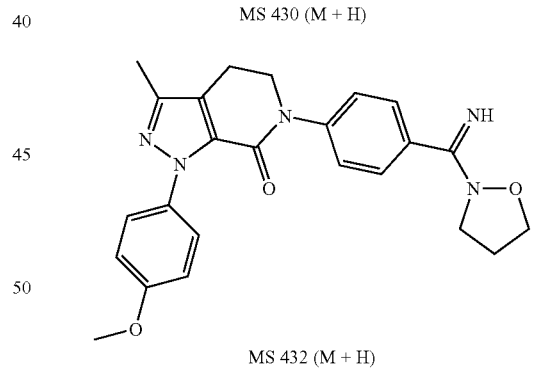
MS 432 (M + H)
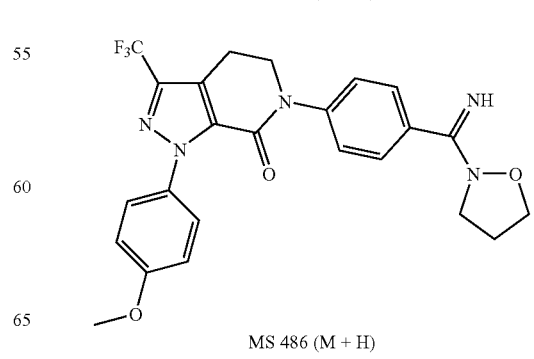
MS 486 (M + H)

Numerous modifications and variations of the present invention are possible in light of the above teachings. It is therefore to be understood that within the scope of the appended claims, the invention may be practiced otherwise that as specifically described herein.

What is claimed is:
1. A compound of Formula I:

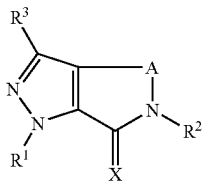

or a stereoisomer or pharmaceutically acceptable salt thereof, wherein;
G is a group of formula IIa:

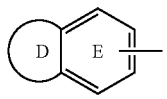

ring D is absent and ring E is phenyl is substituted with R;
R is selected from OH, $OCH_3$, $OCH_2CH_3$, $OCH(CH_3)_2$, and $OCH_2CH_2CH_3$;
A is phenyl;
B is

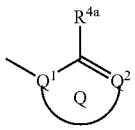

provided that Z and B are attached to different atoms on A and that the $R^{4a}$ shown is other than OH;
$Q^1$ and $Q^2$ are each N;
alternatively, one of $Q^1$ and $Q^2$ is $CR^3$ and $R^{4a}$ is $NR^2R^{2a}$ or $NR^{3a}B_1$, provided that when one of $Q^1$ and $Q^2$ is $CR^3$, then this $R^3$ group optionally forms a ring with the $R^2$ group of $R^{4a}$, this ring is a 5–6 membered ring consisting of, in addition to the C—C—N shown, carbon atoms and from 0–1 additional heteroatoms selected from N, O, and $S(O)_p$, and this ring is substituted with 0–1 $R^5$;
ring Q is a 5–8 membered ring consisting of, in addition to the $Q^1$—$CR^{4a}$=$Q^2$ group shown, carbon atoms and 0–2 heteroatoms selected from N, O, and $S(O)_p$, and the ring is substituted with an additional 0–2 $R^{4a}$;
$R^{1a}$, at each occurrence, is selected from H, —($CR^3R^{3a}$)$_r$—$R^{1b}$, —($CR^3R^{3a}$)$_r$—$CR^3R^{1b}R^{1b}$, —($CR^3R^{3a}$)$_r$—O—($CR^3R^{3a}$)$_r$—$R^{1b}$, —($CR^3R^{3a}$)$_r$—$NR^2$—($CR^3R^{3a}$)$_r$—$R^{1b}$, —($CR^3R^{3a}$)$_r$—$S(O)_p$—($CR^3R^{3a}$)$_r$—$R^{1b}$, —($CR^3R^{3a}$)$_r$—$CO_2$—($CR^3R^{3a}$)$_r$—$R^{1b}$, —($CR^3R^{3a}$)$_r$—$C(O)NR^2$—($CR^3R^{3a}$)$_r$—$R^{1b}$, —($CR^3R^{3a}$)$_r$—C(O)—($CR^3R^{3a}$)$_r$—$R^{1b}$, —$C_{2-6}$ alkenylene-$R^{1b}$, —$C_{2-6}$ alkynylene-$R^{1b}$, and —($CR^3R^{3a}$)$_r$—C(=$NR^{1b}$)$NR^3$ $R^{1b}$, provided that $R^{1a}$ forms other than an N-halo, N—S, O—O, or N—CN bond;
$R^{1b}$ is selected from H, $C_{1-3}$ alkyl, F, Cl, Br, I, —CN, —$NO_2$, —CHO, ($CF_2$)$_r$$CF_3$, ($CR^3R^{3a}$)$_r$$OR^2$, $NR^2R^{2a}$, C(O)$R^{2b}$, $CO_2R^{2b}$, OC(O)$R^2$, CH(CH$_2$OR$^2$)$_2$, ($CF_2$)$_r$$CO_2R^{2a}$, $S(O)_pR^{2b}$, $NR^2(CH_2)_rOR^2$, C(=$NR^{2c}$)$NR^2R^{2a}$, $NR^2C(O)R^{2b}$, $NR^2C(O)NR^2R^{2a}$, $NR^2C(O)_2R^{2a}$, OC(O)$NR^2R^{2a}$, C(O)$NR^2R^{2a}$, C(O)$NR^2(CH_2)_rOR^2$, $SO_2NR^2R^{2a}$, $NR^2SO_2R^2$, C(O)$NR^2SO_2R^2$, $C_{3-6}$ carbocycle substituted with 0–2 $R^{4b}$, and 5–10 membered heterocycle substituted with 0–2 $R^{4b}$ and consisting of carbon atoms and from 1–4 heteroatoms selected from the group consisting of N, O, and $S(O)_p$, provided that $R^{1b}$ forms other than an O—O, N-halo, N—S, or N—CN bond;
$R^2$, at each occurrence, is selected from H, $CF_3$, $C_{1-6}$ alkyl, —($CH_2$)$_r$—$C_{3-10}$ carbocycle substituted with 0–2 $R^{4b}$, and —($CH_2$)$_r$-5–10 membered heterocycle consisting of: carbon atoms and 1–4 heteroatoms selected from the group consisting of N, O, and $S(O)_p$ and substituted with 0–2 $R^{4b}$;
$R^{2a}$, at each occurrence, is selected from H, $CF_3$, $C_{1-6}$ alkyl, —($CH_2$)$_r$—$C_{3-10}$ carbocycle substituted with 0–2 $R^{4b}$, and —($CH_2$)$_r$-5–10 membered heterocycle consisting of: carbon atoms and 1–4 heteroatoms selected from the group consisting of N, O, and $S(O)_p$ and substituted with 0–2 $R^{4b}$;
alternatively, $NR^2R^{2a}$ forms a 5 or 6 membered saturated, partially saturated, or unsaturated ring substituted with 0–2 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;
$R^{2b}$, at each occurrence, is selected from $CF_3$, $C_{1-4}$ alkoxy substituted with 0–2 $R^{4b}$, $C_{1-6}$ alkyl substituted with 0–2 $R^{4b}$, —($CH_2$)$_r$—$C_{3-10}$ carbocycle substituted with 0–2 $R^{4b}$, and —($CH_2$)$_r$-5–10 membered heterocycle consisting of: carbon atoms and 1–4 heteroatoms selected from the group consisting of N, O, and $S(O)_p$ and substituted with 0–2 $R^{4b}$;
$R^{2c}$, at each occurrence, is selected from $CF_3$, OH, $C_{1-4}$ alkoxy, $C_{1-6}$ alkyl, —($CH_2$)$_r$—$C_{3-10}$ carbocycle substituted with 0–2 $R^{4b}$, and —($CH_2$)$_r$-5–10 membered heterocycle containing from 1–4 heteroatoms selected from the group consisting of N, O, and $S(O)_p$ and substituted with 0–2 $R^{4b}$;
$R^3$, at each occurrence, is selected from H, $CH_3$, $CH_2CH_3$, $CH_2CH_2CH_3$, CH($CH_3$)$_2$, $CH_2CH_2CH_2CH_3$, $CH_2CH(CH_3)_2$, CH($CH_3$)$CH_2CH_3$, C($CH_3$)$_3$, benzyl, and phenyl;
$R^{3a}$, at each occurrence, is selected from H, $CH_3$, $CH_2CH_3$, $CH_2CH_2CH_3$, CH($CH_3$)$_2$, $CH_2CH_2CH_2CH_3$, $CH_2CH(CH_3)_2$, CH($CH_3$)$CH_2CH_3$, C($CH_3$)$_3$, benzyl, and phenyl;
alternatively, $NR^3R^{3a}$ forms a 5 or 6 membered saturated, partially unsaturated, or unsaturated ring consisting of: carbon atoms, the nitrogen atom to which $R^3$ and $R^{3a}$ are attached, and 0–1 additional heteroatoms selected from the group consisting of N, O, and $S(O)_p$;
$R^{3b}$, at each occurrence, is selected from H, $CF_3$, $C_{1-6}$ alkyl substituted with 0–2 $R^{1a}$, $C_{2-6}$ alkenyl substituted with 0–2$R^{1a}$, $C_{2-6}$ alkynyl substituted with 0–2 $R^{1a}$, —($C_{0-4}$ alkyl)-5–10 membered carbocycle substituted with 0–3 $R^{1a}$, and —($C_{0-4}$ alkyl)-5–10 membered heterocycle substituted with 0–3 $R^{1a}$ and consisting of: carbon atoms and 1–4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{4a}$, at each occurrence, is selected from H, $(CR^3R^{3a})_r$ $OR^2$, $(CR^3R^{3a})_r$F, $(CR^3R^{3a})_r$Br, $(CR^3R^{3a})_r$Cl, $C_{1-4}$ alkyl, $(CR^3R^{3a})_r$CN, $(CR^3R^{3a})_r$NO$_2$, $(CR^3R^{3a})_r$NR$^2$R$^{2a}$, $(CR^3R^{3a})_r$C(O)R$^{2c}$, $(CR^3R^{3a})_r$NR$^2$C(O)R$^{2b}$, $(CR^3R^{3a})_r$C(O)NR$^2$R$^{2a}$, $(CR^3R^{3a})_r$N=CHOR$^3$, $(CR^3R^{3a})_r$C(O)NH(CH$_2$)$_2$NR$^2$R$^{2a}$, $(CR^3R^{3a})_r$NR$^2$C(O)NR$^2$R$^{2a}$, $(CR^3R^{3a})_r$C(=NR$^2$)NR$^2$R$^{2a}$, $(CR^3R^{3a})_r$NHC(=NR$^2$)NR$^2$R$^{2a}$, $(CR^3R^{3a})_r$SO$_2$NR$^2$R$^{2a}$, $(CR^3R^{3a})_r$NR$^2$SO$_2$NR$^2$R$^{2a}$, $(CR^3R^{3a})_r$NR$^2$SO$_2$—C$_{1-4}$ alkyl, $(CR^3R^{3a})_r$C(O)NHSO$_2$—C$_{1-4}$ alkyl, $(CR^3R^{3a})$ NR$^2$SO$_2$R$^5$, $(CR^3R^{3a})_r$S(O)$_p$R$^{5a}$, $(CR^3R^{3a})_r$(CF$_2$)$_r$CF$_3$, $(CR^3R^{3a})_r$-5–6 membered carbocycle substituted with 0–1 R$^5$, and a $(CR^3R^{3a})_r$-5–6 membered heterocycle consisting of: carbon atoms and 1–4 heteroatoms selected from the group consisting of N, O, and S(O)$_p$ and substituted with 0–1 R$^5$;

$R^{4b}$, at each occurrence, is selected from H, =O, $(CH_2)_r$ OR$^3$, $(CH_2)_r$F, $(CH_2)_r$Cl, $(CH_2)_r$Br, $(CH_2)_r$I, $C_{1-4}$ alkyl, $(CH_2)_r$CN, $(CH_2)_r$NO$_2$, $(CH_2)_r$NR$^3$R$^{3a}$, $(CH_2)_r$C(O)R$^3$, $(CH_2)_r$C(O)OR$^{3c}$, $(CH_2)_r$NR$^3$C(O)R$^{3a}$, $(CH_2)_r$C(O)NR$^3$R$^{3a}$, $(CH_2)_r$NR$^3$C(O)NR$^3$R$^{3a}$, $(CH_2)_r$C(=NR$^3$)NR$^3$R$^{3a}$, $(CH_2)_r$NR$^3$C(=NR$^3$)NR$^3$R$^{3a}$, $(CH_2)_r$SO$_2$NR$^3$R$^{3a}$, $(CH_2)_r$NR$^3$SO$_2$NR$^3$R$^{3a}$, $(CH_2)_r$NR$^3$SO$_2$—C$_{1-4}$ alkyl, $(CH_2)_r$NR$^3$SO$_2$CF$_3$, $(CH_2)_r$NR$^3$SO$_2$-phenyl, $(CH_2)_r$S(O)$_p$CF$_3$, $(CH_2)_r$S(O)$_p$—C$_{1-4}$ alkyl, $(CH_2)_r$S(O)$_p$-phenyl, and $(CH_2)_r$(CF$_2$)$_r$CF$_3$;

$R^5$, at each occurrence, is selected from H, $C_{1-6}$ alkyl, =O, $(CH_2)_r$OR$^3$, F, Cl, Br, I, —CN, NO$_2$, $(CH_2)_r$NR$^3$R$^{3a}$, $(CH_2)_r$C(O)R$^3$, $(CH_2)_r$C(O)OR$^{3c}$, NR$^3$C(O) R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$SO$_2$NR$^3$R$^{3a}$, NR$^3$SO$_2$—C$_{1-4}$ alkyl, NR$^3$SO$_2$CF$_3$, NR$^3$SO$_2$-phenyl, S(O)$_p$CF$_3$, S(O)$_p$—C$_{1-4}$ alkyl, S(O)$_p$-phenyl, (CF$_2$)$_r$CF$_3$, phenyl substituted with 0–2 R$^6$, naphthyl substituted with 0–2 R$^6$, and benzyl substituted with 0–2 R$^6$;

$R^{5a}$, at each occurrence, is selected from $C_{1-6}$ alkyl, $(CH_2)_r$OR$^3$, $(CH_2)_r$NR$^3$R$^{3a}$, $(CH_2)_r$C(O)R$^3$, $(CH_2)_r$C(O)OR$^{3c}$, $(CH_2)_r$NR$^3$C(O)R$^{3a}$, $(CH_2)_r$C(O)NR$^3$R$^{3a}$, (CF$_2$)$_r$CF$_3$, phenyl substituted with 0–2 R$^6$, naphthyl substituted with 0–2 R$^6$, and benzyl substituted with 0–2 R$^6$, provided that R$^5$a does not form a S—N or S(O)$_p$—C(O) bond;

$R^6$, at each occurrence, is selected from H, OH, $(CH_2)_r$ OR$^2$, halo, $C_{1-4}$ alkyl, —CN, NO$_2$, $(CH_2)_r$NR$^2$R$^{2a}$, $(CH_2)_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

p, at each occurrence, is selected from 0, 1, and 2; and r, at each occurrence, is selected from 0, 1, 2, 3, 4, 5, and 6.

2. A compound according to claim 1, wherein:

R is selected from OH, OCH$_3$, OCH$_2$CH$_3$, and OCH (CH$_3$)$_2$;

B is

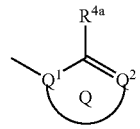

; provided that Z and B are attached to different atoms on A and that the R$^{4a}$ shown is other than OH;

$Q^1$ and $Q^2$ are each N;

alternatively, one of Q$^1$ and Q$^2$ is CR$^3$ and R$^{4a}$ is NR$^2$R$^{2a}$ or NR$^{3a}$B$_1$, provided that when one of Q$^1$ and Q$^2$ is CR$^3$, then this R$^3$ group optionally forms a ring with the R$^2$ group of R$^{4a}$, this ring is a 5–6 membered ring consisting of, in addition to the C—C—N shown, carbon atoms and from 0–1 additional heteroatoms selected from N, O, and S(O)$_p$, and this ring is substituted with 0–1 R$^5$;

ring Q is a 5–6 membered ring consisting of, in addition to the Q$^1$—CR$^{4a}$=Q$^2$ group shown, carbon atoms and 0–2 heteroatoms selected from N, O, and S(O)$_p$, and the ring is substituted with an additional 0–2 R$^{4a}$;

$R^{1a}$, at each occurrence, is selected from H, —(CH$_2$)$_r$— R$^{1b}$, —(CH(CH$_3$))$_r$—R$^{1b}$, —(C(CH$_3$)$_2$)$_r$—R$^{1b}$, —O— (CR$^3$R$^{3a}$)$_r$—R$^{1b}$, —NR$^2$—(CR$^3$R$^{3a}$)$_r$—R$^{1b}$, and —S—(CR$^3$R$^{3a}$)$_r$—R$^{1b}$, provided that R$^{1a}$ forms other than an N-halo, N—S, O—O, or N—CN bond;

$R^{1b}$ is selected from H, CH$_3$, CH$_2$CH$_3$, CH$_2$CH$_2$CH$_3$, CH(CH$_3$)$_2$, F, Cl, Br, I, —CN, —CHO, CF$_3$, OR$^2$, NR$^2$R$^{2a}$, C(O)R$^{2b}$, CO$_2$R$^{2b}$, OC(O)R$^2$, CO$_2$R$^{2a}$, S(O)$_p$ R$^{2b}$, NR$^2$(CH$_2$)$_r$OR$^2$, NR$^2$C(O)R$^{2b}$, NR$^2$C(O)NHR$^2$, NR$^2$C(O)$_2$R$^{2a}$, OC(O)NR$^2$R$^{2a}$, C(O)NR$^2$R$^{2a}$, C(O) NR$^2$(CH$_2$)$_r$OR$^2$, SO$_2$NR$^2$R$^{2a}$, NR$^2$SO$_2$R$^2$, $C_{5-6}$ carbocycle substituted with 0–2 R$^{4b}$, and 5–6 membered heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

$R^2$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, $C_{5-6}$ carbocycle substituted with 0–2 R$^{4b}$, a —CH$_2$—C$_{5-6}$ carbocyclic group substituted with 0–2 R$^{4b}$, and 5–6 membered heterocycle consisting of: carbon atoms and 1–4 heteroatoms selected from the group consisting of N, O, and S(O)$_p$ and substituted with 0–2 R$^{4b}$;

$R^{2a}$, at each occurrence, is selected from H, CF$_3$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 R$^{4b}$, $C_{5-6}$ carbocycle substituted with 0–2 R$^{4b}$, and 5–6 membered heterocycle consisting of: carbon atoms and 1–4 heteroatoms selected from the group consisting of N, O, and S(O)$_p$ and substituted with 0–2 R$^{4b}$;

alternatively, NR$^2$R$^{2a}$ forms a 5 or 6 membered saturated, partially saturated, or unsaturated ring substituted with 0–2 R$^{4b}$ and consisting of: carbon atoms, the nitrogen atom to which R$^2$ and R$^{2a}$ are attached, and 0–1 additional heteroatoms selected from the group consisting of N, O, and S(O)$_p$;

$R^{2b}$, at each occurrence, is selected from CF$_3$, $C_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 R$^{4b}$, C$_{5-6}$ carbocycle substituted with 0–2 R$^{4b}$, and 5–6 membered heterocycle consisting of: carbon atoms and 1–4 heteroatoms selected from the group consisting of N, O, and S(O)$_p$ and substituted with 0–2 R$^{4b}$;

R$^{2c}$, at each occurrence, is selected from CF$_3$, OH, C$_{1-4}$ alkoxy, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, benzyl substituted with 0–2 R$^{4b}$, C$_{5-6}$ carbocycle substituted with 0–2 R$^{4b}$, and 5–6 membered heterocycle containing from 1–4 heteroatoms selected from the group consisting of N, O, and S(O)$_p$ and substituted with 0–2 R$^{4b}$;

R$^3$, at each occurrence, is selected from H, CH$_3$, CH$_2$CH$_3$, CH$_2$CH$_2$CH$_3$, CH(CH$_3$)$_2$, benzyl, and phenyl;

R$^{3a}$, at each occurrence, is selected from H, CH$_3$, CH$_2$CH$_3$, CH$_2$CH$_2$CH$_3$, CH(CH$_3$)$_2$, benzyl, and phenyl;

alternatively, NR$^3$R$^{3a}$ forms a 5 or 6 membered saturated, partially unsaturated, or unsaturated ring consisting of: carbon atoms and the nitrogen atom to which R$^3$ and R$^{3a}$ are attached;

R$^{3b}$, at each occurrence, is selected from H, CF$_3$, CH$_3$, CH$_2$CH$_3$, CH$_2$CH$_2$CH$_3$, CH(CH$_3$)$_2$, —(C$_{0-1}$ alkyl)-5–6 membered carbocycle substituted with 0–1 R$^{1a}$, and —(C$_{0-1}$ alkyl)-5–6 membered heterocycle substituted with 0–1 R$^{1a}$ and consisting of: carbon atoms and 1–4 heteroatoms selected from the group consisting of N, O, and S(O)$_p$;

R$^{3c}$, at each occurrence, is selected from CH$_3$, CH$_2$CH$_3$, CH$_2$CH$_2$CH$_3$, CH(CH$_3$)$_2$, benzyl, and phenyl;

R$^{3d}$, at each occurrence, is selected from H, CH$_3$, CH$_2$CH$_3$, CH$_2$CH$_2$CH$_3$, CH(CH$_3$)$_2$, CH$_2$-phenyl, CH$_2$CH$_2$-phenyl, and C(=O)R$^{3c}$;

R$^{4a}$, at each occurence, is selected from H, CH$_2$OR$^2$, OR$^2$, C$_{1-4}$ alkyl, —CN, CH$_2$CN, NO$_2$, CH$_2$NO$_2$, NR$^2$R$^{2a}$, CH$_2$NR$^2$R$^{2a}$, C(O)R$^{2c}$, CH$_2$C(O)R$^{2c}$, NR$^2$C(O)R$^{2b}$, (CH$_2$)$_r$C(O)NR$^2$R$^{2a}$, NR$^2$C(O)NR$^2$R$^{2a}$, (CH$_2$)$_r$SO$_2$NR$^2$R$^{2a}$, NR$^2$SO$_2$NR$^2$R$^{2a}$, NR$^2$SO$_2$R$^5$, (CH$_2$)$_r$S(O)$_p$R$^{5a}$, CH$_2$CF$_3$, CF$_3$, 5–6 membered carbocycle substituted with 0–1 R$^5$, CH$_2$-5–6 membered carbocycle substituted with 0–1 R$^5$, a 5–6 membered heterocycle consisting of: carbon atoms and 1–4 heteroatoms selected from the group consisting of N, O, and S(O)$_p$ and substituted with 0–1 R$^5$, and a CH$_2$-5–6 membered heterocycle consisting of: carbon atoms and 1–4 heteroatoms selected from the group consisting of N, O, and S(O)$_p$ and substituted with 0–1 R$^5$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, NR$^3$C(O)NR$^3$R$^{3a}$, CH$_2$NR$^3$C(O)NR$^3$R$^{3a}$, C(=NR$^3$)NR$^3$R$^{3a}$, CH$_2$C(=NR$^3$)NR$^3$R$^{3a}$, NR$^3$C(=NR$^3$)NR$^3$R$^{3a}$, CH$_2$NR$^3$C(=NR$^3$)NR$^3$R$^{3a}$, SO$_2$NR$^3$R$^{3a}$, CH$_2$SO$_2$NR$^3$R$^{3a}$, NR$^3$SO$_2$NR$^3$R$^{3a}$, CH$_2$NR$^3$SO$_2$NR$^3$R$^{3a}$, NR$_3$SO$_2$—C$_{1-4}$ alkyl, CH$_2$NR$^3$SO$_2$—C$_{1-4}$ alkyl, NR$^3$SO$_2$CF$_3$, CH$_2$NR$^3$SO$_2$CF$_3$, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, CF$_3$, and CH$_2$CF$_3$;

R$^5$, at each occurrence, is selected from H, =O, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, NR$^3$C(O)NR$^3$R$^{3a}$, CH(=NOR$^{3d}$), C(=NR$^3$)NR$^3$R$^{3a}$, NR$^3$C(=NR$^3$)NR$^3$R$^{3a}$, SO$_2$NR$^3$R$^{3a}$, NR$^3$ SO$_2$NR$^3$R$^{3a}$, NR$_3$SO$_2$—C$_{1-4}$ alkyl, NR$^3$SO$_2$CF$_3$, NR$^3$SO$_2$-phenyl, S(O)$_p$CF$_3$, S(O)—C$_{1-4}$ alkyl, S(O)$_p$-phenyl, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, C(O)R$^{2b}$, CH$_2$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl.

3. A compound according to claim 2, wherein:

G is is 4-methoxy-phenyl,

G is 4-methoxy-phenyl;

B is

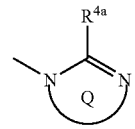

; provided that Z and B are attached to different atoms on A and that the R$^{4a}$ shown is other than OH;

ring Q is a 5–6 membered ring consisting of, in addition to the N—CR$^{4a}$=N group shown, carbon atoms and 0–2 heteroatoms selected from N, O, and S(O)$_p$, and the ring is substituted with an additional 0–2 R$^{4a}$;

R$^{1a}$ is selected from H, R$^{1b}$, CH(CH$_3$)R$^{1b}$, C(CH$_3$)$_2$R$^{1b}$, CH$_2$R$^{1b}$, and CH$_2$CH$_2$R$^{1b}$, provided that R$^{1a}$ forms other than an N-halo, N—S, or N—CN bond;

R$^{1b}$ is selected from H, CH$_3$, CH$_2$CH$_3$, F, Cl, Br, —CN, —CHO, CF$_3$, OR$^2$, NR$^2$R$^{2a}$, C(O)R$^{2b}$, CO$_2$R$^{2b}$, OC(O)R$^2$, CO$_{02}$R$^{2a}$, S(O)$_p$R$^{2b}$, NR$^2$(CH$_2$) $_r$OR$^2$, NR$^2$C(O)R$^{2b}$, C(O)NR$^2$R$^{2a}$, SO$_2$NR$^2$R$^{2a}$, NR$^2$SO$_2$R$^2$, phenyl substituted with 0–2 R$^{4b}$, and 5–6 membered aromatic heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

R$^2$, at each occurrence, is selected from H, CF$_3$, CH$_3$, CH$_2$CH$_3$, CH$_2$CH$_2$CH$_3$, CH(CH$_3$)$_2$, phenyl substituted with 0–2 R$^{4b}$, a benzyl substituted with 0–2 R$^{4b}$, and a 5–6 membered aromatic heterocycle consisting of: carbon atoms and 1–4 heteroatoms selected from the group consisting of N, O, and S(O)$_p$ and substituted with 0–2 R$^{4b}$;

R$^{2a}$, at each occurrence, is selected from H, CF$_3$, CH$_3$, CH$_2$CH$_3$, CH$_2$CH$_2$CH$_3$, CH(CH$_3$)$_2$, benzyl substituted with 0–2 R$^{4b}$, phenyl substituted with 0–2 R$^{4b}$, and 5–6 membered aromatic heterocycle consisting of: carbon atoms and 1–4 heteroatoms selected from the group consisting of N, O, and S(O)$_p$ and substituted with 0–2 R$^{4b}$;

alternatively, NR$^2$R$^{2a}$ forms a 5 or 6 membered saturated, partially saturated, or unsaturated ring substituted with 0–2 R$^{4b}$ and consisting of: carbon atoms, the nitrogen atom to which R$^2$ and R$^{2a}$ are attached, and 0–1 additional heteroatoms selected from the group consisting of N, O, and S(O)$_p$;

R$^{2b}$, at each occurrence, is selected from CF$_3$, C$_{1-4}$ alkoxy, CH$_3$, CH$_2$CH$_3$, CH$_2$CH$_2$CH$_3$, CH(CH$_3$)$_2$, benzyl substituted with 0–2 R$^{4b}$, phenyl substituted with 0–2 R$^{4b}$, and 5–6 membered aromatic heterocycle consisting of: carbon atoms and 1–4 heteroatoms selected from the group consisting of N, O, and S(O)$_p$ and substituted with 0–2 R$^{4b}$;

R$^{2c}$, at each occurrence, is selected from CF$_3$, OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0–2 R$^{4b}$, phenyl substituted with 0–2 R$^{4b}$, and 5–6 membered aromatic heterocycle containing from 1–4 heteroatoms selected from the group consisting of N, O, and S(O)$_p$ and substituted with 0–2 R$^{4b}$;

R$^{3b}$, at each occurrence, is selected from H, CF$_3$, CH$_3$, CH$_2$CH$_3$, CH$_2$CH$_2$CH$_3$, and CH(CH$_3$)$_2$;

R$^{4a}$, at each occurrence, is selected from H, OR$^2$, CH$_2$OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, —CN, NO$_2$, NR$^2$R$^{2a}$, CH$_2$NR$^2$R$^{2a}$, C(O)R$^{2c}$, NR$^2$C(O)R$^{2b}$, C(O)NR$^2$R$^{2a}$, NR$^2$C(O)NR$^2$R$^{2a}$, NR$^2$SO$_2$R$^5$, SO$_2$NR$^2$R$^{2a}$, 6 membered carbocycle substituted with 0–1 R$^5$, and a 5–6 membered heterocycle consisting of: carbon atoms and 1–2 heteroatoms selected from the group consisting of N, O, and S(O)$_p$ and substituted with 0–1 R$^5$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, CH$_2$NR$^3$C(O)R$^{3a}$, C(O)NR$^3$R$^{3a}$, CH$_2$C(O)NR$^3$R$^{3a}$, SO$_2$NR$^3$R$^{3a}$, CH$_2$SO$_2$NR$^3$R$^{3a}$, NR$^3$SO$_2$—C$_{1-4}$ alkyl, CH$_2$NR$^3$SO$_2$—C$_{1-4}$ alkyl, NR$^3$SO$_2$-phenyl, CH$_2$NR$^3$SO$_2$-phenyl, S(O)$_p$CF$_3$, CH$_2$S(O)$_p$CF$_3$, S(O)$_p$—C$_{1-4}$ alkyl, CH$_2$S(O)$_p$—C$_{1-4}$ alkyl, S(O)$_p$-phenyl, CH$_2$S(O)$_p$-phenyl, and CF$_3$;

R$^5$, at each occurrence, is selected from H, =O, CH$_3$, CH$_2$CH$_3$, CH$_2$CH$_2$CH$_3$, CH(CH$_3$)$_2$, OR$^3$, CH$_2$OR$^3$, F, Cl, —CN, NO$_2$, NR$^3$R$^{3a}$, CH$_2$NR$^3$R$^{3a}$, C(O)R$^3$, CH$_2$C(O)R$^3$, C(O)OR$^{3c}$, CH$_2$C(O)OR$^{3c}$, NR$^3$C(O)R$^{3a}$, C(O)NR$^3$R$^{3a}$, SO$_2$NR$^3$R$^{3a}$, CF$_3$, phenyl substituted with 0–2 R$^6$, naphthyl substituted with 0–2 R$^6$, and benzyl substituted with 0–2 R$^6$; and R$^6$, at each occurrence, is selected from H, OH, OR$^2$, F, Cl, CH$_3$, CH$_2$CH$_3$, CH$_2$CH$_2$CH$_3$, CH(CH$_3$)$_2$, —CN, NO$_2$, NR$^2$R$^{2a}$, CH$_2$NR$^2$R$^{2a}$, C(O)R$^{2b}$, CH$_2$(O)R$^{2b}$, NR$^2$C(O)R$^{2b}$, SO$_2$NR$^2$R$^{2a}$, and NR$^2$SO$_2$C$_{1-4}$ alkyl.

4. A compound according to claim 3, wherein:

B is

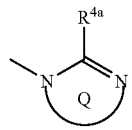

; provided that Z and B are attached to different atoms on A and that the R$^{4a}$ shown is other than OH;

ring Q is a 5–6 membered ring consisting of, in addition to the N—CR$^{4a}$=N group shown, carbon atoms and 0–1 heteroatoms selected from N, O, and S(O)$_p$, and the ring is substituted with an additional 0–2 R$^{4b}$;

R$^{1a}$, at each occurrence, is selected from H, R$^{1b}$, CH(CH$_3$)R$^{1b}$, C(CH$_3$)$_2$R$^{1b}$, and CH$_2$R$^{1b}$, provided that R$^{1a}$ forms other than an N-halo, N—S, or N—CN bond;

R$^{1b}$ is selected from CH$_3$, CH$_2$CH$_3$, F, Cl, Br, —CN, CF$_3$, OR$^2$, NR$^2$R$^{2a}$, C(O)R$^{2b}$, CO$_2$R$^{2b}$, CO$_2$R$^{2a}$, S(O)$_p$R$^{2b}$, C(O)NR$^2$R$^{2a}$, SO$_2$NR$^2$R$^{2a}$, NR$^2$SO$_2$R$^2$, and 5–6 membered aromatic heterocycle consisting of carbon atoms and from 1–4 heteroatoms selected from the group consisting of N, O, and S(O)$_p$, and substituted with 0–2 R$^{4b}$, provided that R$^{1b}$ forms other than an O—O, N-halo, N—S, or N—CN bond;

R$^2$, at each occurrence, is selected from H, CH$_3$, CH$_2$CH$_3$, CH$_2$CH$_2$CH$_3$, CH(CH$_3$)$_2$, phenyl substituted with 0–1 R$^{4b}$, benzyl substituted with 0–1 R$^{4b}$, and 5–6 membered aromatic heterocycle consisting of: carbon atoms and 1–4 heteroatoms selected from the group consisting of N, O, and S(O)$_p$ and substituted with 0–1 R$^{4b}$;

R$^{2a}$, at each occurrence, is selected from H, CH$_3$, CH$_2$CH$_3$, CH$_2$CH$_2$CH$_3$, CH(CH$_3$)$_2$, benzyl substituted with 0–1 R$^{4b}$, phenyl substituted with 0–1 R$^{4b}$, and 5–6 membered aromatic heterocycle consisting of: carbon atoms and 1–4 heteroatoms selected from the group consisting of N, O, and S(O)$_p$ and substituted with 0–1 R$^{4b}$;

alternatively, NR$^2$R$^{2a}$ forms a 5 or 6 membered saturated, partially saturated, or unsaturated ring substituted with 0–1 R$^{4b}$ and consisting of: carbon atoms, the nitrogen atom to which R$^2$ and R$^{2a}$ are attached, and 0–1 additional heteroatoms selected from the group consisting of N, O, and S(O)$_p$;

R$^{2b}$, at each occurrence, is selected from OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0–1 R$^{4b}$, phenyl substituted with 0–1 R$^{4b}$, and 5–6 membered aromatic heterocycle consisting of: carbon atoms and 1–4 heteroatoms selected from the group consisting of N, O, and S(O)$_p$ and substituted with 0–1 R$^{4b}$;

R$^{2c}$, at each occurrence, is selected from OH, OCH$_3$, OCH$_2$CH$_3$, OCH$_2$CH$_2$CH$_3$, OCH(CH$_3$)$_2$, CH$_3$, CH$_2$CH$_3$, CH$_2$CH$_2$CH$_3$, CH(CH$_3$)$_2$, benzyl substituted with 0–1 R$^{4b}$, phenyl substituted with 0–1 R$^{4b}$, and 5–6 membered aromatic heterocycle containing from 1–4 heteroatoms selected from the group consisting of N, O, and S(O)$_p$ and substituted with 0–1 R$^{4b}$;

R$^{3b}$, at each occurrence, is selected from H and CH$_3$;

R$^{4a}$, at each occurrence, is selected from H, OR$^2$, CH$_2$OR$^2$, CH$_3$, CH$_2$CH$_3$, CH$_2$CH$_2$CH$_3$, CH(CH$_3$)$_2$, CH$_2$CH$_2$CH$_2$CH$_3$, CH$_2$CH(CH$_3$)$_2$, CH(CH$_3$)CH$_2$CH$_3$, C(CH$_3$)$_3$, NR$^2$R$^{2a}$, CH$_2$NR$^2$R$^{2a}$, C(O)R$^{2c}$, NR$^2$C(O)R$^{2b}$, C(O)NR$^2$R$^{2a}$, SO$_2$NR$^2$R$^{2a}$, NR$^2$SO$_2$R$^5$, phenyl substituted with 0–1 R$^5$, and a 5–6 membered heterocycle consisting of: carbon atoms and 1 heteroatom selected from the group consisting of N, O, and S(O)$_p$ and substituted with 0–1 R$^5$;

R$^{4b}$, at each occurrence, is selected from H, =O, OR$^3$, CH$_2$OR$^3$, F, Cl, CH$_3$, CH$_2$CH$_3$, CH$_2$CH$_2$CH$_3$, CH(CH$_3$)$_2$, —CN, NO$_2$, NR$^3$R$^{3a}$, CH$_2$NR$^3$R$^{3a}$, C(O)R$^3$, C(O)OR$^{3c}$, NR$^3$C(O)R$^{3a}$, C(O)NR$^3$R$^{3a}$, SO$_2$NR$^3$R$^{3a}$, NR$^3$SO$_2$—C$_{1-4}$ alkyl NR$^3$SO$_2$-phenyl, S(O)$_p$—C$_{1-4}$ alkyl, S(O)$_p$-phenyl, and CF$_3$;

R$^5$, at each occurrence, is selected from H, =O, CH$_3$, CH$_2$CH$_3$, CH$_2$CH$_2$CH$_3$, CH(CH$_3$)$_2$, OR$^3$, NR$^3$R$^{3a}$, C(O)R$^3$, NR$^3$C(O)R$^{3a}$, C(O)NR$^3$R$^{3a}$, SO$_2$NR$^3$R$^{3a}$, and phenyl substituted with 0–2 R$^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

5. A compound according to claim 4, wherein:

B, provided that Z and B are attached to different atoms on A and that the $R^{4a}$ shown is other than OH, is;

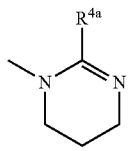

$R^{1a}$, at each occurrence, is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl, provided that $R^{1a}$ forms other than an N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0–1 $R^{4b}$, benzyl substituted with 0–1 $R^{4b}$, and 5 membered aromatic heterocycle consisting of: carbon atoms and 1–4 heteroatoms selected from the group consisting of N, O, and $S(O)_p$ and substituted with 0–1 $R^{4b}$;

$R^{2a}$, at each occurrence, is selected from H, $CH_3$, and $CH_2CH_3$;

alternatively, $NR^2R^{2a}$ forms a 5 or 6 membered saturated, partially saturated, or unsaturated ring substituted with 0–1 $R^{4b}$ and consisting of: carbon atoms, the nitrogen atom to which $R^2$ and $R^{2a}$ are attached, and 0–1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{4a}$, at each occurrence, is selected from H, $OCH_3$, $CH_3$, $CH_2CH_3$, $CH_2CH_2CH_3$, $CH(CH_3)_2$, $NR^2R^{2a}$, $NR^2C(O)R^{2b}$, $NR^2SO_2R^5$, phenyl, 2-oxo-pyrrolidinyl, and 2-oxo-piperidinyl;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$; and $R^5$, at each occurrence, is selected from $CH_3$ and $CH_2CH_3$.

6. A compound according to claim 5, wherein:

A is

B is selected from:

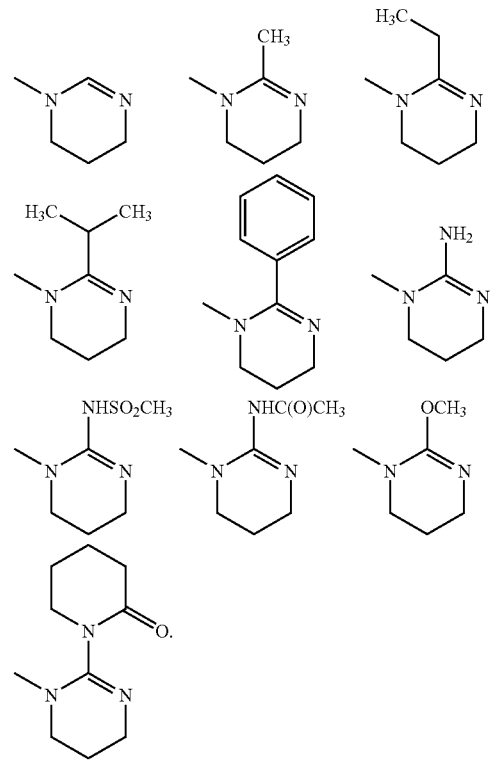

; and

7. A compound according to claim 6, wherein:

A-B is selected from:

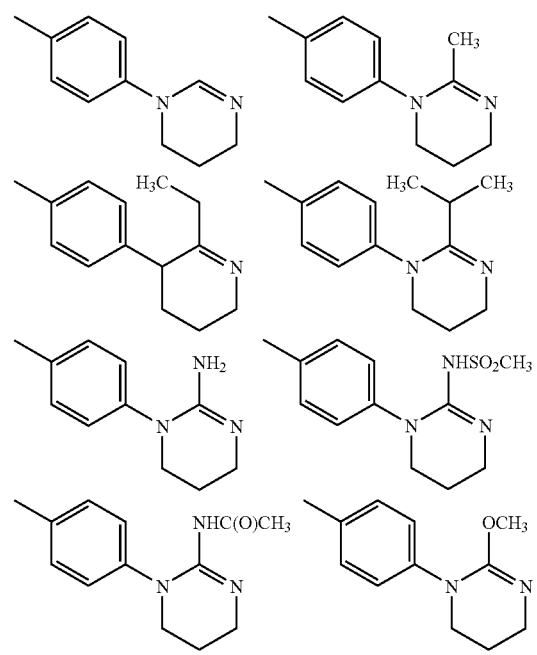

-continued

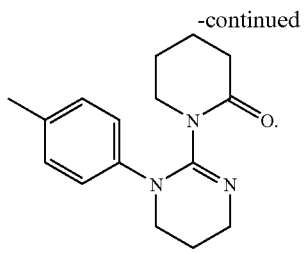

8. A compound according to claim 1, wherein the compound is selected from the group:
  6-[4-(5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one;
  1-(4-methoxy-phenyl)-6-[4-(2-methyl-5,6-dihydro-4H-pyrimidin-1-yl)-phenyl]-3-trifluoromethyl-1,4,5,6-tetrahydro-pyrazolo[3,4-c]pyridin-7-one;
  6-[4-(2-ethyl-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one;
  6-[4-(2-isopropyl-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one;
  1-(4-methoxy-phenyl)-6-[4-(2-phenyl-5,6-dihydro-4H-pyrimidin-1-yl)-phenyl]-3-trifluoromethyl-1,4,5,6-tetrahydro-pyrazolo[3,4-c]pyridin-7-one;
  6-[4-(2-amino-5,6-dihydro-4H-pyrimidin-1-yl)-phenyl]-1-(4-methoxy-phenyl)-3-trifluoromethyl-1,4,5,6-tetrahydro-pyrazolo[3,4-c]pyridin-7-one;
  N-(1-{4-[1-(4-methoxy-phenyl)-7-oxo-3-trifluoromethyl-1,4,5,7-tetrahydro-pyrazolo[3,4-c]pyridin-6-yl]-phenyl}-1,4,5,6-tetrahydro-pyrimidin-2-yl)-methanesulfonamide;
  (1-{4-[1-(4-methoxy-phenyl)-7-oxo-3-trifluoromethyl-1,4,5,7-tetrahydro-pyrazolo[3,4-c]pyridin-6-yl]-phenyl}-1,4,5,6-tetrahydro-pyrimidin-2-yl)-carbamic acid methyl ester;
  N-(1-{4-[1-(4-methoxy-phenyl)-7-oxo-3-trifluoromethyl-1,4,5,7-tetrahydro-pyrazolo[3,4-c]pyridin-6-yl]-phenyl}-1,4,5,6-tetrahydro-pyrimidin-2-yl)-acetamide;
  1-(4-methoxy-phenyl)-6-{4-[2-(2-oxo-piperidin-1-yl)-5,6-dihydro-4H-pyrimidin-1-yl]-phenyl}-3-trifluoromethyl-1,4,5,6-tetrahydro-pyrazolo[3,4-c]pyridin-7-one;
  1-(4-methoxy-phenyl)-6-{4-[2-(2-oxo-pyrrolidin-1-yl)-5,6-dihydro-4H-pyrimidin-1-yl]-phenyl}-3-trifluoromethyl-1,4,5,6-tetrahydro-pyrazolo[3,4-c]pyridin-7-one;
  1-(4-methoxy-phenyl)-6-[4-(2-methyl-5,6-dihydro-4H-pyrimidin-1-yl)-phenyl]-3-cyano-1,4,5,6-tetrahydro-pyrazolo[3,4-c]pyridin-7-one;
  6-[4-(2-amino-5,6-dihydro-4H-pyrimidin-1-yl)-phenyl]-1-(4-methoxy-phenyl)-7-oxo-4,5,6,7-tetrahydro-1H-pyrazolo[3,4-c]pyridine-3-carbonitrile;
  N-(1-{4-[3-cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-methanesulfonamide;
  N-(1-{4-[3-cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-N-methyl-methanesulfonamide;
  N-(1-{4-[3-cyano-1-(4-methoxy-phenyl)-7-oxo-1,4,5,7-tetrahydro-pyrazolo[3,4-c]pyridin-6-yl]-phenyl}-1,4,5,6-tetrahydro-pyrimidin-2-yl)-acetamide;
  6-[4-(2-methoxy-5,6-dihydro-4H-pyrimidin-1-yl)-phenyl]-1-(4-methoxy-phenyl)-7-oxo-4,5,6,7-tetrahydro-1H-pyrazolo[3,4-c]pyridine-3-carbonitrile;
  6-[4-(5,6-dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one;
  3-methanesulfonyl-1-(4-methoxy-phenyl)-6-[4-(2-methyl-5,6-dihydro-4H-pyrimidin-1-yl)-phenyl]-1,4,5,6-tetrahydro-pyrazolo[3,4-c]pyridin-7-one;
  6-[4-(2-isopropyl-5,6-dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one;
  3-methanesulfonyl-1-(4-methoxy-phenyl)-6-[4-(2-phenyl-5,6-dihydro-4H-pyrimidin-1-yl)-phenyl]-1,4,5,6-tetrahydro-pyrazolo[3,4-c]pyridin-7-one;
  6-[4-(2-amino-5,6-dihydro-4H-pyrimidin-1-yl)-phenyl]-3-methanesulfonyl-1-(4-methoxy-phenyl)-1,4,5,6-tetrahydro-pyrazolo[3,4-c]pyridin-7-one;
  3-methanesulfonyl-1-(4-methoxy-phenyl)-6-{4-[2-(2-oxo-piperidin-1-yl)-5,6-dihydro-4H-pyrimidin-1-yl]-phenyl}-1,4,5,6-tetrahydro-pyrazolo[3,4-c]pyridin-7-one;
  6-[4-(5,6-dihydro-4H-pyrimidin-1-yl)-phenyl]-3-isopropoxy-1-(4-methoxy-phenyl)-1,4,5,6-tetrahydro-pyrazolo[3,4-c]pyridin-7-one;
  3-{6-[4-(2-amino-5,6-dihydro-4H-pyrimidin-1-yl)-phenyl]-3-methanesulfonyl-7-oxo-4,5,6,7-tetrahydro-pyrazolo[3,4-c]pyridin-1-yl}-benzamide;
  3-{3-methanesulfonyl-6-[4-(2-methyl-5,6-dihydro-4H-pyrimidin-1-yl)-phenyl]-7-oxo-4,5,6,7-tetrahydro-pyrazolo[3,4-c]pyridin-1-yl}-benzamide;
  1-(3-chloro-phenyl)-6-[4-(2-methyl-5,6-dihydro-4H-pyrimidin-1-yl)-phenyl]-3-trifluoromethyl-1,4,5,6-tetrahydro-pyrazolo[3,4-c]pyridin-7-one; or a pharmaceutically acceptable salt form thereof.

9. A pharmaceutical composition, comprising: a pharmaceutically acceptable carrier and a therapeutically effective amount of a compound of claim 1 or a pharmaceutically acceptable salt form thereof.

10. A method for treating a thromboembolic disorder, comprising: administering to a patient in need thereof a therapeutically effective amount of a compound of claim 1 or a pharmaceutically acceptable salt form thereof.

11. A method according to claim 10, wherein the thromboembolic disorder is selected from the group consisting of arterial cardiovascular thromboembolic disorders, venous cardiovascular thromboembolic disorders, and thromboembolic disorders in the chambers of the heart.

12. A method according to claim 10, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

13. A pharmaceutical composition, comprising: a pharmaceutically acceptable carrier and a therapeutically effective amount of a compound of claim 2 or a pharmaceutically acceptable salt form thereof.

14. A pharmaceutical composition, comprising: a pharmaceutically acceptable carrier and a therapeutically effective amount of a compound of claim 3 or a pharmaceutically acceptable salt form thereof.

15. A pharmaceutical composition, comprising: a pharmaceutically acceptable carrier and a therapeutically effective amount of a compound of claim 4 or a pharmaceutically acceptable salt form thereof.

16. A pharmaceutical composition, comprising: a pharmaceutically acceptable carrier and a therapeutically effective amount of a compound of claim 5 or a pharmaceutically acceptable salt form thereof.

17. A pharmaceutical composition, comprising: a pharmaceutically acceptable carrier and a therapeutically effective amount of a compound of claim 6 or a pharmaceutically acceptable salt form thereof.

18. A pharmaceutical composition, comprising: a pharmaceutically acceptable carrier and a therapeutically effective amount of a compound of claim 7 or a pharmaceutically acceptable salt form thereof.

19. A pharmaceutical composition, comprising: a pharmaceutically acceptable carrier and a therapeutically effective amount of a compound of claim 8 or a pharmaceutically acceptable salt form thereof.

* * * * *